US012428651B2

(12) United States Patent
Howe et al.

(10) Patent No.: US 12,428,651 B2
(45) Date of Patent: Sep. 30, 2025

(54) TRANSCRIPTION FACTORS TO IMPROVE RESISTANCE TO ENVIRONMENTAL STRESS IN PLANTS

(71) Applicant: Board of Trustees of Michigan State University, East Lansing, MI (US)

(72) Inventors: Gregg A. Howe, East Lansing, MI (US); Marcelo Campos, Lago Norte (BR); Yuki Yoshida, Tokyo (JP)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 0 days.

(21) Appl. No.: 18/309,524

(22) Filed: Apr. 28, 2023

(65) Prior Publication Data

US 2023/0365987 A1    Nov. 16, 2023

Related U.S. Application Data

(63) Continuation of application No. 16/323,737, filed as application No. PCT/US2017/048660 on Aug. 25, 2017, now Pat. No. 11,674,151.

(60) Provisional application No. 62/379,773, filed on Aug. 26, 2016.

(51) Int. Cl.
*C12N 15/82*     (2006.01)
(52) U.S. Cl.
CPC ............................... *C12N 15/8286* (2013.01)
(58) Field of Classification Search
None
See application file for complete search history.

(56) References Cited

U.S. PATENT DOCUMENTS

| 8,735,555 | B2 | 5/2014 | Lagarias et al. |
| 11,674,151 | B2 | 6/2023 | Howe et al. |
| 2014/0246036 | A1 | 9/2014 | Qu et al. |
| 2019/0330653 | A1 | 10/2019 | Howe et al. |

FOREIGN PATENT DOCUMENTS

| CN | 101899449 A | 12/2010 |
| CN | 103602686 A | 2/2014 |
| EP | 3504334 B1 | 12/2023 |
| WO | WO-2015124620 A1 | 8/2015 |
| WO | WO-2018039590 A1 | 3/2018 |

OTHER PUBLICATIONS

Leone et al. (New Phytologist, 204:355-367, 2014).*
Niu et al. (J Exp bot., 62:2143-2154, 2011).*
Loulergue et al. (Gene, 225:47-57, 1998).*
Alexandrov et al. (NCBI, GenBank sequence Accession No. NP_001308779, Published Apr. 1, 2016).*
Reed et al. (Plant Cell, 5:147-157, 1993).*
Sheehan et al. (NCBI, GenBank Sequence Accession No. Q6XFQ3, Published Nov. 28, 2006).*
Doerks et al., (TIG, 14:248-250, 1998).*
Smith et al. (Nature Biotechnology, 15:1222-1223, 1997).*
Bork et al. (TIG, 12:425-427, 1996).*
"Canadian Application Serial No. 3,035,084, Response filed Dec. 1, 2023 to Examiners Rule 86(2) Requisition mailed Aug. 1, 2023".
"Brazilian Application Serial No. BR1120190038884, Response filed Mar. 23, 2023 to Office Action mailed Dec. 14, 2022", with English claims, 17 pages.
"Canadian Application Serial No. 3,035,084, Examiners Rule 86(2) Requisition mailed Aug. 1, 2023", 5 pgs.
"U.S. Appl. No. 16/323,737, Non Final Office Action mailed Jun. 9, 2022", 20 pgs.
"U.S. Appl. No. 16/323,737, Notice of Allowance mailed Jan. 30, 2023", 9 pgs.
"U.S. Appl. No. 16/323,737, Preliminary Amendment Filed Feb. 6, 2019", 7 pgs.
"U.S. Appl. No. 16/323,737, Response filed Mar. 7, 2022 to Restriction Requirement mailed Jan. 6, 2022", 9 pgs.
"U.S. Appl. No. 16/323,737, Response filed Oct. 10, 2022 to Non Final Office Action mailed Jun. 9, 2022", 17 pgs.
"U.S. Appl. No. 16/323,737, Restriction Requirement mailed Jan. 6, 2022", 6 pgs.
"Brazilian Application Serial No. BR1120190038884, Office Action mailed Dec. 14, 2022", w/ English Translation, 7 pgs.
"European Application Serial No. 17761766.9, Communication Pursuant to Article 94(3) EPC mailed Apr. 6, 2020", 5 pgs.
"European Application Serial No. 17761766.9, Communication Pursuant to Article 94(3) EPC mailed Jul. 22, 2022", 4 pgs.
"European Application Serial No. 17761766.9, Communication Pursuant to Article 94(3) EPC mailed Aug. 25, 2021", 4 pgs.
"European Application Serial No. 17761766.9, Communication Pursuant to Article 94(3) EPC mailed Nov. 26, 2020", 4 pgs.
"European Application Serial No. 17761766.9, Response filed Apr. 13, 2021 to Communication Pursuant to Article 94(3) EPC mailed Nov. 26, 2020", 12 pgs.
"European Application Serial No. 17761766.9, Response filed Aug. 13, 2020 to Communication Pursuant to Article 94(3) EPC mailed Apr. 6, 2020", 9 pgs.
"European Application Serial No. 17761766.9, Response Filed Dec. 6, 2022 to Communication Pursuant to Article 94(3) EPC mailed Jul. 22, 2022", 168 pgs.
"European Application Serial No. 17761766.9, Response filed Dec. 31, 2021 to Communication Pursuant to Article 94(3) EPC mailed Aug. 25, 2021", 12 pgs.

(Continued)

*Primary Examiner* — Vinod Kumar
(74) *Attorney, Agent, or Firm* — McKee, Voorhees & Sease, PLC

(57) ABSTRACT

Plants, plant cells, and seeds are described herein that grow well and are resistant to environmental stresses such as drought and insects, where the plants have one or more mutations that reduce or eliminate the interaction of MYC transcription factors with the JAZ proteins. The plants can have an additional mutation that reduces or eliminates the function of the PHYB gene, and/or a heterologous PIF4 transgene or PIF4 expression cassette to improve the growth of the myc mutant plants. Methods of making and using such plants, plant cells, and seeds are also described.

12 Claims, 21 Drawing Sheets

Specification includes a Sequence Listing.

(56) References Cited

OTHER PUBLICATIONS

"European Application Serial No. 17761766.9, Response to Response to Communication pursuant to Rules 161(1) and 162 EPC filed Oct. 22, 2019", 8 pgs.
"International Application Serial No. PCT/US2017/048660, International Preliminary Report on Patentability mailed Mar. 7, 2019", 7 pgs.
"International Application Serial No. PCT/US2017/048660, International Search Report mailed Oct. 18, 2017", 6 pgs.
"International Application Serial No. PCT/US2017/048660, Written Opinion mailed Oct. 18, 2017", 5 pgs.
Boccalandro, H. E., et al., "Phytochrome B Enhances Photosynthesis at the Expense of Water-Use Efficiency in *Arabidopsis*", Plant Physiol 150, (2009), 1083-1092.
Bork, Peer, "Go hunting in sequence databases but watch out for the traps", Trends in Genetics, 12(10), (Oct. 1996), 425-427.
Boter, M., et al., "Conserved MYC transcription factors play a key role in jasmonate signaling both in tomato and *Arabidopsis*", Genes Development, 18(13), (2004), 1577-1591.
Campos, M. L., et al., "Rewiring of jasmonate and phytochrome B signalling uncouples plant growth-defense tradeoffs", Nature Communications, 7: Article No. 12570, (2016), 1-10.
Chico, Jose Manuel, et al., "Repression of Jasmonate-Dependent Defenses by Shade Involves Differential Regulation of Protein Stability of MYC Transcription Factors and Their JAZ Repressors in *Arabidopsis*", Plant Cell, 26, (2014), 1967-1980.
Chung, H. S., et al., "A Critical Role for the TIFY Motif in Repression of Jasmonate Signaling by a Stabilized Splice Variant of the JASMONATE ZIM-Domain Protein JAZ10 in *Arabidopsis* C W", The Plant Cell, 21(1), (2009), 131-145.
Doerks, Tobias, et al., "Protein Annotation: detective work for function prediction", Trends in Genetics, vol. 14, No. 6, (1998), 248-250.
Fernandez-Calvo, P., et al., "The *Arabidopsis* bHLH Transcription Factors MYC3 and MYC4 are targets of JAZ repressors and act additively with MYC2 in the activation of jasmonate responses", Plant Cell 23, (2011), 701-715.
Frances, Robson, et al., "Jasmonate and Phytochrome Signaling in Arabidopsis Wound and Shade Responses Are Integrated through JAZ1 Stability", The Plant Cell, (Apr. 1, 2010), 1143-1160.
Gasperini, D., et al., "Multilayered Organization of Jasmonate Signalling in the Regulation of Root Growth", PoOS Genetics, 11(6): e1005300., (2015), 27 pgs.
Goosens, J., et al., "Change of a conserved amino acid in the MYC2 and MYC3 transcription factors leads to release of JAZ repression and increased activity", New Phytoologist, 206, (2015), 1229-1237.
Hoo, Sun Chung, et al., "Top hits in contemporary JAZ: An update on jasmonate signaling", Phytochemistry, (Sep. 1, 2009), vol. 70, No. 13-14, (Sep. 1, 2009), 24 pgs.
Hoo, Sun Chung, et al., "Top hits on contemporary JAZ An update on jasmonate signaling", (Sep. 1, 2009), 1547-1559.
Hornitschek, P., et al., "Phytochrome interacting factors 4 and 5 control seedling growth in changing light conditions by directly controlling auxin signaling", Plant J., 71, (2012), 699-711.
I, Cerrudo, et al., "Low Red/Far-Red Ratios Reduce *Arabidopsis* Resistance to Botrytis cinerea and Jasmonate Responses via COI1-JAZ1O-Dependent Sal icyl ic Acid-Independent Mechanism", Plant Physiology, vol. 158, Rockville Md USA, ISSN 0032-0889 DOI 10.1104/pp 112 193359, (Feb. 27, 2012), 2042-2052.
J, M Chico, et al., "Repression of Jasmonate-Dependent Defenses by Shade Involves Differential Regulation of Protein Stability of MYC Transcription Factors and Their JAZ Repressors in *Arabidopsis*", The Plant Cell, (May 1, 2014).
Kazan, K., et al., "MYC2: The Master in Action", Molecular Plant 6(3), (2013), 686-703.
Leone, Melisa, et al., "To grow or defend? Low red far-red ratios reduce jasmonate sensitivity in *Arabidopsis* seedlings by promoting DELLA degradation and increasing JAZ10 stability", New Phytologist, vol. 204, (2014), 355-367.
Lorenzo, O., et al., "JASMONATE-INSENSISTIVE1 Encodes a MYC Transcription Factor Essential to Discriminate between Differnt Jasmonate-Regulated Defense Responses in *Arabidopsis*", The Plant Cell, vol. 16, (Jul. 2004), 1938-1950.
Major, I. T., "Regulation of growth-defense balance by the Jasmonate Zim-Domain (Jaz)-Myc transcriptional module", The New Phytologist, 215(4), (2017), 1533-1547.
Marcelo, Campos, et al., "Rewiring of jasmonate and phytochrome signalling uncouples plant growth-defense tradeoffs", Nature Communications, (Aug. 30, 2016).
Melisa, Leone, et al., "", New Phytologist; 204, (2014), 355-367.
Moreno, J. E., et al., "Ecological modulation of plant defense via phytochrome control of jasmonate sensitivity", Proc Natl Acad Sci U S A 106, (2009), 4935-4940.
Reed, J. W., et al., "Mutations in the gene for the red/far-red light receptor phytochrome B alter cell elongation and physiological responses throughout *Arabidopsis* development", Plant Cell 5, (1993), 147-157.
Smith, Temple F, et al., The Challenges of Genome Sequence Annotation or "The Devil is in the Details", Nature Biotechnology, 15(12), (Nov. 1997), 1222-1223.
Smolen, G. A., et al., "Dominant Alleles of the Basic Helix-Loop-Helix Transcription Factor ATR2 Activate Stress-Responsive Genes in *Arabidopsis*", Genetics, 161(3), (2002), 1235-1246.
Yang, D. L., et al., "Plant hormone jasmonate prioritizes defense over growth by interfering with gibberellin signaling cascade", Proc. Natl. Acad. Sci. USA, 109(19), (2012), E1192- E1200.
Zhang, F., et al., "Structural basis of JAZ repression of MYC transcription factors in jasmonate signaling", Nature, 525(7568), (2015), 269-273 (17 pgs.).

* cited by examiner

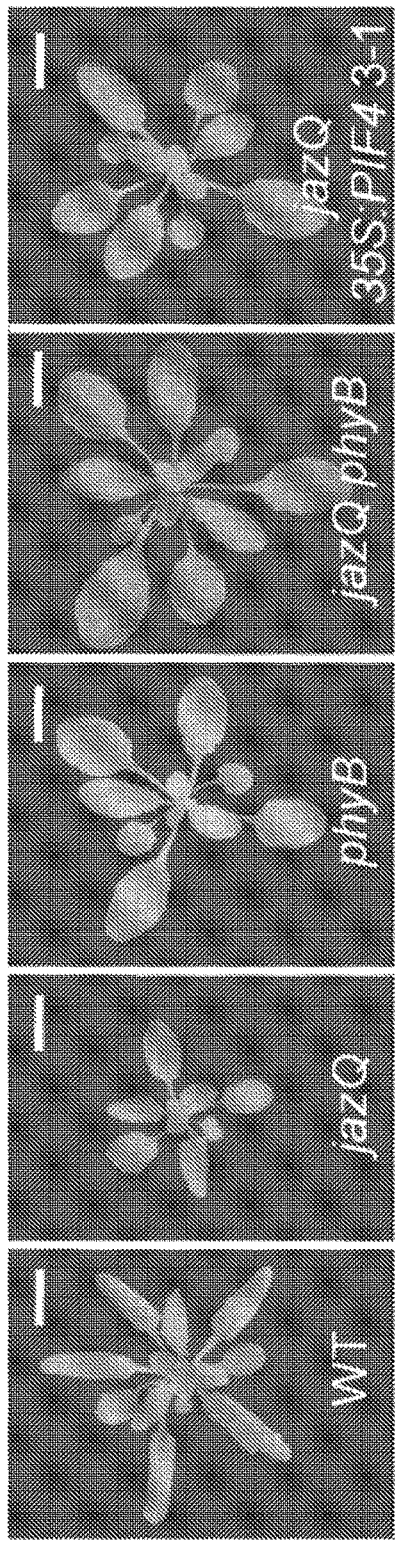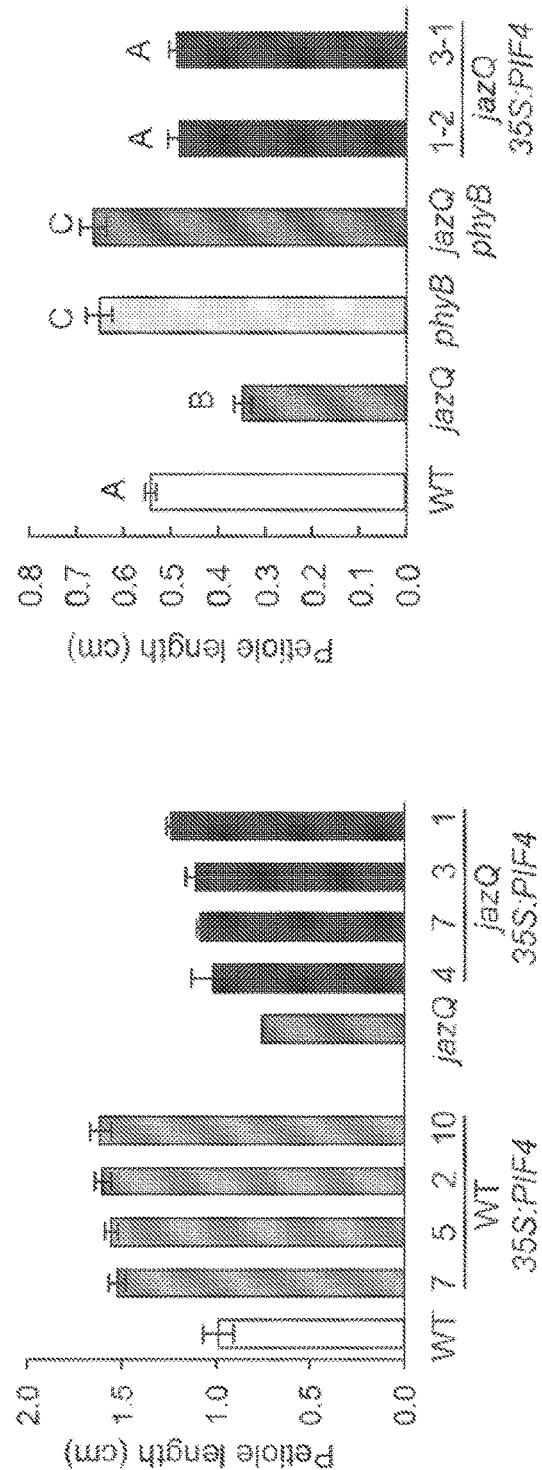
FIG. 5A
FIG. 5B
FIG. 5C

FIG. 6

SEQUENCE LISTING

```
Sequence total quantity: 129
SEQ ID NO: 1            moltype = AA  length = 623
FEATURE                 Location/Qualifiers
source                  1..623
                        mol_type = protein
                        organism = Arabidopsis thaliana
SEQUENCE: 1
MTDYRLQPTM NLWTTDDNAS MMEAFMSSSD ISTLWPPAST TTTTATTETT PTPAMEIPAQ   60
AGFNQETLQQ RLQALIEGTH EGWTYAIFWQ PSYDFSGASV LGWGDGYYKG EEDKANPRRR  120
SSSPPFSTPA DQEYRKKVLR ELNSLISGGV APSDDAVDEE VTDTEWFFLV SMTQSFACGA  180
GLAGKAFATG NAVWVSGSDQ LSGSGCERAK QGGVFGMHTI ACIPSANGVV EVGSTEPIRQ  240
SSDLINKVRI LFNFDGGAGD LSGLNWNLDP DQGENDPSMW INDPIGTPGS NEPGNGAPSS  300
SSQLFSKSIQ FENGSSSTIT ENPNLDPTPS PVHSQTQNPK FNNTFSRELN FSTSSSTLVK  360
PRSGEILNFG DEGKRSSGNP DPSSYSGQTQ FENKRKRSMV LNEDKVLSFG DKTAGESDHS  420
DLEASVVKEV AVEKRPKKRG RKPANGREEP LNHVEAERQR REKLNQRFYA LRAVVPNVSK  480
MDKASLLGDA IAYINELKSK VVKTESEKLQ IKNQLEEVKL ELAGRKASAS GGDMSSSCSS  540
IKPVGMEIEV KIIGWDAMIR VESSKRNHPA ARLMSALMDL ELEVNHASMS VVNDLMIQQA  600
TVKMGFRIYT QEQLRASLIS KIG                                         623

SEQ ID NO: 2            moltype = AA  length = 61
FEATURE                 Location/Qualifiers
source                  1..61
                        mol_type = protein
                        organism = Arabidopsis thaliana
SEQUENCE: 2
YDFSGASVLG WGDGYYKGEE DKANPRRRSS SPPFSTPADQ EYRKKVLREL NSLISGGVAP   60
S                                                                  61

SEQ ID NO: 3            moltype = AA  length = 592
FEATURE                 Location/Qualifiers
source                  1..592
                        mol_type = protein
                        organism = Arabidopsis thaliana
SEQUENCE: 3
MNGTTSSINF LTSDDDASAA AMEAFIGTNH HSSLFPPPPQ QPPQPQFNED TLQQRLQALI   60
ESAGENWTYA IFWQISHDFD SSTGDNTVIL GWGDGYYKGE EDKEKKKNNT NTAEQEHRKR  120
VIRELNSLIS GGIGVSDESN DEEVTDTEWF FLVSMTQSFV NGVGLPGESF LNSRVIWLSG  180
SGALTGSGCE RAGQGQIYGL KTMVCIATQN GVVELGSSEV ISQSSDLMHK VNNLFNFNNG  240
GGNNGVEASS WGFNLNPDQG ENDPALWISE PTNTGIESPA RVNNGNNSNS NSKSDSHQIS  300
KLEKNDISSV ENQNRQSSCL VEKDLTFQGG LLKSNETLSF CGNESSKKRT SVSKGSNNDE  360
GMLSFSTVVR SAANDSDHSD LEASVVKEAI VVEPPEKKPR KRGRKPANGR EEPLNHVEAE  420
RQRREKLNQR FYSLRAVVPN VSKMDKASLL GDAISYINEL KSKLQQAESD KEEIQKKLDG  480
MSKEGNNGKG CGSRAKERKS SNQDSTASSI EMEIDVKIIG WDVMIRVQCG KKDHPGARFM  540
EALKELDLEV NHASLSVVND LMIQQATVKM GSQFFNHDQL KVALMTKVGE NY          592

SEQ ID NO: 4            moltype = AA  length = 55
FEATURE                 Location/Qualifiers
```

```
source                  1..55
                        mol_type = protein
                        organism = Arabidopsis thaliana
SEQUENCE: 4
STGDNTVILG WGDGYYKGEE DKEKKKNNTN TAEQEHRKRV IRELNSLISG GIGVS        55

SEQ ID NO: 5            moltype = AA   length = 589
FEATURE                 Location/Qualifiers
source                  1..589
                        mol_type = protein
                        organism = Arabidopsis thaliana
SEQUENCE: 5
MSPTNVQVTD YHLNQSKTDT TNLWSTDDDA SVMEAFIGGG SDHSSLFPPL PPPPLPQVNE    60
DNLQQRLQAL IEGANENWTY AVFWQSSHGF AGEDNNNNNT VLLGWGDGYY KGEEEKSRKK   120
KSNPASAAEQ EHRKRVIREL NSLISGGVGG GDEAGDEEVT DTEWFFLVSM TQSFVKGTGL   180
PGQAFSNSDT IWLSGSNALA GSSCERARQG QIYGLQTMVC VATENGVVEL GSSEIIHQSS   240
DLVDKVDTFF NFNNGGGEFG SWAFNLNPDQ GENDPGLWIS EPNGVDSGLV AAPVMNNGGN   300
DSTSNSDSQP ISKLCNGSSV ENPNPKVLKS CEMVNFKNGI ENGQEEDSSN KKRSPVSNNE   360
EGMLSFTSVL PCDSNHSDLE ASVAKEAESN RVVVEPEKKP RKRGRKPANG REEPLNHVEA   420
ERQRREKLNQ RFYSLRAVVP NVSKMDKASL LGDAISYISE LKSKLQKAES DKEELQKQID   480
VMNKEAGNAK SSVKDRKCLN QESSVLIEME VDVKIIGWDA MIRIQCSKRN HPGAKFMEAL   540
KELDLEVNHA SLSVVNDLMI QQATVKMGNQ FFTQDQLKVA LTEKVGECP              589

SEQ ID NO: 6            moltype = AA   length = 57
FEATURE                 Location/Qualifiers
source                  1..57
                        mol_type = protein
                        organism = Arabidopsis thaliana
SEQUENCE: 6
NNNNNTVLLG WGDGYYKGEE EKSRKKKSNP ASAAEQEHRK RVIRELNSLI SGGVGGG      57

SEQ ID NO: 7            moltype = AA   length = 751
FEATURE                 Location/Qualifiers
source                  1..751
                        mol_type = protein
                        organism = Oryza sativa
SEQUENCE: 7
MWVLLSPLLT TKNPFHPIPI PTFPLLLFSS SLVGVLFQIK SNLEEEEIEI KSMNLWTDDN    60
ASMMEAFMAS ADLPAFPWGA ASTPPPPPPP PHHHHQQQQQ QVLPPPAAAP AAAAFNQDTL   120
QQRLQSIIEG SRETWTYAIF WQSSIDVSTG ASLLGWGDGY YKGCDDDKRK QRSSTPAAAA   180
EQEHRKRVLR ELNSLIAGAG AAPDEAVEEE VTDTEWFFLV SMTQSFPNGL GLPGQALFAA   240
QPTWIATGLS SAPCDRARQA YTFGLRTMVC LPLATGVLEL GSTDVIFQTG DSIPRIRALF   300
NLSAAAASSW PPHPDAASAD PSVLWLADAP PMDMKDSISA ADISVSKPPP PPPHQIQHFE   360
NGSTSTLTEN PSPSVHAPTP SQPAAPPQRQ QQQQQSSQAQ QGPFRRELNF SDFASNGGAA   420
APPFFKPETG EILNFGNDSS SGRRNPSPAP PAATASLTTA PGSLFSQHTP TLTAAANDAK   480
SNNQKRSMEA TSRASNTNNH PAATANEGML SFSSAPTTRP STGTGAPAKS ESDHSDLEAS   540
VREVESSRVV APPPEAEKRP RKRGRKPANG REEPLNHVEA ERQRREKLNQ RFYALRAVVP   600
NVSKMDKASL LGDAISYINE LRGKLTALET DKETLQSQME SLKKERDARP PAPSGGGGDG   660
GARCHAVEIE AKILGLEAMI RVQCHKRNHP AARLMTALRE LDLDVYHASV SVVKDLMIQQ   720
VAVKMASRVY SQDQLNAALY TRIAEPGTAA R                                 751

SEQ ID NO: 8            moltype = AA   length = 52
FEATURE                 Location/Qualifiers
source                  1..52
                        mol_type = protein
                        organism = Oryza sativa
SEQUENCE: 8
STGASLLGWG DGYYKGCDDD KRKQRSSTPA AAAEQEHRKR VLRELNSLIA GA            52

SEQ ID NO: 9            moltype = AA   length = 705
FEATURE                 Location/Qualifiers
source                  1..705
                        mol_type = protein
                        organism = Zea mays
SEQUENCE: 9
MNLWTDDNAS MMEAFMASAD LPTFPWGAPA GGGNSSAAAA SPPPPQMPAA TAPGFNQDTL    60
QQRLQAMIEG SRETWTYAIF WQSSLDSATG ASLLGWGDGY YKGCDEDKRK QKPLTPSAQA   120
EQEHRKRVLR ELNSLISGAA AAPDEAVEEE VTDTEWFFLV SMTQSFLNGS GLPGQALFAG   180
QPTWIASGLS SAPCERARQA YNFGLRTMVC FPVGTGVLEL GSTDVVFKTA ESMAKIRSLF   240
GGGAGGGSWP PVQPQAPSSQ QPAAGADHAE TDPSMLWLAD APVMDIKDSL SHPSAEISVS   300
KPPPHPPQIH FENGSTSTLT ENPSPSVHAP PPPPAPAAPQ QRQHQHQNQA HQGPFRRELN   360
FSDFASTPSL AATPPFFKPE SGEILSFGAD SNARRNPSPV PPAATASLTT APGSLFSQHT   420
ATMTAAAAND AKNNNKRSME ATSRASNTNH PAATANEGML LSFSSAPTTR PSTGTGAPAK   480
SESDHSDLDA SVREVESSRV VAPPPEAEKR PRKRGRKPAN GREEPLNHVE AERQRREKLN   540
QRFYALRAVV PNVSKMDKAS LLGDAISYIN ELRGKLTSLE TDKETLQTQV EALKKERDAR   600
PPSHSAGLGG HDGGPRCHAV EIDAKILGLE AMIRVQCHKR NHPSARLMTA LRELDLDVYH   660
ASVSVVKDLM IQQVAVKMAS RVYTQDQLSA ALYSRLAEPG SAMGR                  705

SEQ ID NO: 10           moltype = AA   length = 52
```

```
FEATURE                 Location/Qualifiers
source                  1..52
                        mol_type = protein
                        organism = Zea mays
SEQUENCE: 10
ATGASLLGWG DGYYKGCDED KRKQKPLTPS AQAEQEHRKR VLRELNSLIS GA            52

SEQ ID NO: 11           moltype = AA  length = 703
FEATURE                 Location/Qualifiers
source                  1..703
                        mol_type = protein
                        organism = Zea mays
SEQUENCE: 11
MNLWTDDNAS MMEAFMASAD LPAYPWGAPA GGGNPPPPQM PPAMAMAPGF NQDTLQQRLQ     60
AMIEGSRETW TYAIFWQSSL DAATGASLLG WGDGYYKGCD DDKRRHRPPL TPAAQAEQEH    120
RKRVLRELNS LISGGASAAP APAPDEAVEE EVTDTEWFFL VSMTQSFLNG SGLPGQALFA    180
GHHTWIAAGL SSAPCDRARQ AYNFGLRTMV CFPVGTGVLE LGSTDVVFQT AETMAKIRSL    240
FGGGPGGGSW PPVQPQAAPQ QQHAAEADQA AETDPSVLWL ADAPVVDIKD SYSHPSAAEI    300
SVSKPPPPPP PPQIHFENGS TSTLTENPSP SVHAPPAPPA PPQRQQQNQG PFRRELNFSD    360
FASNPSLAAA PPFFKPESGE ILSFGVDSNA QRNPSPAPPA SLTTAPGSLF SQSQHTATAA    420
ANDAKNNNNN NKRSMEATSL ASNTNHHPAA AANEGMLSFS SAPTARPSAG TGAPAKSESD    480
HSDLDASVRE VESSRVVAPP PEAEKRPRKR GRKPANGREE PLNHVEAERQ RREKLNQRFY    540
ALRAVVPNVS KMDKASLLGD AISYINELRG KLTSLESDRE TLQAQVEALK KERDARPHPH    600
PAAGLGGHDA GGPRCHAVEI DAKILGLEAM IRVQCHKRNH PSARLMTALR ELDLDVYHAS    660
VSVVKDLMIQ QVAVKMASRM YSQDQLSAAL YSRLAEPGSV MGR                      703

SEQ ID NO: 12           moltype = AA  length = 53
FEATURE                 Location/Qualifiers
source                  1..53
                        mol_type = protein
                        organism = Zea mays
SEQUENCE: 12
ATGASLLGWG DGYYKGCDDD KRRHRPPLTP AAQAEQEHRK RVLRELNSLI SGG            53

SEQ ID NO: 13           moltype = AA  length = 706
FEATURE                 Location/Qualifiers
source                  1..706
                        mol_type = protein
                        organism = Brachypodium distachyon
SEQUENCE: 13
MNLWTDDNAS MMEAFMASAA DLPTFPWGAA AATPPPPAAV MPQQPAFNQD TLQQRLQAII     60
EGSRETWTYA IFWQSSTDAG AGASLLGWGD GYYKGCDDSF KRAQQPTPA SAAEQEHRKR    120
VLRELNSLIA GGGAAAPDEA VEEEVTDTEW FFLVSMTQSF PNGMGLPGQA LYTRQPTWIA    180
SGLASAPCER ARQAYTFGLR TMVCIPVGTG VLELGATEVI FQTADSLGRI RSLFNLNGGG    240
GGGGAGSSWP PVAPHQQHGG DQAETDPSVL WLTDAPVGDM KESPSVEISV SKPPPPPQIH    300
HFENGSTSTL TENAGPSLHA HQQPATLAPA APPRQNHPH QLQLQHQQSQ QQQQQQQGPF    360
RRELNFSDFA TNASVTVTPP FFKPESGEIL NFGADSTSRR NPSPAPPAAA ASLTTAPGSL    420
FSQHTATVTA PTNEAKNNPK RSMEATSRAS NTNHHPSATA NEGMLSFSSA PTTRPSTGTG    480
APAKSESDHS DLEASVREVE SSRVVPPPEE KRPRKRGRKP ANGREEPLNH VEAERQRREK    540
LNQRFYALRA VVPNVSKMDK ASLLGDAISY INELRGKMTA LESDKDTLHS QIEALKKERD    600
ARPVAPLSGV HDSGPRCHAV EIEAKILGLE AMIRVQCHKR NHPAAKLMTA LRELDLDVYH    660
ASVSVVKDIM IQQVAVKMPN RVYSQDQLNA ALYSRLAEPG APVPIR                   706

SEQ ID NO: 14           moltype = AA  length = 52
FEATURE                 Location/Qualifiers
source                  1..52
                        mol_type = protein
                        organism = Brachypodium distachyon
SEQUENCE: 14
AGASLLGWGD GYYKGCDDAD KRARQQPTPA SAAEQEHRKR VLRELNSLIA GG             52

SEQ ID NO: 15           moltype = AA  length = 707
FEATURE                 Location/Qualifiers
source                  1..707
                        mol_type = protein
                        organism = Sorghum bicolor
SEQUENCE: 15
MNLWTDDNAS MMEAFMASAD LPTFPWGATA GGGNSSAAAA TPPPPPQMPA AAMAPGFNQD     60
TLQQRLQAMI EGSSETWTYA IFWQSSLDAA TGASLLGWGD GYYKGCDDDK RKQRPLTPAA    120
QAEQEHRKRV LRELNSLISG AAAAPDEAVE EVTDTEWFF LVSMTQSFLN GSGLPGQALF    180
AGQPTWIASG LSSAPCERAR QAYNFGLRTM VCFPVGTGVL ELGSTDVVFQ TAESMAKIRS    240
LFGGGAGGGS WPPPQAPSHQ QPAAGPDQAE TDLWLADAPV MDIKDSMSHP SAEISVSKPP    300
PPPPPQIHF ENASTSTLTE NPSPSVHAAP PQPAPAAAPQ RQHQHQNQAH QGPFRRELNF    360
SDFASTNPSS LAATPPFFKP ESGEILSFGA DSNARRNPSP APPAATASLT TAPGSLFSQH    420
TATMTQAAAA NDAKNNNKRS MEATSRASNT NHHPAATANE GMLSFSSAPT TRPSTGTGAP    480
AKSESDHSDL DASVREVESS RVVAPPPEAE KRPRKRGRKP ANGREEPLNH VEAERQRREK    540
LNQRFYALRA VVPNVSKMDK ASLLGDAISY INELRGKLTS LESDKDTLQA QIEALKKERD    600
ARPPAHAAGL GGHDGGPRCH AVEIDAKILG LEAMIRVQCH KRNHPSARLM TALRELDLDV    660
YHASVSVVKD LMIQQVAVKM ASRIYSQDQL NAALYSRLAE PGSAMGR                  707
```

```
SEQ ID NO: 16              moltype = AA   length = 51
FEATURE                    Location/Qualifiers
source                     1..51
                           mol_type = protein
                           organism = Sorghum bicolor
SEQUENCE: 16
ATGASLLGWG DGYYKGCDDD KRKQRPLTPA AQAEQEHRKR VLRELNSLIS G           51

SEQ ID NO: 17              moltype = AA   length = 462
FEATURE                    Location/Qualifiers
VARIANT                    1..462
                           note = Xaa = Any Amino Acid
source                     1..462
                           mol_type = protein
                           organism = Camelina sativa
SEQUENCE: 17
MTDYRLQPTM NLWTTDDNAS MMEAFISSSD ISTLWPMATT TTTTTTATTS APATAMDIPA   60
PAGFNQETLQ QRLQALIEGT NEGWTYAIFW QPSYDFSGAS VLGWGDGYYK GEEDKAKPRQ  120
RSSSPPFSTP ADQEYRKKVL RELNSLISGG VAPSDDAVDE EVTDTEWFFL VSMTQSFACG  180
AGLAGRAFST GNAVWVSGSD QLSGSGCERA KQGGVFGMQT IACIPSANGV VEVGSTEQIR  240
QSSDLINKVR VLFNLDGGAG DLSGLDWNLD PDQGENDPSM WINDPIGAPG SNEPGNGAPS  300
SSSQLFSKSI QFENGSSSTI TENPNPDPTP SPVHSQTQNP KFSNNFSREL NFSTSSSTLV  360
KPRSGEILSF GDDGKRGSGN PDPSSYSGQT QFENKRKKSP NEDKVLSFGD KTTGESDHSD  420
LEASVVKEVA VEKRPKKRGR KPANGREEPL NXMIYVIHSP NP                    462

SEQ ID NO: 18              moltype = AA   length = 80
FEATURE                    Location/Qualifiers
source                     1..80
                           mol_type = protein
                           organism = Camelina sativa
SEQUENCE: 18
QRLQALIEGT NEGWTYAIFW QPSYDFSGAS VLGWGDGYYK GEEDKAKPRQ RSSSPPFSTP   60
ADQEYRKKVL RELNSLISGG                                              80

SEQ ID NO: 19              moltype = AA   length = 689
FEATURE                    Location/Qualifiers
source                     1..689
                           mol_type = protein
                           organism = Solanum lycopersicum
SEQUENCE: 19
MTEYSLPTMN LWNNSTSDDN VSMMEAFMSS DLSFWATNNS TSAAVVGVNS NLPHASSNTP   60
SVFAPSSSTS ASTLSAAATV DASKSMPFFN QETLQQRLQA LIDGARETWT YAIFWQSSVV  120
DFSSPSVLGW GDGYYKGEED KAKRKLSVSS PAYIAEQEHR KKVLRELNSL ISGAPPGTDD  180
AVDEEVTDTE WFFLISMTQS FVNGSGLPGQ ALYSSSPIWV AGTEKLAASH CERVRQAQGF  240
GLQTIVCIPS ANGVVELGST ELIVQSSDLM NKVRVLFNFS NDLGSGSWAV QPESDPSALW  300
LTDPSSSGME VRESLNTVQT NSVPSSNSNK QIAYGNENNH PSGNGQSCYN QQQQKNPPQQ  360
QTQGFFTREL NFSEFGFDGS SNRNGNSSVS CKPESGEILN FGDSTKKSAS SANVNLFTGQ  420
SQFGAGEENN NKNKKRSATS RGSNEEGMLS FVSGTVLPSS GMKSGGGGGE DSEHSDLEAS  480
VVVKEADSSRV VEPEKRPRKR GRKPANGREE PLNHVEAERQ RREKLNQRFY ALRAVVPNVS  540
KMDKASLLGD AISYINELKS KLQNTESDKE DLKSQIEDLK KESRRPGPPP PPNQDLKMSS  600
HTGGKIVDVD IDVKIIGWDA MIRIQCNKKN HPAARLMAAL MELDLDVHHA SVSVVNDLMI  660
QQATVKMGSR HYTEEQLRVA LTSKIAETH                                   689

SEQ ID NO: 20              moltype = AA   length = 53
FEATURE                    Location/Qualifiers
source                     1..53
                           mol_type = protein
                           organism = Solanum lycopersicumv
SEQUENCE: 20
FSSPSVLGWG DGYYKGEEDK AKRKLSVSSP AYIAEQEHRK KVLRELNSLI SGA          53

SEQ ID NO: 21              moltype = AA   length = 464
FEATURE                    Location/Qualifiers
source                     1..464
                           mol_type = protein
                           organism = Solanum lycopersicum
SEQUENCE: 21
MTDYRLWSNT NTTNTCDDTM MMDSFLSSDP SSFWPASTPN RPTPVNGVGE TMPFFNQESL   60
QQRLQALIDG ARESWAYAIF WQSSVVDFAS QTVLGWGDGY YKGEEDKNKR RGSSSSAANF  120
VAEQEHRKKV LRELNSLISG VQASAGNGTD DAVDEEVTDT EWFFLISMTQ SFVNGNGLPG  180
LAMYSSSPIW VTGTEKLAAS QCERARQAQG FGLQTIVCIP SPESREILNF GDSSKRFSGQ  240
SQLGPGPGLM EENKNKNKNK KRSLGSRGNN EEGMLSFVSG VILPTSTMGK SGDSDHSDLE  300
ASVVKEAVVE PEKKPRKRGR KPANGREEPL NHVEAERQRR EKLNQRFYEL RSQIECLRKE  360
LTNKGSSNYS ASPPLNQDVK IVDMDIDVKV IGWDAMIRIQ CSKKNHPAAR LMAALKDLDL  420
DVHHASVSVV NDLMIQQATV KMGSRLYAQE QLRIALTSKI AESR                  464

SEQ ID NO: 22              moltype = AA   length = 54
FEATURE                    Location/Qualifiers
```

```
                            source             1..54
                                               mol_type = protein
                                               organism = Solanum lycopersicum
SEQUENCE: 22
FASQTVLGWG DGYYKGEEDK NKRRGSSSSA ANFVAEQEHR KKVLRELNSL ISGV              54

SEQ ID NO: 23               moltype = AA   length = 692
FEATURE                     Location/Qualifiers
source                      1..692
                            mol_type = protein
                            organism = Solanum tuberosum
SEQUENCE: 23
MTEYSLPTMN LWNNSTSDDN VSMMEAFMSS DLSFWATTNS TTTNSASAAV GVNSNLLHT          60
NNNNPSVFPL SSSTSVSAAA AVDATKSMPF FNQETLQQRL QALIDGARET WTYAIFWQSS        120
VVDFSSPSVL GWGDGYYKGE EDKAKRKLAV SSPAYIAEQE HRKKVLRELN SLISGAPAGT        180
DDDAVDEEVTD TEWFFLISMT QSFVNGSGLP GQALYSSSPI WVAGTEKLAA SHCERVRQAQ       240
GFGLQTIVCI PSANGVVELG STELIVESSD LMNKVRVLFN FSNDLGSGSW AVQPESDPSA        300
LWLTEPSSSG MEVRESLNTV QTNSVPSSNS NKQIAYANEN NHQSGNGQSC YNLQQQQNNP        360
PQQQTQGFFT RELNFSEFGF DGSSNRNGNA SLSCKPESGE ILNFGDSTKK SASSANVNLF        420
TGQSQFGAVE ENNNNKNKKR SATSRGSNEE GMLSFVSGTV LPSSGMKSGG GGGEDSEHSD        480
LEASVVKEAD SSRVVEPEKR PRKRGRKPAN GREEPLNHVE AERQRREKLN QRFYALRAVV        540
PNVSKMDKAS LLGDAISYIN ELKSKLQNTE SDKEDLKSQI EDLKKESRRP GPPPPNQDLK        600
IGGKIVDVDI DVKIIGWDAM IGIQCNKKNH PAARLMAALM ELDLDVHHAS VSVVNDLMIQ        660
QATVKMGSRH YTEEQLRVAL KSKIAETPLE SR                                     692

SEQ ID NO: 24               moltype = AA   length = 53
FEATURE                     Location/Qualifiers
source                      1..53
                            mol_type = protein
                            organism = Solanum tuberosum
SEQUENCE: 24
FSSPSVLGWG DGYYKGEEDK AKRKLAVSSP AYIAEQEHRK KVLRELNSLI SGA                53

SEQ ID NO: 25               moltype = AA   length = 646
FEATURE                     Location/Qualifiers
source                      1..646
                            mol_type = protein
                            organism = Solanum tuberosum
SEQUENCE: 25
MTDYRLWSNS NTTNTSDDNM MMDAFLSSDP SSFWPNRTSI SPTPVNGGVG ETMPFFNQES         60
LQQRLQALID GARESWAYAI FWQSSSTSDF ATPSVLGWGD GYYKGEENKN KRRASSSSTN        120
FVAEQEHRKK VLRELNSLIS GVQATGAGSG GDDAVDEEVT DTEWFFLISM TQSFANGNGL        180
PGLAMYSSSP IWVTGTEKLA GSQCERARQA QGFGLQTIVC IPSANGVVEL GSTELIFESS        240
DLMNKVKYLF NFNIDMGSVT GSGSGSCAVH PEPDPSALWL TDPSSSVVEA KDSLINSSSR        300
DVQLVFGNEN SENGTQNQQH SQQTQGFFTK ELNFSGYGFD GSSTRNKGN SSISCKPETR         360
EILNFGDSSK KSGSLFSGQS QFGPGTGLGL MEENKNNNKK RSLASRGNNE KGMLSFVSGV        420
ILPTSTMGKS GGGGNFDHSD LEASVVKEAI VEPERKPRKR GRKPANGREE PLNHVEAERQ        480
RREKLNQRFY ALRAVVPNVS KMDKASLLGD AIAYINELKS KVQNSDLDKE ELRSQIESLR        540
KELANKGSSN YSSSPPSNQD LKIVDMDIDV KVIGWDAMIR IQCSKKNHPA ARLMAALKDL        600
DLDVHHASVS VVNDLMIQQA TVKMGSRLYA QEQLTIALTS KFAESR                      646

SEQ ID NO: 26               moltype = AA   length = 53
FEATURE                     Location/Qualifiers
source                      1..53
                            mol_type = protein
                            organism = Solanum tuberosum
SEQUENCE: 26
FATPSVLGWG DGYYKGEENK NKRRASSSST NFVAEQEHRK KVLRELNSLI SGV                53

SEQ ID NO: 27               moltype = AA   length = 699
FEATURE                     Location/Qualifiers
source                      1..699
                            mol_type = protein
                            organism = Catharanthus roseus
SEQUENCE: 27
MTDYRLQPKM NLWGTTTNTA ASPIITSDDN SSMMEAFMTS SDPISLWPPS MSVNHHHPPT         60
PTSSAVTTAV DSAKSMPAQP AFFNQENLQQ RLQTLIDGAR ESWTYAIFWQ SSVVEFAGPS        120
VLGWGDGYYK GEEDKGKRKN SSSASSFAEQ EHRKKVLREL NSLIAGPQGT ADDAVDEEVT        180
DTEWFFLISM TQSFVSGSGL PGQALYNSNP VWVTGAGRLA VSHCDRARQA QSFGLQTLVC        240
IPSANGVVEL GSTELIFQSS DLMNKVRILF NFNNIDLGSS SGPWPENDPS SLWLTDPSPS        300
GVGVKEGVNT NNNTSVQGNS IPSGNKQQLV FGNNDNHPTT STLTDHPGAG AVNSYNNSSQ        360
NAQQPQGSFF TRELNFSEYG FERSSVKNGN CKPESGEILN FGGESVTKKN SVSGNGNLFS        420
VQSQFGAGEE NKNKKRPSPV SRGSNDEGML SFTSGVVLST TGVVKSSGGG GGGEDHSDL        480
EASVVKEAES SRVVDPEKRP RKRGRKPANG REEPLNHVEA ERQRREKLNQ RFYALRAVVP        540
NVSKMDKASL LGDAISYINE LKAKLQTTET DKDELKNQLD SLKKELASKE SRLLSSPDQD        600
LKSSNKQSVG NLDMDIDVKI IGREAMIRVQ SSKNNHPAAR VMGALKDLDL ELLHASVSVV        660
NDLMIQQNTV RMGSRFYTQE QLRIALTSRI AGNSMRLLV                              699

SEQ ID NO: 28               moltype = AA   length = 51
```

```
FEATURE                 Location/Qualifiers
source                  1..51
                        mol_type = protein
                        organism = Catharanthus roseus
SEQUENCE: 28
FAGPSVLGWG DGYYKGEEDK GKRKNSSSAS SFAEQEHRKK VLRELNSLIA G        51

SEQ ID NO: 29           moltype =   length =
SEQUENCE: 29
000

SEQ ID NO: 30           moltype = AA  length = 1172
FEATURE                 Location/Qualifiers
source                  1..1172
                        mol_type = protein
                        organism = Arabidopsis thaliana
SEQUENCE: 30
MVSGVGGSGG GRGGGRGGEE EPSSSHTPNN RRGGEQAQSS GTKSLRPRSN TESMSKAIQQ   60
YTVDARLHAV FEQSGESGKS FDYSQSLKTT TYGSSVPEQQ ITAYLSRIQR GGYIQPFGCM  120
IAVDESSFRI IGYSENAREM LGIMPQSVPT LEKPEILAMG TDVRSLFTSS SSILLERAFV  180
AREITLLNPV WIHSKNTGKP FYAILHRIDV GVVIDLEPAR TEDPALSIAG AVQSKLAVR   240
AISQLQALPG GDIKLLCDTV VESVRDLTGY DRVMVYKPHE DEHGEVVAES KRDDLEPYIG  300
LHYPATDIPQ ASRFLFKQNR VRMIVDCNAT PVLVVQDDRL TQSMCLVGST LRAPHGCHSQ  360
YMANMGSIAS LAMAVIINGN EDDGSNVASG RSSMRLWGLV VCHHTSSRCI PFPLRYACEF  420
LMQAFGLQLN MELQLALQMS EKRVLRTQTL LCDMLLRDSP AGIVTQSPSI MDLVKCDGAA  480
FLYHGKYYPL GVAPSEVQIK DVVEWLLANH ADSTGLSTDS LGDAGYPGAA ALGDAVCGMA  540
VAYITKRDFL FWFRSHTAKE IKWGGAKHHP EDKDDGQRMH PRSSFQAFLE VVKSRSQPWE  600
TAEMDAIHSL QLILRDSFKE SEAAMNSKVV DGVVQPCRDM AGEQGIDELG AVAREMVRLI  660
ETATVPIFAV DAGGCINGWN AKIAELTGLS VEEAMGKSLV SDLIYKENEA TVNKLLSRAL  720
RGDEEKNVEV KLKTFSPELQ GKAVPVVVNA CSSKDYLNNI VGVCFVGQDV TSQKIVMDKF  780
INIQGDYKAI VHSPNPLIPP IFAADENTCC LEWNMAMEKL TGWSRSEVIG KMIVGEVFGS  840
CCMLKGPDAL TKFMIVLHNA IGGQDTDKFP FPFFDRNGKF VQALLTANKR VSLEGKVIGA  900
FCFLQIPSPE LQQALAVQRR QDTECFTKAK ELAYICQVIK NPLSGMRFAN SLLEATDLNE  960
DQKQLLETSV SCEKQISRIV GDMDLESIED GSFVLKREEF FLGSVINAIV SQAMFLLRDR 1020
GLQLIRDIPE EIKSIEVFGD QIRIQQLLAE FLLSIIRYAP SQEWVEIHLS QLSKQMADGF 1080
AAIRTEFRMA CPGEGLPPEL VRDMFHSSRW TSPEGLGLSV CRKILKLMNG EVQYIRESER 1140
SYFLIILELP VPRKRPLSTA SGSGDMMLMM PY                              1172

SEQ ID NO: 31           moltype = DNA  length = 4550
FEATURE                 Location/Qualifiers
source                  1..4550
                        mol_type = other DNA
                        organism = Arabidopsis thaliana
SEQUENCE: 31
cttcaattta ttttattggt ttctccactt atctccgatc tcaattctcc ccatttcctt    60
cttcctcaag ttcaaaattc ttgagaattt agctctacca gaattcgtct ccgataacta   120
gtggatgatg attcacccta aatccttcct tgtctcaaga taattctgag aaatttctca   180
aattcaaaat caaacggcat ggtttccgga gtcgggggta gtggcggtgg ccgtggcggt   240
ggccgtggcg gagaagaaga accgtcgtca agtcacactc ctaataaccg aagaggagga   300
gaacaagctc aatcgtcggg aacgaaatct ctcagaccaa gaagcaacac tgaatcaatg   360
agcaaagcaa ttcaacagta caccgtcgac gcaagactcc acgccgtttt cgaacaatcc   420
ggcgaatcag ggaaatcatt cgactactca caatcactcc aaaacgacga gtacggttcc   480
tctgtacctg agcaacagat cacagcttat ctctctcgaa tccagcgagg tggttacatt   540
cagcctttcg gatgtatgat cgccgtcgat gaatccagtt tccggatcat cggttacagt   600
gaaaacgcca gagaaatgtt agggattatg cctcaatcgt ttcctactct tgagaaacct   660
gagattctag ctatgggaac tgatgtgaga tctttgttca cttcttcgag ctcgattcta   720
ctcgagcgtg ctttcgttgc tcgagagatt accttgttaa atccggtttg gatccattcc   780
aagaatactg taaaccgttt tacgccattc ttcataggat tgatgttggt gttgttatt    840
gatttagagc cagctagaac tgaagatcct gcgctttcta ttgctggtgc tgttcaatcg   900
cagaaactcg cggttcgtgc gatttctcag ttacaggctc ttcctggtga agatattaag   960
cttttgtgtg acactgtcgt ggaaagtgtg agggacttga ctggttatga tcgtgttatg  1020
gtttataagt ttcatgaaga tgagcatgga gaagttgtag ctgagagtaa acgagatgat  1080
ttagagcctt atattggact gcattatcct gctactgata ttcctcaagc gtcaaggttc  1140
ttgttttaagc agaaccgtgt ccgaatgata gtagattgca atgccacacc tgttcttgtg  1200
gtccaggacg ataggctaac tcagtctatg tgcttggttg gttctactct tagggctcct  1260
catggttgtc actctcagta tatggctaac atgggatcta ttgcgtcttt agcaatggcg  1320
gttataatca atggaaatga agatgatggg agcaatgtag ctagtggaag aagctcgatg  1380
aggctttggg gtttggttgt ttgccatcac acttcttctc gctgcatacc gtttccgcta  1440
aggtatgctt gtgagttttt gatgcaggct ttccgtttac agttaaacat ggaattgcag  1500
ttagcttttgc aaatgtcaga gaaacgcgtt ttgagaacgc agacactgtt atgtgatatg  1560
cttctgcgtg actcgcctgc tggaattgtt acacagagtc ccagtatcat ggacttagtg  1620
aaatgtgacg gtgcagcatt tctttaccac gggaagtatt acccgttggg tgttgctcct  1680
agtgaagttc agataaaaga tgttgtggag tggttgcttg cgaatcatgc ggattcaacc  1740
ggattaagca ctgatagttt aggcgatgcg gggtatccgg gtgcagctgc gttagggagt  1800
gctgtgtgcg gtatggcagt tgcatatatc acaaaaagag actttctttt ttggtttcga  1860
tctcacactg cgaaagaaat caaatgggga ggcgctaagc atcatccgga ggataaagat  1920
gatgggcaac gaatgcatcc tcgttcgtcc tttcaggctt tccttgaagt tgttaagagc  1980
cggagtcagc catgggaaac tgcggaaatg gatgcgattc actcgctcca gcttattctg  2040
agagactctt taaagaatc tgaggcggct atgaactcta agttgtgga tggtgtggtt  2100
```

-continued

```
cagccatgta gggatatggc gggggaacag gggattgatg agttaggtgc agttgcaaga  2160
gagatggtta ggctcattga gactgcaact gttcctatat tcgctgtgga tgccggaggc  2220
tgcatcaatg gatggaacgc taagattgca gagttgacag gtctctcagt tgaagaagct  2280
atggggaagt ctctggtttc tgatttaata tacaaagaga atgaagcaac tgtcaataag  2340
cttctttctc gtgctttgag aggtatattc agttcttcag ctatgttgta tctgcggtgt  2400
atataccaat tcgcgggtat ttgattattt tgttgcattt ggcaatgcag gggacgagga  2460
aaagaatgtg gaggttaagc tgaaaacttt cagccccgaa ctacaaggga aagcagtttt  2520
tgtggttgtg aatgcttgtt ccagcaagga ctacttgaac aacattgtcg gcgtttgttt  2580
tgttggacaa gacgttacta gtcagaaaat cgtaatggat aagttcatca acatacaagg  2640
agattacaag gctattgtac atagcccaaa ccctctaatc ccgccaattt ttgctgctga  2700
cgagaacacg tgctgcctgg aatgaacat ggcgatggaa aagttacgg gttggtctcg  2760
cagtgaagtg attgggaaaa tgattgtcgg gaagtgttt gggagctgtt gcatgctaaa  2820
gggtcctgat gctttaacca agttcatgat tgtattgcat aatgcgattg gtggccaaga  2880
tacggataag ttcccttttcc cattctttga ccgcaatggg agtttgttc aggctctatt  2940
gactgcaaac aagcgggtta gcctcgaggg aaaggttatt ggggctttct gtttcttgca  3000
aatcccgagc cctgagctgc agcaagcttt agcagtccaa cggaggcagg acacagagtg  3060
tttcacgaag gcaaaagagt tggcttatat ttgtcaggtg ataaagaatc ctttgagcgg  3120
tatgcgtttc gcaaactcat tgttggaggc cacagacttg aacgaggacc agaagcagtt  3180
acttgaaaca agtgttttctt gcgagaaaca gatctcaagg atcgtcgggg acatggatct  3240
tgaaagcatt gaagacgggt gagtatagtt agaatttatc tagaagctag ttttgcttac  3300
ttcacaaaat gtgaccaaat cccaaatttt gttttttttca ttgatcagtt catttgtgct  3360
aaagagggaa gagttttttcc ttggaagtgt cataaacgcg attgtaagtc aagcgatgtt  3420
cttattaagg gacagaggtc ttcagctgat ccgtgacatt cccgaagaga tcaaatcaat  3480
agaggtttt ggagaccaga taaggattca acagctcctg gctgagtttc tgctgagtat  3540
aatccggtat gcaccatctc aagagtgggg ggagatccat ttaagccaac tttcaaagca  3600
aatggctgat ggattcgccg ccatccgcac agaattcagg tacattttcat tgttcccgat  3660
gttgtctcca catatccata accaaaatta tgcaatccgg ttttttttggt tccttatttt  3720
gtacataaag aaaatgaatt tggttttgtt aattacgaat ttgatttagg cgtttaaaga  3780
atttgaggtt ttaaccaatt cactatttgt tttggttatt gtttagttgg aacctagatt  3840
agtttgattt ttgtattcgg tttagtcgac ttgggaactt ttagacacat ccataggcct  3900
agaattagca gtcaaggaat gtaatgtttt caaattgatg aaaaccagct caaaagtgta  3960
aaacttgggg ttcatgtgtt ggtgtctttg ttatgtcttt attcgttgtt tgcagaatgg  4020
cgtgtccagg tgaaggtctg cctccagagc tagtccgaga catgttccat agcagcaggt  4080
ggacaagccc tgaaggttta ggtctaagcg tatgtcgaaa gatttaaag ctaatgaacg  4140
gtgaggttca atacatccga gaatcagaac ggtcctatt cctcatcatt ctggaactcc  4200
ctgtacctcg aaagcgacca ttgtcaactg ctagtggaag tggtgacatg atgctgatga  4260
tgccatatta gtcacacttc agttggtatg agagtttgta tcattgtatg agtgtttgtg  4320
tgtctaacga cgtcggagga ggatagaaag tttttttttt gtttccggtg agattagtag  4380
agaagaggga gattatttgc gttcagctca gctcgccgga aaaaaaacgt aacagtagtt  4440
gtagagaatt tcaagacttt tgtttgtgct gtgtaaattg acaactccga gagaaacaaa  4500
acaatgagat aagaagagag catattaatc gatgaccaat cctttaatt              4550
```

```
SEQ ID NO: 32         moltype = AA  length = 1161
FEATURE               Location/Qualifiers
source                1..1161
                      mol_type = protein
                      organism = Zea mays
SEQUENCE: 32
MASGSRATPT RSPSSARPEA PRHAHHHHHS QSSGGSTSRA GGGAAATESV SKAVAQYTLD   60
ARLHAVFEQS GASGRSFDYS QSLRAPPTPS SEQQIAAYLS RIQRGGHIQP FGCTLAVADD  120
SSFRLLAFSE NSPDLLDLSP HHSVPSLDSS APPHVSLGAD ARLLFSPSSA VLLERAFAAR  180
EISLLNPIWI HSRVSSKPFY AILHRIDVGV VIDLEPARTE DPALSIAGAV QSQKLAVRAI  240
SRLQALPGGD VKLLCDTVVE HVRELTGYDR VMVYRFHEDE HGEVVAESRR DNLEPYLGLH  300
YPATDIPQAS RFLFRQNRVR MIADCHATPV RVIQDPGLSQ PLCLVGSTLR APHGCHAQYM  360
ANMGSIASLV MAVIISSGGD DEQTGRGGIS SAMKLWGLVV CHHTSPRCIP FPLRYACEFL  420
MQAFGLQLNM ELQLAHQLSE KHILRTQTLL CDMLLRDSPT GIVTQSPSIM DLVKCDGAAL  480
YYHGKYYPLG VTPTESQIKD IIEWLTVFHG DSTGLSTDSL ADAGYLGAAA LGEAVCGMAV  540
AYITPSDYLF WFRSHTAKEI KWGGAKHHPE DKDDGQRMHP RSSFKAFLEV VKSRSLPWEN  600
AEMDAIHSLQ LILRDSFRDA AEGTNNSKAI VNGQVQLREL ELRGINELSS VAREMVRLIE  660
TATVPIFAVD TDGCINGWNA KIAELTGLSV EEAMGKSLVN DLIFKESEAT VEKLLSRALR  720
GEEDKNVEIK LKTFGSEQSK GPIFVVVNAC SSRDYTQNIV GVCFVGQDVT GQKVVMDKFV  780
NIQGDYKAIV HNPNPLIPPI FASDENTSCS EWNTAMEKLT GWSRGEVVGK FLIGEVFGNC  840
CRLKGPDALT KFMVIIHNAI GGQDYEKFPF SFFDKNGKYV QALLTANTRS KMDGKSIGAF  900
CFLQIASTEI QQAFEIQRQQ EKKCYARMKE LAYICQEIKN PLSGIRFTNS LLQMTDLNDD  960
QRQFLETSSA CEKQMSKIVK DASLQSIEDG SLVLEQSEFS LGDVMNAVVS QAMLLLRERD 1020
LQLIRDIPDE IKDASAYGDQ CRIQQVLADF LLSMVRSAPS ENGWVEIQVR PNVKQNSDGT 1080
NTELFIFRFA CPGEGLPADV VQDMFSNSQW STQEGVGLST CRKILKLMGG EVQYIRESER 1140
SFFLIVLEQP QPRPAAGREI V                                           1161

SEQ ID NO: 33         moltype = AA  length = 1161
FEATURE               Location/Qualifiers
source                1..1161
                      mol_type = protein
                      organism = Zea mays
SEQUENCE: 33
MASGSRATPT RSPSSARPEA PRHAHHHHHS QSSGGSTSRA GGGAAATESV SKAVAQYTLD   60
ARLHAVFEQS GASGRSFDYS QSLRAPPTPS SEQQIAAYLS RIQRGGHIQP FGCTLAVADD  120
SSFRLLAFSE NSPDLLDLSP HHSVPSLDSS APPHVSLGAD ARLLFSPSSA VLLERAFAAR  180
EISLLNPIWI HSRVSSKPFY AILHRIDVGV VIDLEPARTE DPALSIAGAV QSQKLAVRAI  240
```

```
SRLQALPGGD VKLLCDTVVE HVRELTGYDR VMVYRFHEDE HGEVVAESRR DNLEPYLGLH    300
YPATDIPQAS RFLFRQNRVR MIADCHATPV RVIQDPGLSQ PLCLVGSTLR APHGCHAQYM    360
ANMGSIASLV MAVIISSGGD DEQTGRGGIS SAMKLWGLVV CHHTSPRCIP PPLRYACEFL    420
MQAFGLQLNM ELQLAHQLSE KHILRTQTLL CDMLLRDSPT GIVTQSPSIM DLVKCDGAAL    480
YYHGKYYPLG VTPTESQIKD IIEWLTVFHG DSTGLSTDSL ADAGYLGAAA LGEAVCGMAV    540
AYITPSDYLF WFRSHTAKEI KWGGAKHHPE DKDDGQRMHP RSSFKAFLEV VKSRSLPWEN    600
AEMDAIHSLQ LILRDSFRDA AEGTNNSKAI VNGQVQLREL ELRGINELSS VAREMVRLIE    660
TATVPIFAVD TDGCINGWNA KIAELTGLSV EEAMGKSLVN DLIFKESEAT VEKLLSRALR    720
GEEDKNVEIK LKTFGSEQYK GPIFVVVNAC SSRDYTQNIV GVCFVGQDVT GQKVVMDKFV    780
NIQGDYKAIV HNPNPLIPPI FASDENTSCS EWNTAMEKLT GWSRGEVVGK FLIGEVFGNC    840
CRLKGPDALT KFMVIIHNAI GGQDYEKFPF SFFDKNGKYV QALLTANTRS KMDGKSIGAF    900
CFLQIASTEI QQAFEIQRQQ EKKCYARMKE LAYICQEIKN PLSGIRFTNS LLQMTDLNDD    960
QRQFLETSSA CEKQMSKIVK DASLQSIEDG SLVLEQSEFS LGDVMNAVVS QAMLLLRERD   1020
LQLIRDIPDE IKDASAYGDQ CRIQQVLADF LLSMVRSAPS ENGWVEIQVR PNVKQNSDGT   1080
NTELFIFRFA CPGEGLPADV VQDMFSNSQW STQEGVGLST CRKILKLMGG EVQYIRESER   1140
SFFLIVLEQP QPRPAAGREI V                                            1161

SEQ ID NO: 34          moltype = AA  length = 1166
FEATURE                Location/Qualifiers
source                 1..1166
                       mol_type = protein
                       organism = Zea mays
SEQUENCE: 34
MASDSRPPKR SPSARRVAPR HAHHHHSQSS GGSTSRAGAG GGGGGAAATE SVSKAVAQYN     60
LDARLHAVFE QSGASGRSFD YSQSLRAPPT PSSEQQIAAY LSRIQRGGHI QPLGCTLAVA    120
DDSSFRLLAF SENAADLLDL SPHHSVPSLD SVALPPVSLG ADARLYFSPS SAVLLERAFA    180
AREISLLNPL WIHSRASSKP FYAILHRIDV GVVIDLEPAR TEDPALSIAG AVQSQKLAVR    240
AISRLQALPG GDVKLLCDTV VEHVRELTGY DRVMVYKPHE DEHGEVVAES RRDNLEPYLG    300
LHYPATDIPQ ASRFLFQQNR VRMIADCHAI PVRVIQDPGL SQPLCLVGST LRAPHGCHAQ    360
YMANMGSIAS LVMAVIISSG GDDERTGRGA ISSSMKLWGL VVCHHTSPRC IPFPLRYACE    420
FLMQAFGLQL NMELQAHQL SEKHILRTQT LLCDMLLRDS PAGIITQSPS VMDLVKCDGA    480
ALYYRGKYYP LGVTPTESQI KDIIEWLTVC HGDSTGLSTD SLADAGYLGA VALGDAVCGM    540
AVAYITPSDY LFWFRSHTAK EIKWGGAKHH PEDKDDGQRM HPRSSFKAFL EVVKSRSLSW    600
ENAEMDAIHS LQLILRDSFR DAAEGTSNSK AIVNGQRQLG ELELRGINEL SSVAREMVRL    660
IETATVPIFA VDTDGCINGW NAKIAELTGL SVEEAMGKSL VNDLIFKECD DIVEKLLSRA    720
LRGEEDKNVE IKLKTFGSEQ SKGAIFVIVN ACSSRDYTQN IVGVCFVGQD VTGQKVVMDK    780
FINIQGDYKA IVHNPNPLLP PIFASDENTS CSEWNTAMEK LTGWSREEVV GKFLIGEVFG    840
NCCRLKGPDA LTKFMVVIHN AIEGHDSEKF PFSFFDKNGK YVQALLTANT RSKMDGKSIG    900
AFCFLQIASA EIQQAFEIQR QQEKKCYARM KELAYICQEI KNPSLLQMTDLN    960
DDQRQFLETS SACEKQMSKI VKDASLKSIE DGSLVLEKSE FSLGDVMNAV VSQTMSLLRE   1020
RDLQLIRDIP DEIKDASAYG DQFRIQQVLA DFLLSMAQSA PSENGWVEIQ VRPNVKQNYD   1080
GTDTELFIFR FACPGEGLPA DIVQDMFSNS QWSTQEGVGL STCRKILKLM GGEVQYIRES   1140
ERSFFLIVLE LPQPRLAAGR ENQLIC                                       1166

SEQ ID NO: 35          moltype = AA  length = 1137
FEATURE                Location/Qualifiers
source                 1..1137
                       mol_type = protein
                       organism = Glycine max
SEQUENCE: 35
MASASGAANS SVPPPQIHTS RTKLSHHSSN NNNNIDSMSK AIAQYTEDAR LHAVFEQSGE     60
SGRSFNYSES IRIASESVPE QQITAYLVKI QRGGFIQPFG SMIAVDEPSF RILGYSDNAR    120
DMLGITPQSV PSLDDKNDAA FALGTDVRAL FTHSSALLLE KAFSAREISL MNPIWIHSRT    180
SGKPFYGILH RIDVGIVIDL EPARTEDPAL SIAGAVQSQK LAVRAISQLQ SLPGGDVKLL    240
CDTVVESVRE LTGYDRVMVY KFHEDEHGEV VSESKRPDTL PYIGLHYPAT DIPQASRFLF    300
KQNRVRMIVD CHASAVRVVQ DEALVQPLCL VGSTLRAPHG CHAQYMANMG SIASLVMAVI    360
INGNDEEGVG GRSSMRLWGL VVCHHTSARC IPFPLRYACE FLMQAFGLQL NMELQLAAQS    420
LEKRVLRTQT LLCDMLLRDS PTGIVTQSPS IMDLVKCDGA ALYFQGNYYP LGVTPTEAQI    480
RDIIEWLLAF HGDSTGLSTD SLGDAGYPGA ASLGDAVCGM AVAYITEKDF LFWFRSHTAK    540
EIKWGGAKHH PEDKDDGQRM HPRSSFKAFL EVVKSRSLPW ENAEMDAIHS LQLILRDSFK    600
DAEHRNSKAV VDPHVSEQEL QGVDELSSVA REMVRLIETA TAPIFAVDVD GHVNGWNAKV    660
SELTGLPVEE AMGKSLVHDL VFKESEETMN KLLSRALKGE EDKNVEIKMR TFGPEHQNKA    720
VFLVVNACSS KDFTNNVVGV CFVGQDVTGQ KIVMDKFINI QGDYKAIVHS PNPLIPPIFA    780
SDDNTCCLEW NTAMEKLTGW GRVDVIGKML VGEVFGSCCQ LKGSDSITKF MIVLHNALGG    840
QDTDKFPFSF LDRHGKYVQT FLTANKRVNM EGQIIGAFCF LQIMSPELQQ ALKAQRQQEK    900
NSFGRMKELA YICQGVKNPL SGIRFTNSLL EATSLTNEQK QFLETSVACE KQMLKIIRDV    960
DLESIEDGSL ELEKGEFLLG NVINAVVSQV MLLLRERNLQ LIRDIPEEIK TLAVYGDQLR   1020
IQQVLSDFLL NIVRYAPSPD GWVEIHVRPR IKQISDGLTL LHAEFRMVCP GEGLPPELIQ   1080
DMFNNSRWGT QEGLGLSMSR KILKLMNGEV QYIREAERCY FVVLLELPVT RRSSKKC     1137

SEQ ID NO: 36          moltype = AA  length = 1100
FEATURE                Location/Qualifiers
source                 1..1100
                       mol_type = protein
                       organism = Glycine max
SEQUENCE: 36
MSKAIAQYTE DARLHAVFEQ SGESGRSFNY SESIRIASES VPEQQITAYL VKIQRGGFIQ     60
PFGSMIAVDE PSFRILGYSD NARDMLGITP QSVPSLDDKN DAAFALGTDV RALFTHSSAL    120
LLEKAFSARE ISLMNPIWIH SRTSGKPFYG ILHRIDVGIV IDLEPARTED PALSIAGAVQ    180
```

```
SQKLAVRAIS QLQSLPGGDV KLLCDTVVES VRELTGYDRV MVYKFHEDEH GEVVSESKRP  240
DLEPYIGLHY PATDIPQASR FLFKQNRVRM IVDCHASAVR VVQDEALVQP LCLVGSTLRA  300
PHGCHAQYMA NMGSIASLVM AVIINGNDEE GVGGRSSMRL WGLVVCHHTS ARCIPFPLRY  360
ACEFLMQAFG LQLNMELQLA AQSLEKRVLR TQTLLCDMLL RDSPTGIVTQ SPSIMDLVKC  420
DGAALYFQGN YYPLGVTPTE AQIRDIIEWL LAFHGDSTGL STDSLGDAGY PGAASLGDAV  480
CGMAVAYITE KDFLFWFRSH TAKEIKWGGA KHHPEDKDDG QRMHPRSSFK AFLEVVKSRS  540
LPWENAEMDA IHSLQLILRD SFKDAEHRNS KAVVDPHVSE QELQGVDELS SVAREMVRLI  600
ETATAPIFAV DVDGHVNGWN AKVSELTGLP VEEAMGKSLV HDLVFKESEE TMNKLLSRAL  660
KGEEDKNVEI KMRTFGPEHQ NKAVFLVVNA CSSKDFTNNV VGVCFVGQDV TGQKIVMDKF  720
INIQGDYKAI VHSPNPLIPP IFASDDNTCC LEWNTAMEKL TGWGRVDVIG KMLVGEVFGS  780
CCQLKGSDSI TKFMIVLHNA LGGQDTDKFP FSFLDRHGKY VQTFLTANKR VNMEGQIIGA  840
FCFLQIMSPE LQQALKAQRQ QEKNSFGRMK ELAYICQGVK NPLSGIRFTN SLLEATSLTN  900
EQKQFLETSV ACEKQMLKII RDVDLESIED GSLELEKGEF LLGNVINAVV SQVMLLLRER  960
NLQLIRDIPE EIKTLAVYGD QLRIQQVLSD FLLNIVRYAP SPDGWVEIHV RPRIKQISDG  1020
LTLLHAEFRM VCPGEGLPPE LIQDMFNNSR WGTQEGLGLS MSRKILKLMN GEVQYIREAE  1080
RCYFYVLLEL PVTRRSSKKC                                             1100

SEQ ID NO: 37           moltype = AA   length = 1171
FEATURE                 Location/Qualifiers
source                  1..1171
                        mol_type = protein
                        organism = Oryza sativa
SEQUENCE: 37
MASGSRATPT RSPSSARPAA PRHQHHHSQS SGGSTSRAGG GGGGGGGGGG GAAAAESVSK  60
AVAQYTLDAR LHAVFEQSGA SGRSFDYTQS LRASPTSSEE QQIAAYLSRI QRGGHIQPFG  120
CTLAVADDSS FRLLAYSENT ADLLDLSPHH SVPSLDSSAV PPPVSLGADA RLLFAPSSAV  180
LLERAFAARE ISLLNPLWIH SRVSSKPFYA ILHRIDVGVV IDLEPARTED PALSIAGAVQ  240
SQKLAVRAIS RLQALPGGDV KLLCDTVVEH VRELTGYDRV MVYRFHEDEH GEVVAESRRN  300
NLEPYIGLHY PATDIPQASR FLFRQNRVRM IADCHAAPVR VIQDPALTQP LCLVGSTLRS  360
PHGCHAQYMA NMGSIASLVM AVIISSGGDD DHNIARGSIP SAMKLWGLVV CHHTSPRCIP  420
FPLRYACEFL MQAFGLQLNM ELQLAHQLSE KHILRTQTLL CDMLLRDSPT GIVTQSPSIM  480
DLVKCDGAAL YYHGKYYPLG VTPTEVQIKD IIEWLTMCHG DSTGLSTDSL ADAGYPGAAA  540
LGDAVSGMAV AYITPSDYLF WFRSHTAKEI KWGGAKHHPE DKDDGQRMHP RSSFKAFLEV  600
VKSRSLPWEN AEMDAIHSLQ LILRDSFRDS AEGTSNSKAI VNGQVQLGEL ELRGIDELSS  660
VAREMVRLIE TATVPIFAVD TDGCINGWNA KVAELTGLSV EEAMGKSLVN DLIFKESEET  720
VNKLLSRALR GDEDKNVEIK LKTFGPEQSK GPIFVIVNAC SSRDYTKNIV GVCFVGQDVT  780
GQKVVMDKFI NIQGDYKAIV HNPNPLIPPI FASDENTCCS EWNTAMEKLT GWSRGEVVGK  840
LLVGEVFGNC CRLKGPDALT KFMIVLHNAI GGQDCEKFPF SFFDKNGKYV QALLTANTRS  900
RMDGEAIGAF CFLQIASPEL QQAFEIQRHH EKKCYARMKE LAYIYQEIKN PLNGIRFTNS  960
LLEMTDLKDD QRQFLETSTA CEKQMSKIVK DASLQSIEDG SLVLEKGEFS LGSVMNAVVS  1020
QVMIQLRERD LQLIRDIPDE IKEASAYGDQ YRIQQVLCDF LLSMVRFAPA ENGWVEIQVR  1080
PNIKQNSDGT DTMLFLFRFA CPGEGLPPEI VQDMFNSRW TTQEGIGLSI CRKILKLMGG  1140
EVQYIRESER SFFHIVLELP QPQQAASRGT S                                 1171

SEQ ID NO: 38           moltype = AA   length = 428
FEATURE                 Location/Qualifiers
source                  1..428
                        mol_type = protein
                        organism = Arabidopsis thaliana
SEQUENCE: 38
MEHQGWSFEE NYSLSTNRRS IRPQDELVEL LWRDGQVVLQ SQTHREQTQT QKQDHHEEAL  60
RSSTFLEDQE TVSWIQYPPD EDPFEPDDFS SHFFSTMDPL QRPTSETVKP KSSPEPPQVM  120
VKPKACPDPP PQVMPPPKFR LTNSSSGIRE TEMEQYSVTT VGPSHCGSNP SQNDLDVSMS  180
HDRSKNIEEK LNPNASSSSG GSSGCSFGKD IKEMASGRCI TTDRKRKRIN HTDESVSLSD  240
AIGNKSNQRS GSNRRSRAAE VHNLSERRRR DRINERMKAL QELIPHCSKT DKASILDEAI  300
DYLKSLQLQL QVWMGSGMA AAAASAPMMF PGVQPQQFIR QIQSPVQLPR FPVMDQSAIQ  360
NNPGLVCQNP VQNQIISDRF ARYIGGFPHM QAATQPMEML RFSSPAGQQS QQPSSVPTKT  420
TDGSRLDH                                                           428

SEQ ID NO: 39           moltype = DNA   length = 1747
FEATURE                 Location/Qualifiers
source                  1..1747
                        mol_type = other DNA
                        organism = Arabidopsis thaliana
SEQUENCE: 39
actttctgtc tgtacccaaa agaagtaatg aacctctctc atcttcttct tctctgtttc  60
tttcatgttt tgtgagttgt ttctcaacaa ttttctggtc tcttagagtg agaggagaga  120
gatagagagt tgtgttgggc gtggaacttg actagttcc acatatcagg ttatatagat  180
cttctctttc aacttctgat tcgtccagaa gcttttccta tctgagatct gacatgaaac  240
accaaggttg gagttttgag gagaattata gtttgtccac taatagaaga tctatcaggc  300
cacaagatga actagtggag ttattatggc gagatggaca agtggttctg cagagccaaa  360
ctcatagaga acaaacccaa acccagaac aagatcatca tgaagaagcc ctaagatcca  420
gcacctttct tgaagatcaa gaaactgtct cttggatcca atccctcca gatgaagacc  480
cattcgaacc cgacgactt tcctcccact tcttctcaac catggatccc ctccagagaa  540
caacctcaga gacggttaag cctaagtcca gtcctgaacc tcctcaagtc atggttaagc  600
ctaaggcctg tcctgaccct cctcctcaag tcatgcctcc tccaaaattt aggttaacaa  660
attcatcatc ggggattagg gaaacagaaa tggaacagta ctcggtaacg accgttggac  720
ctagccattg cggaagcaac ccatcacaga acgatctcga tgtctcaatg agtcatgatc  780
gaagcaaaaa catagaagaa aagcttaatc cgaacgcaag ttcctcatca ggtggctcct  840
```

```
ctggttgcag cttttggcaaa gatatcaaag aaatggctag tggaagatgc atcacaaccg    900
accgtaagag aaaacgtata aatcacactg acgaatctgt atctctatca gatgcaatcg    960
gtaacaagtc gaaccaacga tcaggatcaa accgaaggag tcgagcagct gaagttcata    1020
atctctccga aggaggaggg agagatagga tcaatgagag aatgaaggct ttgcaagaac    1080
taatacctca ctgcagtaaa actgataaag cttcgatttt agacgaagcc atagattatt    1140
tgaaatcact tcagttacag cttcaagtga tgtggatggg gagtggaatg cggcggcgg    1200
cggcttcggc tccgatgatg ttccccggag ttcaacctca gcagttcata cgtcagatac    1260
agagcccggt acagttacct cgatttccgg ttatggatca gtctgcaatt cagaacaatc    1320
ccggtttagt ttgccaaaac ccggtacaaa accagatcat ctccgaccgg tttgctagat    1380
acatcggtgg gttcccacac atgcaggccg cgactcagcc gatggagatg ttgagattta    1440
gttcaccggc gggacagcaa agtcaacaac cgtcgtctgt gccgacgaag accaccgacg    1500
gttctcgttt ggaccactag gttggtgagc cacttttta cttccttatt tttggtatgt    1560
ttcttttta tatctatctt tctgaacata cttaaaacgt tcaaggatgt attattatag    1620
agtaaacgtg caacttcatt acgttatttt ctgtatatgt gagtttatgt atgtcaaaat    1680
gacatgatga gatttttgt aaacaacatc ttaaaaacag gacatgtgat ttttgtaatc    1740
gtaaaaa                                                             1747

SEQ ID NO: 40        moltype = AA    length = 397
FEATURE              Location/Qualifiers
source               1..397
                     mol_type = protein
                     organism = Zea mays
SEQUENCE: 40
MQTAIEHACS VVECAATARA AMDMSHYIPD WSSSMGDTFA PLGGEDDDGL IELMWRNGHV    60
VMQAQAPRKP PRPDDDEAAA AQAQAWFQYP VEERADLFSE LFGEAQAAVG GARGEAARQS    120
IRMMPPPPPP PRPAQAPREE KACPGDGGTA TATDGAGSSV LTVVSSLCGS NGNHVQATAP    180
GDVARARDVL MVTSSSTTRS RSCTTKSEQP GPGPGAARRS GKRKHNDATD AEDVGLECEP    240
AQRTTTAKRR RAAQVHNLSE RRRRDRINEK MKALQELIPH CNKADKASML DEAIEYLKSL    300
QLQLQVVWMG GGIAAAGVHQ RTMVAAPGRP PHVASLPASA PDLYTRYLAV DHLPPPPLVP    360
PPRTAAAMGL YPRQNPVPAT SSPSFRTTEN TRKLWQA                            397

SEQ ID NO: 41        moltype = DNA    length = 1492
FEATURE              Location/Qualifiers
source               1..1492
                     mol_type = other DNA
                     organism = Zea mays
SEQUENCE: 41
ccttgccctg ctgcaacttg aacctcctgg cagctcctgt ttcaggcagg cagcaagtag    60
ggaagaggct ctgcagatca gttccatgca gacagcgatc gagcacgcct gctcggtggt    120
ggaatgcgct gcgacagccc gagccgccat ggacatgagc cactacatcc ccgattggag    180
cagcagcatg ggagacacct tcgccactt gggcggcgag gacgacgacg gctcatcga     240
gctcatgtgg cgcaacggcc acgtggtcat gcaggcccag cgcgccgcga agccgccgag    300
acccgacgac gacgaggcgg cggcgcagca ggcgcaggcg tggttccagt acccggtgga    360
ggagagggcc gacctcttct cggagctctt cggggaggcg caggcggccg tcggcggcgc    420
gcgcggggag gccgcgcgcc agagtatccg gatgatgccg ccgccgccgc cgccgccgag    480
gcccgcgcaa gcgccgcggg aggagaaggc gtgcccggga gacggcggca cggcgacggc    540
gacggacggc gccggctcgt ccgtgctcac ggtcgtgtcc agcctctgcg ggagcaacgg    600
caaccacgtg caggcgacgg cgccggggga cgtcgccagg gcccgcgacg tgctgatggt    660
gacctcgtcg tcgacgacgc gttccaggtc atgcaccacc aagagcgagc agccgggtcc    720
cgggcccggc gctgccgcc ggagcggcaa gaggaagcat aacgacgcca ccgatgccga    780
ggacgtgggg ctggagtgcg agccggccgca gaggacgacg actgccaagc ggcgccgca    840
cgcgcaagtc cacaacctct cggagcggag gagacgggca aggatcaacg agaagatgaa    900
ggccctgcag gaactcatac cccactgcaa caaagcggac aaggcgtcga tgctggacga    960
ggcgatcgag tacctcaagt cgctgcagct ccagctgcag gtggtgtgga tgggcggcgg    1020
catcgcggcg gcgggggtgc accagcggac gatggtggcc gcgcccgggc gtcctcccca    1080
cgtggcttcc ctgccggcgt cggcgcccga cctctatacg cgctacctcg ccgtcgacca    1140
cctgccgcca ccgccctttgg tgccaccgcc acgcacggcg gcggcgatgg gcttgtaccc    1200
gcgccagaac cccgtgccgg cgacgtcgtc ccttcctttc cgaacgaccg aaaatacgcg    1260
aaaactatgg caagcctgag attcagatcc ggggtatggt gaccagctga tgggtcatct    1320
agctgcatgc atgtgtgtat gtgttggtag tatggttaag ccttgacaga gacttgtgat    1380
cgagaccgag atcgaccgat aggccgtcac ttctttttc ttccatcttt cagttttgg     1440
ttgataggcc ggagtgtaat ttgaccagtg gtcgagattt gtcaagcgac ac            1492

SEQ ID NO: 42        moltype = AA    length = 562
FEATURE              Location/Qualifiers
source               1..562
                     mol_type = protein
                     organism = Glycine max
SEQUENCE: 42
MNNSIPGWDF ESDTCLTNQR KLIGPDQELV ELLWKNGQVV MHNQTHRKTL GNSSNLRQVQ    60
KSDQSVLRSS GPYGNSSNLD QEDAAPWVQF PLEDPLEQDF CSNLLSELPT CEFESYKPIR    120
QLEEEKFAKF FASGTPHHPT TSSSQPLPPN MKPSCIQGLQ GNPIPMPAPR FHGPDSSQKI    180
HDFGASRKVL NFPQFSTPRN NVPSAPGITQ FREKTTANMS QSEAREYSVI TVGSSHCGSN    240
HIPQEQDVSR ISSTGVWATT NNNTTLSAEP EAVRDVQRP ICPKSGQGKS EMIELTVTSS    300
SGGSGSTGIG RTCSLSTRDH GQKRKGTEEE ALEEQSEDTE LKSADGNKAS QRTRSSRRNR    360
AAEVHNQSER RRRDRINEKM RTLQQLIPNS NKTDKASMLE EAIEYLKSLQ FQLQVMWMGG    420
GMTPVMFPGI QHYMSQMGMG MGAPSLPSIH NPMQLPKVPH DQAMSVLQIP NQNLMCQNPV    480
LGAFNYQNQM QNPCLPEQYA RYMGYHLMQN ASQPMNVFRY GSQAVQHSQT MIAPGNNSSG    540
PMSGTANIDD ADSGKAGSST FN                                             562
```

```
SEQ ID NO: 43            moltype = DNA   length = 2161
FEATURE                  Location/Qualifiers
source                   1..2161
                         mol_type = other DNA
                         organism = Glycine max
SEQUENCE: 43
gaccccgttt tcaactggtc ccgtgttcct tcatttgatg ccacatgtgc agctacccat    60
gttttctcg  ctgttgacga gcacaatata taataaatac catttttttc atgccatatt   120
tgctctcttc tctctttgta ctaataactt ggatctatgc cactgtcctt ctccttgtta   180
aaaactgtgc cacacgtctg tcaccaaact ccctaagcag aagaagcaca tgttcagagg   240
gagtttgtt  tcatcagtct ctagctagca tatatttcta gcttctattc aacaagttgc   300
aaaaaacaga ctttgcctta accaaaagaa aatctgtttt taccttaact cagacaactc   360
gtttggtgaa ccatgaacaa cagtattcct ggttggtagt ttgagagtga tacatgtctc   420
accaaccaaa gaaagctcat agggccggac caagaacttg tagagctcct atggaaaaat   480
gggcaagtag ttatgcacaa ccaaacacat aggaagacac ttgggaattc atctaacttg   540
agacaggtgc agaaaagtga tcaatcagta ttaaggtcta gcggtcccta tggaaactgt   600
agcaactgg  atcaagaaga tgccgcccca tgggtccaat tcccacttga ggacccattg   660
gaacaagatt tttgttcaaa ccttttatct gaactaccaa cttgtgaatt tgaatcttac   720
aagccaatca ggcaattgga agaggaaaag tttgccaaat tttttgcttc cggtaccccc   780
catcatccta caacttcaag ttcacaacca ctaccaccta acatgaaacc ctcatgtatt   840
cagggactcc aagggaatcc tattcctatg ccagctccaa gatttcatgg tcctgattca   900
tctcagaaaa tccatgactt tggagcatca cgaaaggttc taaattttcc tcagttttca   960
acaccccgta ataatgttcc atcagcacct ggtattacac agtttagaga gaaaactact  1020
gctaacatgt cacaaagtga ggctagagag tactcagtga tcacagttgg ttcaagtcac  1080
tgtggcagca atcacatccc tcaggagcaa gatgtaagca ggatttcaag cactggtgtt  1140
tgggccacta ctaataataa tactacttta tctgctgagc ctgaagctgt cagagattat  1200
gtccaaagac cgatttgtcc taagagtggc caaggaaaat cagagatgat tgaactaact  1260
gtgacttcat cttccggtgg ctcgggaagt actggtatcg gaagaacctg ttccctatca  1320
acaagagatc atggccaaaa gagaaaaggg acagaaggaa aagcgttaga ggaacaaagt  1380
gaggacacag aacttaaatc agctgatgga aacaaggctt ctcagcggac gaggtcttcc  1440
agaaggaacc gtgcagcaga agtgcataat caatcagaaa ggagaagaag agataggatc  1500
aacgagaaga tgaggacatt gcagcaactg ataccctaata gtaacaagac agacaaagca  1560
tcaatgttag aagaggcaat cgaatacttg aaatcacttc agtttcagct tcaggttatg  1620
tggatggggg gtggcatgac accagtgatg ttcccaggaa ttcagcacta tatgtcacaa  1680
atgggtatgg gaatgggtgc accttctttg ccttccattc acaacccgat gcaattgcca  1740
aaagtgccac atgatcaagc catgtctgtg cttcagatac aaaccagaa  tttaatgtgt  1800
caaaatccag ttttgggtgc cttaactac caaaaccaga tgcagaaccc gtgccttcca  1860
gaacaatatg cacgttacat gggttaccat cttatgcaaa atgcctctca gcctatgaat  1920
gtgttcagat atggttccca agcagtgcaa cacagtcaaa cgatgattgc caccaggcaat  1980
aatagcagcg gacccatgag tggaacagct aatattgatg atgctgacag tggcaaagcg  2040
ggttcttcca cctttaattg aatagtgaat agcaatacct taaaattact caattggggg  2100
aattacctaa tggagtacgt caatcctcac aagcaccaat atgtgctcca attttatgta  2160
g                                                                 2161

SEQ ID NO: 44            moltype = AA   length = 409
FEATURE                  Location/Qualifiers
source                   1..409
                         mol_type = protein
                         organism = Oryza sativa
SEQUENCE: 44
MNQFVPDWNT TSMGDGFAPL GEDDGLVELL WCNGHVVMQS QAPRKPPRPE KTTAAAAAM    60
AEDESASWFQ YPVDDVLEKD LFTELFGEMT AAGGGGDVR RAACKEERGA VAAFQSRMMP   120
PPWPARGKAE FGDVDDVCGV SEVVMAKMDG AAAAETVGES SMLTIGSSIC GSNHVQTPPV   180
GNGKAGAGTA GAARRAHDTA TVASSSMRSR SCTAKAEPRD VAAAGVGGKR KQRGGAAMES   240
GSPSEDVEFE SAAATCSPAQ KTTTAKRRRA AEVHNLSERR RRDRINEKMK ALQELIPHCN   300
KTDKASMLDE AIEYLKSLQL QLQMMWMGGG MAPPAVMFPA AGVHQYMQRM GAVGMGPPHM   360
ASLPRMPPFM APPPAAVQSS PVVSMADPYA RCLAVDHLQP PPPMFRREY              409

SEQ ID NO: 45            moltype = DNA   length = 1749
FEATURE                  Location/Qualifiers
source                   1..1749
                         mol_type = other DNA
                         organism = Oryza sativa
SEQUENCE: 45
gcgagtcctc ttcctgccct gcccgcccct gccctgcatt cttctttct  ccaccagggg    60
aatccagttc acccccagtg ctgcttctgc tgctgcttct gcatcatctt gcctgttaa   120
aaagacacag tgcccttgtt cttttcgcagt tgcaactagc atctcctcct ctacttgtac   180
tcacttcaca cctcagctca gctcagctca tctcctgtca tctcagctca aagagaaaga   240
gctgaaggtg taagctgatc accaggaagc agaggctttt tttcagatta cagttatctg   300
aaacaaccaa cttcagaatc aatcagcaaa ggtagaaaca agacagagct gctgtgcttc   360
tgtgattaat tagggttgtt aatgccatga accagttcgt ccctgattgg aacaccacca   420
gcatgggcga cggctttgcg ccattaggcg aagacgacgg gctcgtcgag ctgctatggt   480
gcaatggcca cgtcgtcatg cagagccagg cgccgcgaag ccggagagaa               540
cgacggcggcg ggcggcggcg gcgatgcggcg aggatgagtc ggcgtcgtgg tttcagtacc   600
cggtcgacga cgtgctgag  aaggacctgt tcaccgagct gttcggcgaa atgacggcgg   660
ccggcggcgg cggcggcgac gtccgcaggg gcggcgtgcaa ggaggagcgc ggcgcggtcg   720
ccgcgttcca gagcaggatg atgccgccgc cgtggccggc gaggggggaag gcggagtcg   780
gtgacgtcga cgacgtgtgc ggcgtctcgg aggtcgtcat ggcgaagatg gacggggcgg   840
```

```
cggcggcgga  gacggtcggc  gagtcatcga  tgctgacaat  cgggtcgagc  atctgcggga   900
gcaaccacgt  ccagacgccg  ccggtgggga  acgggaaggc  cggcgccggc  accgccggcg   960
ccgcagaag   ggcgcacgac  acggcgacgg  tggcgtcgtc  gtcgatgagg  tcgaggtcct  1020
gcaccgccaa  ggccgagccg  cgcgacgtcg  cagccgccgg  cgtcggcggc  aagcggaagc  1080
agcgcggcgg  cgccgccatg  gagtccggga  gccccaggca  ggacgtggag  ttcgagtccg  1140
ccgccgcaac  gtgctcgccg  gcgcagaaga  cgacgacggc  gaagcggcgg  cgcgccgccg  1200
aggtgcacaa  cctctccgag  aggaggagaa  gagataggat  caatgagaag  atgaaagcat  1260
tacaggagct  catacctcac  tgcaacaaaa  cggacaaagc  atcgatgctg  atgaagcga   1320
tcgagtatct  caagtcactg  cagctccagc  tacagatgat  gtggatgggc  ggcggaattg  1380
cgccgccggc  ggtgatgttc  ccggcggccg  gcgtgcacca  gtacatgcag  cggatgggcg  1440
ccgtcgggat  gggcccacca  cacatggcgt  ccctgccgag  gatgccgccg  ttcatggcgc  1500
cgccgcccgc  cgccgtgcag  agctcgccgg  tggtcagcat  ggccgacccc  tacgcccgct  1560
gcctcgccgt  cgaccacctc  cagccaccgc  ctccgatgtt  tcgacgcgaa  tactagggaa  1620
ggaactaata  tcaaataata  gaaggggtga  gccttcgaat  cgagatcgtc  tagcccacca  1680
ccttatagag  ctagccggaa  ggccctcgag  cgtttctcat  attttcagtt  tcctaagagt  1740
tttttttt                                                               1749

SEQ ID NO: 46          moltype =    length =
SEQUENCE: 46
000

SEQ ID NO: 47          moltype =    length =
SEQUENCE: 47
000

SEQ ID NO: 48          moltype = AA   length = 187
FEATURE                Location/Qualifiers
source                 1..187
                       mol_type = protein
                       organism = Arabidopsis thaliana
SEQUENCE: 48
MSLFPCEASN  MDSMVQDVKP  TNLFPRQPSF  SSSSSSLPKE  DVLKMTQTTR  SVKPESQTAP   60
LTIFYAGQVI  VFNDFSAEKA  KEVINLASKG  TANSLAKNQT  DIRSNIATIA  NQVPHPRKTT  120
TQEPIQSSPT  PLTELPIARR  ASLHRFLEKR  KDRVTSKAPY  QLCDPAKASS  NPQTTGNMSW  180
LGLAAEI                                                                187

SEQ ID NO: 49          moltype = DNA  length = 1527
FEATURE                Location/Qualifiers
source                 1..1527
                       mol_type = other DNA
                       organism = Arabidopsis thaliana
SEQUENCE: 49
atattggagg  taggaagaag  aactctgcaa  ccaaaccaac  caaccccaaa  gccaaacaaa    60
gttttataga  gaccttccat  ttctccctct  cgtgacaaac  gcaatttgca  gagaagcaac   120
agcaacaaca  agaagaagaa  gaaaaagatt  tgagattact  ttgtatcgat  ttagctattc   180
gagaaactct  tgccgtttga  agttttaat   tgttaaagat  gtcgagttct  atggaatgtt   240
ctgagttcgt  cggtagccgg  agatttactg  ggaagaagcc  tagcttctca  cagacgtgta   300
gtcgattgag  tcagtatcta  aaagagaacg  gtagctttgg  agatctgagc  ttaggaatgg   360
catgcaagcc  tgatgtcaat  ggtaagaaac  cttctctttc  tcctagatcc  acttcttttt   420
tcgttttctc  tgttttttat  ttcttgaatc  ttgatcttga  aaacttttca  agaaaatttt   480
gaatcgattt  caaagaaatt  agggagagtt  agtttgctaa  attttgacat  agaaaatgat   540
tggagagagt  tctaactttt  ggatcatata  tatttgcagg  aactttaggc  aactcacgtc   600
agccgacaac  aaccatgagt  ttattcctt   gtgaagcttc  taacatggat  tccatggttc   660
aagatgttaa  accgacgaat  ctgttcctag  gcaaccaag   cttttcttcc  tcatcttcct   720
ctcttccaaa  ggaagatgtt  ttgaaaatga  cacagactac  cagatctgtg  aaaccagagt   780
ctcaaactgc  accattgact  atattctacg  ccgggcaagt  gattgtattc  aatgacttt    840
ctgctgagaa  agccaaagaa  gtgatcaact  tggcagcaa   aggcaccgct  aatagcttag   900
ccaagaatca  aaccgatatc  agaagcaaca  tcgctactat  cgcaaaccaa  gttcctcatc   960
caagaaaaac  cacaacacaa  gagccaatcc  aatcctcccc  aacaccattg  acagaacttc  1020
ctattgctag  aagagcttca  cttcaccggt  tcttggagaa  gagaaaggac  agagttacgt  1080
caaaggcacc  ataccaatta  tgcgatccag  ccaaagcgtc  ttcaaaccct  caaaccacag  1140
gcaacatgtc  gtggctcggt  ttagcagctg  aaatatgaat  gctaaccacc  tcaagccgt   1200
accaagaaat  tcttttgacg  acgttgcttc  aagacaagat  ataaagctc   ctatcttcat  1260
gcttttttgat ttaagataca aactactcaa tgattagtca acttcatata tttgtatgta     1320
ttgattagtg atcaattatt gttagtattc gttatagtct gtttttctac tagttattgt     1380
cgcctgtcta aatccccttg ctatgggtta tctcaaaatt agtttcgtat gtaactaatt     1440
ttgtaagaac aataattttt gttgacgaac catactatca aatactctaa attatatctt     1500
gataaatcta cctatcaggt aagtagg                                          1527

SEQ ID NO: 50          moltype = AA   length = 352
FEATURE                Location/Qualifiers
source                 1..352
                       mol_type = protein
                       organism = Arabidopsis thaliana
SEQUENCE: 50
MERDFLGLGS  KNSPITVKEE  TSESSRDSAP  NRGMNWSFSN  KVSASSSQFL  SFRPTQEDRH   60
RKSGNYHLPH  SGSFMPSSVA  DVYDSTRKAP  YSSVQGVRMF  PNSNQHEETN  AVSMSMPGFQ  120
SHHYAPGGRS  FMNNNNSQP   LVGVPIMAPP  ISILPPPGSI  VGTTDIRSSS  KPIGSPAQLT  180
IFYAGSVCVY  DDISPEKAKA  IMLLAGNGSS  MPQVFSPPQT  HQQVVHHTRA  SVDSSAMPPS  240
```

```
FMPTISYLSP EAGSSTNGLG ATKATRGLTS TYHNNQANGS NINCPVPVSC STNVMAPTVA    300
LPLARKASLA RFLEKRKERV TSVSPYCLDK KSSTDCRRSM SECISSSLSS AT            352

SEQ ID NO: 51           moltype = DNA  length = 3253
FEATURE                 Location/Qualifiers
source                  1..3253
                        mol_type = other DNA
                        organism = Arabidopsis thaliana
SEQUENCE: 51
gcgatttgtt aataaaacta gaaattgcgg tgaattaact tcattccacg ttttttcatt    60
ttctccctca aaagtctctg tttttttttcc tttttccggc gaagctctat ttagcttgat   120
tccggcgttt aacacgcgtt ttaatcgaaa cagacatttg agatcgaatt aatttttgtag   180
cgggctgtgt ctttattata gatggagaga gattttctcg ggttgggttc gaaaaattct    240
ccgatcactg tcaaggagga aaccagcgaa agctctagag attcaggtta tttattactc    300
ttctcaattt ttctgattct gattgttttt aaatcgtaga tttgtttgat tgattaggag    360
ttattaggac tacttgtagt atggaatttg ttttggata gctgattta tggcttgctc     420
gggaactgga attgtcagtt tgttgcttgg agcagaacat tgtcctttgc ttttctcggg    480
agatgtagaa tttggatttg gaaaaactag tgttcttttc caaagccttg tcttaaacat   540
gctttcggtc ggagaaaatta acgagaacta atctcaagct tctaacataa ttaaactcgg   600
taaactttt tttactagag taaattttt tgttttgttt gaagagtctt ataattgaga      660
aatactttat tagtttatac taaaaaaaaaa acgaatacgt aaaatgttgg aaaagagggg   720
atgtatagag actgataaca aaatgataaa atagagacgg ttggtagtag gtagaaagat    780
taaatatact caaagagtg agttggatta gttataaga tgattaactt cttgattgtg     840
tgagttggat tagtttatga gattattaaa atattgattg tgtatttgtg ttgtgtgttg    900
attaagcgga acttgcgtta gaatattgtt caaggtacaa tgtggaaata atagttttct    960
caccacgagg aatataatta tttcaacttt gtttcttat cagccaaaac gtgccacacc    1020
ataaaagtag tgcatcaaca tgtggtgtgg tgtggtgggg ttaaagtttg aatctctctt   1080
taatttaaac tattaaaaca aacttaaatt attggagttt cgtacaatga ctttcaatca   1140
aatgttttag aattagacac ggttttcgaa agtggttttc cctcgttgaa tttgtcaaca    1200
gtatcagatt ctacattgtt ggttactaat cttttccttg aagtaggtgt tgaattaatc    1260
ctctgttgtt tatgtaagga gatctcgaga catttatggt taacagttaa cactacatgt    1320
ttgactttaa actgattatc ttttattctt tttcttttgt agctcccaac agaggaatga    1380
actggtcttt ctcaaacaaa gtatcagctt cttcttctca gtttctatcc ttcaggccaa    1440
ctcaagaaga tagacataga aagtctggaa attatcatct tcctcactct ggttccttca    1500
tgccatcatc agtagctgat gtttatgatt caacccgcaa agctcctac agttctgtac     1560
aggtatttgt catcaaaacc tatgttaacc aagaccctttg tgttttttt atccttcgca    1620
agatagcttt aaaagtgagc cctgttttat gagcatatag taattggttt tgagtctagt    1680
ttagcacaag ttcatggcaa ttagtttgtg gatctaatct tggtttaata ctgattcatt    1740
ttaagtgtaa gctaagcttc tcattttgaa taagttagtt cataaatgc ctcacaccta    1800
ctttatggct tgttactctc agggagtgag gatgttccct aattccaatc aacacgaaga    1860
aactaacgca gtttccatgt cgatgccggg ttttccagtct catcattatg caccaggagg   1920
aagaagcttc atgaacaata acaataactc acaacctttg gtaggagttc ctatcatggc    1980
acctccaatt tcaatccttc ctcctccagg ttccattgta gggactactg atattaggta    2040
cccactagtc atcatatcat acagaaactc tttctacatt tcatagttg actaaagact     2100
tatttttgtc agatcttctt ccaagccaat aggttcacct gcgcagttga cgatctttta    2160
tgccggttca gtttgtgttt acgatgacat atctcctgaa aaggtatctc aatcatttc    2220
ttccatatat gcatctcttt tactcgtaag tatggtact cttttcatttc               2280
tcaggcaaag gcgataatgt tgctagctgg gaacggttcc tctatgcctc aagtctttc    2340
gccgcctcaa actcatcaac aagtggtcca tcatactcgt gcctctgtcg attcttcagc    2400
tatgcctcct agcttcatgc ctacaatatc ttatcttagc cctgaagctg gaagtagcac    2460
aaacggactc ggagccacaa aagcgacaag aggcttgacg tcaacatatc acaacaacca   2520
agctaatgga tccaatatta actgcccagt accagttttc tgttctacca atgtaatggc    2580
tccaacaggt aaaaaacaaa gtcagagacc tgatactaca ttcgccatct aacttactag   2640
tattttcatg gatgtaactt cattctcgtt ctgtttctta tgcagtggca ttacctctgg    2700
ctcgcaaagc atccctggct aggttttttag agaaacgcaa agaaaggtac gcaacacttc    2760
tttagaatac accattcaat agtttcttgg gctaactctc tttctcgctg tgggtttctc    2820
agggtcacga gcgtatcccc atattgctta gacaagaagt catcgacaga ttgtcgcaga    2880
tcaatgtctg aatgcattag ttcttctctc agctctgcaa cctaatttca tctacagtaa    2940
gaaggttgct ttagaccact ccacatccat atttgcattt caatggcggt cttttcaatg    3000
tctcagttaa ttttttcctca ctcgccacac tgagtttctc cttagtctta tatatcgat    3060
agtgtatact ttgtttacat gtttttttgg ggaatggaac ttatgagagc atatcagata    3120
tgtacttggg aaaattagta gaaactgttt gtttctttt ttttaactct gttcttttgt     3180
atatatcact gaagctcgca tatgtataat tcatgtaatg gaattgcatc gcttctgttt    3240
ccctaagtta ttt                                                       3253

SEQ ID NO: 52           moltype = AA  length = 310
FEATURE                 Location/Qualifiers
source                  1..310
                        mol_type = protein
                        organism = Arabidopsis thaliana
SEQUENCE: 52
MERDFLGLGS KLSPITVKEE TNEDSAPSRG MMDWSFSSKV GSGPQFLSFG TSQQETRVNT    60
VNDHLLSSAA MDQNQRTYFS SLQEDRVFPG SSQQDQTTIT VSMSEPNYIN SFINHQHLGG    120
SPIMAPPVSV FPAPTTIRSS SKPLPPQLTI FYAGSVLVYQ DIAPEKAQAI MLLAGNGPHA    180
KPVSQPKPQK LVHHSLPTTD PPTMPPSFLP SISYIVSETR SSGSNGVTGL GPTKTKASLA    240
STRNNQTAAF SMAPTVGLPQ TRKASLARFL EKRKERVINV SPYYVDNKSS IDCRTLMSEC    300
VSCPPAHHLH                                                           310

SEQ ID NO: 53           moltype = DNA  length = 3187
```

| FEATURE | Location/Qualifiers |
|---|---|
| source | 1..3187<br>mol_type = other DNA<br>organism = Arabidopsis thaliana |

SEQUENCE: 53

```
attagaggaa tcataaatcg gcggtgtgtg taacttcaac tcacgttttt catttctctc    60
caaagtcctt caattgttac taattctctc tgatctctca tttcttctct tctccggtga   120
catttttttt ctcccccgcg aaagctaaac cgttttgta ttctcaacga ttgataagcc   180
tgatggagag agatttctc gggctgggat caaagttatc tccgataact gtgaaggagg   240
aaactaacga agattcaggt aattcatctt caacatcttc cattatgatc tgatgattgt   300
gttttcatc tcactttttt ttgtttctat ttttgtaatc tctttttttg ttattgttc   360
aagtacatat atattgtttt tctagcttga ttgggagtcc tactgtctgg ttttttcttg   420
aacaagaaat tttttcttcg ttttctcggg aagagaaaaa ataaattagg gtttctttt   480
tcttgatata tatttaagaa attaggttt agtactatag acagaaattt agctactcga   540
atttgtttga cgtagccgat gaaaaaacac gttttgggac tcgatagtta gaaaattcat   600
acgttcacga tctactttg aagttttttt cattaaatat ttttgcaaa ctacaaatgt   660
acaagtatac aactatacaa gcaaacacca aacttgttga cgttagtaat ttaacaagtg   720
ttagtattat ctttgaaaaa taatattcag agaacaatct tgattttcta ggtgactagg   780
tgatgcatgt ttctaaagct gttggtaatg ttgagtgttt tcaaatact ttcgtttttt   840
tcttcaaaca gccgacaccg acagaacaaa aatgctatat ttttttttgtt gcttacaaaa   900
ttgatcaatt ggtttcaata caatagtatc ttctttagaa aagattgttt ttttcaaagc   960
cggattgaat attgagaatt agaacattgg ctggttattc ttttgaaaa gtttatgcca  1020
tttttaagg tttattaagc aacttgaatt ctatcagtat tattttaaaa cgaagacgtg  1080
aaatgttggg aaaagaatgc gttatatagc gaccggctga cgattagaga tttaacaaca  1140
aatgcaagtc gaattatata aaagcaagat tgattgtgac ttgattaagt tttatttcta  1200
tccaagtaga ctcattgatt aagttaggat catgttgggt attaaattta gatcaagtta  1260
caattttggat gaataattta cttacccacg aggaattaga tagttagttc ttgtcttttt  1320
atattccgaa acgtgccatt tcttgaaagt atttgtatga tcactatttt ccccagtgtg  1380
tttggcttta tgcagatttg ttcattgttg atgaatcaa tgttaagagt cgtccacttt  1440
agcatagcta gatctgagtg tttcctagtt tgataaaatc taaagacatt tgctcatgtt  1500
tcagccccaa gtagaggtat gatggattgg tcattctcaa gcaaagtcgg ttctggtcct  1560
cagtttcttt cttttgggac atcccaacaa gaaacgcgtg taaacacagt caatgatcat  1620
ttgctttctt ctgctgcaat ggatcaaaac cagagaactt acttcagctc actacaggtt  1680
aggctatttc ttgaaaagaa aaaagtagt gataaagtgt gatttagtga ccttgtaaga  1740
aagcttggca attggtttag tttcttctgg tctcaaaatt gatacaaaat gatctcagga  1800
agacagagtg ttcccaggtt ccagtcagca agaccaaaca accatcacag tctccatgtc  1860
cgaaccaaac tacatcaaca gtttcataaa ccaccaacat ttaggaggat ctcctatcat  1920
ggcacctcca gtttcagtat ttcctgctcc aaccactatt aggcatgcac tgcattctat  1980
cttcttctgt ttaacatcag atacagaacc tctttacttc tatagttgac tcgagctcct  2040
ttatgttcat ctccagatct tcttcaaaac cacttccccc tcagttgaca atcttttatg  2100
ccggttcagt attagtttac caagacatag ctcctgaaaa ggtaaccaaa tttccttcaa  2160
tatgtgttac attacagtcc aagctatcca ctgactaagt attcaatcaa agaaataagt  2220
ttcacgtata gacatgctga agttataaa agttactaac ctggtttcaa catacagtat  2280
gttaatgatt catagatatg ataaatcttt gtccttactt cttcatttat tttgtattca  2340
taggcccaag ctatcatgtt gctagccgga aatggaccttc atgctaaacc ggtttcacaa  2400
cctaaacctc aaaaactggt tcatcactct cttccaacca ctgatcctcc aactatgcct  2460
cctagttttcc tgccttccat ctcttacatt gtctctgaaa ccagaagtag tggatccaac  2520
ggggttactg gacttggacc aacaaaaaca aaggcgagtt tagcatccac gcgcaacaac  2580
caaactgctg ccttctctat ggctccaaca ggttataaat gaagtcttaa ctccattaa  2640
tgttttgtca tcaaacttct atcttaggtt tagtttgtta taaccaaaaa atcttgctat  2700
gatttaatac agtgggttta ccacaaacac gcaaagcatc cttggctcgg ttcttagaga  2760
aacgcaaaga aaggtactga gctacaagat tattccttta ttcacaatat caaaacacag  2820
gtttgctgta tattggcttc gttttcttgc agggtcatta acgtatcacc ttattacgta  2880
gacaacaagt catcaataga ctgtagaaca ctgatgtctg aatgtgtaag ctgtcctcca  2940
gctcatcatc tgcactaaaa ccaatttaga ccctcattg ttctaaaggc ttttctttt  3000
ttctctggct ctgtatccta tagactatag tatagttgtt atagcttttg tttattcaga  3060
ttttagtaca ctgggcttgt aaaagcaagt tattatata tatcctataa atttaatttg  3120
gatactgtat gttttgtctt tactcttgca tgtgtataaa aacataaaa gtaagactat  3180
tcaagct                                                             3187
```

| SEQ ID NO: 54 | moltype = AA length = 267 |
|---|---|
| FEATURE | Location/Qualifiers |
| source | 1..267<br>mol_type = protein<br>organism = Arabidopsis thaliana |

SEQUENCE: 54

```
MERDFLGLSD KQYLSNNVKH EVNDDAVEER GLSTKAAREW GKSKVFATSS FMPSSDFQEA    60
KAFPGAYQWG SVSAANVFRR CQFGGAFQNA TPLLLGGSVP LPTHPSLVPR VASSGSSPQL   120
TIFYGGTISV FNDISPDKAQ AIMLCAGNGL KGETGDSKPV REAERMYGKQ IHNTAATSSS   180
SATHTDNFSR CRDTPVAATN AMSMIESFNA APRNMIPSVP QARKASLARF LEKRKERLMS   240
AMPYKKMLLD LSTGESSGMN YSSTSPT                                        267
```

| SEQ ID NO: 55 | moltype = DNA length = 2297 |
|---|---|
| FEATURE | Location/Qualifiers |
| source | 1..2297<br>mol_type = other DNA<br>organism = Arabidopsis thaliana |

SEQUENCE: 55
```
gcaaagagtt aaataagcct ctccaaaagt gtgtctgtaa cattaccaaa acgaaacctt    60
ccttgtggat tcccacttct ttcttctgtt ttcttcttcc tcttctttaa attggatgtt   120
ttgggcaaga aacagagaga aacacgttaa tttgagagtt tgtcattgaa tatttggttt   180
gcaatggaaa gagattttct gggtttgagc gacaagcagt atctaagtaa taacgttaag   240
catgaggtta acgatgatgc tgtcgaagaa cgaggtttgt gttcttgtct cgagaatctt   300
ttatttaat gtttcaagaa gagatcagtt ttcacttta acatagccgt ataaagttgt    360
ttatttaaat ataattttc agattccaaa acttgaaaaa aaaaagattc cattaaatct    420
tttataaaaa tgagattgga tagattagtc aaattgacaa ccataaaaaa tgatacttat   480
agggttaagt acgaaggcag ctagagaatg ggggaagtca aaggttttg ctacttcaag    540
tttcatgcct tcttcagatt tccaggttgg ttcatcttaa aatttaactt actctgtatc   600
agtttcagat gttatggcta atctaatggt tctataagct accgcataat catggtcgtc   660
ttttagcatg tgcaagagga gtactcaatt atggcttga ttaaaaagaa gaatttactt    720
tcaaattatg ttaaacacat caatcacata tttatgagaa aagttgtttt cgtaagagat   780
agccaccgga aaatggtcgg ataaatggcc gaacttatc attttgtgt atgtggccaa     840
tcattaacca gggaaaaaaa attgttggat aagtgctagt taagagctgg tagggtcggt   900
cgtctgccag ccgcaaagtt agggaaaaaa taatttaata ttttgtggcg tttggtgttt   960
ggcgtttgga tcacgtttat ttcttggcat ttttctaaat ttagaatgta caaaaaattt  1020
aaagacgttg acgattaaaa tttgaattta acaaattagg aggctaaggc gtttccgggt  1080
gcataccagt ggggatcagt ttctgcggcc aatgttttcc gcagatgcca atttggtggt  1140
gcgtttcaaa acgcgacgcc gcttttacta ggcggttcag ttcctttacc aactcatcct  1200
tctcttgttc cacggtaatt tccatattat gatgcaaaaa cattcaacaa tttttttgct  1260
cttttcatat tttgatttgg ttatgtgggt ttgtggaaac agagtggctt cctccggatc  1320
atctcctcag ctcacaatct tttatggcgg aactataagc gtcttaatg acatatctcc   1380
cgataaggta tatataatca agattcatac aaataacatt tacataacat ttacatgttc  1440
taaaacggac tattcatgat atgtgagtag gctcaagcca tcatgttatg cgccgggaac  1500
ggtttgaaag gtgaaactgg agatagcaaa ccggttcgag aagctgaaag aatgtatgga  1560
aaacaaatcc ataacactgc tgctacctca tcaagctctg ccactcacac tgataaattc  1620
tcaaggtgta gggacacacc cgttgctgcg actaatgcaa tgagcatgat cgaatcattc  1680
aatgcagctc ctcgtaacat gattccttca ggtatgtgtg tctaatatca acatcaaaac  1740
aaaatataat caagatttt gcttcctcaa atcatatgtc taaactcgaa aattgctttt    1800
ttccagtccc tcaagctcgg aaagcatcct tggctcggtt cttggagaag cgcaaagaga  1860
ggtttgattt tgtattttt ttctttatag aaaatttga ggttttcaa ttgaatctaa     1920
aagaattgat gttgttggtg caggcttatg agtgcaatgc catacaagaa gatgcttctt  1980
gatttgtcga ccggagaatc cagtggaatg aattactctt ctacttctcc tacataaaac  2040
ctacactttt tttttttttt tttacaatgg taatttgtaa ttgtaatcat tagattatga  2100
ttatatagtt accatttata ttcttacgag caggagaaga cgttagggcg tctctgtatt  2160
tgatcattgt ttgtaatgct ttggtctgtt tattgtagga ttacattata actttaagaa  2220
ctaacagata tatgtttgtc atggactcat gtctgtcaag aatttaatat caaataaaat  2280
tcactataat ttttttt                                                2297
```

SEQ ID NO: 56    moltype = AA    length = 197
FEATURE         Location/Qualifiers
source          1..197
                mol_type = protein
                organism = Arabidopsis thaliana
SEQUENCE: 56
```
MSKATIELDF LGLEKKQTNN APKPKFQKFL DRRRSFRDIQ GAISKIDPEI IKSLLASTGN    60
NSDSSAKSRS VPSTPREDQP QIPISPVHAS LARSSTELVS GTVPMTIFYN GSVSVFQVSR   120
NKAGEIMKVA NEAASKKDES SMETDLSVIL PTTLRPKLFG QNLEGDLPIA RRKSLQRFLE   180
KRKERLVSTS PYYPTSA                                                 197
```

SEQ ID NO: 57    moltype = DNA    length = 1927
FEATURE         Location/Qualifiers
source          1..1927
                mol_type = other DNA
                organism = Arabidopsis thaliana
SEQUENCE: 57
```
aaaaactctc acatgagaaa tcagaatccg ttattattcc tccatttatt catctcaaaa    60
cccatatctc tctgtcttga tctctctctc actttctaat aagatcaaag aagatgtcga   120
aagctaccat agaactcgat ttcctcggac ttgagaagaa acaaaccaac aacgctccta   180
agcctaagtt ccagaaattt ctcgatcgcc gtcgtagttt ccgaggttcg tttggttttt   240
agtcgctctc tcttttttt ttcttgcgat aaatcgaatt tattcatatg gaactcctgc    300
agatattcaa ggtgcgattc gaaaatcga tccgagaatc gcc tgttagcttc            360
cactggaaac aattccgatt catcggctaa atctcgttcg gttccgtcta ctccgaggga   420
agatcagcct cagatcccga tttctccggt ccacgcgtct ctcgcaggt atttttgtct    480
ttccggtaaa gttttttttt tctttctaac ttttttggcg ctaccagaaa agacgaaaaa   540
atttgaaatt caaattttca aaacattcat tttcctcagg tctagtaccg aactcgtttc   600
gggaactgtt cctatgacga ttttctacaa tggaagtgtt tcagttttcc aagtgtctcg   660
taacaaagct ggtgaaatta tgaaggtcgc taatgaagca gcatctaaga aagacgagtc   720
gtcgatggag acagatcttt cggtaattct tccgaccact ctaagaccaa agctctttgg   780
ccagaatcta gaaggaggtt agtataataa aaataaaaat cacttagtgc tggattcttc   840
tagaatttta gttacatatt attgcatgta gagatcaag aagagtttgt tgttagagag    900
gaattggttg ctaattagtt tggaattaga tatcaaagag ttaaagacta tagttttatgt  960
ctatacgtat taatatacgt tattaataaa agtataaaca tgttgtttaa tttctgataa   1020
gaaactggtt tatgcgtgtg tatgcagatc ttcccatcgc aaggagaaag tcactgcaac  1080
gttttctcga gaagcgcaag gagaggtaat gattcttcaa caatccaagg attttttaccc 1140
ccaaataatt aaagaaaggt tttattttt ctctctctcg acctttttt tactataagt    1200
tatttaagat agtaattatg ggtcctgcct cttttactct cacatacaac ttaagattca   1260
```

```
actagttttg ttcaacaacg cacatgctta tacgtagata gataatggag atcagtagta  1320
atatcggtat acgtaggtta ctattgtaat ggaactttta aaaagcgcgt tgactttgag  1380
tctttgactc tagttctgtt tgctacaccg acaagttata tttttcaaaa tgatgagaaa  1440
acgaggagaa acaccggaaa aaatttgaa cttttacttt tatcagacca tacggccaaa  1500
gaaagatctg tatattatat aagttatcac aaaacgcgtt ttcacatttt cttttttcgtc  1560
ttgttgtgtt tgcagattag tatcaacatc tccttactat ccgacatcgg cctaaacgat  1620
ctcttttttag attgggacat ggaccaaatt tgtcttttttc aatcggaaga catccatgtt  1680
cgttttttgga tttggcttat ttccaatctt cttttgaagc cttcttcgtc gttgctaaat  1740
cgtatactat tcacgacaaa cgtttttagg agattacgtt acctactaag attatatata  1800
tggtttgtt tttaaaaatg tctattatct ttattgtcat tgatagcttg atttaagaag  1860
ctctctctta tcccgtgacc ttctactttt gttttatttt ttagtatatg gtaaagaaaa  1920
ttataac                                                            1927

SEQ ID NO: 58           moltype = AA   length = 273
FEATURE                 Location/Qualifiers
source                  1..273
                        mol_type = protein
                        organism = Brassica rapa
SEQUENCE: 58
MSSPMESSDF AATRRFSRKP SFSQTCSRLS QYLKENGSFG DLSLGMACKP EVNGISRQPT    60
TTMSLFPCEA SNMEPIGQDV KPKNLFPRQP SFSSSSSSLP KEDILKMTQA TSSTRSVKPE   120
PQTAPLTIFY GGQVIVFNDF SAEKAKEVMD LASKGTANTF TGFTSNVNNN IQSVYTTNLA   180
NNQTEMRSNI APIPNQLPHL MKTTTQNPVQ SSSTAMACEL PIARRASLHR FLAKRKDRVT   240
SKAPYQLNDP AKASSKPQTG DNTTSWLGLA AEM                               273

SEQ ID NO: 59           moltype = AA   length = 252
FEATURE                 Location/Qualifiers
source                  1..252
                        mol_type = protein
                        organism = Brassica oleracea
SEQUENCE: 59
MSSSMECSTT RRSSSGKPSF SLTCSRLSQY LKENGSFGDL SLGMSCKPDT NGMSRKPTTT    60
MSLFPCEASN VGSMAAAQDV KPKNLFPRQP SFSSSSSSIP KEDVPKMTQT TTRSLKPEPQ   120
TAPLTIFYGG QVIVFNDFSA EKAKEVMNLA NKGTANTFTG FTSTLNNNIA PTPNQVPHLM   180
KAATQDPKQT SSAAMACELP IARRASLHRF LAKRKDRVTS KAPYQLNDPA KAYSKPQTGN   240
TTTSWLGLAA DM                                                     252

SEQ ID NO: 60           moltype = AA   length = 233
FEATURE                 Location/Qualifiers
source                  1..233
                        mol_type = protein
                        organism = Zea mays
SEQUENCE: 60
MAASARPGER ATSFAVACSL LSRFVRQNGV AAADLGLRIK GEVEQQRTPA TTNSLPGAEG    60
EEVERRKETM ELFPQSVGFS IKDAAAPREE QGDKEKPKQL TIFYGGKVLV FDDFPADKAK   120
DLMQLASKGS PVVQNVALPQ PSAAAAVTTD KAVLDPVISL AAAKKPARTN ASDMPIMRKA   180
SLHRFLEKRK DRLNAKTPYQ TAPSDAAPVK KEPESQPWLG LGPNAVDSSL NLS         233

SEQ ID NO: 61           moltype = AA   length = 240
FEATURE                 Location/Qualifiers
source                  1..240
                        mol_type = protein
                        organism = Glycine max
SEQUENCE: 61
MSSSSEYLVF SSHHPANSPA EKSTFSQTCS LLSQYIKEKG TFGDLTLGMT CTAETNGSPE    60
TSCHSATTME LFPTIITQRN PTTVDFLSPQ TAYPHHSEVP IMVKSSAFKS MEKEPKAAQL   120
TIFYAGQVVV FDDFPAEKLE EITSLAGKGI SQSQNTSAYA HTHNQQVNHP SFVPNISPQA   180
PSRPLVCDLP IARKASLHRF LSKRKDRIAA KAPYQINNPN SASSKPAESM SWLGLGAQST   240

SEQ ID NO: 62           moltype = AA   length = 244
FEATURE                 Location/Qualifiers
source                  1..244
                        mol_type = protein
                        organism = Oryza sativa
SEQUENCE: 62
MAASARPVGV GGERATSFAM ACSLLSRYVR QNGAAAAELG LGIRGEGEAP RAAPATMSLL    60
PGEAERKKET MELFPQSAGF GQQDAITADS AADAREQEPE KRQLTIFYGG KVLVFNDFPA   120
DKAKGLMQLA SKGSPVAPQN AAAPAPAAVT DNTKAPMAVP APVSSLPTAQ ADAQKPARAN   180
ASDMPIARKA SLHRFLEKRK DRLNAKTPYQ ASPSDATPVK KEPESQPWLG LGPNAVVKPI   240
ERGQ                                                              244

SEQ ID NO: 63           moltype = AA   length = 391
FEATURE                 Location/Qualifiers
source                  1..391
                        mol_type = protein
                        organism = Zea mays
SEQUENCE: 63
MERDFLAAIG KEQQHPRKEK AGGGAEESAY FGAAAVPAMD WSFASKPCAA PALMSFRSAA    60
REEPSFPQFS ALDGTKNTAP RMLTHQRSFG PDSTQYAALH RAQNGARVVP VSSPFSQSNP   120
```

```
MFRVQSSPSL PNSTAFKQPP FAISNAVASS TVGSYGGTRD AVRPRTAQLT IFYAGSVNVF    180
NNVSAEKAQE LMFLASRGSS APVACKPEAP PTLAPAKVTA PEVLLPAKQM LFQKPQHLSP    240
PPSSVPGILQ SAALPRSASS SSNLDSPAPK SSVPLAVPPV SQAPPATLIA TTTAAAIMPR    300
AVPQARKASL ARFLEKRKER VTTAAPYPSA KSPLESSDTF GSGSASANAN DKSSCTDIAL    360
SSNHEESLCL GGQPRSIISF SEESPSTKLQ I                                   391

SEQ ID NO: 64           moltype = AA   length = 386
FEATURE                 Location/Qualifiers
source                  1..386
                        mol_type = protein
                        organism = Glycine max
SEQUENCE: 64
MEREFFGLSS KNGAWTTMKD DAVNKSRDQV RSSGMQWSFP NKVSALPQFL SFKTNQEDKP     60
RKTILEPLAS SGYMAMSTQY AFDSNQKSFL GLTNRNLSIS KHAAGNKQGM TVYPLQCCDA    120
QSEEARIFSV SNQSNQVSPV LQSNLASTGL NMVNSVIKPQ PFGSKSSGTP LSILPSIGSI    180
VGSTDLRNNS KSSTMPTQLT IFYAGSVCVY DDISPEKAKA IMLMAGNGYT PTEKMELPTV    240
KLQPAISIPS KDDGFMISQS YPPSTFPTPL PLTSHVNSQP GGGSSSNKEI SIIRQVGPST    300
APTNHLESPI IGSIGSASKE KAQPVCLPQA RKASLARFLE KRKGRMMRTS PYLYMSKKSP    360
ECSSSGSDSV SFSLNFSGSC SLPATN                                        386

SEQ ID NO: 65           moltype = AA   length = 416
FEATURE                 Location/Qualifiers
source                  1..416
                        mol_type = protein
                        organism = Oryza sativa
SEQUENCE: 65
MERDFLGAIG KDEEQRRHAE ERKESDYFGA GGGAAAAAMD WSFASRAALM SFRSSSSAAA     60
AAAREETREL AFPHFSALDG AKMQQASHVL ARQKSFGAES HGIPQYAAAA AVHGAHRGQP    120
PHVLNGARVI PASSPFNPNN PMFRVQSSPN LPNAVGAGGG AFKQPPFAMG NAVAGSTVGV    180
YGTRDMPKAK AAQLTIFYAG SVNVFNNVSP EKAQELMFLA SRGSLPSAPT TVARMPEAHV    240
FPPPAKVTVPE VSPTKPMMLQ KPQLVSSPVP AISKPISVVS QATSLPRSAS SSNVDSNVTK    300
SSGPLVVPPT SLPPPAQPET LATTTAAAIM PRAVPQARKA SLARFLEKRK ERVTTVAPYP    360
LAKSPLESSD TMGSANDNKS SCTDIALSSN RDESLSGQP RTISFCEESP STKLQI         416

SEQ ID NO: 66           moltype = AA   length = 404
FEATURE                 Location/Qualifiers
source                  1..404
                        mol_type = protein
                        organism = Zea mays
SEQUENCE: 66
MAKSGASFPE SSWMERDFLA AIGKEQQHPH KEEAGAEESA YFGGAGAAAA APAMDWSFAS     60
KPGAAPALMS FRSASFPQFS SFDGAKNPAP RILTHQRSFG PDSTHYAAAH RTQHALNGAR    120
VTPVSSPFNQ NSPMFRVQSS PSLPNGTAFK QPPFAINNNA AASSTVGFYG TRDVVRPKTA    180
QLTIFYAGSV NVFDNVSAEK AQELMLLASR GSLPSSAPVA RKPEAPILAP AKVTAPEVLH    240
ATQMLFQKPQ HVSPPSSAIS KPIPGILQAA SLPRSASSSN LDSPFPKSSV PFPVSPVSQA    300
PRAQPATIAA TTAAAIMPRA VPQARKASLA RFLEKRKERV TTAAPYPSAK SPMESSDTFG    360
SGSSANDKSSC TDIALSSNHE ESLCLGQPRN ISFIQESPST KLQI                    404

SEQ ID NO: 67           moltype = AA   length = 340
FEATURE                 Location/Qualifiers
source                  1..340
                        mol_type = protein
                        organism = Glycine max
SEQUENCE: 67
MERDFMGLNL KEPLAVVKEE MNNDGCKNSG FKKGRIAQWP FSNKVSALPH LMSFKASQDD     60
KTKNTVSDTL SSSGFMSILS QEAFDTSQKR SAGEPQMFSV PNQAISVSLG NPFLKNHFAA    120
AGQKPLLGGI PVTTSHSVLP SAVAVAGMTE SCNSVKPSAQ LTIFYAGTVN IFDDISAEKA    180
QAIMLLAGNS LSAASNMAQP NVQVPISKLG AGAGVPVSQP ANTSPGSGLS SPLSVSSHTG    240
VQSGSGLTST DEFLAAKTTG VPNTPICNVE PPKVVSATTM LTSAVPQARK ASLARFLEKR    300
KERVMSAAPY NLNKKSEECA TAEYAGVNFS ATNTVLAKQG                          340

SEQ ID NO: 68           moltype = AA   length = 427
FEATURE                 Location/Qualifiers
source                  1..427
                        mol_type = protein
                        organism = Oryza sativa
SEQUENCE: 68
MERDFLGAIW RKEEAAGKPE EHSDYRGGGG GASAAMWQQF PATKVGAASS AFMSFRSSAA     60
AAREEDPKEA AVFDRFSLSG FRPPPRPSPG DAFDGAAAMK QRQFGFNGRQ QYAAAAQHGH    120
REQGVDSYGV AAPHHFPSPS PSPRHPVPFG HANPMLRVHS LPNVAGGSPY RNQSFSVGNS    180
VAGSTVGVYG GPRDLQNPKV TQMTIFYDGL NVFDNIPVE KAQELMLLAS RASIPSPPSA    240
ARKSDSPISA AAKLTVPEAL PARQIVVQKP EASVPLVSGV SNPITIVSGV VTLPKSFSSS    300
NDSAGPKSGG LPLAVTPLSQ ASPSQPIPVA TTNASAIMPR AVPQARKASL ARFLEKRKER    360
VSSVAPYPSS KSPLESSDTI GSPSTPSKSS CTDITPSTNN CEDSLCLGQP RNISFSSQEP    420
PSTKLQI                                                              427

SEQ ID NO: 69           moltype = AA   length = 353
FEATURE                 Location/Qualifiers
```

```
source                          1..353
                                mol_type = protein
                                organism = Zea mays
SEQUENCE: 69
MDWSFASKPC AAPALMSFRS AAREEPSFPQ FSALDGTKNT APRMLTHQRS FGPDSTQYAA    60
LHRAQNGARV VPVSSPFSQS NPMFRVQSSP SLPNSTAFKQ PPFAISNAVA SSTVGSYGGT   120
RDAVRPRTAQ LTIFYAGSVN VFNNVSAEKA QELMFLASRG SSAPVACKPE APPTLAPAKV   180
TAPEVLLPAK QMLFQKPQHL SPPPSSVPGI LQSAALPRSA SSSSNLDSPA PKSSVPLAVP   240
PVSQAPPATL IATTTAAAIM PRAVPQARKA SLARFLEKRK ERVTTAAPYP SAKSPLESSD   300
TFGSGSASAN ANDKSSCTDI ALSSNHEESL CLGGQPRSII SFSEESPSTK LQI          353

SEQ ID NO: 70                   moltype = AA  length = 338
FEATURE                         Location/Qualifiers
source                          1..338
                                mol_type = protein
                                organism = Glycine max
SEQUENCE: 70
MERDFMGLNL KEPLAVVKEE MNNDGCKNSG FKKGRIAQWP FSNKVSALPH LMSFKASQDD    60
KTKNTVSDTL SSSGFMSILS QEAFDTSQKR SAGEPQMFSV PNQAISVSLG NPFLKNHFAA   120
AGQKPLLGGI PVTTSHSVLP SAVAVAGMTE SCVKPSAQLT IFYAGTVNIF DDISAEKAQA   180
IMLLAGNSLS AASNMAQPNV QVPISKLGAG AGVPVSQPAN TSPGSGLSSP LSVSSHTGVQ   240
SGSGLTSTDE FLAAKTTGVP NTPICNVEPP KVVSATTMLT SAVPQARKAS LARFLEKRKE   300
RVMSAAPYNL NKKSEECATA EYAGVNFSAT NTVLAKQG                           338

SEQ ID NO: 71                   moltype = AA  length = 308
FEATURE                         Location/Qualifiers
source                          1..308
                                mol_type = protein
                                organism = Oryza sativa
SEQUENCE: 71
MQQASHVLAR QPPHVLNGAR VIPASSPFNP NNPMFRVQSS PNLPNAVGAG GGAFKQPPFA    60
MGNAVAGSTV GVYGTRDMPK AKAAQLTIFY AGSVNVFNNV SPEKAQELMF LASRGSLPSA   120
PTTVARMPEA HVFPPAKVTV PEVSPTKPMM LQKPQLVSSP VPAISKPISV VSQATSLPRS   180
ASSSNVDSNV TKSSGPLVVP PTSLPPPAQP ETLATTTAAA IMPRAVPQAR KASLARFLEK   240
RKERVTTVAP YPLAKSPLES SDTMGSANDN KSSCTDIALS SNRDESLSLG QPRTISFCEE   300
SPSTKLQI                                                            308

SEQ ID NO: 72                   moltype = AA  length = 218
FEATURE                         Location/Qualifiers
source                          1..218
                                mol_type = protein
                                organism = Zea mays
SEQUENCE: 72
MAGHAPARDK TTTGFAATCS LLSQFLKEKK GGLQGLGGLA MAPAPAAGAG AFRPPTTMNL    60
LSALDAAKAT VGEPEGHGQR TGGNPREAAG EEAQQLTIFY GGKVVVFDRF PSAKVKDLLQ   120
IVSPPGADAV VDGAGAGAAV PTQNLPRPSH DSLSADLPIA RRNSLHRFLE KRKDRITAKA   180
PYQVNSSVGA EASKAEKPWL GLGQEQEGSD GRQAGEEM                           218

SEQ ID NO: 73                   moltype = AA  length = 201
FEATURE                         Location/Qualifiers
source                          1..201
                                mol_type = protein
                                organism = Glycine max
SEQUENCE: 73
MAAGVTVKSE VLESSPPEGV CSNTVENHLV QTNLSDGSPN KSVPASGLDA VIPSANQLTI    60
FYNGSVCVYD GIPAEKVHEI MLIAAAAAKS TEMKKIGTQT TLISPAPSRP SSPHGITNNI   120
GSSQKSSICR LQAEFPIARR HSLQRFLEKR RDRLGSKTPY PSSPTTKVAD NIENNFCADN   180
APELISLNRS EEEFQPTVSA S                                             201

SEQ ID NO: 74                   moltype = AA  length = 188
FEATURE                         Location/Qualifiers
source                          1..188
                                mol_type = protein
                                organism = Oryza sativa
SEQUENCE: 74
MSTRAPVELD FLGLRAAAAD ADDRHAKSGG SSASSSSSIR GMETSAIARI GPHLLRRVIA    60
AAGPPPPPST APVPEEMPGA AAAAPMTLF YNGSVAVFDV SHDKAEAIMR MATEATKAKG    120
LARGNAIVGN FAKEPLTRTK SLQRFLSKRK ERLTSLGPYQ VGGPAAVGAT TSTTTKSFLA   180
KEEEHTAS                                                            188

SEQ ID NO: 75                   moltype = DNA  length = 20
FEATURE                         Location/Qualifiers
misc_feature                    1..20
                                note = A synthetic primer
source                          1..20
                                mol_type = other DNA
                                organism = synthetic construct
SEQUENCE: 75
accgagacac attcccgatt                                                20
```

```
SEQ ID NO: 76          moltype = DNA   length = 20
FEATURE                Location/Qualifiers
misc_feature           1..20
                       note = A synthetic primer
source                 1..20
                       mol_type = other DNA
                       organism = synthetic construct
SEQUENCE: 76
catcaggctt gcatgccatt                                                    20

SEQ ID NO: 77          moltype = DNA   length = 25
FEATURE                Location/Qualifiers
misc_feature           1..25
                       note = A synthetic primer
source                 1..25
                       mol_type = other DNA
                       organism = synthetic construct
SEQUENCE: 77
acgaataaga gcgtccattt tagag                                              25

SEQ ID NO: 78          moltype = DNA   length = 24
FEATURE                Location/Qualifiers
misc_feature           1..24
                       note = A synthetic primer
source                 1..24
                       mol_type = other DNA
                       organism = synthetic construct
SEQUENCE: 78
gtggagtggt ctaaagcaac cttc                                               24

SEQ ID NO: 79          moltype = DNA   length = 23
FEATURE                Location/Qualifiers
misc_feature           1..23
                       note = A synthetic primer
source                 1..23
                       mol_type = other DNA
                       organism = synthetic construct
SEQUENCE: 79
ataacgctgc ggacatctac att                                                23

SEQ ID NO: 80          moltype = DNA   length = 21
FEATURE                Location/Qualifiers
misc_feature           1..21
                       note = A synthetic primer
source                 1..21
                       mol_type = other DNA
                       organism = synthetic construct
SEQUENCE: 80
tcaggaagac agagtgttcc c                                                  21

SEQ ID NO: 81          moltype = DNA   length = 21
FEATURE                Location/Qualifiers
misc_feature           1..21
                       note = A synthetic primer
source                 1..21
                       mol_type = other DNA
                       organism = synthetic construct
SEQUENCE: 81
tgcgtttctc taagaaccga g                                                  21

SEQ ID NO: 82          moltype =    length =
SEQUENCE: 82
000

SEQ ID NO: 83          moltype = DNA   length = 20
FEATURE                Location/Qualifiers
misc_feature           1..20
                       note = A synthetic primer
source                 1..20
                       mol_type = other DNA
                       organism = synthetic construct
SEQUENCE: 83
ttgggtgatg gttcacgtag                                                    20

SEQ ID NO: 84          moltype = DNA   length = 21
FEATURE                Location/Qualifiers
misc_feature           1..21
                       note = A synthetic primer
```

```
                          source            1..21
                                            mol_type = other DNA
                                            organism = synthetic construct
SEQUENCE: 84
taccgcataa tcatggtcgt c                                                    21

SEQ ID NO: 85             moltype = DNA   length = 21
FEATURE                   Location/Qualifiers
misc_feature              1..21
                          note = A synthetic primer
source                    1..21
                          mol_type = other DNA
                          organism = synthetic construct
SEQUENCE: 85
tcatgctcat tgcattagtc g                                                    21

SEQ ID NO: 86             moltype = DNA   length = 22
FEATURE                   Location/Qualifiers
misc_feature              1..22
                          note = A synthetic primer
source                    1..22
                          mol_type = other DNA
                          organism = synthetic construct
SEQUENCE: 86
ctttgaagac gtggttggaa cg                                                   22

SEQ ID NO: 87             moltype = DNA   length = 22
FEATURE                   Location/Qualifiers
misc_feature              1..22
                          note = A synthetic primer
source                    1..22
                          mol_type = other DNA
                          organism = synthetic construct
SEQUENCE: 87
atttctcgat cgccgtcgta gt                                                   22

SEQ ID NO: 88             moltype = DNA   length = 25
FEATURE                   Location/Qualifiers
misc_feature              1..25
                          note = A synthetic primer
source                    1..25
                          mol_type = other DNA
                          organism = synthetic construct
SEQUENCE: 88
gccaaagagc tttggtctta gagtg                                                25

SEQ ID NO: 89             moltype = DNA   length = 25
FEATURE                   Location/Qualifiers
misc_feature              1..25
                          note = A synthetic primer
source                    1..25
                          mol_type = other DNA
                          organism = synthetic construct
SEQUENCE: 89
gtctaagcgt caatttgttt acacc                                                25

SEQ ID NO: 90             moltype = DNA   length = 25
FEATURE                   Location/Qualifiers
misc_feature              1..25
                          note = A synthetic primer
source                    1..25
                          mol_type = other DNA
                          organism = synthetic construct
SEQUENCE: 90
atgtcgagtt ctatggaatg ttctg                                                25

SEQ ID NO: 91             moltype = DNA   length = 26
FEATURE                   Location/Qualifiers
misc_feature              1..26
                          note = A synthetic primer
source                    1..26
                          mol_type = other DNA
                          organism = synthetic construct
SEQUENCE: 91
tcatatttca gctgctaaac cgagcc                                               26

SEQ ID NO: 92             moltype = DNA   length = 21
FEATURE                   Location/Qualifiers
```

```
misc_feature              1..21
                          note = A synthetic primer
source                    1..21
                          mol_type = other DNA
                          organism = synthetic construct
SEQUENCE: 92
atggagagag attttctcgg g                                             21

SEQ ID NO: 93             moltype = DNA  length = 23
FEATURE                   Location/Qualifiers
misc_feature              1..23
                          note = A synthetic primer
source                    1..23
                          mol_type = other DNA
                          organism = synthetic construct
SEQUENCE: 93
ttaggttgca gagctgagag aag                                           23

SEQ ID NO: 94             moltype = DNA  length = 20
FEATURE                   Location/Qualifiers
misc_feature              1..20
                          note = A synthetic primer
source                    1..20
                          mol_type = other DNA
                          organism = synthetic construct
SEQUENCE: 94
atggagagag attttctcgg                                               20

SEQ ID NO: 95             moltype = DNA  length = 20
FEATURE                   Location/Qualifiers
misc_feature              1..20
                          note = A synthetic primer
source                    1..20
                          mol_type = other DNA
                          organism = synthetic construct
SEQUENCE: 95
cagatgatga gctggaggac                                               20

SEQ ID NO: 96             moltype = DNA  length = 24
FEATURE                   Location/Qualifiers
misc_feature              1..24
                          note = A synthetic primer
source                    1..24
                          mol_type = other DNA
                          organism = synthetic construct
SEQUENCE: 96
atggaaagag attttctggg tttg                                          24

SEQ ID NO: 97             moltype = DNA  length = 29
FEATURE                   Location/Qualifiers
misc_feature              1..29
                          note = A synthetic primer
source                    1..29
                          mol_type = other DNA
                          organism = synthetic construct
SEQUENCE: 97
ttatgtagga gaagtagaag agtaattca                                     29

SEQ ID NO: 98             moltype = DNA  length = 22
FEATURE                   Location/Qualifiers
misc_feature              1..22
                          note = A synthetic primer
source                    1..22
                          mol_type = other DNA
                          organism = synthetic construct
SEQUENCE: 98
atgtcgaaag ctaccataga ac                                            22

SEQ ID NO: 99             moltype = DNA  length = 30
FEATURE                   Location/Qualifiers
misc_feature              1..30
                          note = A synthetic primer
source                    1..30
                          mol_type = other DNA
                          organism = synthetic construct
SEQUENCE: 99
gatagtaagg agatgttgat actaatctct                                    30

SEQ ID NO: 100            moltype = DNA  length = 24
```

```
FEATURE                 Location/Qualifiers
misc_feature            1..24
                        note = A synthetic primer
source                  1..24
                        mol_type = other DNA
                        organism = synthetic construct
SEQUENCE: 100
atggctgatg gtgaagacat tcaa                                              24

SEQ ID NO: 101          moltype = DNA  length = 24
FEATURE                 Location/Qualifiers
misc_feature            1..24
                        note = A synthetic primer
source                  1..24
                        mol_type = other DNA
                        organism = synthetic construct
SEQUENCE: 101
tcagaagcac ttcctgtgaa caat                                              24

SEQ ID NO: 102          moltype = DNA  length = 19
FEATURE                 Location/Qualifiers
misc_feature            1..19
                        note = A synthetic primer
source                  1..19
                        mol_type = other DNA
                        organism = synthetic construct
SEQUENCE: 102
aagcagcgta atcggtagg                                                    19

SEQ ID NO: 103          moltype = DNA  length = 21
FEATURE                 Location/Qualifiers
misc_feature            1..21
                        note = A synthetic primer
source                  1..21
                        mol_type = other DNA
                        organism = synthetic construct
SEQUENCE: 103
gcacagcaat cgggtataaa g                                                 21

SEQ ID NO: 104          moltype = DNA  length = 24
FEATURE                 Location/Qualifiers
misc_feature            1..24
                        note = A synthetic primer
source                  1..24
                        mol_type = other DNA
                        organism = synthetic construct
SEQUENCE: 104
ggagaactca cgatgggagc gatt                                              24

SEQ ID NO: 105          moltype = DNA  length = 24
FEATURE                 Location/Qualifiers
misc_feature            1..24
                        note = A synthetic primer
source                  1..24
                        mol_type = other DNA
                        organism = synthetic construct
SEQUENCE: 105
gcgtcgtggc tttcgataac caga                                              24

SEQ ID NO: 106          moltype = DNA  length = 17
FEATURE                 Location/Qualifiers
misc_feature            1..17
                        note = A synthetic primer
source                  1..17
                        mol_type = other DNA
                        organism = synthetic construct
SEQUENCE: 106
gctggcggtt cgacatg                                                      17

SEQ ID NO: 107          moltype = DNA  length = 21
FEATURE                 Location/Qualifiers
misc_feature            1..21
                        note = A synthetic primer
source                  1..21
                        mol_type = other DNA
                        organism = synthetic construct
SEQUENCE: 107
gccattcctc tgcgaattag a                                                 21
```

```
SEQ ID NO: 108              moltype = DNA   length = 26
FEATURE                     Location/Qualifiers
misc_feature                1..26
                            note = A synthetic primer
source                      1..26
                            mol_type = other DNA
                            organism = synthetic construct
SEQUENCE: 108
agaaactcca aatcaagaac cagctc                                       26

SEQ ID NO: 109              moltype = DNA   length = 26
FEATURE                     Location/Qualifiers
misc_feature                1..26
                            note = A synthetic primer
source                      1..26
                            mol_type = other DNA
                            organism = synthetic construct
SEQUENCE: 109
ccggttttaat cgaagaacac gaagac                                      26

SEQ ID NO: 110              moltype = AA   length = 4
FEATURE                     Location/Qualifiers
REGION                      1..4
                            note = A synthetic protein
source                      1..4
                            mol_type = protein
                            organism = synthetic construct
SEQUENCE: 110
GWGD                                                               4

SEQ ID NO: 111              moltype = AA   length = 4
FEATURE                     Location/Qualifiers
REGION                      1..4
                            note = A synthetic protein
source                      1..4
                            mol_type = protein
                            organism = synthetic construct
SEQUENCE: 111
DFSG                                                               4

SEQ ID NO: 112              moltype = AA   length = 11
FEATURE                     Location/Qualifiers
REGION                      1..11
                            note = A synthetic protein
source                      1..11
                            mol_type = protein
                            organism = synthetic construct
SEQUENCE: 112
RELNSLISGG V                                                       11

SEQ ID NO: 113              moltype = AA   length = 10
FEATURE                     Location/Qualifiers
REGION                      1..10
                            note = A synthetic protein
source                      1..10
                            mol_type = protein
                            organism = synthetic construct
SEQUENCE: 113
DTEWFFLVSM                                                         10

SEQ ID NO: 114              moltype = AA   length = 15
FEATURE                     Location/Qualifiers
REGION                      1..15
                            note = A synthetic protein
source                      1..15
                            mol_type = protein
                            organism = synthetic construct
SEQUENCE: 114
VVNDLMIQQA TVKMG                                                   15

SEQ ID NO: 115              moltype = AA   length = 32
FEATURE                     Location/Qualifiers
REGION                      1..32
                            note = A synthetic protein
source                      1..32
                            mol_type = protein
                            organism = synthetic construct
SEQUENCE: 115
KRGRKPANGR EEPLNHVEAE RQRREKLNQR FY                                32
```

```
SEQ ID NO: 116          moltype = AA  length = 49
FEATURE                 Location/Qualifiers
REGION                  1..49
                        note = A synthetic protein
source                  1..49
                        mol_type = protein
                        organism = synthetic construct
SEQUENCE: 116
GDNTVILGWG DGYYKGEEDK EKKKNNTNTA EQEHRKRVIR ELNSLISGG                   49

SEQ ID NO: 117          moltype = AA  length = 51
FEATURE                 Location/Qualifiers
REGION                  1..51
                        note = A synthetic protein
source                  1..51
                        mol_type = protein
                        organism = synthetic construct
SEQUENCE: 117
NNNTVLLGWG DGYYKGEEEK SRKKKSNPAS AAEQEHRKRV IRELNSLISG G                51

SEQ ID NO: 118          moltype = AA  length = 52
FEATURE                 Location/Qualifiers
REGION                  1..52
                        note = A synthetic protein
source                  1..52
                        mol_type = protein
                        organism = synthetic construct
SEQUENCE: 118
GAGASLLGWG DGYYKGCDDA DKRARQQPTP ASAAEQHRKR VLRELNSLIA GG               52

SEQ ID NO: 119          moltype = AA  length = 53
FEATURE                 Location/Qualifiers
REGION                  1..53
                        note = A synthetic protein
source                  1..53
                        mol_type = protein
                        organism = synthetic construct
SEQUENCE: 119
ATGASLLGWG DGYYKGCDDD KRRHRPPLTP AAQAEQEHRK RVLRELNSLI SGG              53

SEQ ID NO: 120          moltype = AA  length = 53
FEATURE                 Location/Qualifiers
REGION                  1..53
                        note = A synthetic protein
source                  1..53
                        mol_type = protein
                        organism = synthetic construct
SEQUENCE: 120
STGASLLGWG DGYYKGCDDD KRKQRSSTPA AAAEQEHRKR VLRRELNSLI AGA              53

SEQ ID NO: 121          moltype = AA  length = 52
FEATURE                 Location/Qualifiers
REGION                  1..52
                        note = A synthetic protein
source                  1..52
                        mol_type = protein
                        organism = synthetic construct
SEQUENCE: 121
ATGASLLGWG DGYYKGCDED KRKQKPLTPS AQAEQEHRKR VLRELNSLIS GA               52

SEQ ID NO: 122          moltype = AA  length = 52
FEATURE                 Location/Qualifiers
REGION                  1..52
                        note = A synthetic protein
source                  1..52
                        mol_type = protein
                        organism = synthetic construct
SEQUENCE: 122
ATGASLLGWG DGYYKGCDDD KRKQRPLTPA AQAEQEHRKR VLRELNSLIS GA               52

SEQ ID NO: 123          moltype = AA  length = 55
FEATURE                 Location/Qualifiers
REGION                  1..55
                        note = A synthetic protein
source                  1..55
                        mol_type = protein
                        organism = synthetic construct
```

```
SEQUENCE: 123
FSGASVLGWG DHYYKGEEDK AKPRQRSSSP PFSTPADQEY RKKVLRELNS LISGG         55

SEQ ID NO: 124          moltype = AA  length = 55
FEATURE                 Location/Qualifiers
REGION                  1..55
                        note = A synthetic protein
source                  1..55
                        mol_type = protein
                        organism = synthetic construct
SEQUENCE: 124
FSGASVLGWG DGYYKGEEDK ANPRRRSSSP PFSTPADQEY RKKVLRELNS LISGG         55

SEQ ID NO: 125          moltype = AA  length = 53
FEATURE                 Location/Qualifiers
REGION                  1..53
                        note = A synthetic protein
source                  1..53
                        mol_type = protein
                        organism = synthetic construct
SEQUENCE: 125
FSSPSVLGWG DGYYKGEEDK AKRKLSVSSP AYIAEQEHRK KVLRELNSLI SGA           53

SEQ ID NO: 126          moltype = AA  length = 54
FEATURE                 Location/Qualifiers
REGION                  1..54
                        note = A synthetic protein
source                  1..54
                        mol_type = protein
                        organism = synthetic construct
SEQUENCE: 126
FASQTVLGWG DGYYKGEEDK NKRRGSSSSA ANFCAEQEHR KKVLRELNSL ISGV          54

SEQ ID NO: 127          moltype = AA  length = 55
FEATURE                 Location/Qualifiers
REGION                  1..55
                        note = A synthetic protein
source                  1..55
                        mol_type = protein
                        organism = synthetic construct
SEQUENCE: 127
RSGQQVLGWG DGCCREPNEE EESKVVRSYN FNNMGAEEET WQDMRKRVLQ KLHRL         55

SEQ ID NO: 128          moltype = AA  length = 55
FEATURE                 Location/Qualifiers
REGION                  1..55
                        note = A synthetic protein
source                  1..55
                        mol_type = protein
                        organism = synthetic construct
SEQUENCE: 128
KAGDLVLCWG DGYCREPKEG EKSEIVRILS MGREEETHQT MRKRVLQKLH DLFGG         55

SEQ ID NO: 129          moltype = DNA  length = 23
FEATURE                 Location/Qualifiers
misc_feature            1..23
                        note = A synthetic primer
source                  1..23
                        mol_type = other DNA
                        organism = synthetic construct
SEQUENCE: 129
acggttcctc tatgcctcaa gtc                                            23
```

TRANSCRIPTION FACTORS TO IMPROVE RESISTANCE TO ENVIRONMENTAL STRESS IN PLANTS

CROSS REFERENCE TO RELATED APPLICATIONS

This application is a divisional of U.S. patent application Ser. No. 16/323,737, filed Feb. 6, 2019, which is a national stage application filed under 35 U.S.C. § 371 from International Application Serial No. PCT/US2017/048660, filed 25 Aug. 2017 and published as WO 2018/039590 on 1 Mar. 2018, which claims benefit of priority to the filing date of U.S. Provisional Application Ser. No. 62/379,773, filed Aug. 26, 2016, and the contents of each application are specifically incorporated herein by reference in their entirety.

FEDERAL FUNDING

This invention was made with government support under DE-FG02-91ER20021 awarded by the U.S. Department of Energy, and under GM057795 awarded by the National Institutes of Health, and under IOS1139329 awarded by the National Science Foundation. The government has certain rights in the invention.

INCORPORATION BY REFERENCE OF SEQUENCE LISTING

A Sequence Listing is provided herewith as an xml file, "2329982.xml" created on Apr. 28, 2023 and having a size of 181,631 bytes. The content of the xml file is incorporated by reference herein in its entirety.

BACKGROUND OF THE INVENTION

Plants integrate developmental and environmental cues to prioritize the allocation of photosynthetic products to growth, defense and other physiological processes. Investments in defense often suppress growth, whereas rapid growth, such as that triggered by competition for light, attenuates defense.

SUMMARY

In plants, investments in defense often suppress growth, reducing overall biomass yields. For example, dense planting of crops such as corn suppresses the plant immune system through active repression of the jasmonate signaling pathway. As described herein, selected jasmonate and phytochrome gene deletions can unlink growth and defense tradeoffs in plants. As also described herein, selected mutations in transcription factors can obviate jasmonate inhibition and improve plant resistance to environmental stresses, but plants with such transcription factor mutations may not grow optimally. By combining the transcription factor mutations with loss-of-function phytochrome gene mutations can improve plant growth while retaining environmental stress resistance. The resulting phenotype observed in plants includes robust growth and less insect infestation. Such modifications enhance biomass output, and allows crops to be densely planted. Such modified plants can have significant utility in agriculture.

Described herein are plants, plant cells, and plant seeds that can have a PhyB loss-of-function mutation, and (a) a modified MYC nucleic acid encoding a mutant MYC protein comprising at least one mutation within or outside of a JAZ-interacting domain (JID) polypeptide region, (b) a loss-of-function mutation in at least one gene encoding a transcriptional repressor of jasmonic acid response (JAZ) protein; or (c) a combination of (a) and (b).

Also described here are methods of making such plants, plant cells, and seeds. For example, one method can include (a) providing one or more plant cell that has a PhyB loss-of-function mutation; (b) introducing into at least one of the one or more plant cells at least one transgene or expression cassette encoding a mutant MYC nucleic acid segment that encodes a mutant MYC protein to generate one or more transformed plant cells; and (c) generating a plant from the one or more transformed plant cell(s). The mutant MYC nucleic acid can, for example, have a dominant MYC mutation. Such a mutant MYC protein can have reduced binding to a JAZ protein selected from a JAZ1 protein, JAZ2 protein, JAZ3 protein, JAZ4 protein, JAZ5 protein, JAZ6 protein, JAZ7 protein, JAZ8 protein, JAZ9 protein, JAZ10 protein, JAZ11 protein, JAZ12 protein, JAZ13 protein, or a combination thereof, where for example the binding is reduced by at least 20% compared to a corresponding wild type MYC protein that does not have the MYC mutation(s).

Another exemplary method can include (a) providing one or more plant cells with a loss-of-function mutation in at least one gene encoding a transcriptional repressor of jasmonic acid response (JAZ) protein; (b) introducing into the one or more plant cells a PhyB loss-of-function mutation to generate one or more modified plant cells; and (c) generating a plant from the one or more modified plant cell(s). For example, the method can involve providing one or more plant cells with a loss-of-function mutation in jaz1, jaz3, jaz4-1, jaz9, and jaz10 genes.

Such methods can provide plants that exhibit resistance to environmental stress compared to a wild type plant of the same species under the same environmental conditions.

For example, the modified plants and plants grown from the modified seeds described herein can have 5% less, or 10% less, or 20% less, or 30% less, or 40% less, or 50% less, or 60% less, or 70% less, or 80% less, or 90% less, or 100% less leaf damage from insect feeding than a wild type plant (without the mutations described herein) of the same species grown under the same conditions. In some cases, the modified plants and plants grown from the modified seeds described herein can have at least about 10%, or at least about 20%, or at least about 30%, or at least about 40%, or at least about 50%, or at least about 60%, or at least about 70%, or at least about 80%, or at least about 90% fewer insects or insect larvae than a wild type plant of the same species grown under the same conditions.

The modified plants and plants grown from the modified seeds described herein grow as well as or better than wild type plants. For example, the rosette dry weight of the modified plants and plants grown from the modified seeds described herein is about the same as the rosette dry weight of wild type plants (without the genetic modifications described herein) grown for the same time and under the same conditions. For example, the rosette dry weight of the modified plants, and plants grown from the modified seeds, described herein is about 80% to about 120%, or about 90% to about 110% of the rosette dry weight of wild type plants grown for the same time and under the same conditions.

In some cases, the average primary root length of the modified plants and plants grown from the modified seeds described herein can be 1.5-fold longer, of 2-fold longer, or 2.3-fold longer, or 2.5-fold longer, or 2.7-fold longer, or

DESCRIPTION OF FIGURES

FIG. 1A shows a simple model of the jasmonate (JA)-gibberellic acid (GA) signaling network that governs growth and defense against environmental stress. FIG. 1B shows an image of wild-type (WT) and jazQ (jQ) seedlings grown in the absence or presence of 25 µM methyl-jasmonic acid (MJ or MeJA). FIG. 1C graphically illustrates accumulation of glucosinolates in WT (open bar) and jazQ mutant (shaded bar) seedlings. Compound abbreviations: 3MSP=3-methylsulfinylpropylglucosinolate; 4MSB=4-methylsulfinylbutylglucosinolate; 5MSP=5-methylsulfinylpentylglucosinolate; 4OHI3M=4-hydroxyindol-3-ylmethylglucosinolate; 7MSH=7-methylsulfinylheptylglucosinolate; 4MTB=4-methylthiobutylglucosinolate; 8MSO=8-methylsulfinyloctylglucosinolate; I3M=indol-3-ylmethylglucosinolate; 4MI3M=4-methoxyindol-3-ylmethylglucosinolate; 1MI3M=1-methoxyindol-3-ylmethylglucosinolate; 7MTH=7-methylthioheptylglucosinolate; 8MTO, 8-methylthiooctylglucosinolate. FIG. 1D graphically illustrates anthocyanin accumulation in petioles of 4-week-old plants. FIG. 1E graphically illustrates *Trichoplusia ni* weight after feeding on WT (33 larvae) and mutant jazQ (38 larvae) plants for 10 days. FIG. 1F shows an image of 4-week old soil-grown WT and jazQ plants. Data in all graphs represent the mean±standard error (s.e.) of at least 10 biological replicates. Asterisks in FIGS. 1C, 1D, and 1E denote significant differences between WT and jazQ mutants at P<0.05 (Student's t-test). FIG. 1G is a schematic diagram showing T-DNA insertion lines used for construction of jazQ mutations. The organization of each JAZ gene is depicted by white and grey boxes representing untranslated regions (UTRs) and exons, respectively. The identity and position of the T-DNA insertion is shown. Arrows show the position of primers used to test expression by RT-PCR. FIG. 1H shows a gel illustrating RT-PCR analysis of JAZ gene expression in WT and mutant jazQ seedlings. RNA was obtained from seedlings grown for eight days on plates containing 25 µM MeJA. The ACTIN1 gene (ACT1, At2g37620) was used as a positive control. FIG. 1I graphically illustrates root length of WT, jaz10-1 mutant, and jazQ mutant seedlings grown for eight days on MS medium supplemented with 5, 10 or 25 µM MeJA. Control seedlings were grown in the absence of MeJA (0 µM). Data shown are the mean±s.e. of measurements on at least 12 seedlings per genotype. P-values are shown for two-way ANOVA comparisons (inset). Asterisks represent statistical difference between mutant and WT according to Tukey HSD test (P<0.05). Single asterisks denote a significant difference between mutant and WT, whereas double asterisks denote a significant difference between jaz10-1 and jazQ mutants at a given concentration of MeJA.

FIG. 2A shows images of five week-old WT, jazQ mutant, and sjg11 mutant plants. The sjg11 plants have a mutation in the PHYB gene that suppresses the growth phenotype of jazQ. Hence, jazQ sjg11 mutant plants are about the same size as wild type plants. FIG. 2B illustrates Trichoplusia ni weight after feeding for 10 days on WT (31 larvae), mutant jazQ (31 larvae), and mutant sjg11 (37 larvae) plants. Data shown are the mean±standard error (s.e.) of at least 12 independent replicates. FIG. 2C shows images of four week-old plants grown in soil. FIG. 2D graphically illustrates rosette dry weight of WT, mutant jazQ, mutant phyB and mutant jazQ/phyB plants. FIG. 2E graphically illustrates anthocyanin accumulation in petioles of WT, mutant jazQ, mutant phyB and mutant jazQ/phyB plants. Data shown in FIG. 2D-2E are the mean±standard error (s.e.) of ten plants per genotype. FIG. 2F graphically illustrates T ni larval weight after feeding for 10 days on WT (23 larvae), mutant jazQ (29 larvae), and mutant jazQ phyB (27 larvae) plants. Data show the mean larval weight±s.e. of insects reared on 12 plants per host genotype. Capital letters denote statistical differences according to Tukey HSD-test (P<0.05). Scale bars=1 cm. FIG. 2G shows a schematic diagram of the PHYB gene in sjg11. Sequence analysis identified a cytosine (C) to thymine (T) transition that creates a TGA nonsense mutation at the CGA codon for R322. This mutation truncates the PHYB apoprotein in the chromophore-binding GAF domain and is a null mutation. FIG. 2H graphically illustrates the number of days to bolting of wild type, jazQ, and jazQ sjg11 plants. Data show the mean±standard error (s.e.) of at least 12 independent replicates. Letters indicate statistical differences between genotypes (Tukey HSD-test, P<0.05).

FIG. 4A shows a heat map of photosystem II quantum efficiency ($\Phi_{II}$) in response to varying light regimes. Chlorophyll fluorescence values for the indicated mutants were normalized to Col-0. Plants were exposed to three consecutive 16 hr/day light regimes: constant light (day 1, left panel); sinusoidal increase and decrease in light intensity (day 2, middle panel); and sinusoidal light with higher intensity pulses (day 3, right panel). FIG. 4B graphically illustrates the photosynthetic rate in response to increasing light as measured by gas exchange in 6-9 plants per genotype. The inset shows non-linear curve-fitting to model the maximum velocity of Rubisco determined from foliage photosynthetic rates in response to increasing $CO_2$. FIG. 4C graphically illustrates Rubisco concentration in leaves from 54-day-old plants (n=4). FIG. 4D graphically illustrates total chlorophyll concentration in leaves from 54-day-old plants (n=4). FIG. 4E graphically illustrates the thickness of 22-day-old rosette leaves (n=4). Data shown in FIGS. 4B-4E are the mean±s.e., and capital letters indicate statistical difference at P<0.05 (Tukey HSD-test). In d, WT and mutant jazQ phyB means are different at P<0.1.

FIGS. 5A-5E illustrate that overexpression of PIF4 in the mutant jazQ background leads to partial rescue of growth without compromising defense. FIG. 5A shows images of representative 21-d-old plants of the indicated genotype. Two independent T3 lines (#1-2 and #3-1) of jazQ 35S:PIF4 were characterized but only the latter is shown. Scale bars=1 cm. FIG. 5B graphically illustrates petiole length of the third true leaf of independent jazQ 35S:PIF4 T2 lines (n=6 plants per line). T2 lines #1 and #3 are parents of T3 lines #1-2 and #3-1 described in panels c-e below. As a control to demonstrate the expected effects of PIF4 overexpression on petiole length, WT Col-0 plants were also transformed with the 35S:PIF4 transgene. Data for four independent T2 lines is shown. FIG. 5C graphically illustrates petiole length of the third true leaf of 21-d-old jazQ 35S:PIF4 plants compared to WT and mutant jazQ (n=10). FIG. 5D graphically illustrates anthocyanin content in petioles of 21-d-old plants of the indicated genotype (n>10 plants). FIG. 5E graphically illustrates the weight of $T.$ $ni$ larvae recovered after 10 d feeding on 12 plants per genotype: WT plants (37 larvae), jazQ mutant plants (31 larvae), jazQ 35S:PIF4 #1-2 mutant plants (27 larvae), and jazQ 35S:PIF4 #3-1 mutant plants (25 larvae). Data show the mean±s.e. Capitalized letters indicate statistical differences (Tukey HSD-test, P<0.05).

Figure 6:
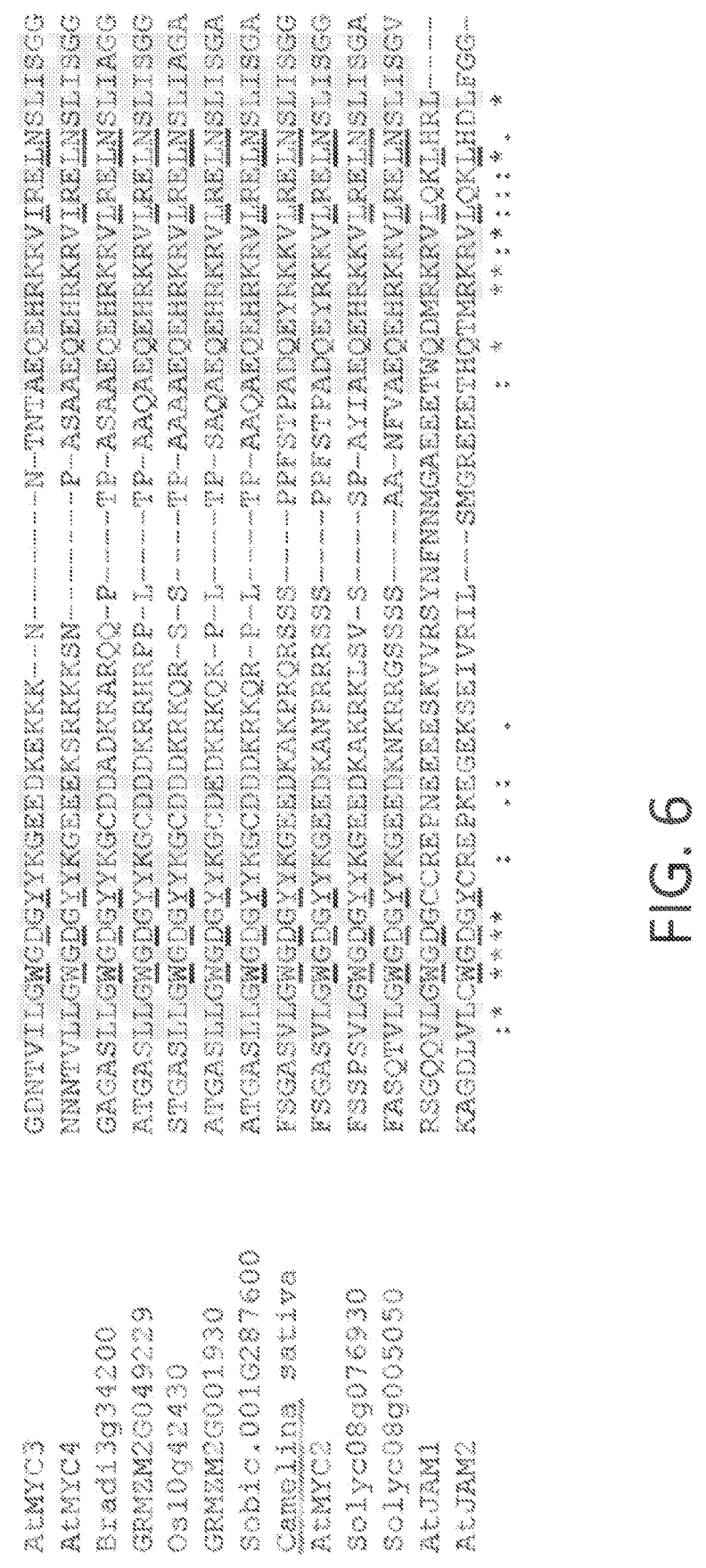

FIG. 6 shows a sequence alignment of the JAZ-interacting domain (JID) from various MYC transcription factors (SEQ ID NOs: 116 (AtMYC3), 117 (AtMYC4), 118 (Bradi3g34200), 119 (GRMZM2G049229), 120 (Os10g42430), 121 (GRMZM2G001930), 122 (Sobic.001G287600), 123 (*Camelina sativa*), 124 (AtMYC2), 125 (Solyc08g076930), 126 (Solyc08g005050), 127 (AtJAM1), 128 (AtJAM2)). Underlining identifies those conserved amino acids that interact directly with JAZ9. These amino acid residues are targets for site directed mutagenesis, to generate modified MYC transcription factors that are insensitive to inhibition by JAZ repressors.

FIG. 7A schematically illustrates the domain architecture of *Arabidopsis thaliana* MYC3 (AtMYC3) and two alternative splice forms of *Arabidopsis thaliana* JAZ10 (AtJAZ10). FIG. 7B shows schematic diagrams of X-ray crystal structures of MYC3 in complex with JAZ10's CMID (left) or Jas domain (center), and an overlay of the two structures (see, e.g., Zhang et al., 2017). FIG. 7C shows results of yeast two-hybrid analyses of MED25 and JAZ10.4 (bait) interactions with wild-type MYC3 and MYC3 point mutants (prey, identified at the top). Darker color (blue in the original) denotes protein-protein interaction. Asterisks (*) denote two novel MYC3 mutants that fail to interact with the CMID of JAZ10.4 but retain interaction with the MED25 co-activator. FIG. 7D shows that overexpression of the MYC3$^{D94N}$ dominant transcription factor (but not wild-type MYC3) in the phyB mutant background confers resistance to 5-methyl-tryptophan (5-MT). Plants were grown for 3 weeks in MS medium containing 50 µM 5-methyl-tryptophan or in mock treatment without methyl-tryptophan. FIG. 7E graphically illustrates that overexpression of a dominant MYC2 mutant transcription factor (MYC2$^{D105N/E165K}$) in phyB-9-defective mutant *Arabidopsis* plants reduces primary root inhibition caused by treatment with 5-methyl-tryptophan. As shown, the non-transgenic (NT) phyB-9 mutant plants that do not express the (MYC2$^{D105N/E165K}$) protein exhibit smaller primary roots, indicating the presence of 5-methyl-tryptophan has inhibited growth. Transgenic expression of additional wild type MYC2 improves primary root length the phyB-9-defective mutant *Arabidopsis* plants. However, expression of the dominant MYC2 mutant transcription factor (MYC2$^{D105N/E165K}$) provides the best primary root growth in the phyB-9-defective mutant *Arabidopsis* plants.

DETAILED DESCRIPTION

Figure 1A:
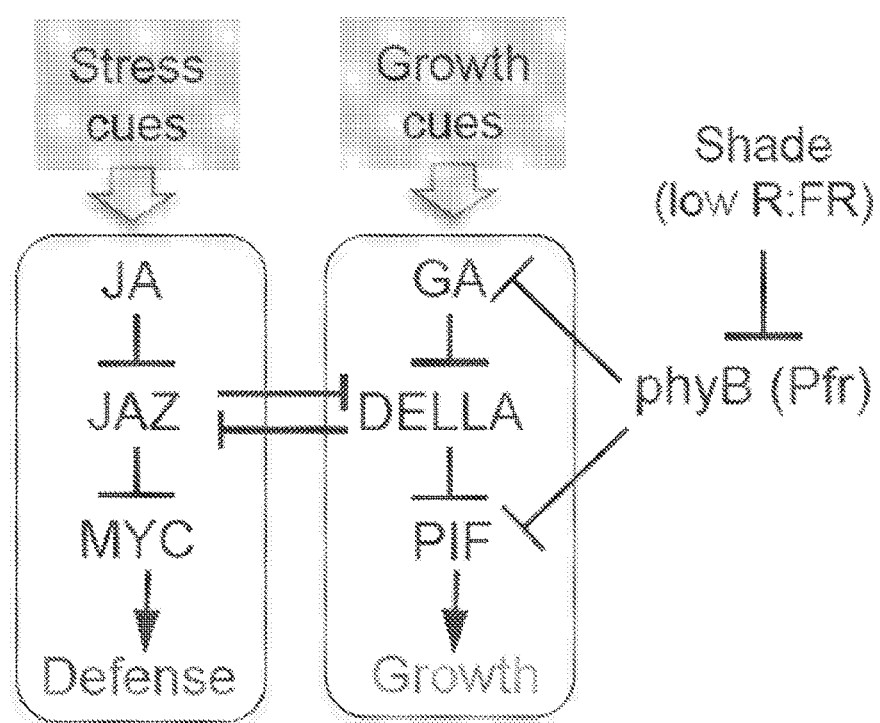
FIGS. 1A-1I illustrate development of a JAZ quintuple mutant (jazQ) that exhibits reduced growth and enhanced defense.

Plants and methods of making such plants are described herein that grow well and are resistant to environmental stresses such as drought and insects. The plants have mutations that reduce or eliminate the expression or function of proteins that modulate jasmonic acid responses (e.g., JAZ genes/proteins). Plants with such mutations are referred to herein as jaz mutants or jaz plants. Such reduction/elimination of jasmonic acid regulatory protein expression and/or function improves the insect resistance (compared to wild type plants) of jaz mutant plants. An additional mutation that reduces or eliminates the function of the PHYB gene improves the growth of jaz mutant plants. Hence, the combination of jaz and phyB loss-of-function mutations provides robustly growing plant lines that are also resistant to insects. Seeds of such jaz and phyB loss-of-function mutants, and methods of making and using such seeds and plants are also described herein.

Plants described herein can have one or more mutations that reduce or eliminate the interaction of MYC transcription factors with the JAZ proteins. MYC2 mediates stress responses through the action of plant stress hormones such as jasmonate (JA). In plant cells containing high levels of jasmonate, MYC transcription factors bind to the promoter region of JA-response genes to promote their transcriptional activation. However, simple overexpression of MYC2 is insufficient to constitutively activate defense responses. This is because MYC transcription factors are strongly repressed by direct binding of members of the JAZ family of repressor proteins. This application describes mutated MYC transcription factors that do not bind JAZ repressor proteins. Such mutations can be dominant MYC mutations. These plants that express mutant MYC proteins are capable of strongly activated defense responses in the presence of JAZ proteins. Such strong defense responses can reduce plant growth. By expressing mutant MYC proteins in a mutant phyB loss-of-function background, the plants exhibit strong defenses against environmental stress and also grow well.

Jasmonic acid and its various metabolites regulate plant responses to abiotic and biotic stresses as well as plant growth and development. The JAZ proteins typically inhibit the activation of defense responses that are controlled by jasmonic acid, and reduce the resistance of plants to environmental stresses such as drought, insects, and other environmental stresses. Reduction or elimination of JAZ functions tends to increase jasmonic acid expression and/or function, increase the activity of MYC transcription factors, and thereby improve drought and insect resistance (compared to wild type plants). Plants that produce mutated MYC proteins unable to bind JAZ proteins are phenotypically similar (increased resistance and reduced growth) to plants in which JAZ function is reduced or eliminated. An additional mutation that reduces or eliminates the function of the PHYB gene improves the growth of the myc mutant plants. Hence, the combination of myc and phyB loss-of-function mutations provides robustly growing plant lines that are also resistant to environmental stresses. Seeds of such myc and phyB loss-of-function mutants, and methods of making and using such seeds and plants are also described herein.

Mutations

Plants and seeds have one or more genomic deletions, insertions, or substitutions in at least part of the MYC, JAZ, and PHYB genes. Such deletions, insertions, or substitutions can be generated by site-specific recombination-mediated methods. The mutations can range in size from one or two nucleotides to thousands of nucleotides (or any value therebetween). Deletions, insertions, and/or substitutions are created at a desired location in the genome. For example, borders (end points) of the deletions, insertions, or substitutions can be at defined locations to control the size of the deletions, insertions, or substitutions.

The mutation(s) can reduce or eliminate expression of endogenous JAZ and/or PhyB genes within plant cells, plants, and seeds. For example, the mutations can eliminate transcription and/or translation of from JAZ and PHYB genes encoding JAZ1, JAZ3, JAZ4, JAZ9, JAZ10, PHYB, and combinations thereof. The mutations can also eliminate transcription and/or translation of from genes related to the JAZ and PHYB genes encoding JAZ1, JAZ3, JAZ4, JAZ9, JAZ10, PHYB, and combinations thereof. For example, transcription and/or translation can be reduced by at least 20%, or at least 30%, or at least 40%, or at least 50%, or at least 60%, or at least 70%, or at least 80%, or at least 90%, or at least 95%, or at least 97%, or at least 99% compared to wild type plant cells, plants, and seeds of the same species (that do not have the JAZ and/or PhyB mutation(s)).

The mutation(s) can reduce or eliminate MYC protein interaction with one or more JAZ protein. For example, the mutation(s) can reduce or eliminate MYC protein interaction with JAZ1 protein, JAZ2 protein, JAZ3 protein, JAZ4 protein, JAZ5 protein, JAZ6 protein, JAZ7 protein, JAZ8 protein, JAZ9 protein, JAZ10 protein, JAZ11 protein, JAZ12 protein, JAZ13 protein, and combinations thereof. For example, interaction between a MYC protein and a JAZ protein, or binding between such mutant MYC protein and any of such JAZ proteins can be reduced by at least 20%, or at least 30%, or at least 40%, or at least 50%, or at least 60%, or at least 70%, or at least 80%, or at least 90%, or at least 95%, or at least 97%, or at least 99% compared to wild type plant cells, plants, and seeds of the same species (that do not have the MYC mutation(s)).

Non-limiting examples of methods of introducing a modification into the genome of a plant cell can include microinjection, viral delivery, recombinase technologies, homologous recombination, TALENS, CRISPR, and/or ZFN, see, e.g. Clark and Whitelaw Nature Reviews Genetics 4:825-833 (2003); which is incorporated by reference herein in its entirety.

For example, nucleases such as zinc finger nucleases (ZFNs), transcription activator like effector nucleases (TALENs), and/or meganucleases can be employed with guide nucleic acid that allows the nuclease to target the genomic MYC, JAZ and PHYB site(s). In some cases of the various aspects described herein, a targeting vector can be used to introduce a deletion or modification of the genomic MYC, JAZ and PHYB chromosomal sites.

A "targeting vector" is a vector generally has a 5' flanking region and a 3' flanking region homologous to segments of the gene of interest. The 5' flanking region and a 3' flanking region can surround a DNA sequence comprising a modification and/or a foreign DNA sequence to be inserted into the gene. For example, the genomic MYC, JAZ and PHYB site(s) can be disrupted by insertion of T-DNA. In another example, the foreign DNA to be inserted may encode a selectable marker, such as an antibiotics resistance gene. Examples for suitable selectable markers include chloramphenicol resistance, gentamycin resistance, kanamycin resistance, spectinomycin resistance (SpecR), neomycin resistance gene (NEO) and hygromycin β-phosphotransferase markers (genes). The 5' flanking region and the 3' flanking region can be homologous to regions within the gene, or such flanking regions can flank the coding region of gene to be deleted, mutated, or replaced with the unrelated DNA sequence. In some cases, the targeting vector does not comprise a selectable marker. DNA comprising the targeting vector and the native gene of interest are contacted under conditions that favor homologous recombination (e.g., by transforming plant cell(s) with the targeting vector).

A typical targeting vector contains nucleic acid fragments of not less than about 0.1 kb nor more than about 10.0 kb from both the 5' and the 3' ends of the genomic locus which encodes the gene to be modified (e.g. the genomic MYC, JAZ and/or PHYB site(s)). These two fragments can be separated by an intervening fragment of nucleic acid that includes the modification to be introduced. When the resulting construct recombines homologously with the chromosome at this locus, it results in the introduction of the modification, e.g. an insertion, substitution, or a deletion of a portion of the genomic MYC, JAZ and/or PHYB site(s).

In some cases, a Cas9/CRISPR system can be used to create a modification in genomic MYC, JAZ and/or PHYB site(s). Clustered regularly interspaced short palindromic repeats (CRISPR)/CRISPR-associated (Cas) systems are useful for, e.g. RNA-programmable genome editing (see e.g., Marraffini and Sontheimer. Nature Reviews Genetics 11: 181-190 (2010); Sorek et al. Nature Reviews Microbiology 2008 6: 181-6; Karginov and Hannon. Mol Cell 2010 1:7-19; Hale et al. Mol Cell 2010:45:292-302; Jinek et al. Science 2012 337:815-820; Bikard and Marraffini Curr Opin Immunol 2012 24:15-20; Bikard et al. Cell Host & Microbe 2012 12: 177-186; all of which are incorporated by reference herein in their entireties). A CRISPR guide RNA can be used that can target a Cas enzyme to the desired location in the genome, where it generates a double strand break. This technique is available in the art and described, e.g. at Mali et al. Science 2013 339:823-6; which is incorporated by reference herein in its entirety and kits for the design and use of CRISPR-mediated genome editing are commercially available, e.g. the PRECISION X CAS9 SMART NUCLEASE™ System (Cat No. CAS900A-1) from System Biosciences, Mountain View, CA.

In other cases, a cre-lox recombination system of bacteriophage P1, described by Abremski et al. 1983. Cell 32:1301 (1983), Sternberg et al., *Cold Spring Harbor Symposia on Quantitative Biology*, Vol. XLV 297 (1981) and others, can be used to promote recombination and alteration of the genomic MYC, JAZ and/or PHYB site(s). The cre-lox system utilizes the cre recombinase isolated from bacteriophage P1 in conjunction with the DNA sequences (termed lox sites) it recognizes. This recombination system has been effective for achieving recombination in plant cells (U.S. Pat. No. 5,658,772), animal cells (U.S. Pat. Nos. 4,959,317 and 5,801,030), and in viral vectors (Hardy et al., J. Virology 71:1842 (1997).

The plant cells, plants, and plant seeds can have genomic mutations that alter one or more amino acids in the encoded MYC, JAZ and/or PHYB proteins. For example, plant cells, plants, and seeds can be modified so that at least one amino acid of a MYC, JAZ and/or PHYB polypeptide is deleted or mutated to reduce the function of MYC, JAZ and/or PHYB proteins. In some cases, a conserved amino acid or a conserved domain of the MYC, JAZ and/or PHYB polypeptide is modified. For example, a conserved amino acid or several amino acids in a conserved domain of the MYC, JAZ and/or PHYB polypeptide can be modified to change the physical and/or chemical properties of the conserved amino acid(s). For example, to change the physical and/or chemical properties of the conserved amino acid(s), the amino acid(s) can be deleted or replaced by amino acid(s) of another class, where the classes are identified in the following Table 1.

TABLE 1

| Classification | Genetically Encoded | Genetically Non-Encoded |
| --- | --- | --- |
| Hydrophobic | | |
| Aromatic | F, Y, W | Phg, Nal, Thi, Tic, Phe(4-Cl), Phe(2-F), Phe(3-F), Phe(4-F), Pyridyl Ala, Benzothienyl Ala |
| Apolar | M, G, P | |
| Aliphatic | A, V, L, I | t-BuA, t-BuG, MeIle, Nle, MeVal, Cha, bAla, MeGly, Aib |
| Hydrophilic | | |
| Acidic | D, E | |
| Basic | H, K, R | Dpr, Orn, hArg, Phe(p-NH$_2$), DBU, A$_2$ BU |
| Polar | Q, N, S, T, Y | Cit, AcLys, MSO, hSer |
| Cysteine-Like | C | Pen, hCys, β-methyl Cys |

Different types of amino acids can be in the mutant myc, jazQ and/or phyB polypeptide(s), such as any of those listed in Table 2.

TABLE 2

| Amino Acid | One-Letter Symbol | Common Abbreviation |
| --- | --- | --- |
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |
| β-Alanine | | bAla |
| N-Methylglycine (sarcosine) | | MeGly |
| Ornithine | | Orn |
| Citrulline | | Cit |
| N-methylisoleucine | | MeIle |
| Phenylglycine | | Phg |
| Norleucine | | Nle |
| Penicillamine | | Pen |
| Homoarginine | | hArg |
| N-acetyl lysine | | AcLys |
| p-Aminophenylalanine | | Phe(pNH$_2$) |
| N-methylvaline | | MeVal |
| Homocysteine | | hCys |
| Homoserine | | hSer |

For example, modified MYC proteins can have any naturally occurring amino acid within the protein replaced with any of the amino acids listed in Tables 1 or 2. Positions within MYC protein that can have such replacements include, for example, amino acid positions 94, 97, 102, 105, 107, 125, 128, 129, 148, 152, 155, 163, 165, 169, and/or 172.

In some cases, myc, jaz and/or phyB mutations are introduced by insertion of foreign DNA into the gene of interest. For example, this can involve the use of either transposable elements (see, e.g., Parinov et al., Plant Cell 11, 2263-2270 (1999)) or T-DNA. The foreign DNA not only disrupts the expression of the gene into which it is inserted but also acts as a marker for subsequent identification of the mutation. Because some plant introns are small, and because there can be very little intergenic material in plant chromosomes, the insertion of a piece of T-DNA on the order of 5 to 25 kb in length generally produces a dramatic disruption of gene function. If a large enough population of T-DNA-transformed lines is available, one has a very good chance of finding a plant carrying a T-DNA insert within any gene of interest.

Mutations that are homozygous lethal can be maintained in the population in the form of heterozygous plants.

MYC Proteins and Modifications Thereof

The bHLH-type transcription factor (TF) MYC2, together with related members of this family (e.g., MYC3 and MYC4 in *Arabidopsis*), promote myriad plant responses to biotic and abiotic stress (Kazan & Manners, 2013). MYC2 executes biotic and abiotic stress responses primarily through the stress hormones jasmonate and abscisic acid (ABA). For example, in some cases the MYC transcription factors can promote jasmonate-triggered defense responses against pathogen and insect pests. In plant cells containing high levels of jasmonate, MYC transcription factors bind to the promoter region of JA-response genes to promote their transcriptional activation.

Previous studies have shown that simple overexpression of MYC2 from a strong promoter such as the 35S cauliflower mosaic virus promoter is insufficient to constitutively activate defense responses in tomato/potato and *Arabidopsis* (Boter et al., 2004; Lorenzo et al., 2004). The reason for this is now clear: MYC transcription factors are strongly repressed via direct binding by members of the JAZ family of repressor proteins (of which there are thirteen in *Arabidopsis*, JAZ1-JAZ13).

JAZ proteins contain a C-terminal Jas motif that interacts directly with the JAZ-interacting domain (JID) of MYC transcription factors, thus inhibiting transcriptional activation of jasmonate response genes (Fernandez-Calvo et al., 2011; Zhang et al., 2015). Mutated derivatives of MYC2 (e.g. MYC2D105N) and MYC3 (e.g. MYC3D94N) fail to interact with most JAZ proteins, and are capable of activating jasmonate-responsive target genes in the presence of JAZs. This has been demonstrated from co-transfection assays (Goossens et al., 2015) and characterization of an *Arabidopsis* atr2D mutant (which harbors an Asp-to-Asn, MYC3D94N mutation) (Smolen et al., 2002). Based on these findings, it was stated that "Ultimately, the transferability of the Asp-to-Asn amino acid change might facilitate the design of hyperactive transcription factors for plant engineering" (Goossens et al., 2015). However, such mutations do not inhibit interactions with JAZ1 and JAZ10, which are potent repressors of MYC transcription factors.

Depending upon the location of a mutation, some mutations of MYC transcription factors may still be subject to repression by JAZ1 and JAZ10 because these two JAZ proteins harbor a cryptic MYC-interaction domain (CMID). By changing the MYC contact points with the CMID domain, which in some cases may be within the JID domain and in some cases outside of the JID domain, MYC transcription factors are generated that escape repression by all JAZ proteins. Such MYC transcription factors therefore are highly potent in their capacity to promote the expression of JA-response genes (i.e., MYC transcription factors that avoid repression by all JAZs).

This technology is useful not only for design of crops with increased resistance to pests, but also for enhancing the production of plant-derived medicinal compounds. One example is the anti-cancer drug taxol, whose production in taxus cells is promoted by the JA pathway via MYC transcription factors. Engineering of mutant (e.g., dominant mutant) MYC transcription factors into taxus cells could significantly increase taxol production. This same approach can be used to increase the production of any plant compound whose synthesis is controlled by MYC transcription factors (this includes many if not most plant secondary metabolites).

Examples of MYC protein sequences are provided herein that have one or more amino acid mutations, substitutions, replacements, insertions, or deletions within their JAZ-interacting domains (JIDs). In some cases, one or more mutations, substitutions, replacements, insertions, or deletions that are outside of the JAZ-interacting domain (JID) of the MYC proteins provided herein, for example, in regions that may interact with JAZ cryptic MYC-interaction domains (CMIDs).

For example, any of the MYC or MYC-related proteins described herein have at least one amino acid, or at least two amino acids, or at least three amino acids, or at least four amino acids, or at least five amino acid mutations, substitutions, replacements, insertions, or deletions in their JAZ-interacting domains (JIDs) on in regions that interact with JAZ cryptic MYC-interaction domains (CMIDs), or in both JID and CMID-interacting domains of a MYC protein. For example, MYC2 regions that interact with JAZ cryptic MYC-interaction domains (CMIDs) and/or MYC2 JAZ-interacting domains (JID) of a modified MYC protein can have less than 100%, or at less than 99.5%, or at less than 99%, or less than 98%, or at less than 97%, or less than 96%, or less than 95%, or less than 94%, or less than 93%, or less than 92%, or less than 91%, or less than 90% sequence identity with any of the CMID-interacting domains, JID, MYC or MYC related sequences described herein. However, in some cases the modified MYC protein have at least 40%, or at least 50%, or at least 60%, or at least 70%, or at least 80%, or at least 90%, or at least 95%, or at least 97%, or at least 99% sequence identity compared to the MYC or MYC-related sequences described herein.

For example, an *Arabidopsis thaliana* MYC2 sequence is shown below as SEQ ID NO:1, where the JAZ-interacting domain (JID) is shown in bold and with underlining.

```
  1  MTDYRLQPTM NLWTTDDNAS MMEAFMSSSD ISTLWPPAST
 41  TTTTATTETT PTPAMEIPAQ AGFNQETLQQ RLQALIEGTH
 81  EGWTYAIFWQ PSYDFSGASV LGWGDGYYKG EEDKANPRRR
121  SSSPPFSTPA DQEYRKKVLR ELNSLISGGV APSDDAVDEE
161  VTDTEWFFLV SMTQSFACGA GLAGKAFATG NAVWVSGSDQ
201  LSGSGCERAK QGGVFGMHTI ACIPSANGVV EVGSTEPIRQ
241  SSDLINKVRI LFNFDGGAGD LSGLNWNLDP DQGENDPSMW
281  INDPIGTPGS NEPGNGAPSS SSQLFSKSIQ FENGSSSTIT
321  ENPNLDPTPS PVHSQTQNPK FNNTFSRELN FSTSSSTLVK
361  PRSGEILNFG DEGKRSSGNP DPSSYSGQTQ FENKRKRSMV
401  LNEDKVLSFG DKTAGESDHS DLEASVVKEV AVEKRPKKRG
441  RKPANGREEP LNHVEAERQR REKLNQRFYA LRAVVPNVSK
481  MDKASLLGDA IAYINELKSK VVKTESEKLQ IKNQLEEVKL
521  ELAGRKASAS GGDMSSSCSS IKPVGMEIEV KIIGWDAMIR
561  VESSKRNHPA ARLMSALMDL ELEVNHASMS VVNDLMIQQA
601  TVKMGFRIYT QEQLRASLIS KIG
```

The JAZ-interacting domain (JID) of the SEQ ID NO:1 *Arabidopsis thaliana* MYC2 protein is shown below as SEQ ID NO:2.

```
 81  YDFSGASV LGWGDGYYKG EEDKANPRRR
121  SSSPPFSTPA DQEYRKKVLR ELNSLISGGV APS
```

In some cases, the MYC2 protein with SEQ ID NO:1 can have one or more mutations within the JID, and/or one or more mutations outside of the JID region. Thus modified MYC proteins described herein have less than 100% sequence identity to SEQ ID NO:1 and/or to SEQ ID NO:2.

Several amino acid positions of the MYC2 proteins can be modified, including for example, positions 94, 97, 102, 105, 107, 125, 128, 129, 148, 152, 155, 163, 165, 169, 172, or combinations thereof. MYC2 from different plant species can have variations in sequence. Hence, MYC2 from species other than *Arabidopsis thaliana* can have modifications at positions corresponding to positions 94, 97, 102, 105, 107, 125, 128, 129, 148, 152, 155, 163, 165, 169, and/or 172 from *Arabidopsis thaliana*.

For example, in some cases position 165 of the SEQ ID NO:1 MYC2 sequence can be a lysine rather than a glutamic acid (i.e., an E165K mutation). Such an E165K mutation is a gain-of-function allele of MYC2. The E165K mutation is in the transcriptional activation domain (TAD) of MYC2, which lies outside the JAZ-interacting domain, as described by Gasperini et al. PLOS Genetics 11(6): e1005300 (2015).

Other examples of MYC2 mutations include MYC2 D105N; MYC2 D105N+E165K; MYC2 M172A; MYC2 E165A+M172; and MYC2 L169A mutations.

An *Arabidopsis thaliana* MYC3 sequence is shown below as SEQ ID NO:3, where the JAZ-interacting domain (JID) is shown in bold and with underlining.

```
  1  MNGTTSSINF LTSDDDASAA AMEAFIGTNH HSSLFPPPPQ
 41  QPPQPQFNED TLQQRLQALI ESAGENWTYA IFWQISHDFD
 81  SSTGDNTVIL GWGDGYYKGE EDKEKKKNNT NTAEQEHRKR
121  VIRELNSLIS GGIGVSDESN DEEVTDTEWF FLVSMTQSFV
161  NGVGLPGESF LNSRVIWLSG SGALTGSGCE RAGQGQIYGL
201  KTMVCIATQN GVVELGSSEV ISQSSDLMHK VNNLFNFNNG
241  GGNNGVEASS WGFNLNPDQG ENDPALWISE PTNTGIESPA
281  RVNNGNNSNS NSKSDSHQIS KLEKNDISSV ENQNRQSSCL
321  VEKDLTFQGG LLKSNETLSF CGNESSKKRT SVSKGSNNDE
361  GMLSFSTVVR SAANDSDHSD LEASVVKEAI VVEPPEKKPR
401  KRGRKPANGR EEPLNHVEAE RQRREKLNQR FYSLRAVVPN
441  VSKMDKASLL GDAISYINEL KSKLQQAESD KEEIQKKLDG
481  MSKEGNNGKG CGSRAKERKS SNQDSTASSI EMEIDVKIIG
521  WDVMIRVQCG KKDHPGAREM EALKELDLEV NHASLSVVND
561  LMIQQATVKM GSQFFNHDQL KVALMTKVGE NY
```

The JAZ-interacting domain (JID) of the SEQ ID NO:3 *Arabidopsis thaliana* MYC3 protein is shown below as SEQ ID NO:4.

81 STGDNTVIL GWGDGYYKGE EDKEKKKNNT NTAEQEHRKR

121 VIRELNSLIS GGIGVS

In some cases, the MYC3 protein with SEQ ID NO:3 can have one or more mutations within the JID, and/or one or more mutations outside of the JID region. Thus modified MYC proteins described herein have less than 100% sequence identity to SEQ ID NO:3 and/or to SEQ ID NO:4.

Several amino acid positions of the MYC3 proteins can be modified, including for example, positions 94, 97, 102, 105, 107, 125, 128, 129, 148, 152, 155, 163, 165, 169, 172, or combinations thereof. MYC3 from different plant species can have variations in sequence. Hence, MYC3 from species other than *Arabidopsis thaliana* can have modifications at positions corresponding to positions 94, 97, 102, 105, 107, 125, 128, 129, 148, 152, 155, 163, 165, 169, and/or 172 from *Arabidopsis thaliana*.

For example, the glutamic acid at position 148 of the MYC3 protein with SEQ ID NO:3 corresponds to the glutamic acid at position 165 of the MYC2 protein, and can be lysine rather than glutamic acid (E148K) or an alanine rather than glutamic acid (E148A). In addition the aspartic acid at position 94 of the MYC3 protein with SEQ ID NO:3 or SEQ ID NO:4 can be an asparagine (D94N). Modified MYC3 proteins can also have a combination of E148K and D94N mutations.

Other MYC3 modifications can include an MYC3 M155A mutation, an MYC3 L152A mutation, and combinations thereof. The MYC3 M155A mutation, and/or MYC3 L152A mutation can be combined with E148K, E148A, and/or D94N mutation.

An *Arabidopsis thaliana* MYC4 sequence is shown below as SEQ ID NO:5, where the JAZ-interacting domain (JID) is shown in bold and with underlining.

```
  1 MSPTNVQVTD YHLNQSKTDT TNLWSTDDDA SVMEAFIGGG
 41 SDHSSLFPPL PPPPLPQVNE DNLQQRLQAL IEGANENWTY
 81 AVFWQSSHGF AGEDNNNNNT VLLGWGDGYY KGEEEKSRKK
121 KSNPASAAEQ EHRKRVIREL NSLISGGVGG GDEAGDEEVT
161 DTEWFFLVSM TQSFVKGTGL PGQAFSNSDT IWLSGSNALA
201 GSSCERARQG QIYGLQTMVC VATENGVVEL GSSEIIHQSS
241 DLVDKVDTFF NFNNGGGEFG SWAFNLNPDQ GENDPGLWIS
281 EPNGVDSGLV AAPVMNNGGN DSTSNSDSQP ISKLCNGSSV
321 ENPNPKVLKS CEMVNFKNGI ENGQEEDSSN KKRSPVSNNE
361 EGMLSFTSVL PCDSNHSDLE ASVAKEAESN RVVVEPEKKP
401 RKRGRKPANG REEPLNHVEA ERQRREKLNQ RFYSLRAVVP
441 NVSKMDKASL LGDAISYISE LKSKLQKAES DKEELQKQID
481 VMNKEAGNAK SSVKDRKCLN QESSVLIEME VDVKIIGWDA
521 MIRIQCSKRN HPGAKFMEAL KELDLEVNHA SLSVVNDLMI
561 QQATVKMGNQ FFTQDQLKVA LTEKVGECP
```

The JAZ-interacting domain (JID) of the SEQ ID NO:5 *Arabidopsis thaliana* MYC4 protein is shown below as SEQ ID NO:6.

81 NNNNNT VLLGWGDGYY KGEEEKSRKK

121 KSNPASAAEQ EHRKRVIREL NSLISGGVGG G

A comparison of the *Arabidopsis thaliana* MYC4 sequence with SEQ ID NO:5 and the *Arabidopsis thaliana* MYC2 sequence having SEQ ID NO:1 is shown below.

```
50.2% identity in 630 residues overlap; Score: 1225.0; Gap frequency: 12.4
Seq 1     9 TMNLWTTDDNASMMEAEMSS-
SDISTLWPPASTTTTTATTETTPTPTPAMEIPAQAGFNQET
Seq 5    20 TTNLWSTDDDASVMEAFIGGGSDHSSLEPPLP-----------PPPLPQV------
NEDN
            * *** *** ** ****   ** * * **            * *        *

Seq 1    68 LQQRLQALIEGTHEGWTYAIFWQPSYDFSGAS-------
VLGWGDGYYKGEEDKANPRRR
Seq 5    63 LQQRLQALIEGANENWTYAVFWQSSHGFAGEDNNNNNTVLLGWGDGYYKGEEEKS--
RKK
            **********  * **** *** *  *  *       ************ *   *

Seq 1   121
SSSPPFSTPADQEYRKKVLRELNSLISGGVAPSDDAVDEEVTDTEWFFLVSMTQSFACGA
Seq 5   121 KSNR--
ASAAEQEHRKPVIRELNSLISGGVGGGDEAGDEEVTDTEWFFLVSMTQSFVKGT
              *    * ** ** * ***********  * * ******************
*

Seq 1   181
GLAGKAFATGNAVWVSGSDQLSGSGCERAKQGGVFGMHTIACIPSANGVVEVGSTEPIRQ
Seq 5   179
GLPGQAFSNSDTIWLSGSNALAGSSCERARQGQIYGLQTMVCVATENGVVELGSSEIIHQ
              ** * **    * ***  * *** * ** **** **  *  *    ***** ** * **

Seq 1   241
SSDLINKVRILFNFDGGAGDLSGLNWNLDPDQGENDPSMWINDPIGTPGSNEPGNGAPSS
Seq 5   239 SSDLVDKVDTFFNFNNGGGEFGSWAFNLNPDQGENDPGLWISEPNGV-------------
            ****  **  **** ***  *  ** ******** ** **  * *

Seq 1   301
SSQLFSKSIQFENGSSSTITENPNLDPTPSPVHSQTQNPKFNNTFSRELNFSTSSSTLVK
Seq 5   286 DSGLVAAPVMNNGGNDSTSNSDSQ------PISKLCNGSSVENPNPKVL-----------
             * *        *  **       *          *      *       *
```

-continued

```
Seq 1  361
PRSGEILNFGDEGKRSSGNPDPSSYSGQTQFENKRKRSMVLNEDKVLSFGDKTAGESDHS
Seq 5  329-KSCEMVN--KNGIENGQEEDSS--------
NKKRSPVSNNEEGMLSFTSVLPCDSNHS
            *  *  **          *    **          **        **      ***          *
**

Seq 1  421DLEASVVKE-------
VAVEKRPKKRGRKPANGREEPLNHVEAERQRREKLNQRFYALPA
Seq 5  378
DLEASVAKEAESNRVVVEPEKKPRKRGRKPANGREEPLNHVEAERQRREKLNQRFYSLRA
        ****** **        *  ** * *****************************
***

Seq 1  474
VVPNVSKMDKASLLGDAIAYINELKSKVVKTESEKLQIKNQLEEVKLELAGRKASASGGD
Seq 5  438
VVPNVSKMDKASLLGDAISYISELKSKLQKAESDKEELQKQIDVMNKEAGNAKSSVKDRK
        ****************** ** *****  * ** *       *        *     *  *

Seq 1  534
MSSSCSSIKPVGMEIEVKIIGWDAMIRVESSKRNHPAARLMSALMDLELEVNHASMSVVN
Seq 5  498CLNQESSVL-
IEMEVDVKIIGWDAMIRIQCSKRNHPGAKFMEALKELDLEVNHASLSVVN
               **      **  **********  ******  *   *  **   * *******
****

Seq 1  594DLMIQQATVKMGFRIYTQEQLRASLISKIG
Seq 5  557DLMIQQATVKMGNQFFTQDQLKVALTEKVG
         ************    ** **    *    * *
```

In some cases, the *Arabidopsis thaliana* MYC4 protein with SEQ ID NO:5 can have one or more mutations within the JID, and/or one or more mutations outside of the JID region. Thus modified MYC4 proteins described herein have less than 100% sequence identity to SEQ ID NO:5 and/or to SEQ ID NO:6.

Several amino acid positions of the MYC proteins can be modified, including for example, positions 94, 97, 102, 105, 107, 125, 128, 129, 148, 152, 155, 163, 165, 167, 169, 170, 172, or combinations thereof. MYC4 from different plant species can have variations in sequence. Hence, MYC4 from species other than *Arabidopsis thaliana* can have modifications at positions corresponding to positions 94, 97, 102, 105, 107, 125, 128, 129, 148, 152, 155, 163, 165, 167, 169, 170, and/or 172 from the *Arabidopsis thaliana* MYC2 protein (highlighted in bold and with underlining in the comparison above). In some cases the amino acid positions in the MYC4 protein can vary from those in the corresponding *Arabidopsis thaliana* MYC2 protein by 1-10 positions.

For example, modified MYC4 proteins can have D107N mutations, E163K mutations, M170A mutations, L167A mutations, or combinations thereof. Other MYC proteins can have the same types of mutations but the location can vary. For example, the aspartic acid (D) that is at position 107 of the MYC4 protein with SEQ ID NO:5, at be at different positions in other MYC proteins. For example, such an aspartic acid can be at ±5 positions from position 107. However, such an aspartic acid is readily identified by sequence comparisons such as those illustrated herein because a selected amino acid at a particular position can be aligned via its adjoining sequence with the sequence of a related protein, and even if there are sequence variations between the two proteins the skilled person can find the selected amino acid in the related protein.

Similarly, for example, a selected amino acid at a particular position, such an aspartic acid at position 107 in one protein can readily be identified in another protein as being at position 102 because that aspartic acid it is typically found within a sequence that is conserved between the two proteins. For example an aspartic acid at position 102 or 107 in different proteins can readily be identified because it is at the end of a conserved GWGD (SEQ ID NO:110) sequence. Other conserved segments of MYC protein sequences are illustrated in the sequence comparisons shown herein, including for example, the DFSG (SEQ ID NO:111) sequence, the RELNSLISGGV (SEQ ID NO:112) sequence, the DTEWFFLVSM (SEQ ID NO:113) sequence, the VVNDLMIQQATVKMG (SEQ ID NO:114) sequence, and/or the KRGRKPANGREEPLNHVEAERQRREKLNQRFY (SEQ ID NO:115) sequence. Such segments of conserved sequences facilitate alignment of related amino acid sequences so that corresponding amino acids can be identified despite position and some sequence variation.

MYC-related proteins can also be modified and expressed in a variety of plants, for example, instead of or in addition to a native MYC protein. An example of a MYC-related protein is a rice (*Oryza sativa*) MYC7E protein, which has at least 47% sequence identity to the MYC2 sequence with SEQ ID NO:1. This rice MYC7E protein sequence is shown below as SEQ ID NO:7, where the JAZ-interacting domain (JID) is shown in bold and with underlining.

```
  1  MWVLLSPLLT  TKNPFHPIPI  PTFPLLLFSS  SLVGVLFQIK

41  SNLEEEEIEI  KSMNLWTDDN  ASMMEAFMAS  ADLPAFPWGA

81  ASTPPPPPPP  PHHHHQQQQQ  QVLPPPAAAP  AAAAFNQDTL

121  QQRLQSIIEG  SRETWTYAIF  WQSSIDVSTG  ASLLGWGDGY

161  YKGCDDDKRK  QRSSTPAAAA  EQEHRKRVLR  ELNSLIAGAG

201  AAPDEAVEEE  VTDTEWFFLV  SMTQSFPNGL  GLPGQALFAA

241  QPTWIATGLS  SAPCDRARQA  YTFGLRTMVC  LPLATGVLEL

281  GSTDVIFQTG  DSIPRIRALF  NLSAAAASSW  PPHPDAASAD

321  PSVLWLADAP  PMDMKDSISA  ADISVSKPPP  PPPHQIQHFE
```

```
361 NGSTSTLTEN PSPSVHAPTP SQPAAPPQRQ QQQQQSSQAQ

401 QGPFRRELNF SDFASNGGAA APPFFKPETG EILNFGNDSS

441 SGRRNPSPAP PAATASLTTA PGSLFSQHTP TLTAAANDAK

481 SNNQKRSMEA TSRASNTNNH PAATANEGML SFSSAPTTRP

521 STGTGAPAKS ESDHSDLEAS VREVESSRVV APPPEAEKRP

561 RKRGRKPANG REEPLNHVEA ERQRREKLNQ RFYALRAVVP

601 NVSKMDKASL LGDAISYINE LRGKLTALET DKETLQSQME

641 SLKKERDARP PAPSGGGGDG GARCHAVEIE AKILGLEAMI

681 RVQCHKRNHP AARLMTALRE LDLDVYHASV SVVKDLMIQQ

721 VAVKMASRVY SQDQLNAALY TRIAEPGTAA R
```

A comparison of the rice MYC7E protein sequence having SEQ ID NO:7 with the MYC2 protein sequence having SEQ ID NO:1 is shown below, where the asterisks identify positions that are identical in the two proteins.

The JAZ-interacting domain (JID) of the rice MYC7E protein sequence having SEQ ID NO:7 is shown below as SEQ ID NO:8.

```
121                               STG ASLLGWGDGY

161      YKGCDDDKRK QRSSTPAAAA EQEHRKRVLR ELNSLIAGA
```

In some cases, the MYC7E protein with SEQ ID NO:7 can have one or more mutations within the JID, and/or one or more mutations outside of the JID region. Thus modified MYC proteins described herein have less than 100% sequence identity to SEQ ID NO:7 and/or to SEQ ID NO:8.

For example, MYC7E from *Oryza sativa* can have modifications at positions corresponding to positions 94, 97, 102, 105, 107, 125, 128, 129, 148, 152, 155, 163, 165, 167, 169, 170, and/or 172 from the *Arabidopsis thaliana* MYC2 protein (highlighted in bold and with underlining in the comparison above). In some cases the amino acid positions

```
47.2% identity in 705 residues overlap; Score: 1039.0; Gap frequency: 14.8%
UserSeq 1     9 TMNLWTTDDNASMMEAFMSSSDISTL-WPPASTTTTTATT---------ETTPTPAMEIP
UserSeq 7    52 SMNLWT-DDNASMMEAFMASADLPAFTWGPASTPPPPPPPPHHHHQQQQQQVLPPPAAAP
                ***** *********** * *      *A  ***                     *  *

UserSeq 1    59 AQAGFNQETLQQRLQALIEGTHEGWTYAIFWQPSYDFS-GASVLGWGDGYYKGEEDKANP
UserSeq 7   111 AAAAFNQDTLQQRLQSIIEGSRETWTYAIFWQSSIDVSTGASLLGWGDGYYKGCDDDKR-
                * * *** ******** ***  * ******** * * *** **********   *

UserSeq 1   118 RRRSSSPPFSTPADQEYRKKVLRELNSLISGGVAPSDDAVDEEVTDTEWFFLVSMTQSFA
UserSeq 7   170 KQRSSTP--AAAAEQEHRKRVLRELNSLIAGAGAAPDEAVEEEVTDTEWFFLVSMTQSFP
                  *** *        * ** ********* *   * ** * ** *****************

UserSeq 1   178 CGAGLAGKAFATGNAVWVSGSDQLSGSGCERAKQGGVFGMHTIACIPSANGVVEVGSTEP
UserSeq 7   228 NGLGLPGQALFAAQPTWIATG--LSSAPCDRARQAYTFGLRTMVCLPLATGVLELGSTDV
                * ** * *             *  ** * **   *   * * * ** ***

UserSeq 1   238 IRQSSDLINKVRILFNFDGGAGDLSGLNWNLDPDQGENDPS-MWIND--PIGTPGSNEPG
UserSeq 7   286 IFQTGDSIPRIRALFNLSAAAAS----SWPPHPDAASADPSVLWLADAPPMDMKDSISAA
                * * *  *     ***       *    *   ***   *   *  *  *

UserSeq 1   295 NGAPSSSSQLFSKSIQ-FENGSSSTITENPNID---PTPS----PVHSQTQNPKFNNT--
UserSeq 7   342 DISVSKPPPPPPHQIQHFENGSTSTLTENPSPSVHAPTPSQPAAPPQRQQQQQQSSQAQQ
                         *   ** ***** ** ***** *   ****    *        * *

UserSeq 1   345 --FSRELFSTSSST-------LVKPRSGEILNFGDEGKRSSGNRDPSSYSGQTQF----
UserSeq 7   402 GPFRRELNFSDFASNGGAAAPPFFKPETGEILNFGNDSSGRRNPSPAPPAATASLTTAP
                  * ******  *                ** *******      ** *

UserSeq 1   392 -------------------ENKRKRSMVLNE--------------DKVLSF---------
UserSeq 7   462 GSLFSQHTPTLTAAANDAKSNNQKRSMEATSRASNTNNHPAATANEGMLSFSSAPTTRRS
                                    *   ****                   ***

UserSeq 1   410 ---GDKTAGESDHSDLEASVVKEVA---------VEKRPKKRGRKPANGREEPLNHVEAE
UserSeq 7   522 TGTGAPAKSESDHSDLEASVREVESSRVVAPPPEAEKRPRKRGRKPANGREEPLNHVEAE
                     *   **********          ****  ******************

UserSeq 1   458 RQRREKLNQRFYALRTAVVPNVSKMDKASLLGFAIAYINELKSKVVKTESEKLQIKNQLEE
UserSeq 7   582 RQRREKLNQRFYALRVVPNVSKMDKASLLGDAISYINELRGKLTALETDKETLQSQMES
                ***************   ************** *  ****  *   *  **  * * *

UserSeq 1   518 VKLELAGRKASASGGDMSSSCSSIKPVGMEIEVKIIGWDAMIRVESSKRNHPAARLMSAL
UserSeq 7   642 LKKERDARPPAPSGG---GGDGGARCHAVEIEAKILGLEAMIRVQCHKRNHPAARLMTAL
                 *  *   ***        ***  *  *** *      ******   *********  **

UserSeq 1   578 MDLELEVNHASMSVVNDLMIQQATVKMGFRIYTQEQLRASLISKI
UserSeq 7   699 RELDLDVYHASVSVVKDLMIQQVAVKMASPVYSQDQLNAALYTRI
                  * *** *** *** ******  *** *  * * *** * *
``` in the endogenous *Oryza sativa* MYC protein can vary from those in the corresponding *Arabidopsis thaliana* MYC2 protein by 1-10 positions.

An example of another MYC protein is a maize (*Zea mays*) MYC4 protein, which has at least 47% sequence identity to the *Arabidopsis* MYC2 sequence with SEQ ID NO:1. This maize MYC4 protein sequence is shown below as SEQ ID NO:9, where the JAZ-interacting domain (JID) is shown in bold and with underlining.

```
  1 MNLWTDDNAS MMEAFMASAD LPTFPWGAPA GGGNSSAAAA

41 SPPPPQMPAA TAPGFNQDTL QQRLQAMIEG SRETWTYAIF

81 WQSSLDSATG ASLLGWGDGY YKGCDEDKRK QKPLTPSAQA

121 EQEHRKRVLR ELNSLISGAA AAPDEAVEEE VTDTEWFFLV

161 SMTQSFLNGS GLPGQALFAG QPTWIASGLS SAPCERARQA

201 YNFGLRTMVC FPVGTGVLEL GSTDVVFKTA ESMAKIRSLF

241 GGGAGGGSWP PVQPQAPSSQ QPAAGADHAE TDPSMLWLAD

281 APVMDIKDSL SHPSAEISVS KPPPHPPQIH FENGSTSTLT

321 ENPSPSVHAP PPPPAPAAPQ QRQHQHQNQA HQGPFRRELN

361 FSDFASTPSL AATPPFFKPE SGEILSFGAD SMARRNPSPV

401 PPAATASLTT APGSLFSQHT ATMTAAAAND AKNNNKRSME

441 ATSRASNTNH HPAATANEGM LSFSSAPTTR PSTGTGAPAK

481 SESDHSDLDA SVREVESSRV VAPPPEAEKR PRKRGRKPAN

521 GREEPLNHVE AERQRREKLN QRFYALRAVV PNVSKMDKAS

561 LLGDAISYIN ELRGKLTSLE TDKETLQTQV EALKKERDAR

601 PPSHSAGLGG HDGGPRCHAV EIDAKILGLE AMIRVQCHKR

641 NHPSARLMTA LRELDLDVYH ASVSVVKDLM IQQVAVKMAS

681 RVYTQDQLSA ALYSRLAEPG SAMGR*
```

A comparison of the maize MYC4 protein sequence having SEQ ID NO:9 with the MYC2 protein sequence having SEQ ID NO:1 is shown below.

```
47.2% identity in 703 residues overlap; Score: 1048.0; Gap frequency: 13.8%
UserSeq 1   10 MNLWTTDDNASMMEAFMSSSDISTL-W-PPASTTTTTATTETTPTPAMEIPAQAGFNQET
UserSeq 9    1 MNLMT-DDNASMMEAFMASADLPTFPWGAPAGGGNSSAAAASPPPPQMPAATAPGFNQDT
               ***** ************ *  *   **        *    * * *      **** *

UserSeq 1   68 LQQRLQALIEGTHEGWTYAIFWQPSYDFS-GASVLGWGDGYYKGEEDKANPRRRSSSPPF
UserSeq 9   60 LQQRLQAMIEGSRETWTYAIFWQSSLDSATGASLLGWGDGYYKGCDED---KRKQKPLTP
               ******* *** * ********* * *  *** **********  **    * *   *

UserSeq 1  127 STPADQEYRKKVLRELNSLISGGVAPSDDAVDEEVTDTEWFFLVSMTQSFACGAGLAGKA
UserSeq 9  117 SAQAEQEHRKRVLRELNSLISGAAAAPDEAVEEEVTDTEWFFLVSMTQSFLNGSGLPGQA
               *  * ** ** ********** * *  *  * ************* ***  ** * ** *

UserSeq 1  187 FATGNAVWVSGSDQLSGSGCERAKQGGVFGMHTIACIPSANGVVEVGSTEPIRQSDLIN
UserSeq 9  177 LFAGQPTWIASG--LSSAPCERARQAYNFGLRTMVCFPVGTGVLELGSTDVVFKTAESMA
                ** *   * ***       ***     *     *  *   ** **** *  *  * *

UserSeq 1  247 KVRILFNFDGGAGDL--------SGLNWNLDPDQGENDPSM-WIND-PIGT--PGSNEPG
UserSeq 9  235 KIRSLFGGGAGGGSWPPVQPQAPSSQQPAAGADHAETDPSMLWLADAPVMDIKDSLSHPS
               * * **    **             *       * * **** * *   *         *

UserSeq 1  295 NGAPSSSSQLFSKSIQFENGSSSTITENPNLD-----PTPSPV-----HSQTQNPKFNNT
UserSeq 9  295 AEISVSKPPPHPPQIHFENGSTSTLTENPSPSVHAPPPPPAPAAPQQRQHQHQNQAHQGP
                *      *    *  ***** ** ****                 *  * *   * **

UserSeq 1  345 FSRELNFSTSSST--------LVKPRSGEILNFG-DEGKRSSGNPDP------------S
UserSeq 9  355 FRRELNFSDFASTPSLAATPPFFKPESGEILSFGADSNARRNPSPVPPAATASLTTAPGS
               * ******  **         ** *  **** **    *  ** *               *

UserSeq 1  384 SYSGQT---------QFENKRKRSMVLNE--------------DKVLSF-----------
UserSeq 9  415 LFSQHTATMTAAAANDAKNNKRSMEATSRASNTNHHPAATANEGMLSFSSAPTTRPSTG
                 *  *         * ****                    ***

UserSeq 1  410 -GDKTAGESDHSDLEASVVKEVA---------VEKRPKKRGRKPANGREEPLNHVEAERQ
UserSeq 9  475 TGAPAKSESDHSDLDASVREVESSRVVAPPPEAEKRPRKRGRKPANGREEPLNHVEAERQ
                    *******  *** ***         **** ****** *************

UserSeq 1  460 RREKLNQRFYALRAVVPNVSKMDKASLLGDAIAYINELKSKVVKTESEKLQIKNQLEEVK
UserSeq 9  535 RREKLNQRFYALRAVVPNVSKMDKASLLGDAISYINELRGKLTSLETDKETLQTQVEALK
               ******************************* ***** *   * * **  *   *  *

UserSeq 1  520 LELAGRKASASGGDMSSSCSSIKPVGMEIEVKIIGWDAMIRVESSKRNHPAARLMSALMD
UserSeq 9  595 KERDARPPSHSAG-LGGHDGGPRCHAVEIDAKILGLEAMIRVQCHKRNHPSARLMTALRE
                *  *         *      ** * ** *** *********  ***** **** **

UserSeq 1  580 LELEVNHASMSVVNDLMIQQATVKMGFRIYTQEQLRASLISKI
UserSeq 9  654 LDLDVYHASVSVVKDLMIQQVAVKMASRVYTQDQLSAALYSRL
               * * * *** *** ****** *** *  **** ** ** * *
```

The JAZ-interacting domain (JID) of the maize MYC4 protein sequence having SEQ ID NO:9 is shown below as SEQ ID NO:10.

```
 81           ATG ASLLGWGDGY YKGCDEDKRK QKPLTPSAQA
121     EQEHRKRVLR ELNSLISGA
```

In some cases, the maize MYC4 protein with SEQ ID NO:9 can have one or more mutations within the JID, and/or one or more mutations outside of the JID region. Thus modified MYC proteins described herein have less than 100% sequence identity to SEQ ID NO:9 and/or to SEQ ID NO:10.

For example, such a MYC4 from *Zea mays* can have modifications at positions corresponding to positions 94, 97, 102, 105, 107, 125, 128, 129, 148, 152, 155, 163, 165, 167, 169, 170, and/or 172 from the *Arabidopsis thaliana* MYC2 protein (highlighted in bold and with underlining in the comparison above). In some cases the amino acid positions in the endogenous *Zea mays* MYC4 protein can vary from those in the corresponding *Arabidopsis thaliana* MYC2 protein by 1-10 positions.

An example of another MYC-related protein is a maize (*Zea mays*) MYC4-like protein, shown below as SEQ ID NO:11, where the JAZ-interacting domain (JID) is shown in bold and with underlining.

```
  1 MNLWTDDNAS MMEAFMASAD LPAYPWGAPA GGGNPPPPQM
 41 PPAMAMAPGF NQDTLQQRLQ AMIEGSRETW TYAIFWQSSL
 81 DAATGASLLG WGDGYYKGCD DDKRRHRPPL TPAAQAEQEH
121 RKRVLRELNS LISGGASAAP APAPDEAVEE EVTDTEWFFL
```

```
161 VSMTQSFLNG SGLPGQALFA GHHTWIAAGL SSAPCDRARQ
201 AYNFGLRTMV CFPVGTGVLE LGSTDVVFQT AETMAKIRSL
241 FGGGPGGGSW PPVQPQAAPQ QQHAAEADQA AETDPSVLWL
281 ADAPVVDIKD SYSHPSAAEI SVSKPPPPPP PPQIHFENGS
321 TSTLTENPSP SVHAPPAPPA PPQRQQQNQG PFRRELNFSD
361 FASNPSLAAA PPFFKPESGE ILSFGVDSNA QRNPSPAPPA
401 SLTTAPGSLF SQSQHTATAA ANDAKNNNNN NKRSMEATSL
441 ASNTNHHPAA AANEGMLSFS SAPTARPSAG TGAPAKSESD
481 HSDLDASVRE VESSRVVAPP PEAEKRPRKR GRKPANGREE
521 PLNHVEAERQ RREKLNQRFY ALRAVVPNVS KMDKASLLGD
561 AISYINELRG KLTSLESDRE TLQAQVEALK KERDARPHPH
601 PAAGLGGHDA GGPRCHAVEI DAKILGLEAM IRVQCHKRNH
641 PSARLMTALR ELDLDVYHAS VSVVKDLMIQ QVAVKMASRM
681 YSQDQLSAAL YSRLAEPGSV MGR
```

The JAZ-interacting domain (JID) of the maize MYC4-like protein sequence having SEQ ID NO:11 is shown below as SEQ ID NO:12.

```
 81     ATGASLLG WGDGYYKGCD DDKRRHRPPL TPAAQAEQEH
121     RKRVLRELNS LISGG
```

A comparison of the *Arabidopsis* MYC4 protein with SEQ ID NO:5 with the *Zea mays* MYC4-like having SEQ ID NO:11 is shown below.

```
41.5% identity In 689 residues overlap; Score: 710.0; Gap frequency: 19.7%
Seq 5    25
STDDDASVMEAFIGGGSDHSSLFPPLPPPPLPQVNEDNLQQRLQALIEGANENWTYAVFW
Seq 11   18 SADLPAYPWGAPAGGGNPPPPQMPPAMAMA-
PGFNQDTLQQRLQAMIEGSRETWTYAIFW
              *  *  *    *  ***       **       *   *  * *******  ***   * ****
**

Seq 5    85 QSSHGFAGEDNNNNNTVLLGWGDGYYKGEEEKSRKKKS--
NPASAAEQHRKRVIRELNS
Seq 11   77 QSSLDAA------
TGASLLGWGDGYYKGCDDDKRRHRPPLTPAAQAEQEHRKRVLRELNS
                *** *           ********** *      **  ********
*****

Seq 5   143 LISGGVGGG-----
DEAGDEEVTDTEWFFLVSMTQSFVKGTLPGQAFSNSDTIWLSGSN
Seq 11  131
LISGGASAAPAPAPDEAVEEEVTDTEWFFLVSMTQSFLNGSGLPGQALFAGHHTWIAAG-
        *****           ***  ****************  *  ******       *

Seq 5   198 ALAGSSCERARQGQIYGLQTMVCVATENGVVELGSSEIIHQSSDLVDKVDTFFNFNNGGG
Seq 11  190 -
LSSAPCDRARQAYNFGLRTMVCFPVGTGVLELGSTDVVFQTAETMAKIRSLFGGGPGGG
               *   * **** ** ****  ** ****    *   *   *
***

Seq 5   258 EFGSWAFNLNPDQ---------GENDPG-LWI------------
SEPNGVDSGLVAAP--
Seq 11  249
SWPPVQPQAAPQQQHAAEADQAAETDPSVLWLADAPVVDIKDSYSHPSAAEISVSKPPPP
            * *         * **  **                * *           *

Seq 5   294 -----VMNNGGNDSTSNSDSQP-----------------------------
--
```

-continued
```
Seq 11 309
PPPPQIHFENGSTSTLTENPSPSVHAPPAPPAPPQRQQQNQGPFRRELNFSDFASNPSLA
                  *  **      *

Seq 5  311--------------ISKLCNGSSVENPNPKVLKSC---------
EMVNFKNGIEGQEEDS
Seq 11 369
AAPPFFKPESGEILSFGVDSNAQRNPSPAPPASLTTAPGSLFSQSQHTATAANDAKNNN
                              *     ** *    *                  *

Seq 5  349SNKKRS-------------PVSNNEEGMLSFTSV------------
LPCDSNHSDLEASV
Seq 11 429
NNNKRSMEATSLASNTNHHPAAAANEGMLSFSSAPTARPSAGTGAPAKSESDHSDLDASV
         * ***        *      ******  *                * ****
***

Seq 5  384AKEAESNRVVVEP---
EKKPRKRGRKPANGREEPLNHVEAERQPREKLNQRFYSLRAVVP
Seq 11 489-
REVESSRVVAPPPEAEKRPRKRGRKPANGREEPLNHVEAERQRREKLNQRFYALRAVVP
          *  ** ***    *   **  ******************************
******

Seq 5  441
NVSKMDKASLLGDAISYISELKSKLQKAESDKEELQKQIDVMNKEAGNAKSSVKDRKCLN
Seq 11 548
NVSKMDKASLLGDAISYINELRGKLTSLESDRETLQAQVEALKKERDARPHPHPAAGLGG
       ******************  **   **    *** * **  *            **

Seq 5  501QESSV--
LIEMEVDVKIIGWDAMIRIQCSKRNHPGAKFMEALKELDLEVNHASLSVVNDL
Seq 11 608
HDAGGPRCHAVEIDAKILGLEAMIRVQCHKRNHPSARLMTALRELDLDVYHASVSVVKDL
         *  * **  *    ****  ** ***** *   *  **  ****  *  *** ***
**

Seq 5  559MIQQATVKMGNQFFTQDQLKVALTEKVGE
Seq 11 668MIQQVAVKMASRMYSQDQLSAALYSRLAE
          ****  ***        ****   **         *
```

In some cases, the MYC4-like protein with SEQ ID NO:11 can have one or more mutations within the JID, and/or one or more mutations outside of the JID region. Thus modified MYC proteins described herein have less than 100% sequence identity to SEQ ID NO:11 and/or to SEQ ID NO:12.

For example, such a Zea mays MYC4-like protein can have modifications at positions corresponding to positions 94, 97, 102, 105, 107, 125, 128, 129, 148, 152, 155, 163, 165, 167, 169, 170, and/or 172 from the *Arabidopsis thaliana* MYC2 protein (highlighted in bold and with underlining in the comparison above). In some cases the amino acid positions in the endogenous *Zea mays* MYC4 protein can vary from those in the corresponding *Arabidopsis thaliana* MYC2 protein by 1-10 positions.

An example of another MYC-related protein is a Brachypodium distachyon MYC4-like protein, shown below as SEQ ID NO:13, where the JAZ-interacting domain (JID) is shown in bold and with underlining.

```
  1 MNLWTDDNAS MMEAFMASAA DLPTFPWGAA AATPPPPAAV

41 MPQQPAFNQD TLQQRLQAII EGSRETWTYA IFWQSSTDAG

81 AGASLLGWGD GYYKGCDDAD KRARQQPTPA SAAEQEHRKR

121 VLRELNSLIA GGGAAAPDEA VEEEVTDTEW FFLVSMTQSF

161 PNGMGLPGQA LYTRQPTWIA SGLASAPCER ARQAYTFGLR

201 TMVCIPVGTG VLELGATEVI FQTADSLGRI RSLFNLNGGG

241 GGGGAGSSWP PVAPHQQHGG DQAETDPSVL WLTDAPVGDM
```

-continued
```
281 KESPSVEISV SKPPPPPQIH HFENGSTSTL TENAGPSLHA

321 HQQPATLAPA APPRQNQHPH QLQLQHQQSQ QQQQQQQGPF

361 RRELNFSDFA TNASVTVTPP FFKPESGEIL NFGADSTSRR

401 NPSPAPPAAA ASLTTAPGSL FSQHTATVTA PTNEAKNNPK

441 RSMEATSRAS NTNHHPSATA NEGMLSFSSA PTTRPSTGTG

481 APAKSESDHS DLEASVREVE SSRVVPPPEE KRPRKRGRKP

521 ANGREEPLNH VEAERQRREK LNQRFYALRA VVPNVSKMDK

561 ASLLGDAISY INELRGKMTA LESDKDTLHS QIEALKKERD

601 ARPVAPLSGV HDSGPRCHAV EIEAKILGLE AMIRVQCHKR

641 NHPAAKLMTA LRELDLDVYH ASVSVVKDIM IQQVAVKMPN

681 RVYSQDQLNA ALYSRLAEPG APVPIR
```

The JAZ-interacting domain (JID) of the Brachypodium distachyon MYC4-like protein sequence having SEQ ID NO:13 is shown below as SEQ ID NO:14.

```
                                                             G
 80
 81 AGASLLGWGD GYYKGCDDAD KRARQQPTPA SAAEQEHRKR

121 VLRELNSLIA GG
```

In some cases, the Brachypodium distachyon MYC4-like protein with SEQ ID NO:13 can have one or more mutations within the JID, and/or one or more mutations outside of the JID region. Thus modified MYC proteins described herein have less than 100% sequence identity to SEQ ID NO:13 and/or to SEQ ID NO:14.

For example, such a MYC4-like from Brachypodium distachyon can have modifications at positions corresponding to positions 94, 97, 102, 105, 107, 125, 128, 129, 148, 152, 155, 163, 165, 167, 169, 170, and/or 172 from *Arabidopsis thaliana*.

An example of another MYC-related protein is a *Sorghum bicolor* MYC-like protein, shown below as SEQ ID NO:15, where the JAZ-interacting domain (JID) is shown in bold and with underlining.

```
  1 MNLWTDDNAS MMEAFMASAD LPTFPWGATA GGGNSSAAAA

41 TPPPPPQMPA AAMAPGFNQD TLQQRLQAMI EGSSETWTYA

81 IFWQSSLDAA TGASLLGWGD GYYKGCDDDK RKQRPLTPAA

121 QAEQEHRKRV LRELNSLISG AAAAPDEAVE EEVTDTEWFF

161 LVSMTQSFLN GSGLPGQALF AGQPTWIASG LSSAPCERAR

201 QAYNFGLRTM VCFPVGTGVL ELGSTDVVFQ TAESMAKIRS

241 LFGGGAGGGS WPPPQAPSHQ QPAAGPDQAE TDLWLADAPV

281 MDIKDSMSHP SAEISVSKPP PPPPPPQIHF ENASTSTLTE

321 NPSPSVHAAP PQPAPAAAPQ RQHQHQNQAH QGPFRRELNF

361 SDFASTNPSS LAATPPFFKP ESGEILSFGA DSNARRNPSP

401 APPAATASLT TAPGSLFSQH TATMTQAAAA NDAKNNNKRS

441 MEATSRASNT NHHPAATANE GMLSFSSAPT TRPSTGTGAP

481 AKSESDHSDL DASVREVESS RVVAPPPEAE KRPRKRGRKP

521 ANGREEPLNH VEAERQRREK LNQRFYALRA VVPNVSKMDK

561 ASLLGDAISY INELRGKLTS LESDKDTLQA QIEALKKERD

601 ARPPAHAAGL GGHDGGPRCH AVEIDAKILG LEAMIRVQCH

641 KRNHPSARLM TALRELDLDV YHASVSVVKD LMIQQVAVKM

681 ASRIYSQDQL NAALYSRLAE PGSAMGR
```

The JAZ-interacting domain (JID) of the *Sorghum bicolor* MYC-like protein sequence having SEQ ID NO:15 is shown below as SEQ ID NO:16.

```
 81            A TGASLLGWGD GYYKGCDDDK RKORPLTPAA

121 QAEQEHRKRV LRELNSLISG
```

In some cases, the *Sorghum bicolor* MYC-like protein with SEQ ID NO:15 can have one or more mutations within the JID, and/or one or more mutations outside of the JID region. Thus modified MYC proteins described herein have less than 100% sequence identity to SEQ ID NO:15 and/or to SEQ ID NO:16. For example, although any of the amino acids in the SEQ ID NO:15 or 16 protein be modified, modification of the amino acids in the JAZ-interacting domain (JID), and/or modification of the serine at position 136 of the SEQ ID NO:15 or at the corresponding position of SEQ ID NO:16 can be useful to reduce interaction of the MYC-related protein with one or more JAZ proteins.

In other cases, such a *Sorghum bicolor* MYC-like protein can have modifications at positions corresponding to positions 94, 97, 102, 105, 107, 125, 128, 129, 148, 152, 155, 163, 165, 167, 169, 170, and/or 172 from *Arabidopsis thaliana*.

An example of another MYC-related protein is a *Camelina sativa* MYC2-like protein, shown below as SEQ ID NO:17, where the JAZ-interacting domain (JID) is shown in bold and with underlining.

```
  1 MTDYRLQPTM NLWTTDDNAS MMEAFISSSD ISTLWPMATT

41 TTTTTTATTS APATAMDIPA PAGFNQETLQ QRLQALIEGT

81 NEGWTYAIFW QPSYDFSGAS VLGWGDGYYK GEEDKAKPRQ

121 RSSSPPFSTP ADQEYRKKVL RELNSLISGG VAPSDDAVDE

161 EVTDTEWFFL VSMTQSFACG AGLAGRAFST GNAVWVSGSD

201 QLSGSGCERA KQGGVFGMQT IACIPSANGV VEVGSTEQIR

241 QSSDLINKVR VLFNLDGGAG DLSGLDWNLD PDQGENDPSM

281 WINDPIGAPG SNEPGNGAPS SSSQLFSKSI QFENGSSSTI

321 TENPNPDPTP SPVHSQTQNP KFSNNFSREL NFSTSSSTLV

361 KPRSGEILSF GDDGKRGSGN PDPSSYSGQT QFENKRKKSP

401 NEDKVLSFGD KTTGESDASD LEASVVKEVA VEKRPKKRGR

441 KPANGREEPL NXMIYVIHSP NP
```

The JAZ-interacting domain (JID) of the *Camelina sativa* MYC2-like protein sequence having SEQ ID NO:17 is shown below as SEQ ID NO:18.

```
 41                            QRLQALIEGT

81 NEGWTYAIFW QPSYDFSGAS VLGWGDGYYK GEEDKAKPRQ

121 RSSSPPFSTP ADQEYRKKVL RELNSLISGG
```

In some cases, the *Camelina sativa* MYC2-like protein with SEQ ID NO:17 can have one or more mutations within the JID, and/or one or more mutations outside of the JID region. Thus modified MYC proteins described herein have less than 100% sequence identity to SEQ ID NO:17 and/or to SEQ ID NO:18.

For example, such a *Camelina sativa* MYC2-like protein can have modifications at positions corresponding to positions 94, 97, 102, 105, 107, 125, 128, 129, 148, 152, 155, 163, 165, 167, 169, 170, and/or 172 from *Arabidopsis thaliana*.

An example of another MYC-related protein is a *Solanum lycopersicum* MYC2-like protein, shown below as SEQ ID NO:19, where the JAZ-interacting domain (JID) is shown in bold and with underlining.

```
  1 MTEYSLPTMN LWNNSTSDDN VSMMEAFMSS DLSFWATNNS

41 TSAAVVGVNS NLPHASSNTP SVFAPSSSTS ASTLSAAATV

81 DASKSMPFFN QETLQQRLQA LIDGARETWT YAIFWQSSVV

121 DFSSPSVLGW GDGYYKGEED KAKRKLSVSS PAYIAEQEHR

161 KKVLRELNSL ISGAPPGTDD AVDEEVTDTE WFFLISMTQS

201 FVNGSGLPGQ ALYSSSPIWV AGTEKLAASH CERVRQAQGF

241 GLQTIVCIPS ANGVVELGST ELIVQSSDLM NKVRVLFNFS

281 NDLGSGSWAV QPESDPSALW LTDPSSSGME VRESLNTVQT

321 NSVPSSNSNK QIAYGNENNH PSGNGQSCYN QQQQKNPPQQ
```

```
361 QTQGFFTREL NFSEFGFDGS SNRNGNSSVS CKPESGEILN

401 FGDSTKKSAS SANVNLFTGQ SQFGAGEENN NKNKKRSATS

441 RGSNEEGMLS FVSGTVLPSS GMKSGGGGGE DSEHSDLEAS

481 VVKEADSSRV VEPEKRPRKR GRKPANGREE PLNHVEAERQ

521 RREKLNQRFY ALRAVVPNVS KMDKASLLGD AISYINELKS

561 KLQNTESDKE DLKSQIEDLK KESRRPGPPP PPNQDLKMSS

601 HTGGKIVDVD IDVKIIGWDA MIRIQCNKKN HPAARLMAAL

641 MELDLDVHHA SVSVVNDLMI QQATVKMGSR HYTEEQLRVA

681 LTSKIAETH
```

The JAZ-interacting domain (JID) of the *Solanum lycopersicum* MYC2-like protein sequence having SEQ ID NO:19 is shown below as SEQ ID NO:20.

```
121 FSSPSVLGW GDGYYKGEED KAKRKLSVSS PAYIAEQEHR

161 KKVLRELNSL ISGA
```

A comparison of the *Arabidopsis thaliana* MYC2 sequence having SEQ ID NO:1 with the *Solanum lycopersicum* MYC2-like protein with SEQ ID NO:19 is shown below.

```
54.0% identity in 641 residues overlap; Score: 1333.0; Gap frequency: 8.7%
Seq 1   27
SSSDISTLWPPASTTTTTATTETTPTPAMEIPAQAGFNQETLQQRLQALIEGTHEGWTYA
Seq 19  56 SSNTESVFAPSSSTSASTLSAAATVDASKSMPF---
FNQETLQQRLQALIDGARETWTYA
           **  *  *  **   *      *      ************** * *
****

Seq 1   87 IFWQPSY-
DFSGASVLGWGDGYYKGEEDKANPRRRSSSPPFSTPADQEYRKKVLRELNSL
Seq 19 113 IFWQSSVVDFSSPSVLGWGDGYYKGEEDKAKRKLSVSSPAYI--
AEQEHRKKVLRELNSL
            ****  *   ***  *****************    ***    *  **
***********

Seq 1  146
ISGGVAPSDDAVDEEVTDTEWFFLVSMTQSFACGAGLAGKAFATGNAVWVSGSDQLSGSG
Seq 19 171
ISGAPPGTDDAVDEEVTDTEWFFLISMTQSFVNGSGLPGQALYSSSPIWVAGTEKLAASH
           ***    ****************** ***** * ** * *   ** *  *  *

Seq 1  206
CEPAKQGGVEGMHTIACIPSANGVVEVGSTEPIRQSSDLINKVRILFNFDGGAGDLSGLN
Seq 19 231 CERVPQAQGFGLQTIVCIPSANGVVELGSTELIVQSSDLMNKVRVLFNF---
SNDLGSGS
           **  *    **  ** ********** ****   *****  **** **** ****   **

Seq 1  266 WNLDPDQGENDPS-MWINDPIGTPGS-
NEPGNGAPSSSSQLFSKSIQFENGSSSTITENP
Seq 19 288 WAVQP---
ESDPSALWLTDPSSSGMEVRESLNTVQTNSVPSSNSNKQIAYGNENNHPSGN
           *  *      *  *  *** * **          *  *    *        * *

Seq 1  324 NLDPTPSPVHSQTQNPKFNNTFSRELNFST-----------
SSSTLVKPRSGEILNFGDE
Seq 19 345
GQSCYNQQQQKNPPQQQTQGFFTRELNFSEFGFDGSSNRGNSSVSCKPESGEILNFGDS
                            * ******    **   ** *********

Seq 1  373 GKRSSGNPDPSSYSGQTQF------ENKRKR----SMVLNEDKVLSF---------
GDKT
Seq 19 405
TKKSASSANVNLFTGQSQFGAGEENNNKNKKRSATSRGSNEEGMLSFVSGTVLPSSGMKS
             * *            ** **   ** **   *  *   * **  ***        * *

Seq 1  414 AG----ESDHSDLEASVVKE------
VAVEKRPKKRGRKPANGREEPLNHVEAERQRREK
Seq 19 465
GGGGGEDSEHSDLEASVVKEADSSRVVEPEKRPRKRGRKPANGREEPLNHVEAERQRREK
               *     **********    *     * **********    * *******
************************

Seq 1  464
LNQRFYALRAVVPNVSKMDKASLLGDAIAYINELKSKVVKTESKLQIKNQLEEVKLELA
Seq 19 525
LNQRFYALRAVVPNVSKMDKASLLGDAISYINELKSKLQNTESDKEDLKSQIEDLKKESR
           ***************************  ********* ****     *  *  *  * *
```

-continued

```
Seq 1   524--
GRKASASGGDMSSSCSSIKPVGMEIEVKIIGWDAMIRVESSKRNHPAARLMSALMDLE
Seq 19  585
RPGPPPPPNQDLKMSSHTGGKIVDVDIDVKIIGWDAMIRIQCNKKNHPAARLMAALMELD
           *      **     *  *   * **********     * ********  *** *

Seq 1   582 LEVNHASMSVVNDLMIQQATVKMGFRIYTQEQLRASLISKI
Seq 19  645 LDVHHASVSVVNDLMIQQATVKMGSRHYTEEOLRVALTSKI
            * * *** **************** * ** ****  * ***
```

In some cases, the *Solanum lycopersicum* MYC2-like protein with SEQ ID NO:19 can have one or more mutations within the JID, and/or one or more mutations outside of the JID region. For example, *Solanum lycopersicum* MYC2-like proteins can have mutations at positions 132, 190, 194, 197, or combinations thereof. In some cases, the positions of mutations can be at one position on either side of positions 132, 190, 194, or 197. Examples of mutations in *Solanum lycopersicum* MYC2-like proteins include mutations such as D132N, E190K, M197A, L194A, and combinations thereof. Thus modified MYC proteins described herein have less than 100% sequence identity to SEQ ID NO:19 and/or to SEQ ID NO:20.

In other examples, such a *Solanum lycopersicum* MYC2-like protein can have modifications at positions corresponding to positions 94, 97, 102, 105, 107, 125, 128, 129, 132, 148, 152, 155, 163, 165, 167, 169, 170, and/or 172 from *Arabidopsis thaliana* MYC2 protein (highlighted in bold and with underlining in the comparison above). In some cases the amino acid positions in the endogenous *Zea mays* MYC4 protein can vary from those in the corresponding *Arabidopsis thaliana* MYC2 protein by 1-10 positions.

An example of another MYC-related protein is a *Solanum lycopersicum* protein, shown below as SEQ ID NO:21, where the JAZ-interacting domain (JID) is shown in bold and with underlining.

```
  1  MTDYRLWSNT NTTNTCDDTM MMDSFLSSDP SSFWPASTPN
 41  RPTPVNGVGE TMPFFNQESL QQRLQALIDG ARESWAYAIF
 81  WQSSVVDFAS QTVLGWGDGY YKGEEDKNKR RGSSSSAANF
121  VAEQEHRKKV LRELNSLISG VQASAGNGTD DAVDEEVTDT
161  EWFFLISMTQ SFVNGNGILPG LAMYSSSPIW VTGTEKLAAS
201  QCERARQAQG FGLQTIVCIP SPESREILNF GDSSKRFSGQ
241  SQLGPGPGLM EENKNENKNK KRSLGSRGNN EEGMLSFVSG
281  VILPTSTMGK SGDSDHSDLE ASVVKEAVVE PEKKPRKRGR
321  KPANGREEPL NHVEAERQRR EKLNQRFYEL RSQIECLRKE
361  LTNKGSSNYS ASPPLNQDVK IVDMDIDVKV IGWDAMIRIQ
401  CSKKNHPAAR LMAALKDLDL DVHHASVSVV NDLMIQQATV
441  KMGSRLYAQE QLRIALTSKI AESR
```

The JAZ-interacting domain (JID) of the *Solanum lycopersicum* MYC-related protein sequence having SEQ ID NO:21 is shown below as SEQ ID NO:22.

```
 81           FAS QTVLGWGDGY YKGEEDKNKR RGSSSSAANF
121  VAEQEHRKKV LRELNSLISG V
```

In some cases, the *Solanum lycopersicum* MYC-related protein with SEQ ID NO:21 can have one or more mutations within the JID, and/or one or more mutations outside of the JID region. For example, such *Solanum lycopersicum* MYC-related proteins can have mutations at positions 98, 161, 165, 168, or combinations thereof. In some cases, the positions of mutations can be at one position on either side of positions 98, 161, 165, or 168. Examples of mutations in *Solanum lycopersicum* MYC2-like proteins include mutations such as D98N, E161K, M168A, L165A, and combinations thereof. Thus modified MYC proteins described herein have less than 100% sequence identity to SEQ ID NO:21 and/or to SEQ ID NO:22.

An example of another MYC-related protein is a *Solanum tuberosum* MYC protein, shown below as SEQ ID NO:23, where the JAZ-interacting domain (JID) is shown in bold and with underlining.

```
  1  MTEYSLPTMN LWNNSTSDDN VSMMEAFMSS DLSFWATTNS
 41  TTTNSASAAV VGVNSNLLHT NNNNPSVFPL SSSTSVSAAA
 81  AVDATKSMPF FNQETLQQRL QALIDGARET WTYAIFWQSS
121  VVDFSSPSVL GWGDGYYKGE EDKAKRKLAV SSPAYIAEQE
161  HRKXVLRELN SLISGAPAGT DDAVDEEVTD TEWFFLiSMT
201  QSFVNGSGLP GQALYSSSPI WVAGTEKLAA SHCERVRQAQ
241  GFGLQTIVCI PSANGVVELG STELIVESSD LMNKVRVLFN
281  FSNDLGSGSW AVQPESDPSA LWLTEPSSSG MEVRESLNTV
321  QTNSVPSSNS NKQIAYANEN NHQSGNGQSC YNLQQQQNNP
361  PQQQTQGFFT RELNFSEFGF DGSSNRNGNA SLSCKPESGE
401  ILNFGDSTKK SASSANVNLF TGQSQFGAVE ENNNNKNKKR
441  SATSRGSNEE GMLSFVSGTV LPSSGMKSGG GGGEDSEHSD
481  LEASVVKEAD SSRVVEPEKR PRKRGRKPAN GREEPLNHVE
521  AERQRREKLN QRFYALRAMV PNVSKMDKAS LLGDAISYIN
561  ELKSKLQNTE SDKEDLKSQI EDLKKESRRP GPPPPNQDLK
601  IGGKIVDVDI DVKJIGWDAM IGIQCNKKNE PAARLMAALM
641  ELDLDVHHAS VSVVNDLMIQ QATVKMGSRH YTEEQLRVAL
681  KSKIAETPLE SR
```

The JAZ-interacting domain (JID) of the *Solanum tuberosum* MYC protein sequence having SEQ ID NO:23 is shown below as SEQ ID NO:24.

```
121       FSSPSVL GWGDGYYKGE EDKAKRKLAV SSPAYIAEQE
161  HRKKVLRELN SLISGA
```

In some cases, the *Solanum tuberosum* MYC protein with SEQ ID NO:23 can have one or more mutations within the JID, and/or one or more mutations outside of the JID region.

Thus modified MYC proteins described herein have less than 100% sequence identity to SEQ ID NO:23 and/or to SEQ ID NO:24.

For example, such a *Solanum tuberosum* MYC protein with SEQ ID NO:23 can have modifications at positions corresponding to positions 94, 97, 102, 105, 107, 125, 128, 129, 132, 148, 152, 155, 163, 165, 167, 169, 170, and/or 172 from *Arabidopsis thaliana* MYC2 protein (highlighted in bold and with underlining in the comparison above). In some cases the amino acid positions in the endogenous *Solanum tuberosum* MYC protein can vary from those in the corresponding *Arabidopsis thaliana* MYC2 protein by 1-10 positions.

An example of another MYC-related protein is a *Solanum tuberosum* MYC protein, shown below as SEQ ID NO:25, where the JAZ-interacting domain (JID) is shown in bold and with underlining.

```
  1  MTDYRLWSNS NTTNTSDDNM MMDAFLSSDP SSFWPNRTSI
 41  SPTPVNGGVG ETMPFFNQES LQQRLQALID GARESWAYAI
 81  FWQSSSTSDF ATPSVLGWGD GYYKGEENKN KRRASSSSTN
121  EVAEQEHRKK VLRELNSLIS GVQATGAGSG GDDAVDEEVT
161  DTEWFFLISM TQSFANGNGL PGLAMYSSSP IWVTGTEKLA
201  GSQCERARQA QGFGLQTIVC IPSANGVVEL GSTELIFESS
241  DLMNKVKYLF NFNIDMGSVT GSGSGSCAVH PEPDPSALWL
281  TDPSSSVVEA KDSLINSSSR DVQLVFGNEN SENGTQNQQH
321  SQQTQGFFTK ELNFSGYGFD GSSTRNKNGN SSISCKPETR
361  EILNFGDSSK KSGSLFSGQS QFGPGTGLGL MEENKNNNKK
401  RSLASRGNNE KGMLSFVSGV ILPTSTMGKS GGGGNFDHSD
441  LEASVVKEAI VEPERKPRKR GRKPANGREE PLNHVEAERQ
481  RREKLNQRFY ALRAVVPNVS KMDKASLLGD AIAYINELKS
521  KVQNSDLDKE ELRSQIESLR KELANKGSSN YSSSPPSNQD
561  LKIVDMDIDV KVIGWDAMIR IQCSKKNHPA ARLMAALKDL
601  DLDVHHASVS VVNDLMIQQA TVKMGSRLYA QEQLTIALTS
641  KFAESR
```

The JAZ-interacting domain (JID) of the *Solanum tuberosum* MYC protein sequence having SEQ ID NO:25 is shown below as SEQ ID NO:26.

```
 81          F ATPSVLGWGD GYYKGEENKN KRRASSSSTN
121  FVAEQEHRKK VLRELNSLIS GV
```

In some cases, the *Solanum tuberosum* MYC protein with SEQ ID NO:25 can have one or more mutations within the JID, and/or one or more mutations outside of the JID region. Thus modified MYC proteins described herein have less than 100% sequence identity to SEQ ID NO:25 and/or to SEQ ID NO:26.

An example of another MYC-related protein is a *Catharanthus roseus* MYC2 protein, shown below as SEQ ID NO:27, where the JAZ-interacting domain (JID) is shown in bold and with underlining.

```
  1  MTDYRLQPKM NLWGTTTNTA ASPIITSDDN SSMMEAFMTS
 41  SDPISLWPPS MSVNHHHPPT PTSSAVTTAV DSAKSMPAQP
 81  AFFNQENLQQ RLQTLIDGAR ESWTYAIFWQ SSVVEFAGPS
121  VLGWGDGYYK GEEDKGKRKN SSSASSFAEQ EHRKKVLREL
161  NSLIAGPQGT ADDAVDEEVT DTEWFFLISM TQSFVSGSGL
201  PGQALYNSNP VWVTGAGRLA VSHCDRARQA QSFGLQTLVC
241  IPSANGVVEL GSTELIFQSS DLMNKVRILF NFNNIDLGSS
281  SGPWPENDPS SLWLTDPSPS GVGVKEGVNT NNNTSVQGNS
321  IPSGNKQQLV FGNNDNHPTT STLTDHPGAG AVNSYNNSSQ
361  NAQQPQGSFF TRELNFSEYG FERSSVKNGN CKPESGEILN
401  FGGESVTKKN SVSGNGNLFS VQSQFGAGEE NKNKKRPSPV
441  SRGSNDEGML SFTSGVVLPS TGVVKSSGGG GGGDSDHSDL
481  EASVVKEAES SRVVDPEKRP RKRGRKPANG REEPLNHVEA
521  ERQRREKLNQ RFYALRAVVP NVSKMDKASL LGDAISYINE
561  LKAKLQTTET DKDELKNQLD SLKKELASKE SRLLSSPDQD
601  LKSSNKQSVG NLDMDIDVKI IGREAMIRVQ SSKNNHPAAR
641  VMGALKDLDL ELLHASVSVV NDLMIQQNTV RMGSRFYTQE
681  QLRIALTSRI AGNSMRLLV
```

A comparison of the *Catharanthus roseus* MYC2 protein sequence having SEQ ID NO:27 with the MYC2 protein sequence having SEQ ID NO:1 is shown below.

```
54.1% identity in 693 residues overlap; Score: 1363.0; Gap frequency: 10.7%
UserSeq 1   1 MTDYRLQPTMNLW-----------TTDDNASMMEAFMSSSDISTLWPRAST------T
UserSeq 27  1 MTDYRLQPKMNLWGTTTNTAASPITTSDDNSSMMEAFMTSSDPISLWPPSMSVNHHHPPT
              ******** ****        * *** ******* ***   ****            *

UserSeq 1  42 TTTATTETTPTPAMEIPAQ-AGFNQETLQQRLQALIEGTHEGWTYAIFWQPSY-DFSGAS
UserSeq 27 61 PTSSAVTTAVDSAKSMPAQPAFFNQENLQQRLQTLIDGARESWTYAIFWQSSVVEFAGPS
              *    *     *** * **** ****** ** * * ********  *   *

UserSeq 1  100 VLGWGDGYYKGEEDKANPRRRSSSPPFSTPADQEYRKKVLRELNSLISGGVAPSDDAVDE
UserSeq 27 121 VLGWGDGYYGEEDKGKRKNSSSASSF---AEQEHRKKVLRELNSLIAGPQGTADDAVDE
               **************     **   *  ** ************  *       ******
```

-continued

```
UserSeq    1 160 EVTDTEWFFLVSMTQSFACGAGLAGKAFATGNAVWVSGSDQLSGSGCERKQGGVFGMHT
UserSeq 27178 EVTDTEWFFLISMTQSFVSGSGLPGQALYNSNPVWVTGAGRLAVSHCDRARQAQSFGLQT
                 ********** ****** * ** * *   * *** *  *  * * **  *  **   *

UserSeq    1 220 IACIPSANGVVEVGSTEPIRQSSDLINKVRILFNFDG-GAGDLSGLNWNLDPDQ-GENDP
UserSeq 27238 LVCIPSANGVVELGSTELIFQSSDLMNKVRILFNFNNIDLGSSSGPWPENDPSSLWLTDP
                 ********** **** * ***** ********    *  **       **    **

UserSeq    1 278 S---MWINDPIGTPGSNE-PGNGAPSSSSQLFSKSIQFENGSSSTITENPNLDPTPSPVH
UserSeq 27298 SPSGVGVKEGVNTNNNTSVQGNSIPSGNKQQLVFGNNDNHPTTSTLTDHPGAGAVNSYNN
                 *           *      **  **    *                ** *   *    *

UserSeq    1 334 S-QTQNPKFNNTFSRELNES-------TSSSTLVKPRSGEILNFGDEG--KRSSGNPDPS
UserSeq 27358 SSQNAQQPQGSFFTRELNFSEYGFERSSVKNGNCKPESGEILNFGGESVTKKNSVSGNGN
                 * *         * ******       **  ********  *  *

UserSeq    1 384 SYSGQTQE----ENKRKR-----SMVLNEDKVLSF--------------GDKTAGESDH
UserSeq 27418 LFSVQSQFGAGEENKNKKRPSPVSRGSNDEGMLSFTSGVVLPSTGVVKSSGGGGGGDSDH
                  * * **    *** *      *  *   ***              *    *  * ***

UserSeq    1 420 SDLEASVVKE------VAVEKRPKKRGRKPANGREEPLNHVEAERQRREKLNQRFYALRA
UserSeq 27478 SDLEASVVKEAESSRVVDPEKRPRKRGRKPANGREEPLNHVEAERQRREKLNQRFYALRA
                 **********      *  ****  ***********************************

UserSeq    1 474 VVPNVSKMDKASLLGDAIAYINELKSKVVKTESEKLQIKNQLEEVKLELAGRKA---SAS
UserSeq 27538 VVPNVSKMDKASLLGDAISYINELKAKLQTTETDKDELKNQLDSLKKELASKESRLLSSP
                 ****************** ****** *   ** *   **** *   *****   *  *

UserSeq    1 531 GGDM-SSSCSSIKPVGMEIEVKIIGWDAMIRVESSKRNHPAARLMSALMDLELEVNHASM
UserSeq 27598 DQDLKSSNKQVGNLDMDIDVKIIGREAMIRVQSSKNNHPAARVMGALKDLDLELLHASV
                  * **   *    * * ***** ** ****** ***** ****** * *** *** ** ***

UserSeq    1 590 SVVNDLMIQQATVKMGFRIYTQEQLRASLISKI
UserSeq 27658 SVVNDLMIQQNTVRMGSRFYTQEQLRIALTSRI
                 **********  ** ** * ********    *  *  *
```

The JAZ-interacting domain (JID) of the *Catharanthus roseus* MYC2 protein sequence having SEQ ID NO:27 is shown below as SEQ ID NO:28.

```
 81                                              FAGPS
121   VLGWGDGYYK GEEDKGKRKN SSSASSFAEQ EHRKKVLREL
161   NSLIAG
```

In some cases, the *Catharanthus roseus* MYC protein with SEQ ID NO:27 can have one or more mutations within the JID, and/or one or more mutations outside of the JID region. Thus modified MYC proteins described herein have less than 100% sequence identity to SEQ ID NO:27 and/or to SEQ ID NO:28.

For example, such a *Catharanthus roseus* MYC protein with SEQ ID NO:27 can have modifications at positions corresponding to positions 94, 97, 102, 105, 107, 125, 128, 129, 132, 148, 152, 155, 163, 165, 167, 169, 170, and/or 172 from *Arabidopsis thaliana* MYC2 protein (highlighted in bold and with underlining in the comparison above). In some cases the amino acid positions in the endogenous *Catharanthus roseus* MYC protein can vary from those in the corresponding *Arabidopsis thaliana* MYC2 protein by 1-10 positions.

PhyB and Modifications of PhyB to Enhance Growth

Although jasmonate and MYC transcription factors are potent activators of defense responses, the jasmonate hormone is also a potent inhibitor of plant growth. Plants cells in which the jasmonate pathway and MYC transcription factors are activated exhibit slow growth and low yield. For example, treatment of taxus cells with exogenous jasmonate is currently used to boost taxol production, but the downside of such treatment is that such cells stop dividing and growing. Also, plants having the dominant atr2D mutant of MYC3 (a D94N missense mutation in the JAZ-interacting domain (JID)) grow very slowly. Hence even if expression of such MYC3 proteins can relieve repression by JAZ proteins and improve the environmental stress resistance of plants, use of such an atr2D mutation by itself may not be particularly useful.

The PhyB gene encodes a regulatory photoreceptor protein (Phytochrome B (PHYB)) that exists in two forms. The two forms are reversibly interconvertible by light, where a Pr form absorbs maximally in the red region of the spectrum and where a Pfr form absorbs maximally in the far-red region. As described herein phyB gene mutations improve plant growth, for example, in myc mutant plants that have increased resistance to environmental challenges such as insects. Plant cells, plants, and seeds from selected plant species can be modified to have loss-of-function phyB mutations to improve cell growth.

One example of an *Arabidopsis thaliana* phytochrome B (PHYB) protein sequence is shown below (SEQ ID NO:30). The codon encoding the arginine (R) at position 322 that is highlighted (in bold and with underlining) is replaced by a termination signal (TGA) in some of the mutant phyB plant lines described herein that have improved plant growth. This genetic mutation in such a mutant phyB is a C→T substitution, causing the arginine codon (CGA) to become a termination codon (TGA). Hence, mutant phyB plant lines with phyB loss of function mutations (e.g., deletions) exhibit improved plant growth, for example, when present in a mutant jaz genetic background.

```
  1   MVSGVGGSGG GRGGGRGGEE EPSSSHTPNN RRGGEQAQSS
 41   GTKSLRPRSN TESMSKAIQQ YTVDARLHAV FEQSGESGKS
```

```
 81  FDYSQSLKTT TYGSSVPEQQ ITAYLSRIQR GGYIQPFGCM
121  IAVDESSFRI IGYSENAREM LGIMPQSVPT LEKPEILAMG
161  TDVRSLFTSS SSILLERAFV AREITLLNPV WIHSKNTGKP
201  FYAILHRIDV GVVIDLEPAR TEDPALSIAG AVQSQKLAVR
241  AISQLQALPG GDIKLLCDTV VESVRDLTGY DRVMVYKFHE
281  DEHGEVVAES KRDDLEPYIG LHYPATDIPQ ASRFLFKQNR
321  VRMIVDCNAT PVLVVQDDRL TQSMCLVGST LRAPHGCHSQ
361  YMANMGSIAS LAMAVIINGN EDDGSNVASG RSSMRLWGLV
401  VCHHTSSRCI PFPLRYACEF LMQAFGLQLN MELQLALQMS
441  EKRVLRTQTL LCDMLLRDSP AGIVTQSPSI MDLVKCDGAA
481  FLYHGKYYPL GVAPSEVQIK DVVEWLLANH ADSTGLSTDS
521  LGDAGYPGAA ALGDAVCGMA VAYITKRDFL FWFRSHTAKE
561  IKWGGAKHHP EDKDDGQRMH PRSSFQAFLE VVKSRSQPWE
601  TAEMDAIHSL QLILRDSFKE SEAAMNSKVV DGVVQPCRDM
641  AGEQGIDELG AVAREMVPLI ETATVPIFAV DAGGCINGWN
681  AKIAELTGLS VEEAMGKSLV SDLIYKENEA TVNKLLSRAL
721  RGDEEKNVEV KLKTFSPELQ GKAVFVVVNA CSSKDYLNNI
761  VGVCFVGQDV TSQKIVMDKF INIQGDYKAI VHSPNPLIPP
801  IFAADENTCC LEWNMAMEKL TGWSRSEVIG KMIVGEVFGS
841  CCMLKGPDAL TKFMIVLHNA IGGQDTDKFP FPFFDRNGKF
881  VQALLTANKR VSLEGKVIGA FCFLQIPSPE LQQALAVQRR
921  QDTECFTKAK ELAYICQVIK NPLSGMRFAN SLLEATDLNE
961  DQKQLLETSV SCEKQISRIV GDMDLESIED GSFVLKREEF
1001 FLGSVINAIV SQAMFLLRDR GLQLIRDIPE EIKSIEVFGD
1041 QIRIQQLLAE FLLSIIRYAP SQEWVEIHLS QLSKQMADGF
1081 AAIRTEFRMA CPGEGLPPEL VRDMFHSSRW TSPEGLGLSV
1121 CRKILKLMNG EVQYIRESER SYFLIILELP VPRKRPLSTA
1151 SGSGDMMLMM PY
```

A chromosomal DNA sequence for the *Arabidopsis thaliana* phytochrome B (PHYB) protein with SEQ ID NO:30 is shown below as SEQ ID NO:31.

```
   1 CTTCAATTTA TTTTATTGGT TTCTCCACTT ATCTCCGATC
  41 TCAATTCTCC CCATTTTCTT CTTCCTCAAG TTCAAAATTC
  81 TTGAGAATTT AGCTCTAGCA GAATTCGTCT CCGATAACTA
 121 GTGGATGATG ATTCACCCTA AATCCTTCCT TGTCTCAAGG
 161 TAATTCTGAG AAATTTCTCA AATTCAAAAT CAAACGGCAT
 201 GGTTTCCGGA GTCGGGGGTA GTGGCGGTGG CCGTGGCGGT
 241 GGCCGTGGCG GAGAAGAAGA ACCGTCGTCA AGTCACACTC
 281 CTAATAACCG AAGAGGAGGA GAACAAGCTC AATCGTCGGG
 321 AACGAAATCT CTCAGACCAA GAAGCAACAC TGAATCAATG
 361 AGCAAAGCAA TTCAACAGTA CACCGTCGAC GCAAGACTCC
 401 ACGCCGTTTT CGAACAATCC GGCGAATCAG GGAAATCATT
 441 CGACTACTCA CAATCACTCA AAACGACGAC GTACGGTTCC
 481 TCTGTACCTG AGCAACAGAT CACAGCTTAT CTCTCTCGAA
 521 TCCAGCGAGG TGGTTACATT CAGCCTTTCG GATGTATGAT
 561 CGCCGTCGAT GAATCCAGTT TCCGGATCAT CGGTTACAGT
 601 GAAAACGCCA GAGAAATGTT AGGGATTATG CCTCAATCTG
 641 TTCCTACTCT TGAGAAACCT GAGATTCTAG CTATGGGAAC
 681 TGATGTGAGA TCTTTGTTCA CTTCTTCGAG CTCGATTCTA
 721 CTCGAGCGTG CTTTCGTTGC TCGAGAGATT ACCTTGTTAA
 761 ATCCGGTTTG GATCCATTCC AAGAATACTG GTAAACCGTT
 801 TTACGCCATT CTTCATAGGA TTGATGTTGG TGTTGTTATT
 841 GATTTAGAGC CAGCTAGAAC TGAAGATCCT GCGCTTTCTA
 881 TTGCTGGTGC TGTTCAATCG CAGAAACTCG CGGTTCGTGC
 921 GATTTCTCAG TTACAGGCTC TTCCTGGTGG AGATATTAAG
 961 CTTTTGTGTG ACACTGTCGT GGAAAGTGTG AGGGACTTGA
1001 CTGGTTATGA TCGTGTTATG GTTTATAAGT TCATGAAGA
1041 TGAGCATGGA GAAGTTGTAG CTGAGAGTAA ACGAGATGAT
1081 TTAGAGCCTT ATATTGGACT GCATTATCCT GCTACTGATA
1121 TTCCTCAAGC GTCAAGGTTC TTGTTTAAGC AGAACCGTGT
1161 CCGAATGATA GTAGATTGCA ATGCCACACC TGTTCTTGTG
1201 GTCCAGGACG ATAGGCTAAC TCAGTCTATG TGCTTGGTTG
1241 GTTCTACTCT TAGGGCTCCT CATGGTTGTC ACTCTCAGTA
1281 TATGGCTAAC ATGGGATCTA TTGCGTCTTT AGCAATGGCG
1321 GTTATAATCA ATGGAAATGA AGATGATGGG AGCAATGTAG
1361 CTAGTGGAAG AAGCTCGATG AGGCTTTGGG GTTTGGTTGT
1401 TTGCCATCAC ACTTCTTCTC GCTGCATACC GTTTCCGCTA
1441 AGGTATGCTT GTGAGTTTTT GATGCAGGCT TTCGGTTTAC
1481 AGTTAAACAT GGAATTGCAG TTAGCTTTGC AAATGTCAGA
1521 GAAACGCGTT TTGAGAACGC AGACACTGTT ATGTGATATG
1561 CTTCTGCGTG ACTCGCCTGC TGGAATTGTT ACACAGAGTC
1601 CCAGTATCAT GGACTTAGTG AAATGTGACG GTGCAGCATT
1641 TCTTTACCAC GGGAAGTATT ACCCGTTGGG TGTTGCTCCT
1681 AGTGAAGTTC AGATAAAAGA TGTTGTGGAG TGGTTGCTTG
1721 CGAATCATGC GGATTCAACC GGATTAAGCA CTGATAGTTT
1761 AGGCGATGCG GGGTATCCCG GTGCAGCTGC GTTAGGGGAT
1801 GCTGTGTGCG GTATGGCAGT TGCATATATC ACAAAAGAG
1841 ACTTTCTTTT TTGGTTTCGA TCTCACACTG CGAAAGAAAT
1881 CAAATGGGGA GGCGCTAAGC ATCATCCGGA GGATAAAGAT
1921 GATGGGCAAC GAATGCATCC TCGTTCGTCC TTTCAGGCTT
1961 TTCTTGAAGT TGTTAAGAGC CGGAGTCAGC CATGGGAAAC
```

```
2001  TGCGGAAATG GATGCGATTC ACTCGCTCCA GCTTATTCTG
2041  AGAGACTCTT TTAAAGAATC TGAGGCGGCT ATGAACTCTA
2081  AAGTTGTGGA TGGTGTGGTT CAGCCATGTA GGGATATGGC
2121  GGGGGAACAG GGGATTGATG AGTTAGGTGC AGTTGCAAGA
2161  GAGATGGTTA GGCTCATTGA GACTGCAACT GTTCCTATAT
2201  TCGCTGTGGA TGCCGGAGGC TGCATCAATG GATGGAACGC
2241  TAAGATTGCA GAGTTGACAG GTCTCTCAGT TGAAGAAGCT
2281  ATGGGGAAGT CTCTGGTTTC TGATTTAATA TACAAAGAGA
2321  ATGAAGCAAC TGTCAATAAG CTTCTTTCTC GTGCTTTGAG
2361  AGGTATATTC AGTTCTTCAG CTATGTTGTA TCTGCGGTGT
2401  ATATACCAAT TCGCGGGTAT TTGATTATTT TGTTGCATTT
2441  GGCAATGCAG GGGACGAGGA AAAGAATGTG GAGGTTAAGC
2481  TGAAAACTTT CAGCCCCGAA CTACAAGGGA AAGCAGTTTT
2521  TGTGGTTGTG AATGCTTGTT CCAGCAAGGA CTACTTGAAC
2561  AACATTGTCG GCGTTTGTTT TGTTGGACAA GACGTTACTA
2601  GTCAGAAAAT CGTAATGGAT AAGTTCATCA ACATACAAGG
2641  AGATTACAAG GCTATTGTAC ATAGCCCAAA CCCTCTAATC
2681  CCGCCAATTT TTGCTGCTGA CGAGAACACG TGCTGCCTGG
2721  AATGGAACAT GGCGATGGAA AAGCTTACGG GTTGGTCTCG
2761  CAGTGAAGTG ATTGGGAAAA TGATTGTCGG GGAAGTGTTT
2801  GGGAGCTGTT GCATGCTAAA GGGTCCTGAT GCTTTAACCA
2841  AGTTCATGAT TGTATTGCAT AATGCGATTG GTGGCCAAGA
2881  TACGGATAAG TTCCCTTTCC CATTCTTTGA CCGCAATGGG
2921  AAGTTTGTTC AGGCTCTATT GACTGCAAAC AAGCGGGTTA
2961  GCCTCGAGGG AAAGGTTATT GGGGCTTTCT GTTTCTTGCA
3001  AATCCCGAGC CCTGAGCTGC AGCAAGCTTT AGCAGTCCAA
3041  CGGAGGCAGG ACACAGAGTG TTTCACGAAG GCAAAAGAGT
3081  TGGCTTATAT TTGTCAGGTG ATAAAGAATC CTTTGAGCGG
3121  TATGCGTTTC GCAAACTCAT TGTTGGAGGC CACAGACTTG
3161  AACGAGGACC AGAAGCAGTT ACTTGAAACA AGTGTTTCTT
3201  GCGAGAAACA GATCTCAAGG ATCGTCGGGG ACATGGATCT
3241  TGAAAGCATT GAAGACGGGT GAGTATAGTT AGAATTTATC
3281  TAGAAGCTAG TTTTGCTTAC TTCACAAAAT GTGACCAAAT
3321  CCCAAATTTT GTTTTTTTCA TTGATCAGTT CATTTGTGCT
3361  AAAGAGGGAA GAGTTTTTCC TTGGAAGTGT CATAAACGCG
3401  ATTGTAAGTC AAGCGATGTT CTTATTAAGG GACAGAGGTC
3441  TTCAGCTGAT CCGTGACATT CCCGAAGAGA TCAAATCAAT
3481  AGAGGTTTTT GGAGACCAGA TAAGGATTCA ACAGCTCCTG
3521  GCTGAGTTTC TGCTGAGTAT AATCCGGTAT GCACCATCTC
3561  AAGAGTGGGT GGAGATCCAT TTAAGCCAAC TTTCAAAGCA
3601  AATGGCTGAT GGATTCGCCG CCATCCGCAC AGAATTCAGG
3641  TACATTTCAT TGTTCCCGCT GTTGTCTCCA CATATCCATA
3681  ACCAAAATTA TGCAATCCGG TTTTTTTGGT TCCTTATTTT
3721  GTACATAAAG AAAATGAATT TGGTTTGGTT AATTACGAAT
3761  TTGATTTAGG CGTTTAAAGA ATTTGAGGTT TTAACCAATT
3801  CACTATTTGT TTTGGTTATT GTTTAGTTGG AACCTAGATT
3841  AGTTTGATTT TTGTATTCGG TTTAGTCGAC TTGGGAACTT
3881  TTAGACACAT CCATAGGCCT AGAATTAGCA GTCAAGGAAT
3921  GTAATGTTTT CAAATTGATG AAAACCAGCT CAAAAGTGTA
3961  AAACTTGGGT TTCATGTGTT GGTGTCTTTG TTATGTCTTT
4001  ATTCGTTGTT TGCAGAATGG CGTGTCCAGG TGAAGGTCTG
4041  CCTCCAGAGC TAGTCCGAGA CATGTTCCAT AGCAGCAGGT
4081  GGACAAGCCC TGAAGGTTTA GGTCTAAGCG TATGTCGAAA
4121  GATTTTAAAG CTAATGAACG GTGAGGTTCA ATACATCCGA
4161  GAATCAGAAC GGTCCTATTT CCTCATCATT CTGGAACTCC
4201  CTGTACCTCG AAAGCGACCA TTGTCAACTG CTAGTGGAAG
4241  TGGTGACATG ATGCTGATGA TGCCATATTA GTCACACTTC
4281  AGTTGGTATG AGAGTTTGTA TCATTGTATG AGTGTTTGTG
4321  TGTCAACGA CGTCGGAGGA GGATAGAAAG TTTTTTTTTT
4361  GTTTCCGGTG AGATTAGTAG AGAAGAGGGA GATTATTTGC
4401  GTTCAGCTCA GCTCGCCGGA AAAAAACGT AACAGTAGTT
4441  GTAGAGAATT TCAAGACTTT TGTTTGTGCT GTGTAAATTG
4481  ACAACTCCGA GAGAAACAAA ACAATGAGAT AAGAAGAGAG
4081  CATATTAATC GATGACCAAT CCTTTTAATT
```

Chromosomal sequences that encode phytochrome B and/or phytochrome B-related polypeptides from many plant types and species can be modified to reduce or eliminate the expression and/or function of the encoded polypeptide. For example, chromosomal sequences encoding phytochrome B and/or phytochrome B-related polypeptides from agriculturally important plants such as alfalfa (e.g., forage legume alfalfa), algae, avocado, barley, broccoli, Brussels sprouts, cabbage, canola, cassava, cauliflower, cole vegetables, collards, corn, crucifers, grain legumes, grasses (e.g., forage grasses), jatropa, kale, kohlrabi, maize, miscanthus, mustards, nut sedge, oats, oil firewood trees, oilseeds, potato, radish, rape, rapeseed, rice, rutabaga, sorghum, soybean, sugar beets, sugarcane, sunflower, switchgrass, tobacco, tomato, turnips, and/or wheat can be modified reduce or eliminate the expression and/or function of one or more encoded phytochrome B and/or phytochrome B-related polypeptides.

In some cases, more than one gene or chromosomal segment encoding a phytochrome B and/or phytochrome B-related polypeptide can be modified to reduce or eliminate the expression and/or function of the encoded protein(s).

The following are examples of "phytochrome B-related" proteins and nucleic acids that can be modified to reduce or eliminate the expression and/or function thereof, and thereby generate plants with improved growth.

An uncharacterized *Zea mays* protein referred to as LOC100383702 (NCBI accession no. NP_001169810.1 (GI: 293335473) has significant sequence identity to the *Arabi-* dopsis thaliana PHYB protein with SEQ ID NO:30, as illustrated by the sequence comparison shown below. Domains of sequence homology are identified by asterisks below the sequence comparisons.

```
73.1% identity in 1139 residues overlap; Score: 4271.0; Gap frequency: 0.9%
Seq 30    22 PSSSHTPNNRRGGEQAQSSGTKSLRPRSNTESMSKAIQQYTVDARLHAVFEQSGESGKSF
Seq 32    18 PEAPRHAHHHHSQSSGGSTSRAGGGAAATESVSKAVAQYTLDARLHAVFEQSGASGRSF
                      *                    *       *** ***   *** ************ **
              **

Seq 30    82 DYSQSLKTTTYGSSVPEQQITAYLSRIQRGGYIQPFGCMIAV-
             DESSFRIIGYSENAPEM
Seq 32    78 DYSQSLRAPPTPSS--
             EQQIAAYLSRIQRGGHIQPFGCTLAVADDSSFRLLAFSENSPDL
              ******       **  **** **********  ******  ** * ****   ***

Seq 30   141 LGIMPQ-SVPTLEK--
             PEILAMGTDVRSLFTSSSSILLERAFVAREITLLNPVWIHSKNT
Seq 32   136 LDLSPHHSVPSLDSSAPPHVSLGADARLLFSPSSAVLLERAFAAREISLLNPIWIHSRVS
                 *   *     *          *  *  **  **  ******* **** **** ****

Seq 30   198 GKPFYAILHRIDVGVVIDLEPARTEDPALSIAGAVQSQKLAVRAISQLQALPGGDIKLLC
Seq 32   196 SKPFYAILHRIDVGVVIDLEPARTEDPALSIAGAVQSQKLAVRAISRLQALPGGDVKLLC
              ************************************************** ********
             ****

Seq 30   258 DTVVESVRDLTGYDRVMVYKFHEDEHGEVVAESKRDDLEPYIGLHYPATDIPQASRFLFK
Seq 32   256 DTVVEHVRELTGYDRVMVYRFHEDEHGEVVAESRRDNLEPYLGLHYPATDIPQASRFLFR
              *****  ** ********** ************ *** **** ****** *****************

Seq 30   318 QNRVRMIVDCNATPVLVVQDDRLTQSMCLVGSTLRAPHGCHSQYMANMGSIASLAMAVII
Seq 32   316 QNRVRMIADCHATPVRVIQDPGLSQPLCLVGSTLRAPHGCHAQYMANMGSIASLVMAVII
              ******* ** **** * **   *  * ************** ************ ************
             *****

Seq 30   378 NGNEDDGSNVASGRSS-
             MRLWGLVVCHHTSSRCIPFPLRYACEFLMQAFGLQLNMELQLA
Seq 32   376 SSGGDDEQTGRGGISSAMKLWGLVVCHHTSPRCIPFPLRYACEFLMQAFGLQLNMELQLA
                 **        *  **  * ***********
             ****************************

Seq 30   437 LQMSEKRVLRTQTLLCDMLLRDSPAGIVTQSPSIMDLVKCDGAAFLYHGKYYPLGVAPSE
Seq 32   436 HQLSEKHILRTQTLLCDMLLRDSPTGIVTQSPSIMDLVKCDGAALYYHGKYYPLGVTPTE
               * *** ******************* ******************** ********** **

Seq 30   497 VQIKDVVEWLLANHADSTGLSTDSLGDAGYPGAAALGDAVCGMAVAYITKRDFLFWFRSH
Seq 32   496 SQIKDIIEWLTVFHGDSTGLSTDSLADAGYLGAAALGEAVCGMAVAYITPSDYLFWFRSH
               ****  ****    *  **********  ****  ******  ************ *
             *******

Seq 30   557 TAKEIKWGGAKHHPEDKDDGQRMHPRSSFQAFLEVVKSRSQPWETAEMDAIHSLQLILRD
Seq 32   556 TAKEIKWGGAKHHPEDKDDGQRMHPRSSFKAFLEVVKSRSLPWENAEMDAIHSLQLILRD
              ****************************  *********** *** ************ ***
             ***************

Seq 30   617 SFKES-
             EAAMNSKVVDGVVQPCRDMAGEQGIDELGAVAREMVRLIETATVPIFAVDAGGC
Seq 32   616 SFRDAAEGTNNSKAIVNGQVQLRELE-
             LRGINELSSVAREMVRLIETATVPIFAVDTDGC
                 **   *  ***        *       **  ** *******************
              **
```

```
Seq 30   676
INGWNAKIAELTGLSVEEAMGKSLVSDLIYKENEATVNKLLSRALRGDEEKNVEVKLKTF
Seq 32   675
INGWNAKIAELTGLSVEEAMGKSLVNDLIFKESEATVEKLLSRALRGEEDKNVEIKLKTF
         ************************ *** ** **** ********* * ****
*****

Seq 30   736
SPELQGKAVFVVVNACSSKDYLNNIVGVCFVGQDVTSQKIVMDKFINIQGDYKAIVHSPN
Seq 32   735
GSEQSKGPIFVVVNACSSRDYTQNIVGVCFVGQDVTGQKVVMDKFVNIQGDYKAIVHNPN
            *   ********* **  ************* ** ***** ***********
**

Seq 30   796
PLIPPIFAADENTCCLEWNMAMEKLTGWSRSEVIGKMIVGEVFGSCCMLKGPDALTKFMI
Seq 32   795
PLIPPIFASDENTSCSEWNTAMEKLTGWSRGEVVGKFLIGEVFGNCCRLKGPDALTKFMV
******** **** * *** ********** ** **     ***** ** ***********

Seq 30   856
VLHNAIGGQDTDKFPFPFFDRNGKFVQALLTANKRVSLEGKVIGAFCFLQIPSPELQQAL
Seq 32   855
IIHNAIGGQDYEKFPFSFFDKNGKYVQALLTANTRSKMDGKSIGAFCFLQIASTEIQQAF
 ********   **** *** *** ******** *    ** ********* *  * ***

Seq 30   916
AVQRRQTECFTKAKELAYICQVIKNPLSGMRFANSLLEATDLNEDQKQLLETSVSCEKQ
Seq 32   915
EIQRQQEKKCYARMKELAYICQEIKNPLSGIRFTNSLLQMTDLNDDQRQFLETSSACEKQ
  ** *   *    ******** ******* ** **** ****  ** * **** * ****
****

Seq 30   976
ISRIVGDMDLESIEDGSFVLKREEFFLGSVINAIVSQAMFLLRDRGLQLIRDIPEEIKSI
Seq 32   975
MSKIVKDASLQSIEDGSLVLEQSEFSLGDVMNAVVSQAMLLLRERDLQLIRDIPDEIKDA
  * *  *  * ****** **   ** ** * **** *****  * ******** ***

Seq 30  1036 EVFGDQIRIQQLLAEFLLSIIRYAPSQE-
WVEIHLSQLSKQMADGFAAIRTEFRMACPGE
Seq 32  1035
SAYGDQCRIQQVLADFLLSMVRSAPSENGWVEIQVRPNVKQNSDGTNTELFIFRFACPGE
    ***  **** ** **** **  * ****   **  * ***       **  *****
*****

Seq 30  1095
GLPPELVRDMFHSSRWTSPEGLGLSVCRKILKLMNGEVQIRESERSYFLIILELPVPR
Seq 32  1095
GLPADVVQDMFSNSWSTQEGVGLSTCRKILKLMGGEVQYIRESERSFFLIVLEQPQPR
*** *  *** *   ** ** *** ******** ****  ****** *** ** * *
**
```

This PHYB-related *Zea mays* protein referred to as LOC100383702 (NCBI accession no. NP_001169810.1 (GI: 293335473) has the following sequence (SEQ ID NO:32).

```
  1   MASGSRATPT RSPSSARPEA PRHAHHHHHS QSSGGSTSRA
 41   GGGAAATESV SKAVAQYTLD ARLHAVFEQS GASGRSFDYS
 81   QSLRAPPTPS SEQQIAAYLS RIQRGGHIQP FGCTLAVADD
121   SSFRLLAFSE NSPDLLDLSP HHSVPSLDSS APPHVSLGAD
161   ARLLFSPSSA VLLERAFAAR EISLLNPIWI HSRVSSKPFY
201   AILHRIDVGV VIDLEPARTE DPALSIAGAV QSQKLAVRAI
241   SRLQALPGGD VKLLCDTVVE HVRELTGYDR VMVYRFHEDE
281   HGEVVAESRR DNLEPYLGLH YPATDIPQAS RFLFRQNRVR
321   MIADCHATPV RVIQDPGLSQ PLCLVGSTLR APHGCHAQYM
361   ANMGSIASLV MAVIISSGGD DEQTGRGGIS SAMKLWGLVV
401   CHHTSPRCIP FPLRYACEFL MQAFGLQLNM ELQAHQLSE
441   KHILRTQTLL CDMLLRDSPT GIVTQSPSIM DLVKCDGAAL
481   YYHGKYYPLG VTPTESQIKD IIEWLTVFHG DSTGLSTDSL
521   ADAGYLGAAA LGEAVCGMAV AYITPSDYLF WFRSHTAKEI
561   KWGGAKHHPE DKDDGQRMHP RSSFKAFLEV VKSRSLPWEN
601   AEMDAIHSLQ LILRDSFRDA AEGTNNSKAI VNGQVQLREL
641   ELRGINELSS VAREMVRLIE TATVPIFAVD TDGCINGWNA
681   KIAELTGLSV EEAMGKSLVN DLIFKESEAT VEKLLSRALR
721   GEEDKNVEIK LKTFGSEQSK GPIFVVVNAC SSRDYTQNIV
761   GVCFVGQDVT GQKVVMDKFV NIQGDYKAIV HNPNPLIPPI
801   FASDENTSCS EWNTAMEKLT GWSRGEVVGK FLIGEVFGNC
841   CRLKGPDALT KFMVIIHNAI GGQDYEKFPF SFFDKNGKYV
881   QALLTANTRS KMDGKSIGAF CFLQIASTEI QQAFEIQRQQ
```

```
 921   EKKCYARMKE LAYICQEIKN PLSGIRFTNS LLQMTDLNDD

961   QRQFLETSSA CEKQMSKIVK DASLQSIEDG SLVLEQSEFS

1001   LGDVMNAVVS QAMLLLRERD LQLIRDIPDE IKDASAYGDQ

1041   CRIQQVLADF LLSMVRSAPS ENGWVEIQVR PNVKQNSDGT

1081   NTELFIFRFA CPGEGLPADV VQDMFSNSQW STQEGVGLST

1121   CRKILKLMGG EVQYIRESER SFFLIVLEQP QPRPAAGREI

1161   V
```

A codon encoding the arginine at position 320 of the SEQ ID NO:32 protein is equivalent to the codon encoding the arginine at position 322 of the SEQ ID NO:30 protein; a mutant phyB with a sequence encoding the first 319 amino acids of SEQ ID NO:32 can have a C→T substitution, causing the arginine codon (CGA) at position 320 to become a termination codon (TGA).

A cDNA encoding the SEQ ID NO:32 protein is available as NCBI accession number NM_001176339.1 (GI: 293335472), and a chromosomal segment encoding the SEQ ID NO:32 protein is on *Zea mays* chromosome 1 at NC_024459.1 (50023180.50034310), sequence available as NCBI accession number NC_024459.1 (GI:662250330).

A *Zea mays* protein referred to as phytochromeB1 (NCBI accession no. DAA45039.1 (GI:414866482) has significant sequence identity to the *Arabidopsis thaliana* PHYB protein with SEQ ID NO:30, as illustrated by the sequence comparison shown below. Domains of sequence homology are identified by asterisks below the sequence comparison.

```
73.1% identity in 1139 residues overlap; Score: 4270.0; Gap frequency: 0.9%
Seq 30    22
PSSSHTPNNRRGGEQAQSSGTKSLRPRSNTESMSKAIQQYTVDARLHAVFEQSGESGKSF
Seq 33    18
PEAPRHAHHHHHSQSSGGSTSRAGGGAAATESVSKAVAQYTLDARLHAVFEQSGASGRSF
              *                  *      *** ***  *** ************ **
**

Seq 30    82 DYSQSLKTTTYGSSVPEQQITAYLSRIQRGGYIQPFGCMIAV-
DESSFRIIGYSENAPEM
Seq 33    78 DYSQSLRAPPTPSS--
EQQIAAYLSRIQRGGHIQPFGCTLAVADDSSFRLLAFSENSPDL
                ******         **  **** **********  ******   *  * ****    ***

Seq 30   141 LGIMPQ-SVPTLEK--
PEILAMGTDVRSLFTSSSSILLERAFVAREITLLNPVWIHSKNT
Seq 33   136
LDLSPHHSVPSLDSSAPPHVSLGALARLLFSPSSAVLLERAFAAREISLLNPIWIHSRVS
                *   *  *** *     *     * *  * **  **  ****** **** **** ****

Seq 30   198
GKPFYAILHRIDVGVVIDLEPARTEDPALSIAGAVQSQKLAVRAISQLQALPGGDIKLLC
Seq 33   196
SKPFYAILHRIDVGVVIDLEPARTEDPALSIAGAVQSQKLAVRAISRLQALPGGDVKLLC
                 **********************************************  ********
****

Seq 30   258
DTVVESVRDLTGYDRVMVYKFHEDEHGEVVAESKRDDLEPYIGLHYPATDIPQASRFLFK
Seq 33   256
DTVVEHVRELTGYDRVMVYRFHEDEHGEVVAESRRDNLEPYLGLHYPATDIPQASRFLFR
                *****  ** ********** **************  ** **** ******************

Seq 30   318
QNRVRMIVDCNATPVLVVQDDRLTQSMCLVGSTLRAPHGCHSQYMANMGSIASLAMAVII
Seq 33   316
QNPVRMIADCHATPVRVIQDPGLSQPLCLVGSTLRAPHGCHAQYMANMGSIASLVMAVII
                ** *****  ** ****  *   *  *   ** *************** ************* ******
*****

Seq 30   378 NGNEDDGSNVASGRSS-
MRLWGLVVCHHTSSRCIPFPLRYACEFLMQAFGLQLNMELQLA
Seq 33   376
SSGGDDEQTGRGGISSAMKLWGLVVCHHTSPRCIPFPLPYACEFLMQAFGLQLNMELQLA
                     **       *  **  *  ***********
*****************************

Seq 30   437
LQMSEKRVLRTQTLLCDMLLRDSPAGIVTQSPSIMDLVKCDGAAFLYHGKYYPLGVAPSE
Seq 33   436
HQLSEKHILRTQTLLCDMLLRDSPTGIVTQSPSIMDLVKCDGAALYYHGKYYPLGVTPTE
                * ***  ***************** ******************** ********** **

Seq 30   497
VQIKDVVEWLLANHADSTGLSTDSLGDAGYPGAAALGDAVCGMAVAYITKRDFLFWFRSH
Seq 33   496
SQIKDIIEWLTVFHGDSTGLSTDSLADAGYLGAAALGEAVCGMAVAYITPSDYIFWFRSH
                 ****  ****    * ********  ****  ****** ****************      *   *******
*******
```

-continued

```
Seq 30   557
TAKEIKWGGAKHHPEDKDDGQRMHPRSSFQAFLEVVKSRSQPWETAEMDAIHSLQLILRD
Seq 33   556
TAKEIKWGGAKHHPEDKDDGQRMHPRSSFKAFLEVVKSRSLPWENAEMDAIHSLQLILRD
         ******************************* ********** ***
***************

Seq 30   617 SFKES-
EAAMNSKVVDGVVQPCRDMAGEQGIDELGAVAREMVRLIETATVPIFAVDAGGC
Seq 33   616 SFRDAAEGTNNSKAIVNGQVQLRELE-
LRGINELSSVAREMVRLIETATVPIFAVDTDGC
             **    *   ***       *     ** ** ******************
**

Seq 30   676
INGTRNAKIAELTGLSVEEAMGKSLVSDLIYKENEATVNKLLSRALRGDEEKNVEVKLKTF
Seq 33   675
INGWNAKIAELTGLSVEEAMGKSLYNDLIFKESEATVEKLLSRALRGEEDKNVEIKLKTF
         *** ******************* *** ** **** ********* * ****
*****

Seq 30   736
SPELQGKAVFVVVNACSSKDYLNNIVGVCFVDQDVTSQKLIVMDKFINIQGDYKAIVHSPN
Seq 33   735
GSEQYKGPIFVVVNACSSRDYTQNIVGVCFVGQDVTGQKVVMDKFVNIQGDYKAIVHNPN
           *       ********* **  ************* **** ***** ***********
**

Seq 30   796
PLIPPIFAADENTCCLEWNMAMEKLTGWSRSEVIGKMIVGEVFGSCCMLKGPDALTKFMI
Seq 33   795
PLIPPIFASDENTSCSEWNTAMEKLTGWSRGEVVGKFLIGEVFGNCCRLKGPDALTKFMV
         ******** **** * *** ********** ** **    ***** ** ***********

Seq 30   856
VLHNAIGGQDTDKFPFPFFDRNGKFVQALLTANKRVSLEGKVIGAFCFLQIPSPELQQAL
Seq 33   855
IIHNAIGGQYEKFPFSFFDKNGKYVQALLTANTRSKMDGKSIGAFCFLQTASTEIQQAF
          ******** **** *** *** ******** *    ** ********* * * ***

Seq 30   916
AVQRRQTECFTKAKELAYICQVIKNPLSGMRFANSLLEATDLNEDQKQLLETSVSCEKQ
Seq 33   915
EIQRQQEKKCYARMKELAYICQEIKNPLSGIRFTNSLLQMTDLNDDQRQFLETSSACEKQ
          ** *    *      ******* ******* *** **** **** ** * ****
****

Seq 30   976
ISRIVGDMDLESIEDGSFVLKREEFFLGSVINAIVSQAMFLLPDRGLQLIRDIPEEIKSI
Seq 33   975
MSKIVKDASLQSIEDGSLVLEQEFSLGDVMNAVVSQAMLLLRERDLQLIRDIPDEIKDA
          * *  *   * ******  ** * *  * ** ***** ** * * ******** ***

Seq 30   1036 EVFGQIRIQQLLAEFLLSIIRYAPSQE-
WVEIHLSQLSKQMADGFAAIRTEFRMACPGE
Seq 33   1035
SAYGDQCRIQQVIADFLLSMVRSAPSENGWVEIQVRPNVYQNSDGTNTELFIFRFACPGE
             ***  **  ** **** * **** * ***      **  **       ** ** ** **
*****

Seq 30   1095
GLPPELVRDMFHSSRWTSPEGLGLSVCRKILKLMNGEVQYIRESERSYFLIILELPVPR
Seq 33   1095
GLPADVVQDMFSNSQWSTQEGVGLSTCRKILKLMGGEVQYIRESERSFFLIVLEQPQPR
         ***   * *** *  *** ** *** ******** *********** *** ** * *
**
```

This PHYB-related *Zea mays* protein referred to as phytochromeB1 (NCBI accession no. DAA45039.1 (GI: 414866482) has the following sequence (SEQ ID NO:33).

```
  1   MASGSRATPT RSPSSARPEA PRHAHHHHHS QSSGGSTSRA
 41   GGGAAATESV SKAVAQYTLD ARLHAVFEQS GASGRSFDYS
 81   QSLRAPPTPS SEQQIAAYLS RIQRGGHIQP FGCTLAVADD
121   SSFRLLAFSE NSPDLLDLSP HESVPSLDSS APPHVSLGAD
161   ARLLFSPSSA VLLERAFAAR EISLLNPIWI HSRVSSKPFY
201   AILHRIDVGV VIDLEPARTE DPALSIAGAV QSQKLAVRAI
241   SRLQALPGGD VKLLCDTVVE AVRELTGYDR VMVYRFHEDE
281   HGEVVAESRR DNLEPYLGLH YPATDIPQAS RFLFRQNRVR
321   MIADCHATPV RVIQDPGLSQ PLCLVGSTLR APHGCHAQYM
```

```
361  ANMGSIASLV MAVIISSGGD DEQTGRGGIS SAMKLWGLVV
401  CHHTSPRCIP FPLRYACEFL MQAFGLQLNM ELQLAHQLSE
441  KHILRTQTLL CDMLLRDSPT GIVTQSPSIM DLVKCDGAAL
481  YYHGKYYPLG VTPTESQIKD IIEWLTVFHG DSTGLSTDSL
521  ADAGYLGAAA LGEAVCGMAV AYITPSDYLF WFRSHTAKEI
561  KWGGAKHHPE DKDDGQRMHP RSSFKAFLEV VKSRSLPWEN
601  AEMDAIHSLQ LILRDSFRDA AEGTNNSKAI VNGQVQLREL
641  ELRGINELSS VAREMVRLIE TATVPIFAVD TDGCINGWNA
681  KIAELTGLSV EEAMGKSLVN DLIFKESEAT VEKLLSRALR
721  GEEDKNVEIK LKTFGSEQYK GPIFVVVNAC SSRDYTQNIV
761  GVCFVGQDVT GQKVVMDKFV NIQGDYKALV HNPNPLIPPI
801  FASDENTSCS EWNTAMEKLT GWSRGEVVGK FLIGEVFGNC
841  CRLKGPDALT KFMVIIHNAI GGQDYEKFPF SFFDKNGKYV
881  QALLTANTRS KMDGKSIGAF CFLQIASTEI QQAFEIQRQQ
921  EKKCYARMKE LAYICQEIKN PLSGIRFTNS LLQMTDLNDD
961  QRQFLETSSA CERQMSKIVK DASLQSIEDG SLVLEQSEFS
1001 LGDVMNAVVS QAMLLLRERD LQLIRDIPDE IKDASAYGDQ
1041 CRIQQVLADF LLSMVRSAPS ENGWVEIQVR PNVKQNSDGT
1081 NTELFIFRFA CPGEGLPADV VQDMFSNSQW STQEGVGLST
1121 CRKILKLMGG EVQYIRESER SFFLIVLEQP QPRPAAGREI
1161 V
```

A codon encoding the arginine at position 320 of the SEQ ID NO:33 protein is equivalent to the codon encoding the arginine at position 322 of the SEQ ID NO:30 protein. A codon encoding the arginine at position 320 of the SEQ ID NO:33 protein can be changed to a termination codon. Hence, the PHYB-related *Zea mays* protein referred to as phytochromeB1 (NCBI accession no. DAA45039.1 (GI: 414866482) with sequence SEQ ID NO:33) can be inactivated in a manner similar to the PhyB loci described above.

A chromosomal segment encoding the SEQ ID NO:33 protein is on *Zea mays* chromosome 1 at NC_024459.1 (50023180.50034310), sequence available as NCBI accession number NC_024459.1 (GI:662250330).

A *Zea mays* referred to as phytochromeB2 (NCBI accession no. NP_001168077.1 (GI:293336623) has significant sequence identity to the *Arabidopsis thaliana* PHYB protein with SEQ ID NO:30, as illustrated by the sequence comparison shown below. Domains of sequence homology are identified with asterisks below the sequence comparison.

```
72.3% identity in 1135 residues overlap; Score: 4203.0; Gap frequency: 0.9%
Seq 30    26
HTPNNRRGGEQAQSSGTKSLRPRSNTESMSKAIQQTVDARLHAVFEQSGESGKSFDYSQ
Seq 34    24
HHHSQSSGGSTSRAGAGGGGGGAAATESVSKAVAQYNLDARLHAVFEQSGASGRSFDYSQ
          *      **                ***  ***   **  ************  **
******

Seq 30    86 SLKTTTYGSSVPEQQITAYLSRIQRGGYIQPFGCMIAV-
DESSFRIIGYSENAREMLGIM
Seq 34    84 SLRAPPTPSS--
EQQIAAYLSRIQRGGHIQPLGCTLAVADDSSFRLLAFSENAADLLDLS
             **        **  **** **********  ***  ** **  *  ****      ****   *

Seq 30    145 PQ-SVPTLEKPEI--
LAMGTDVRSLFTSSSSILLERAFVAREITLLNPVWIHSKNTGKPF
Seq 34    142
PHHSVPSLDSVALPPVSLGADARLYFSPSSAVLLERAFAAREISLLNPLWIHSRASSKPF
              *   *** *                 * *  *  * **  ****** **** **** ****
***

Seq 30    202
YAILHRIDVGVVIDLEPARTEDPALSIAGAVQSQKLAVRAISQLQALPGGDIKLLCDTVV
Seq 34    202
YAILHRIDVGVVIDLEPARTEDPALSIAGAVQSQLAVPAISRLQALPGGDVKLLCDTVV
              *********************************************  ********
********

Seq 30    262
ESVRDLTGYDRVMVYKFHEDEHGEVVAESKRDDLEPYIGLHYPATDIPQASRFLFKQNRV
Seq 34    262
EHVRELTGYDRVMVYKFHEDEHGEVVAESRRDNLEPYLGLHYPATDIPQASRFLFQQNRV
              * ** ************************ ** ****  *******************
****

Seq 30    322 RMIVDCNATPVLVVQDDRLTQSMCLVGSTLRAPHGCHSQMANMGSIASLAMAVIIN-
GN
Seq 34    322
RMIADCHAIPVRVIQDPGLSQQLCLVGSTLRAPHGCHAQYMANMGSIASLVMAVIISSGG
              *** **  * ** ** *  *   ************** *  *********** ****** *
```

-continued

```
Seq 30  381
EDDGSNVASGRSSMRLWGLVVCHHTSSRCIPFPLRYACEFLMQAFGLQLNMELQLALQMS
Seq 34  382
DDERTGRGAISSSMKLWGLVVCHHTSPRCIPFPLRYACEFLMQAFGLQLNMELQAHQLS
          *   *** ********** ************************ **

Seq 30  441
EKRVLRTQTLLCDMLLRDSPAGIVTQSPSIMDLVKCDGAAFLYHGKYYPLGVAPSEVQIK
Seq 34  442
EKHILRTQTLLCDMLLRDSPAGIITQSPSVMDLVKCDGAALYYRGKYYPLGVTPTESQIK
  ** ****************** ***** **********  ********* *  *
***

Seq 30  501
DVVEWLLANHADSTGLSTDSLGDAGYPGAAALGDAVCGMAVAYITKRDELFWFRSHTAKE
Seq 34  502
DIIEWLTVCHGDSTGLSTDSLADAGYLGAVALGDAVCGMAVAYITPSDYLFWFRSHTAKE
 *  ***   * ********* **** ** ************** *  ********** *
**********

Seq 30  561
IKWGGAKHHPEDKDDGQRMHPRSSFQAFLEVVKSRSQPWETAEMDAIHSLQLILRDSFKE
Seq 34  562
IKWGGAKHHPEDKDDGQRMHPRSSFKAFLEVVKSRSLSWENAEMDAIHSLQLILRDSFRD
************************ ********** ** ****************

Seq 30  621 S-
EAAMNSKVVDGVVQPCRDMAGEQGIDELGAVAREMVRLIETATVPIFAVDAGGCINGW
Seq 34  622 AAEGTSNSKAIVNGQRQLGELE-
LRGINELSSVAREMVRLIETATVPIFAVDTDGCINGW
              *   ***              ** **  *******************
******

Seq 30  680
NAKIAELTGLSVEEAMGKSLVSDLIYKENEATVNKLLSRALRGDEEKNVEVKLKTFSPEL
Seq 34  681
NAKIAELTGLSVEEAMGKSLVNDLIFKECDDIVEKLLSRALRGEEDKNVEIKLKTFGSEQ
********************* *** ***    ********* *  *****  *****  *

Seq 30  740
QGKAVFVVVNACSSKDYLNNIVGVCFVGQDVTSQKIVMDKFINIQGDYKAIVHSPNPLIP
Seq 34  741
SKGAIFVIVNACSSRDYTQNIVGVCFVGQDVTGQKVVMDKFINIQGDYKAIVHNPNPLLP
  ** ****** ** **  ************ ** *****************  **** *

Seq 30  800
PIFAADENTCCLEWNMMEKLTGWSRSEVIGKMIVGEVFGSCCMLKGPDALTKFMIVLHN
Seq 34  801
PIFASDENTSCSEWNTAMEKLTGWSREEVVGKFLIGEVFGNCCRLKGPDALTKFMVVIHN
****  **** * *   *********  ** **   *****  *  *********** *
**

Seq 30  860
AIGGQDTDKFPFPFFDRNGKFVQALLTANKRVSLEGKVIGAFCFLQIPSPELQQALAVQR
Seq 34  861
AIEGHDSEKFPFSFFDKNGKYWALLTANTRSKMDGKSIGAFCFLQIASAEIQQAFEIQR
** *  * **** *** *** **** *** * * ** ******** *  ****   **
**

Seq 30  920
RQDTECFTKAKELAYICQVIKNPLSGMRFANSLLEATDLNEDQKQLLETSVSCEKQISRI
Seq 34  921
QQEKKCYARMKELAYICQEIKNPLSGIRFTNSLLQMTDLNDDQRQFLETSSACEKQMSKI
  *   *   ******** ****** ** **** ***** ** *  **** *****  *

Seq 30  980
VGDMDLESIEDGSFVLKREEFFLGSVINAIVSQAMFLLRDRGLQLIRDIPEEIKSIEVFG
Seq 34  981
VKDASLKSIEDGSLVLEKSEFSLGDVMNAVVSQTMSLLRERDLQLIRDIPDEIKDASAYG
*  *    ****** ** *  ** *  ** *** *  *** ********* ***    *

Seq 30  1040 DQIRIQQLLAEFLLSIIPYAPSQE-
WVEIHLSQLSKQMADGFAAIRTEFRMACPGEGLPP
Seq 34  1041
DQFRIQQVLADFLLSMAQSAPSENGWVEIQVRPNVKQNYDGTDTELFIFRFACPGEGLPA
  ** **** ** **      ***   ****       *   *          ** ** 
********

Seq 30  1099 ELVRDMFHSSRWTSPEGLGLSVCRKILKLMNGEVQYIRESERSYFLIILELPVPR
Seq 34  1101 DIVQDMFSNSQWSTQEGVGLSTCRKILKLMGGEVQYIRESERSFFLIVLELPQPR
       * ***  *  **  ** *** ************ ************* *** ****  **
```

This PHYB-related *Zea mays* protein referred to as phytochromeB2 (NCBI accession no. NP_001168077.1 (GI: 293336623) has the following sequence (SEQ ID NO:34).

```
   1  MASDSRPPKR SPSARRVAPR AAEEHHSQSS GGSTSRAGAG
  41  GGGGGAAATE SVSKAVAQYN LDARLHAVFE QSGASGRSFD
  81  YSQSLRAPPT PSSEQQIAAY LSRIQRGGHI QPLGCTLAVA
 121  DDSSFRLLAF SENAADLLDL SPHHSVPSLD SVALPPVSLG
 161  ADARLYFSPS SAVLLERAFA AREISLLNPL WIHSRASSKP
 201  FYAILHRIDV GVVIDLEPAR TEDPALSIAG AVQSQKLAVR
 241  AISRLQALPG GDVKLLCDTV VEHVRELTGY DRVMVYKFHE
 281  DEHGEVVAES RRDNLEPYLG LHYPATDIPQ ASRFLFQQNR
 321  VRMIADCHAI PVRVIQDPGL SQQLCLVGST LRAPHGCHAQ
 361  YMANMGSIAS LVMAVIISSG GDDERTGRGA ISSSMKLWGL
 401  VVCHHTSPRC IPFPLRYACE FLMQAFGLQL NMELQLAHQL
 441  SEKHILRTQT LLCDMLLRDS PAGIITQSPS VMDLVKCDGA
 481  ALYYRGKYYP LGVTPTESQI KDIIEWLTVC HGDSTGLSTD
 521  SLADAGYLGA VALGDAVCGM AVAYITPSDY LFWFRSHTAK
 561  EIKWGGAKHE PEDKDDGQRM HPRSSFKAFL EVVKSRSLSW
 601  ENAEMDAIHS LQLILRDSFR DAAEGTSNSK AIVNGQRQLG
 641  ELELRGINEL SSVAREMVRL IETATVPIFA VDTDGCINGW
 681  NAKIAELTGL SVEEAMGKSL VNDLIFKECD DIVEKLLSRA
 721  LRGEEDKNVE IKLKTFGSEQ SKGAIFVIVN ACSSRDYTQN
 761  IVGVCFVGQD VTGQKVVMDK FINIQGDYKA IVHNPNPLLP
 801  PIFASDENTS CSEWNTAMEK LTGWSREEVV GKFLIGEVFG
 841  NCCRLKGPDA LTKFMVVIHN AIEGHDSEKF PFSFFDKNGK
 881  YVQALLTANT RSKMDGKSIG AFCFLQIASA EIQQAFEIQR
 921  QQEKKCYARM KELAYICQEI KNPLSGIRFT NSLLQMTDLN
 961  DDQRQFLETS SACEKQMSKI VKDASLKSIE DGSLVLEKSE
1001  FSLGDVMNAV VSQTMSLLRE RDLQLIRDIP DEIKDASAYG
1041  DQFRIQQVLA DFLLSMAQSA PSENGWVEIQ VRPNVKQNYD
1081  GTDTELFIFR FACPGEGLPA DIVQDMFSNS QWSTQEGVGL
1121  STCRKILKLM GGEVQYIRES ERSFFLIVLE LPQPRLAAGR
1161  ENQLIC
```

A codon encoding the arginine at position 322 of the SEQ ID NO:34 protein is equivalent to the codon encoding the arginine at position 322 of the SEQ ID NO:30 protein. A codon encoding the arginine at position 322 of the SEQ ID NO:34 protein can be changed to a termination codon. Hence, the PHYB-related *Zea mays* protein referred to as phytochromeB2 (NCBI accession no. NP_001168077.1 (GI: 293336623) with sequence SEQ ID NO:34) can be inactivated in a manner similar to the PhyB loci described above.

A cDNA encoding the SEQ ID NO:34 protein is available as NCBI accession number NM_001174606.1 (GI: 293336622), and a chromosomal segment encoding the SEQ ID NO:32 protein is on *Zea mays* chromosome 9 at NC_024467.1 (135245613.135251739, complement), sequence available as NCBI accession number NC_024467.1 (GI:662248440).

A *Glycine max* protein referred to as phytochrome B (NCBI accession no. NP_001240097 XP_003533157; NP_001240097.1 (GI:358248221)) has significant sequence identity to the *Arabidopsis thaliana* PHYB protein with SEQ ID NO:30, as illustrated by the sequence comparison shown below. Domains of sequence homology are identified with asterisks below the sequence comparison.

```
77.4% identity in 1109 residues overlap; Score: 4478.0; Gap frequency: 1.1%
Seq 30    49
SNTESMSKAIQQYTVDARLHAVFEQSGESGKSFDYSQSLKTTTYGSSVPEQQITAYLSRI
Seq 35    33 NNIDSMSKAIAQYTEDARLHAVFEQSGESGRSFNYSESIRIAS--
ESVPEQQITAYLVKI
             *  ****** *** *************** ** ** *          ************

Seq 30   109 QRGGYIQPFGCMIAVDESSFRIIGYSENAREMLGIMPQSVPTLEKPE--
ILAMGTDVRSL
Seq 35    91
QRGGFIQPFGSMIAVDEPSFRILGYSDNARDMLGITPQSVPSLDDKNDAAFALGTDVRAL
             **** ***** ****** **** *** *** **** *****  *        *  *****
*

Seq 30   167
FTSSSSILLERAFVAREITLLNPVWIHSKNTGKPFYAILHRIDVGVVIDLEPARTEDPAL
Seq 35   151
FTHSSALLLEKAFSAREISLMNPIWIHSRTSGKPFYGILHRIDVGIVIDLEPARTEDPAL
             ** **  *** ** **** * ** ****   ***** ********
**************

Seq 30   227
SIAGAVQSQKLAVRAISQLQALPGGDIKLLCDTVVESVRDLTGYDRVMVYKFHEDEHGEV
Seq 35   211
SIAGAVQSQKLAVRAISQLQSLPGGDVKLLCDTVVESVRELTGYDRVMVYKFHEDEHGEV
             ******************** ***** *********** *********************
**************
```

-continued

```
Seq 30   287
VAESKRDDLEPYIGLHYPATDIPQASRFLFKQNRVRMIVDCNATPVLVVQDDRLTQSMCL
Seq 35   271
VSESKRPDLEPYIGLHYPATDIRQASRELFKQNRVRMIVDCHASAVRVVQDEALVQPLCL
         * **** ********************************  *  * ****  * *
**

Seq 30   347
VGSTLRAPHGCHSQYMANMGSIASLAMAVIINGNEDDGSNVASGRSSMRLWGLVVCHHTS
Seq 35   331 VGSTLRAPHGCHAQYMANMGSIASLVMAVIINGNDEEG---
VGGRSSMRLWGLVVCHHTS
             ************ ************ ********   *
*****************

Seq 30   407
SRCIPFPLRYACEFLMQAFGLQLNMELQLALQMSEKRVLRTQTLLCDMLLRDSPAGIVTQ
Seq 35   388
ARCIPFPLRYACEFLMQAFGLQLNMELQLAAQSLEKRVLRTQTLLCDMLLRDSPTGIVTQ
          ****************************  *  ******************* ****
*****

Seq 30   467
SPSIMDLVKCDGAAFLYHGKYYPLGVAPSEVQIKDVVEWLLANHADSTGLSTDSLGDAGY
Seq 35   448
SPSIMDLVKCDGAALYFQGNYYPLGVTPTEAQIRDIIEWLLAFHGDSTGLSTDSLGDAGY
         **************  *  ****** * ** *  * ***** * **************
***************

Seq 30   527
PGAAALGDAVCGMAVAYITKRDFLFWFRSHTAKEIKWGGAKHHPEDKDDGQRMHPRSSFQ
Seq 35   508
PGAASLGDAVCGMAVAYITEKDFLFWFRSHTAKEIKWGGAKHHPEDKDDGQRMHPRSSFK
         **** ************** ***************************************

Seq 30   587
AFLEVVKSRSQPWETAEMDAIHSLQLILRDSFKESEAAMNSKVVDGVVQPCRDMAGEQGI
Seq 35   568 AFLEVVKSRSLPWENAEMDAIHSLQLILRDSFKDAEHRNSKAVVD----
PHVSEQELQGV
             ********** *** *****************  *   *** *         **

Seq 30   647
DELGAVAREMVRLIETATVPIFAVDAGGCINGWNAKIAELTGLSVEEAMGKSLVSDLIYK
Seq 35   624
DELSSVAREMVRLIETATAPIFAVDVDGHVNGWNAKVSELTGLPVEEAMGKSLVHDLVFK
         *** ************** ****** ** ****** * ***** ********* ** **
*

Seq 30   707
ENEATVNKLLSRALRGDEEKNVEVKLKTFSPELQGKAVFVVVNACSSKDYLNNIVGVCFV
Seq 35   684
ESEETMNKLLSRALKGEEDKNVEIKMRTFGPEHQNKAVFLVVNACSSKDFTNNVVGVCFV
         * * * ********  *  **** *  ** **  **** ********    ********
******

Seq 30   767
GQDVTSQKIVMDKFINIQGDYKAIVHSPNPLIPPIFAADENTCCLEWNMAMEKLTGWSRS
Seq 35   744
GQDVTGQKIVMDKFINIQGDYKAIVHSPNPLIPPIFASDDNTCCLEWNTAMEKLTGWGRV
         ***** ******************************  ******** ******** * *

Seq 30   827
EVIGKMIVGEVFGSCCMLKGPDALTKFMIVLHNAIGGQDTDKFPFPFFDRNGKFVQALLT
Seq 35   804
DVIGKMLVGEVFGSCCQLKGSDSITKFMIVLHNALGGQDTDKFPFSFLDRHGKYVQTFLT
          ***** ********* *** *  ********* *********** * ** ** **  **

Seq 30   887
ANKRVSLEGKVIGAFCFLQIPSPELQQALAVQRRQDTECFTKAKELAYICQVIKNPLSGM
Seq 35   864
ANKRVNMEGQIIGAFCFLQIMSPELQQALKAQRQQEKNSFGRMKELAYICQGVKNPLSGI
         *****  ** ********* *********  **  *  *   ******** *******

Seq 30   947
RFANSLLEATDLNEDQKQLLETSVSCEKQISRIVGDMDLESIEDGSFVLKREEFFLGSVI
Seq 35   924
RFTNSLLEATSLTNEQKQFLETSVACEKQMLKIIRDVDLESIEDGSLELEKGEFLLGNVI
         ** ******* *  ***  ****** ****   *   ********    *  ** ** **
**
```

```
                                     -continued
Seq 30 1007 NAIVSQAMFLLRDRGLQLIRDIPEEIKSIEVFGDQIRIQQLLAEFLLSIIRYAPSQE-
WV
Seq 35  984
NAVVSQVMLLLRERNLQLIRDIPEEIKTLAVYGDQLRIQQVLSDFLLNIVRYAPSPDGWV
              ** *** * *** * ************   * *** **** *  *** * *****
**
Seq 30 1066
EIHLSQLSKQMADGFAAIRTEFRMACPGEGLPPELVRDMFHSSRWTSPEGLGLSVCRKIL
Seq 35 1044
EIHVRPRIKQISDGLTLLHAEFRMVCPGEGLPPELIQDMFNNSRWGTQEGLGLSMSRKIL
            ***      ** **      **** **********  ***  ***   ******
****
Seq 30 1126 KLMNGEVQYIRESERSYFLIILELPVPRK
Seq 35 1104 KLMNGEVQYIREAERCYFYVLLELPVTRR
            ************ ** **  ***** *
```

This PHYB-related *Glycine max* protein referred to as phytochrome B (NCBI accession no. NP_001240097 XP_003533157; NP_001240097.1 (GI:358248221)) has the following sequence (SEQ ID NO:35).

```
  1  MASASGAANS SVPPPQIHTS RTKLSHHSSN NNNNIDSMSK
 41  AIAQYTEDAR LHAVFEQSGE SGRSFNYSES IRIASESVPE
 81  QQITAYLVKI QRGGFIQPFG SMIAVDEPSF RILGYSDNAR
121  DMLGITPQSV PSLDDKNDAA FALGTDVRAL FTHSSALLLE
161  KAFSAREISL MNPIWIHSRT SGKPFYGILH RIDVGIVIDL
201  EPARTEDPAL SIAGAVQSQK LAVRAISQLQ SLPGGDVKLL
241  CDTVVESVRE LTGYDRVMVY KFHEDEHGEV VSESKRPDLE
281  PYIGLHYPAT DIPQASRFLF KQNRVRMIVD CHASAVRVVQ
321  DEALVQPLCL VGSTLRAPHG CHAQYMANMG SIASLVMAVI
361  INGNDEEGVG GRSSMRLWGL VVCHHTSARC IPFPLRYACE
401  FLMQAFGLQL NMELQLAAQS LEKRVLRTQT LLCDMLLRDS
441  PTGIVTQSPS IMDLVKCDGA ALYFQGNYYP LGVTPTEAQI
481  RDIIEWLLAF HGDSTGLSTD SLGDAGYPGA ASLGDAVCGM
521  AVAYITEKDF LFWFRSHTAK EIKWGGAKHH PEDKDDGQRM
561  HPRSSFKAFL EVVKSRSLPW ENAEMDAIHS LQLILRDSFK
601  DAEHRNSKAV VDPHVSEQEL QGVDELSSVA REMVRLIETA
641  TAPIFAVDVD GHVNGWNAKV SELTGLPVEE AMGKSLVHDL
681  VFKESEETMN KLLSRALKGE EDKNVEIKMR TFGPEHQNKA
721  VFLVVNACSS KDFTNNVVGV CFVGQDVTGQ KIVMDKFINI
761  QGDYKAIVAS PNPLIPPIFA SDDNTCCLEW NTAMEKLTGW
801  GRVDVIGKML VGEVFGSCCQ LKGSDSITKF MIVLHNALGG
841  QDTDKFPFSF LDRHGKYVQT FLTANKRVNM EGQIIGAFCF
881  LQIMSPELQQ ALKAQRQQEK NSFGRMKELA YICQGVKNPL
921  SGIRFTNSLL EATSLTNEQK QFLETSVACE KQMLKIIRDV
961  DLESIEDGSL ELEKGEFLLG NVINAVVSQV MLLLRERNLQ
1001 LIRDIPEEIK TLAVYGDQLR IQQVLSDFLL NIVRYAPSPD
1041 GWVEIHVRPR IKQISDGLTL LHAEFRMVCP GEGLPPELIQ
1081 DMFNNSRWGT QEGLGLSMSR KILKLMNGEV QYIREAERCY
1121 FYYLLELPVT RRSSKKC
```

A codon encoding the arginine at position 306 of the SEQ ID NO:35 protein is equivalent to the codon encoding the arginine at position 322 of the SEQ ID NO:30 protein. A codon encoding the arginine at position 306 of the SEQ ID NO:35 protein can be changed to a termination codon. Hence, the PHYB-related *Glycine max* protein referred to as phytochrome B (NCBI accession no. NP_001240097 XP_003533157; NP_001240097.1 (GI:358248221)) with sequence SEQ ID NO:35) can be inactivated in a manner similar to the PhyB loci described above.

A cDNA encoding the SEQ ID NO:35 protein is available as NCBI accession number NM_001253168.1 (GI: 358248220), and a chromosomal segment encoding the SEQ ID NO:35 protein is on *Glycine max* chromosome 9 at NC_016096.2 (2960478 . . . 2966704, complement), sequence available as NCBI accession number NC_016096.2 (GI:952545307).

Another *Glycine max* protein referred to as phytochrome B (NCBI accession no. ACJ61499.1 (GI:214011498)) also has significant sequence identity to the *Arabidopsis thaliana* PHYB protein with SEQ ID NO:30, as illustrated by the sequence comparison shown below. Domains of sequence homology are identified with asterisks below the sequence comparison.

```
77.5% identity in 1104 residues overlap; Score: 4466.0; Gap frequency: 1.1%
Seq 30    54
MSKAIQQYTVDARLHAVFEQSGESGKSFDYSQSLKTTTYGSSVPEQQITAYLSRIQRGGY
Seq 36     1 MSKAIAQYTEDARLHAVFEQSGESGRSFNYSESIRIAS--
ESVPEQQITAYLVKIQRGGF
               ***** *** *************** *** ** ** *         *********** *****

Seq 30   114 IQPFGCMIAVDESSFRIIGYSENAREMLGIMPQSVPTLEKPE--
ILAMGTDVRSLFTSSS
Seq 36    59
IQPFGSMIAVDEPSFRILGYSDNARDMLGITPQSVPSLDDKNDAAFALGTDVRALFTHSS
             ***** ****** **** **** *** ***** ***** *       *   * ***** ***
**
```

-continued

```
Seq 30   172
SILLERAFVAREITLLNPVWIHSKNTGKPFYAILHRIDVGVVIDLEPARTEDPALSIAGA
Seq 36   119
ALLLEKAFSAREISLMNPIWIHSRTSGKPFYGILHPIDVGIVIDLEPAPTEDPALSIAGA
         *** ** **** * ** ****  ***** ********
******************

Seq 30   232
VQSQKLAVRAISQLQALPGGDIKLLCDTVVESVRDLTGYDRVMVYKFHEDEHGEVVAESK
Seq 36   179
VQSOKLAVRAISQLQSLPGGDVKLLCDTVVESVRELTGYDRVMVYKFHEDEHGEVVSESK
         *************** ***** ************* ********************
***

Seq 30   292 RDDLEPYIGLHYPATDIPQASRFLFKQNRVRMIVDCNATPVLVVQDDRLTQSMCLVGSTL
Seq 36   239 RPDLEPYIGLHYPATDIPQASRFLEKQNRVRMIVDCHASAVRVVQDEALVQPLCLVGSTL
             * ********************** *********  *  **** * *
             *******

Seq 30   352
RAPHGCHSQYMANMGSIASLAMAVIINGNEDDGSNVASGRSSMRLWGLVVCHHTSSRCIP
Seq 36   299 RAPHGCHAQYMANMGSIASLVMAVIINGNDEEG---
VGGRSSMRLWGLVVCHHTSARCIP
             ******* ************ ********   *      *****************
****

Seq 30   412
FPLRYACEFLMQAFGLQLNMELQLALQMSEKRVLRTQTLLCDMLLRDSPAGIVTQSPSIM
Seq 36   356
FPLRYACEFLMQAFGLQLNMELQLAAQSLEKRVLRTQTLLCDMLLRDSPTGIVTQSPSIM
         ************************ *  ******************** **********
**********

Seq 30   472
DLNKCDGAAFLYHGKYYPLGVAPSEVQIKDVVEWLLANHADSTGLSTDSLGDAGYPGAAA
Seq 36   416
DLNKCDGAALYFQGNYYPLGVTPTEAQIRDIIEWLLAFHGDSTGLSTDSLGDAGYPGAAS
         ********* *   * ***** *  * ** * *****  ******************

Seq 30   532
LGDAVCGMAVAYITKRDFLEWFRSHTAKEIKWGGAKHHPEDKDDGQRMHPRSSFQAFLEV
Seq 36   476
LGDAVCGMAVAYITEKDFLFWFRSHTAKEIKWGGAKHHPEDKDDGQRMHPRSSFKAFLEV
         ************** **** ************************************** ****
*****

Seq 30   592
VKSRSQPWETAEMDAIHSLQLILRDSFKESEAAMNSKVVDGVVQPCRDMAGEQGIDELGA
Seq 36   536 VKSRSLPWENAEMDAIHSLQLILRDSFKDAEHRNSKAVVD----
PHVSEQELQGVDELSS
             ***** *** ****************  *    ***  *        ** ***

Seq 30   652
VAREMVRLIETATVPIFAVDAGGCINGWNAKIAELTGLSVEEAMGKSLVSDLIYKENEAT
Seq 36   592
VAREMVRLIETATAPIFAVDVDGHVNGWNAKVSELTGLPVEEAMGKSLVHDLVFKESEET
         ************* ****** **  ****** ***** **********  ** ** *
*

Seq 30   712
VNKLLSRALRGDEEKNVEVKLKTFSPELQGKAVFVVVNACSSKDYLNNIVGVCFVGQDVT
Seq 36   652
MNKLLSRALKGEEDKNVEIKMRTFGPEHQNKAVFLVVNACSSKDFTNNVVGVCFVGQDVT
         ********* *  ***** *  ** ** ***** ********* **  *********
***********

Seq 30   772
SQKIVMDKFINIQGDYKAIVHSPNPLIPPIFAADENTCCLEWNMAMEKLTGWSRSEVIGK
Seq 36   712
GQKIVMDKFINIQGDYKAIVHSPNPLIPPIFASDDNTCCLEWNTAMEKLTGWGRVDVIGK
          ******************************* * ******** ********  * *
****

Seq 30   832
MIVGEVFGSCCMLKGPDALTKFMIVLHNAIGGQDTDKFPFPFFDRNGKFVQALLTANKRV
Seq 36   772
MLVGEVFGSCCQLKGSDSITKFMIVLHNALGGQDTDKFPFSFLDRHGKYVQTFLTANKRV
         * ********* *** *  ********* ********** * ** ** ** ** ******
*******
```

```
Seq 30  892
SLEGKVIGAFCFLQIPSPELQQALAVQRRQDTECFTKAKELAYICQVIKNPLSGMRFANS
Seq 36  832
NMEGQIIGAFCFLQIMSPELQQALKKRQQEKNSFGRMKELAYICQGVKNPLSGIRFTNS
              **  ********* ********  ** *    *  ********  ****** **
**

Seq 30  952
LLEATDLNEDQKQLLETSVSCEKQISRIVGDMDLESIEDGSFVLKREEFFLGSVINAIVS
Seq 36  892
LLEATSLTNEQKQFLETSVACEKQMLKIIRDVDLESIEDGSLELEKGEFLLGNVINAVVS
              ***** *  *** ***** ****   *  * *********  *  ** ** ****
**

Seq 30 1012 QAMFLLRDRGLQLIRDIPEEIKSIEVFGDQIRIQOLLAEFLLSIIRYAPSQE-
WVEIHLS
Seq 36  952
QVMLLLRERNLQLIRDIPEEIKTLAVYGDQLRIQQVLSDFLLNIVRYAPSPDGWVEIHVR
              * *  *** * ************  * *** **** *  *** * *****     *****

Seq 30 1071
QLSKQMADGFAAIRTEFRMACPGEGLPPELVRDMFHSSRWTSPEGLGLSVCRKILKLMNG
Seq 36 1012
PRIKQISDGLTLLHAEFRMVCPGEGLPPELIQDMFNNSRWGTQEGLGLSMSRKILKLMNG
               **  **          **** **********  *** ***    ******
*********

Seq 30 1131 EVQYIRESERSYFLIILELPVPRK
Seq 36 1072 EVQYIRRAERCYFYVLLELPVTRR
              ******* ** **    ***** *
```

This PHYB-related *Glycine max* protein referred to as phytochrome B (NCBI accession no. ACJ61499.1 (GI: 214011498)) has the following sequence (SEQ ID NO:36).

```
   1  MSKAIAQYTE DARLEAVFEQ SGESGRSFNY SESIRIASES
  41  VPEQQITAYL VKIQRGGFIQ PFGSMIAVDE PSFRILGYSD
  81  NARDMLGITP QSVPSLDDKN DAAHALGTDV RALFTHSSAL
 121  LLEKAFSARE ISLMNPIWIH SRTSGKPFYG ILHRIDVGIV
 161  IDLEPARTED PALSIAGAVQ SQKLAVRAIS QLQSLPGGDV
 201  KLLCDTVVES VRELTGYDRV MVYKFHEDEH GEVVSESKRP
 241  DLEPYIGLHY PATDIPQASR FLFKQNRVRM IVDCHASAVR
 281  VVQDEALVQP LCLVGSTLRA PHGCHAQYMA NMGSIASLVM
 321  AVIINGNDEE GVGGRSSMRL WGLVVCHHTS ARCIPFPLRY
 361  ACEFLMQAFG LQLNMELQLA AQSLEKRVLR TQTLLCDMLL
 401  RDSPTGIVTQ SPSIMDLVKC DGAALYFQGN YYPLGVTPTE
 441  AQIRDIIEWL LAFHGDSTGL STDSLGDAGY PGAASLGDAV
 481  CGMAVAYITE KDFLFWFRSH TAKEIKWGGA KHHPEDKDDG
 521  QRMHPRSSFK AFLEVVKSRS LPWENAEMDA IHSLQLILRD
 561  SFKDAEHRNS KAVVDPHVSE QELQGVDELS SVAREMVRLI
 601  ETATAPIFAV DVDGHVNGWN AKVSELTGLP VEEAMGKSLV
 641  HDLVFKESEE TMNKLLSRAL KGEEDKNVEI KMRTFGPEHQ
 681  NKAVFLVVNA CSSKDFTNNV VGVCFVGQDV TGQKIVMDKF
 721  INIQGDYKAI VHSPNPLIPP IFASDDNTCC LEWNTAMEKL
 761  TGWGRVDVIG KMLVGEVFGS CCQLKGSDSI TKFMIVLHNA
 801  LGGQDTDKFP FSFLDRHGKY VQTFLTANKR VNMEGQIIGA
 841  FCFLQIMSPE LQQALKAQRQ QEKNSFGRMK ELAYICQGVK
 881  NPLSGIRFTN SLLEATSLTN EQKQFLETSV ACEKQMLKII
 921  RDVDLESIED GSLELEKGEF LLGNVINAVV SQVMLLLRER
 961  NLQLIRDIPE EIKTLAVYGD QLRIQQVLSD FLLNIVRYAP
1001  SPDGWVEIHV RPRIKQISDG LTLLHAEFRM VCPGEGLPPE
1041  LIUMFMNSR WGTQEGLGLS MSRKILKLMN GEVQYIREAE
1081  RCYFYVLLEL PVTRRSSKKC
```

A codon encoding the arginine at position 269 of the SEQ ID NO:36 protein is equivalent to the codon encoding the arginine at position 322 of the SEQ ID NO:30 protein. A codon encoding the arginine at position 269 of the SEQ ID NO:36 protein can be changed to a termination codon. Hence, the PHYB-related *Glycine max* protein referred to as phytochrome B (NCBI accession no. ACJ61499.1 (GI: 214011498) with sequence SEQ ID NO:36) can be inactivated in a manner similar to the PhyB loci described above.

A chromosomal segment encoding the SEQ ID NO:36 protein is on *Glycine max* chromosome 9, and also at NC_016096.2 (2960478 . . . 2966704, complement), with a sequence available as NCBI accession number NC_016096.2 (GI:952545307).

An *Oryza sativa* protein referred to as phytochrome B (NCBI accession no. AFK31004.1 (GI:388458276)) has significant sequence identity to the *Arabidopsis thaliana* PHYB protein with SEQ ID NO:30, as illustrated by the sequence comparison shown below. Domains of sequence homology are identified with asterisks below the sequence comparison.

75.6% identity in 1113 residues overlap; Score: 4309.0; Gap frequency: 1.3%

```
Seq 30    52 ESMSKAIQQYTVDARLHAVFEQGESGKSFDYSQSLKTTTYGSSVPEQQTAYLSRIQRG
Seq 37    56 ESVSKAVAQYTLDARLHAVFEQSGASGRSFDYTQSLRASPTPSS--EQQIAAYLSRIQRG
                ** *** *** ************ ** **** ***       ** ****
             *********

Seq 30   112 GYIQPFGCMIAV-DESSFRIIGYSENAREMLGIMPQ-SVPTLEK---PEILAMGTDVRSL
Seq 37   114 GHIQPFGCTLAVADDSSFRLLAYSENTADLLDLSPHHSVPSLDSSAVPPPVSLGADARLL
              * ****** ** * **** **** ****    *     *** *     *   * * *
             *

Seq 30   167 FTSSSSILLERAFVAREITLLNPVWIHSKNTGKPFYAILHRIDVGVVIDLEPARTEDPAL
Seq 37   174 FAPSSAVLLERAFAAREISLLNPLWIHSRVSSKPFYAILHRIDVGVVIDLEPARTEDPAL
              *  ** ****** **** **** **** ****
             ***************************

Seq 30   227 SIAGAVQSQKLAVRAISQLQALPGGDIKLLCDTVVESVRDLTGYDRVMVYKFHEDEHGEV
Seq 37   234 SIAGAVQSQKLAVRAISRLQALPGGDVKLLCDTVVEHVRELTGYDRVMVYRFHEDEHGEV
             ***************** ******** ******** ** ********** **********
             *********

Seq 30   287 VAESKRDDLEPYIGLHYPATDIPQASRELFKQNRVRMIVDCNATPVLVVQDDRLTQSMCL
Seq 37   294 VAESRRNNLEPYIGLHYPATDIPQASRFLFRQNRVRMIADCEAAPVRVIQDPALTQPLCL
             ****  *  ****************** ** ******* **   **  *     ** ***
             **

Seq 30   347 VGSTLRAPHGCHSQYMANMGSIASLAMAVIINGNEDDGSNVASGR--SSMRLWGLVVCHH
Seq 37   354 VGSTLRSPHGCHAQYMANMGSIASLVMAVIISSGGDDDHNIARGSIPSAMKLWGLVVCHH
             ****** ***** *********** ***** *    **  *  *  *  ***********
             *********

Seq 30   405 TSSRCIPFPLRYACEFLMQAFGLQLNMELQLALQMSEKRVLRTQTLLCDMLLRDSPAGIV
Seq 37   414 TSPRCIPFPLRYACEFLMQAFGLQLNMELQLAHQLSEKHILRTQTLLCDMLLRDSPTGIV
              ** ******************************* *** *** ****************
             ***

Seq 30   465 TQSPSIMDLVKCDGAAFLYHGRYYPLGVAPSEVQIKDVVEWLLANHADSTGLSTDSLGDA
Seq 37   474 TQSPSIMDLVKCDGAALYYHGKYYPLGVTPTEVQIKDIIEWLTMCHGDSTGLSTDSLADA
             **************** ***** ***** ** ****** **** *    ***********
             **

Seq 30   525 GYPGAAALGDAVCGMAVAYITKRDFLFWFRSHTAKEIKWGGAKHHPEDKDDGQRMHPRSS
Seq 37   534 GYPGAAALGDAVSGMAVAYITPSDYLFWFRSHTAKEIKWGGAKHHPEDKDDGQRMHPRSS
             ************ ******** *  ***********************************
             ***********************************

Seq 30   585 FQAFLEVVKSRSQPWETAEMDAIHSLQLILRDSFKES-EAAMNSK-VVDGVVVQPCRDMAG
Seq 37   594 FKAFLEVVKSRSLPWENAEMDAIHSLQLILRDSFRDSAEGTSNSKAIVNGQVQ--LGELE
              * ********** *** **************** **   * ****  *  * *   * **

Seq 30   643 EQGIDELGAVAREMVRLIETATVPIFAVDAGGCINGWNAKIAELTGLSVEEAMGKSLVSD
Seq 37   652 LRGIDELSSVAREMVRLIETATVPIFAVDTDGCINGWNAKVAELTGLSVEEAMGKSLVND
              ****** ******************** ********** ******************* **
             *
```

```
Seq 30  703
LIYKENEATVNKLLSRALRGDEEKNVEVKLKTFSPELQGKAVFVVVNACSSKDYLNNIVG
Seq 37  712
LIFKESEETVNKLLSRALRGDEDKNVEIKLKTFGPEQSKGPIFVIVNACSSRDYTKNIVG
            ** **  **************  ****  *****  **        ** ****** **
****

Seq 30  763
VCFVGQDVTSQKIVMDKFINIQGDYKAIVHSPNPLIPPIFAADENTCCLEWNMAMEKLTG
Seq 37  772
VCFVGQDVTGQKVVMDKFINIQGDYKAIVHNPNPLIPPIFASDENTCCSEWNTAMEKLTG
         ********* ** ****************** ********** ****** ***
*******

Seq 30  823
WSRSEVIGKMIVGEVFGSCCMLKGPDALTKFMIVLHNAIGGQDTDKFPFPFFDRNGKFVQ
Seq 37  832
WSRGEVVGKLLVGEVFGNCCRLKGPDALTKFMIVLHNAIGGQDCEKFPFSFFDKNGKYVQ
         *** ** **  ****** ** ********************  **** ****  *** ***
**

Seq 30  883
ALLTANKRVSLEGKVIGAFCFLQIPSPELQQALAVQRRQDTECFTKAKELAYICQVIKNP
Seq 37  892
ALLTANTRSRMDGEAIGAFCFLQIASPELQQAFEIQRHHEKKCYARMKELAYIYQEIKNP
         ******  *  *   ********* ******* *  **  ** **   * ****** *
****

Seq 30  943
LSGMRFANSLLEATDLNEDQKQLLETSVSCEKQISRIVGDMDLESIEDGSFVLKREEFFL
Seq 37  952
LNGIRFTNSLLEMTDLKDDQRQFLETSTACEKQMSKIVKDASLQSIEDGSLVLEKGEFSL
         * * ** ***** ***  ***  ***** ***** * ** *   * *******  **   **
*

Seq 30  1003
GSVINAIVSQAMFLLRDRGLQLIRDIPEEIKSIEVFGDQIRIQQLLAEFLLSIIRYAPSQ
Seq 37  1012
GSVMNAVVSQVMIQLRERDLQLIRDIPDEIKEASAYGDQYRIQQVLCDFLLSMVRFAPAE
         ***  ** ***  *  ** *********  ***     **** **** *  ****  * **

Seq 30  1063 E-
WVEIHLSQLSKQMADGFAAIRTEFRMACPGEGLPPELVRDMFHSSRWTSPEGLGLSVC
Seq 37  1072
NGWVEIQVRPNIKQNSDGTDTMLFLFRFACPGEGLPPEIVQDMFSNSRWTTQEGIGLSIC
           ****        **  **   ** **********  *  ***  ****  ****  ** ***
*

Seq 30  1122 RKILKLMNGEVQYIRESERSYFLIILELPVPRK
Seq 37  1132 RKILKLMGGEVQYIRESERSFFHIVLELPQPQQ
              *******  ***********   *  * ****  *
```

This PHYB-related *Oryza sativa* protein referred to as phytochrome B (NCBI accession no. AFK31004.1 (GI: 388458276)) has the following sequence (SEQ ID NO:37).

```
  1  MASGSRATPT RSPSSARPAA PRAQHHHSQS SGGSTSRAGG
 41  GGGGGGGGGG GAAAAESVSK AVAQYTLDAR LHAVFEQSGA
 81  SGRSFDYTQS LRASPTPSSE QQIAAYLSRI QRGGHIQPFG
121  CTLAVADDSS FRLLAYSENT ADLLDLSPHH SVPSLDSSAV
161  PPPVSLGADA RLLFAPSSAV LLERAFAARE ISLLNPLWIH
201  SRVSSKPFYA ILHRIDVGVV IDLEPARTED PALSIAGAVQ
241  SQKLAVRAIS RLQALPGGDV KLLCDTVVEH VRELTGYDRV
281  MVYRFHEDEH GEVVAESRRN NLEPYIGLHY PATDIPQASR
321  FLFRQNRVRM IADCHAAPVR VIQDPALTQP LCLVGSTLRS
361  PHGCHAQYMA NMGSIASLVM AVIISSGGDD DHNIARGSIP
401  SAMKLWGLVV CHHTSPRCIP FPLRYACEFL MQAFGLQLNM
441  ELQLAHQLSE KHILRTQTLL CDMLLRDSPT GIVTQSPSIM
481  DLVKCDGAAL YYHGKYYPLG VTPTEVQIKD IIEWLTMCHG
521  DSTGLSTDSL ADAGYPGAAA LGDAVSGMAV AYITPSDYLF
561  WFRSHTAKEI KWGGAKHHPE DKDDGQRMHP RSSFKAFLEV
601  VKSRSLPWEN AEMDAIHSLQ LILRDSFRDS AEGTSNSKAI
641  VNGQVQLGEL ELRGIDELSS VAREMVRLIE TATVPIFAVD
681  TDGCINGWNA KVAELTGLSV EEAMGKSLVN DLIFKESEET
721  VNKLLSRALR GDEDKNVEIK LKTFGPEQSK GPIFVIVNAC
761  SSRDYTKNIV GVCFVGQDVT GQKVVMDKFI NIQGDYKAIV
801  HNPNPLIPPI FASDENTCCS EWNTAMEKLT GWSRGEVVGK
841  LLVGEVFGNC CRLKGPDALT KFMIVLHNAI GGQDCEKFPF
881  SFFDKNGKYV QALLTANTRSRMDGEAIGAF CFLQIASPEL
```

```
 921  QQAFEIQRHH  EKKCYARMKE  LAYIYQEIKN  PLNGIRFTNS

961  LLEMTDLKDD  QRQFLETSTA  CEKQMSKIVK  DASLQSIEDG

1001  SLVLEKGEFS  LGSVMNAVVS  QVMIQLRERD  LQLIRDIPDE

1041  IKEASAYGDQ  YRIQQVLCDF  LLSMYRFAPA  ENGWVEIQVR

1081  PNIKQNSDGT  DTMLFLFRFA  CPGEGLPPEI  VQDMFSNSRW

1121  TTQEGIGLSI  CRKILKLMGG  EVQYIRESER  SFFHIVLELP

1181  QPQQAASRGT  S
```

A codon encoding the arginine at position 329 of the SEQ ID NO:37 protein is equivalent to the codon encoding the arginine at position 322 of the SEQ ID NO:30 protein. A codon encoding the arginine at position 329 of the SEQ ID NO:37 protein can be changed to a termination codon. Hence, PHYB-related *Oryza sativa* protein referred to as phytochrome B (NCBI accession no. AFK31004.1 (GI: 388458276) with sequence SEQ ID NO:37) can be inactivated in a manner similar to the PhyB loci described above.

A chromosomal segment encoding the SEQ ID NO:37 protein is on *Oryza sativa* chromosome 3 at NC_029258.1 (11020017 . . . 11028186), sequence available as NCBI accession number NC_029258.1 (GI:996703430).

Chromosomal sites encoding any of the conserved amino acids and conserved domains illustrated by the sequence comparisons shown above can be deleted or mutated to reduce the activity of the proteins described herein.

For example, a wild type plant can express PHYB polypeptides or PHYB-related polypeptides with at least 70%, or at least 75%, or at least 80%, or at least 85%, or at least 90%, or at least 95%, or at least 97%, or at least 98%, or at least 99% sequence identity to any of SEQ ID NOs:30, 32, 33, 34, 35, 36, or 37.

However, the mutant phyB plant cells, plants, and/or seeds with reduced PHYB function and improved plant growth can have mutations that delete at least a portion of the phyB loci or that delete at least a portion of phyB-related loci (so that PHYB function is reduced or lost altogether). Mutant phyB plant cells, plants, and/or seeds with reduced PHYB function and improved plant growth can express mutant phyB and/or mutant phyB-related polypeptides that have reduced activity. Such PHYB and/or PHYB-related polypeptides that have reduced PHYB activity can have less than 99%, or less than 98%, or less than 95%, or less than 90%, or less than 85%, or less than 75%, or less than 60%, or less than 50%, or less than 40%, or less than 30%, or less than 20% sequence identity to any of SEQ ID NOs:30, 32, 33, 34, 35, 36, or 37. In other words, mutations can delete or modify chromosomal PhyB or PhyB-related chromosomal sites so that a truncated polypeptide, a highly mutated polypeptide, or no polypeptide is expressed.

The mutant PHYB and/or PHYB-related can, for example, have mutations in at least one conserved amino acid position, or at least two conserved amino acid positions, or at least three conserved amino acid positions, or at least five conserved amino acid positions, or at least seven conserved amino acid positions, or at least eight conserved amino acid positions, or at least ten conserved amino acid positions, or at least fifteen amino acid positions, or at least twenty conserved amino acid positions, or at least twenty-five amino acid positions. In some cases, an entire conserved PhyB and/or PhyB-related domain or the entire endogenous PHYB and/or PHYB-related gene, loci, or chromosomal segment is deleted or mutated.

The conserved amino acids and/or domains are in some cases mutated by deletion or replacement with amino acids that have dissimilar physical and/or chemical properties. Examples of amino acids with different physical and/or chemical properties that can be used are shown in Tables 1 and 2.

Pif4

As described herein, overexpression of PIF4 can improve myc mutant plant growth without compromising defense against insects. Hence, the mutant plants described herein can also express PIF4, for example, by transformation of plants having a myc, myc-related, phyB, and/or phyB-related mutant genomic background with an expression cassette or expression vector that encodes PIF4.

One example of an *Arabidopsis thaliana* PIF4 protein sequence is shown below as SEQ ID NO:38.

```
  1  MEHQGWSFEE  NYSLSTNRRS  IRPQDELVEL  LWRDGQVVLQ

41  SQTHREQTQT  QKQDHHEEAL  RSSTFLEDQE  TVSWIQYPPD

81  EDPFEPDDFS  SHFFSTMDPL  QRPTSETVKP  KSSPEPPQVM

121  VKPKACPDPP  PQVMPPPKFR  LTNSSSGIRE  TEMEQYSVTT

161  VGPSHCGSNP  SQNDLDVSMS  HDRSKNIEEK  LNPNASSSSG

201  GSSGCSFGKD  IKEMASGRCI  TTDRKRKRIN  HTDESVSLSD

241  AIGNKSNQRS  GSNRRSRAAE  VHNLSERRRR  DRINERMKAL

281  QELIPHCSKT  DKASILDEAI  DYLKSLQLQL  QVMWMGSGMA

321  AAAASAPMMF  PGVQPQQFIR  QIQSPVQLPR  FPVMDQSAIQ

361  NNPGLVCQNP  VQNQIISDRF  ARYIGGFPAM  QAATQPMEML

401  RFSSPAGQQS  QQPSSVPTKT  TDGSRLDH
```

A cDNA that encodes the SEQ ID NO:38 PIF4 protein can have nucleotide sequence SEQ ID NO:39, shown below.

```
  1  ACTTTCTGTC  TGTACCCAAA  AGAAGTAATG  AACCTCTCTC

41  ATCTTCTTCT  TCTCTGTTTC  TTTCATGTTT  TGTGAGTTGT

81  TTCTCAACAA  TTTTCTGGTC  TCTTAGAGTG  AGAGGAGAGA

121  GATAGAGAGT  TGTGTTGGGC  GTGGAACTTG  GACTAGTTCC

161  ACATATCAGG  TTATATAGAT  CTTCTCTTTC  AACTTCTGAT

201  TCGTCCAGAA  GCTTTCCTAA  TCTGAGATCT  GACATGGAAC

241  ACCAAGGTTG  GAGTTTTGAG  GAGAATTATA  GTTTGTCCAC

281  TAATAGAAGA  TCTATCAGGC  CACAAGATGA  ACTAGTGGAG

321  TTATTATGGC  GAGATGGACA  AGTGGTTCTG  CAGAGCCAAA

361  CTCATAGAGA  ACAAACCCAA  ACCCAGAAAC  AAGATCATCA

401  TGAAGAAGCC  CTAAGATCCA  GCACCTTTCT  TGAAGATCAA

441  GAAACTGTCT  CTTGGATCCA  ATACCCTCCA  GATGAAGACC

481  CATTCGAACC  CGACGACTTC  TCCTCCCACT  TCTTCTCAAC

521  CATGGATCCC  CTCCAGAGAC  CAACCTCAGA  GACGGTTAAG

561  CCTAAGTCCA  GTCCTGAACC  TCCTCAAGTC  ATGGTTAAGC

601  CTAAGGCCTG  TCCTGACCCT  CCTCCTCAAG  TCATGCCTCC

641  TCCAAAATTT  AGGTTAACAA  ATTCATCATC  GGGGATTAGG
```

```
681  GAAACAGAAA TGGAACAGTA CTCGGTAACG ACCGTTGGAC
721  CTAGCCATTG CGGAAGCAAC CCATCACAGA ACGATCTCGA
761  TGTCTCAATG AGTCATGATC GAAGCAAAAA CATAGAAGAA
801  AAGCTTAATC CGAACGCAAG TTCCTCATCA GGTGGCTCCT
841  CTGGTTGCAG CTTTGGCAAA GATATCAAAG AAATGGCTAG
```

-continued

```
881  TGGAAGATGC ATCACAACCG ACCGTAAGAG AAAACGTATA
921  AATCACACTG ACGAATCTGT ATCTCTATCA GATGCAATCG
961  GTAACAAGTC GAACCAACGA TCAGGATCAA ACCGAAGGAG
1001 TCGAGCAGCT GAAGTTCATA ATCTCTCCGA AAGGAGGAGG
1041 AGAGATAGGA TCAATGAGAG AATGAAGGCT TTGCAAGAAC
1081 TAATACCTCA CTGCAGTAAA ACTGATAAAG CTTCGATTTT
1121 AGACGAAGCC ATAGATTATT TGAAATCACT TCAGTTACAG
1161 CTTCAAGTGA TGTGGATGGG GAGTGGAATG GCGGCGGCGG
1201 CGGCTTCGGC TCCGATGATG TTCCCCGGAG TTCAACCTCA
1241 GCAGTTCATA CGTCAGATAC AGAGCCCGGT ACAGTTACCT
1281 CGATTTCCGG TTATGGATCA GTCTGCAATT CAGAACAATC
1321 CCGGTTTAGT TTGCCAAAAC CCGGTACAAA ACCAGATCAT
1361 CTCCGACCGG TTTGCTAGAT ACATCGGTGG GTTCCCACAC
1401 ATGCAGGCCG CGACTCAGCC GATGGAGATG TTGAGATTTA
1441 GTTCACCGGC GGGACAGCAA AGTCAACAAC CGTCGTCTGT
1481 GCCGACGAAG ACCACCGACG GTTCTCGTTT GGACCACTAG
1521 GTTGGTGAGC CACTTTTTTA CTTCCTTATT TTTGGTATGT
1561 TTCTTTTTTA TATCTATCTT TCTGAACATA CTTAAAACGT
1601 TCAAGGATGT ATTATTATAG AGTAAACGTG CAACTTCATT
1641 ACGTTATTTT CTGTATATGT GAGTTTATGT ATGTCAAAAT
1681 GACATGATGA GATTTTTTGT AAACAACATC TTAAAAACAG
1721 GACATGTGAT TTTTGTAATC GTAAAAA
```

Nucleic acids from a variety of plant types that encode PIF4 and/or PIF4-related polypeptides can be transformed into plants as transgenes. For example, such nucleic acids that encode PIF4 and/or PIF4-related polypeptides can be incorporated into expression cassettes or expression vectors that are introduced into selected plant cells, for example, plant cells with a mutant myc, JAZ, and/or phyB genetic background. Plant lines can be generated from the plant cells.

A PIF4-related protein from *Zea mays* referred as a putative HLH DNA-binding domain superfamily protein (NCBI accession no. NP_001146660.1 (GI:226502090)) has substantial homology to the *Arabidopsis thaliana* PIF4 SEQ ID NO:38 protein sequence, as illustrated below. Domains of sequence homology are identified with asterisks below the sequence comparison.

```
63.6% identity in 99 residues overlap; Score: 316.0; Gap fre-
quency: 0.0%
Seq 38 224
RKRKRINHTDESVSLSDAIGNKSNQRSGSNRRSRAAEVHNLSERRRRDRINERMKALQEL
Seq 40 218
RRSGKRKHNDATDAEDVGLECEPAQRTTTAKRRRAAQVHNLSERRRRDRINEKMKKLQEL
 *  * *                  **     * ***  **************
*******

Seq 38 234 IPHCSKTDKASILDEAIDYLKSLQLQLQVMWMGSGMAAA
Seq 40 278 IPHCNKADKASMLDEAIEYLKSLQLQLQVVWMGGGIAAA
           ****  **** ***** ***********  ***  * ***
```

The *Zea mays* protein referred as a putative HLH DNA-binding domain superfamily protein (NCBI accession no. NP_001146660.1 (GI:226502090)) has the following sequence SE ID NO:40).

```
  1 MQTAIEHACS VVECAATARA AMDMSHYIPD WSSSMGDTFA
 41 PLGGEDDDGL IELMWRNGHV VMQAQAPRKP PRPDDDEAAA
 81 AQAQAWFQYP VEERADLFSE LFGEAQAAVG GARGEAARQS
121 IRMMPPPPPP PRPAQAPREE KACPGDGGTA TATDGAGSSV
161 LTVVSSLCGS NGNHVQATAP GDVARARDVL MVTSSSTTRS
201 RSCTTKSEQP GPGPGAARRS GKRKHNDATD AEDVGLECEP
241 AQRTTTAKRR RAAQVHNLSE RRRRDRINEK MKALQELIPH
281 CNKADKASML DEAIEYLKSL QLQLQVVWMG GGIALAGVHQ
321 RTMVAAPGRP PHVASLPASA PDLYTRYLAV DHLPPPPLVP
361 PPRTAAAMGL YPRQNPVPAT SSPSFRTTEN TRKLWQA
```

A cDNA encoding the *Zea mays* protein referred as a putative HLH DNA-binding domain superfamily protein (NCBI accession no. NP_001146660.1 (GI:226502090); SEQ ID NO:38) has the following nucleotide sequence (SEQ ID NO:41).

```
  1 CCTTGCCCTG CTGCAACTTG AACCTCCTGG CAGCTCCTGT
 41 TTCAGGCAGG CAGCAAGTAG GGAAGAGGCT CTGCAGATCA
 81 GTTCCATGCA GACAGCGATC GAGCACGCCT GCTCGGTGGT
121 GGAATGCGCT GCGACAGCCC GAGCCGCCAT GGACATGAGC
161 CACTACATCC CCGATTGGAG CAGCAGCATG GGAGACACCT
201 TCGCGCCACT GGGCGGCGAG GACGACGACG GCTCATCGA
241 GCTCATGTGG CGCAACGGCC ACGTGGTCAT GCAGGCCCAG
281 GCGCCGCGGA AGCCGCCGAG ACCCGACGAC GACGAGGCGG
321 CGGCGGCGCA GGCGCAGGCG TGGTTCCAGT ACCCGGTGGA
```

```
-continued
361  GGAGAGGGCC GACCTCTTCT CGGGAGCTCTT CGGGGAGGCG
401  CAGGCGGCCG TCGGCGGCGC GCGCGGGGAG GCCGCGCGCC
441  AGAGTATCCG GATGATGCCG CCGCCGCCGC CGCCGCCGAG
481  GCCCGCGCAA GCGCCGCGGG AGGAGAAGGC GTGCCCGGGA
521  GACGGCGGCA CGGCGACGGC GACGGACGGC GCCGGCTCGT
561  CCGTGCTCAC GGTCGTGTCC AGCCTCTGCG GGAGCAACGG
601  CAACCACGTG CAGGCGACGG CGCCGGGGGA CGTCGCCAGG
641  GCCCGCGACG TGCTGATGGT GACCTCGTCG TCGACGACGC
681  GTTCCAGGTC ATGCACCACC AAGAGCGAGC AGCCGGGTCC
```

```
-continued
1321 AGCTGCATGC ATGTGTGTAT GTGTTGGTAG TATGGTTAAG
1361 CCTTGACAGA GACTTGTGAT CGAGACCGAG ATCGACCGAT
1401 AGGCCGTCAC TTCTTTTTTC TTCCATCTTT CAGTTTTTGG
1441 TTGATAGGCC GGAGTGTAAT TTGACCAGTG GTCGAGATTT
1481 GTCAAGCGAC AC
```

A PIF4-related protein from *Glycine max* referred as a transcription factor PIF4 (NCBI accession no. XP_006575634.1 (GI:571442111)) has substantial homology to the *Arabidopsis thaliana* PIF4 SEQ ID NO:38 protein sequence, as illustrated below. Domains of sequence homology are identified with asterisks below the sequence comparison.

```
41.7% identify in 240 residues overlap; Score: 357.0; Gap frequency: 7.5%
Seq 38 139 EKLNPNASSSSGGSSGCSFGKDIKEMASGRCITTD-
RKRKRINHTDESVSLSDAIGNKSN
Seq 42 291
EMIELTVTSSSGGSGSTGIGRTCSLSTRDHGQKRKGTEEEALEEQSEDTELKSADGNKAS
                    *      ******   *                  *  *  * ***

Seq 38 248
QRSGSNRRSRAAEVHNLSERRRRDRINERMKALQELIPHCSKTDKASILDEAIDYLKSLQ
Seq 42 351
QRTRSSRRNPAAEVHNQSERRRRDPINEKMRTLQQLIPNSNKTDKASMLEEAIEYLKSLQ
        **  *  ** ******* ************  *  ** ***   ****** * ***
******

Seq 38 308 LQLQVMWMGSGMAAAAASKPMMFPGANVQPQQF----IRQIQSPVQLPRFPVMDQSAIQN-
-
Seq 42 411
FQLQVMWMGGGMTPVMFPGIQHYMSQMGMGMGAPSLPSIHNPMQLPKVPHDQAMSVLQIP
        ******** **                            *  * *** *

Seq 38 362 NPGLVCQNPV----------
QNQIISDRFARYIGGFPHMQAATQPMEMLRFSSPAGQQSQ
Seq 42 471 NQNLMCQNPVLGAFNYQNQMQNPCLPEQYARYMG-
YHLMQNASQPMNVFRYGSQAVQHSQ
           *  * *****        **     *** *    ** * ***    *   *    *
**
```

```
-continued
721  CGGGCCCGGC GCTGCCCGCC GGAGCGGCAA GAGGAAGCAT
761  AACGACGCCA CCGATGCCGA GGACGTGGGG CTGGAGTGCG
801  AGCCGGCGCA GAGGACGACG ACTGCCAAGC GGCGCCGCGC
841  CGCGCAAGTC CACAACCTCT CGGAGCGGAG GAGACGGGAC
881  AGGATCAACG AGAAGATGAA GGCCCTGCAG GAACTCATAC
921  CCCACTGCAA CAAAGCGGAC AAGGCGTCGA TGCTGGACGA
961  GGCGATCGAG TACCTCAAGT CGCTGCAGCT CCAGCTGCAG
1001 GTGGTGTGGA TGGGCGGCGG CATCGCGGCG GCGGGGGTGC
1041 ACCAGCGGAC GATGGTGGCC GCGCCCGGGC GTCCTCCCCA
1081 CGTGGCTTCC CTGCCGGCGT CGGCGCCCGA CCTCTATACG
1121 CGCTACCTCG CCGTCGACCA CCTGCCGCCA CCGCCCTTGG
1161 TGCCACCGCC ACGCACGGCC GCGGCGATGG GCTTGTACCC
1201 GCGCCAGAAC CCCGTGCCGG CGACGTCGTC TCCTTCCTTC
1241 CGAACGACCG AAAATACGAG AAAACTATGG CAAGCCTGAG
1281 ATTCAGATCC GGGGTATGGT GACCAGCTGA TGGGTCATCT
```

The PIF4-related protein from *Glycine max* referred as a transcription factor PIF4 (NCBI accession no. XP_006575634.1 (GI:571442111)) has the following sequence (SEQ ID NO:42).

```
  1 MNNSIPGWDF ESDTCLTNQR KLIGPDQELV ELLWKNGQVV
 41 MHNQTHRKTL GNSSNLRQVQ KSDQSVLRSS GPYGNSSNLD
 81 QEDAAPWVQF PLEDPLEQDF CSNLLSELPT CEFESYKPIR
121 QLEEEKFAKF FASGTPHHPT TSSSQPLPPN MKPSCIQGLQ
161 GNPIPMPAPR FHGPDSSQKI HDFGASRKVL NFPQFSTPRN
201 NVPSAPGITQ FREKTTANMS QSEAREYSVI TVGSSHCGSN
241 HIPQEQDVSR ISSTGVWATT NNNTTLSAEP EAVRDYVQRP
281 ICPKSGQGKS EMIELTVTSS SGGSGSTGIG RTCSLSTRDH
321 GQKRKGTEEE ALEEQSEDTE LKSADGNKAS QRTRSSRRNR
361 AAEVHNQSER RRDRINEKM RTLQQLIPMS NKTDKASMLE
401 EAIEYLKSLQ FQLQVMWMGG GMTPVMFPGI QHYMSQMGMG
```

-continued

```
441 MGAPSLPSIH NPMQLPKVPH DQAMSVLQIP NQNLMCQNPV

481 LGAFNYQNQM QNPCLPEQYA RYMGYELMQN ASQPMNVFRY

521 GSQAVQHSQT MIAPGNNSSG PMSGTANIDD ADSGKAGSST

561 FN
```

A cDNA encoding the PIF4-related protein from *Glycine max* referred as a transcription factor PIF4 (NCBI accession no. XP_006575634.1 (GI:571442111); SEQ ID NO:42) is shown below as SEQ ID NO: 43.

```
   1 GACCCCGTTT TCAACTGGTC CCGTGTTCCT TCATTTGATG

41 CCACATGTGC AGCTAGCCAT GTTTTTCTCG CTGTTGACGA

81 GCACAATATA TAATAAATAC CATTTTTTTC ATGCCATATT

121 TGCTCTCTTC TCTCTTTGTA CTAATAACTT GGATCTATGC

161 CACTGTCCTT CTCCTTGTTA AAAACTGTGC CACACGTCTG

201 TCACCAAACT CCCTAAGCAG AAGAAGCACA TGTTCAGAGG

241 GAGTTTTGTT TCATCAGTCT CTAGCTAGCA TATATTTCTA

281 GCTTCTATTC AACAAGTTGC AAAAAACAGA CTTTGCCTTA

321 ACCAAAAGAA AATCTGTTTT TACCTTAACT CAGACAACTC

361 GTTTGGTGAA CCATGAACAA CAGTATTCCT GGTTGGGATT

401 TTGAGAGTGA TACATGTCTC ACCAACCAAA GAAAGCTCAT

441 AGGGCCGGAC CAAGAACTTG TAGAGCTCCT ATGGAAAAAT

481 GGGCAAGTAG TTATGCACAA CCAAACACAT AGGAAGACAC

521 TTGGGAATTC ATCTAACTTG AGACAGGTGC AGAAAAGTGA

561 TCAATCAGTA TTAAGGTCTA GCGGTCCCTA TGGAAACTCA

601 AGCAACTTGG ATCAAGAAGA TGCCGCCCCA TGGGTCCAAT

641 TCCCACTTGA GGACCCATTG GAACAAGATT TTTGTTCAAA

681 CCTTTTATCT GAACTACCAA CTTGTGAATT TGAATCTTAC

721 AAGCCAATCA GGCAATTGGA AGAGGAAAAG TTTGCCAAAT

761 TTTTTGCTTC CGGTACCCCC CATCATCCTA CAACTTCAAG

801 TTCACAACCA CTACCACCTA ACATGAAACC CTCATGTATT

841 CAGGGACTCC AAGGGAATCC TATTCCTATG CCAGCTCCAA

881 GATTTCATGG TCCTGATTCA TCTCAGAAAA TCCATGACTT

921 TGGAGCATCA CGAAAGGTTC TAAATTTTCC TCAGTTTTCA

961 ACACCCCGTA ATAATGTTCC ATCAGCACCT GGTATTACAC

1001 AGTTTAGAGA GAAAACTACT GCTAACATGT CACAAAGTGA

1041 GGCTAGAGAG TACTCAGTGA TCACAGTTGG TTCAAGTCAC

1081 TGTGGCAGCA ATCACATCCC TCAGGAGCAA GATGTAAGCA

1121 GGATTTCAAG CACTGGTGTT TGGGCCACTA CTAATAATAA

1161 TACTACTTTA TCTGCTGAGC CTGAAGCTGT CAGAGATTAT

1201 GTCCAAAGAC CGATTTGTCC TAAGAGTGGC CAAGGAAAAT

1241 CAGAGATGAT TGAACTAACT GTGACTTCAT CTTCCGGTGG

1281 CTCGGGAAGT ACTGGTATCG GAAGAACCTG TTCCCTATCA

1321 ACAAGAGATC ATGGCCAAAA GAGAAAAGGG ACAGAAGAAG

1361 AAGCGTTAGA GGAACAAAGT GAGGACACAG AACTTAAATC

1401 AGCTGATGGA AACAAGGCTT CTCAGCGGAC GAGGTCTTCC

1441 AGAAGGAACC GTGCAGCAGA AGTGCATAAT CAATCAGAAA

1481 GGAGAAGAAG AGATAGGATC AACGAGAAGA TGAGGACATT

1521 GCAGCAACTG ATACCTAATA GTAACAAGAC AGACAAAGCA

1561 TCAATGTTAG AAGAGGCAAT CGAATACTTG AAATCACTTC

1601 AGTTTCAGCT TCAGGTTATG TGGATGGGGG GTGGCATGAC

1641 ACCAGTGATG TTCCCAGGAA TTCAGCACTA TATGTCACAA

1681 ATGGGTATGG GAATGGGTGC ACCTTCTTTG CCTTCCATTC

1721 ACAACCCGAT GCAATTGCCA AAAGTGCCAC ATGATCAAGC

1761 CATGTCTGTG CTTCAGATAC AAACCAGAA TTTAATGTGT

1801 CAAAATCCAG TTTTGGGTGC CTTTAACTAC CAAAACCAGA

1841 TGCAGAACCC GTGCCTTCCA GAACAATATG CACGTTACAT

1881 GGGTTACCAT CTTATGCAAA ATGCCTCTCA GCCTATGAAT

1921 GTGTTCAGAT ATGGTTCCCA AGCAGTGCAA CACAGTCAAA

1961 CGATGATTGC ACCAGGCAAT AATAGCAGCG GACCCATGAG

2001 TGGAACAGCT AATATTGATG ATGCTGACAG TGGCAAAGCG

2041 GGTTCTTCCA CCTTTAATTG AATAGTGAAT AGCAATACCT

2081 TAAAATTACT CAATTGGGGG AATTACCTAA TGGAGTACGT

2121 CAATCCTCAC AAGCACCAAT ATGTGCTCCA ATTTTATGTA

2161 G
```

A PIF4-related protein from *Oryza sativa* referred as a transcription factor PIF4 isoform X3 (NCBI accession no. XP_015618080.1 (GI:1002309425)) has substantial homology to the *Arabidopsis thaliana* PIF4 SEQ ID NO:38 protein sequence, as illustrated below. Domains of sequence homology are identified with asterisks below the sequence comparison.

36.8% identity in 323 residues overlap; Score: 322.0; Gap frequency: 8.4%
Seq 38    25
DELVELLWRDGQWLQSQTHREQTQTQKQDHHEEALRSSTFLEDQETVSWIQYPPDEDPF
Seq 44    24 DGLVELLWCNGHVVMQSQAPRKPPRPEKT-----TAAAAAAMAEDESASWFQYPVD-
DVL
              * ******  *  *  *          *    *  * * *

Seq 38    85
EPDDFSSHFFSTMDPLQRPTSETVKPKSSPEPPQVMVKPKACPDPPPQVMPPPKFRLTNS
Seq 44    78 EKDLFTE-
LFGEMTAAGGGGGDVRRAACKEERGAVAAFQSRMMPPPWPARGKAEFGDVDD
           * * *   *    *                    * *         **          *

Seq 38    145 SSGIRETEMEQY------------SVTTVGPSHCGSNPSQND-
LDVSMSHDRSKNIEEKL
Seq 44    137
VCGVSEVVMAKMDGAAAAETVGESSMLTIGSSICGSNHVQTPPVGNGKAGAGTAGAARRA
              *  *  *              *  *  * **** *

Seq 38    192 NPNAS--SSSGGSSGCSFGKDIKEMASGRCITTDRKR----
KRINHTDESVSLSDAIGNK
Seq 44    197
HDTATVASSSMRSRSCTAKAEPRDVAAAGVGGKRKQRGGAAMESGSPSEDVEFESAAATC
                * ***  * *      *            *           *       * *   *

Seq 38    246 SN-
QRSGSNRRSRAAEVHNLSERRRRDRINERMKALQELIPHCSKTDKASILDEAIDYLK
Seq 44    257
SPAQKTTTAKRRRAAEVHNLSERRRRDRINEKMKALQELIPHCNKTDKASMLDEAIEYLK
              *  *     * ***************** ******* ** ***
***

Seq 38    305 SLQLQLQVMWMGSGMAAAAASAP
Seq 44    317 SLQLQLQMMWMGGGMAPPAVMFP
              *****  *  *   *

This PIF4-related protein from *Oryza sativa* referred as a transcription factor PIF4 isoform X3 (NCBI accession no. XP_015618080.1 (GI:1002309425)) has the following sequence (SEQ ID NO:44).

```
  1 MNQFVPDWNT TSMGDGFAPL GEDDGLVELL WCNGHWMQS

41 QAPRKPPRPE KTTAAAAAAM AEDESASWFQ YPVDDVLEKD

81 LFTELFGEMT AAGGGGGDVR RAACKEERGA VAAFQSRMMP

121 PPWPARGKAE FGDVDDVCGV SEWMAKMDG AAAAETVGES

161 SMLTIGSSIC GSMHVQTPPV GNGKAGAGTA GAARRAHDTA

201 TVASSSMRSR SCTAKAEPRD VAAAGVGGKR KQRGGAAMES

241 GSPSEDVEFE SAAATCSPAQ KTTTAKRRRA AEVHNLSERR

281 RRDRINEKMK ALQELIPHCN KTDKASMLDE AIEYLKSLQL

321 QLQMMWMGGG MAPPAVMFPA AGVHQYMQRM GAVGMGPPHM

361 ASLPRMPPFM APPPAAYQSS PVYSMADPYA RCLAVDHLQP

401 PPPMFRREY
```

A cDNA encoding the PIF4-related protein from *Oryza sativa* referred as a transcription factor PIF4 isoform X3 (NCBI accession no. XP_015618080.1 (GI:1002309425); SEQ ID NO:44) has the following sequence (SEQ ID NO:45).

```
  1 GCGAGTCCTC TTCCTGCCCT GCCCTGCCCT GCCCTGCATT

41 CTTTCTTTCT CCACCAGGGG AATCCAGTTC ACCCCCAGTG

81 CTGCTTCTGC TGCTGCTTCT GCATCATCTT GCCCTGTTAA
```

```
-continued
121 AAAGACACAG TGCCCTTGTT CTTTCGCAGT TGCAACTAGC

161 ATCTCCTCCT CTACTTGTAC TCACTTCACA CCTCAGCTCA

201 GCTCAGCTCA TCTCCTGTCA TCTCAGCTCA AAGAGAAAGA

241 GCTGAAGGTG TAAGCTGATC ACCAGGAAGC AGAGGCTTTT

281 TTTCAGATTA CAGTTATCTG AAACAACCAA CTTCAGAATC

321 AATCAGCAAA GGTAGAAACA AGACAGAGCT GCTGTGCTTC

361 TGTGATTAAT TAGGGTTGTT AATGCCATGA ACCAGTTCGT

401 CCCTGATTGG AACACCACCA GCATGGGCGA CGGCTTTGCG

441 CCATTAGGCG AAGACGACGG GCTCGTCGAG CTGCTATGGT

481 GCAATGGCCA CGTCGTCATG CAGAGCCAGG CGCCGCGGAA

521 GCCGCCGAGG CCGGAGAAGA CGACGGCGGC GGCGGCGGCG

561 GCGATGGCGG AGGATGAGTC GGCGTCGTGG TTTCAGTACC

601 CGGTCGACGA CGTGCTTGAG AAGGACCTGT TCACCGAGCT

641 GTTCGGCGAA ATGACGGCGG CCGGCGGCGG CGGCGGCGAC

681 GTCCGCAGGG CGGCGTGCAA GGAGGAGCGC GGCGCGGTCG

721 CCGCGTTCCA GAGCAGGATG ATGCCGCCGC CGTGGCCGGC

761 GAGGGGGAAG GCGGAGTTCG GTGACGTCGA CGACGTGTGC

801 GGCGTCTCGG AGGTCGTCAT GGCGAAGATG GACGGGGCGG

841 CGGCGGCGGA GACGGTCGGC GAGTCATCGA TGCTGACAAT

881 CGGGTCGAGC ATCTGCGGGA GCAACCACGT TCAGACGCCG

921 CCGGTGGGGA ACGGGAAGGC CGGCGCCGGC ACCGCCGGCG
```

```
                      -continued
 961  CCGCCAGAAG GGCGCACGAC ACGGCGACGG TGGCGTCGTC

1001  GTCGATGAGG TCGAGGTCCT GCACCGCCAA GGCCGAGCCG

1041  CGCGACGTCG CAGCCGCCGG CGTCGGCGGC AAGCGGAAGC

1081  AGCGCGGCGG CGCCGCCATG GAGTCCGGGA GCCCCAGCGA

1121  GGACGTGGAG TTCGAGTCCG CCGCCGCAAC GTGCTCGCCG

1161  GCGCAGAAGA CGACGACGGC GAAGCGGCGG CGCGCCGCCG

1201  AGGTGCACAA CCTCTCCGAG AGGAGGAGAA GAGATAGGAT

1241  CAATGAGAAG ATGAAAGCAT TACAGGAGCT CATACCTCAC

1281  TGCAACAAAA CGGACAAAGC ATCGATGCTG GATGAAGCGA

1321  TCGAGTATCT CAAGTCACTG CAGCTCCAGC TACAGATGAT

1361  GTGGATGGGC GGCGGAATGG CGCCGCCGGC GGTGATGTTC

1401  CCGGCGGCGG GCGTGCACCA GTACATGCAG CGGATGGGCG

1441  CCGTCGGGAT GGGCCCACCA CACATGGCGT CCCTGCCGAG

1481  GATGCCGCCG TTCATGGCGC CGCCGCCGGC CGCCGTGCAG

1521  AGCTCGCCGG TGGTCAGCAT GGCCGACCCC TACGCCCGCT

1561  GCCTCGCCGT CGACCACCTC CAGCCACCGC CTCCGATGTT

1601  TCGACGCGAA TACTAGGGAA GGAACTAATA TCAAATAATA

1641  GAAGGGGTGA GCCTTCGAAT CGAGATCGTC TAGCCCACCA

1681  CCTTATAGAG CTAGCCGGAA GGCCCTCGAG CGTTTCTCAT

1721  ATTTTCAGTT TCCTAAGAGT TTTTTTTTT
```

Expression cassettes and expression vectors can include a nucleic acid segment encoding a PIF4 protein where the nucleic acid segment is operably linked to a promoter. The nucleic acid segment can encode a PIF4 protein with at least 70% sequence identity, or at least 80% sequence identity, or at least 85% sequence identity, or at least 90% sequence identity, or at least 95% sequence identity, or at least 97% sequence identity, or at least 98% sequence identity, or at least 99% sequence identity to any of amino acid sequences identified as SEQ ID NO: 38, 40, 42, or 44. For example, the Pif4 nucleic acid segment can have at least 70% sequence identity, or at least 80% sequence identity, or at least 85% sequence identity, or at least 90% sequence identity, or at least 95% sequence identity, or at least 97% sequence identity, or at least 98% sequence identity, or at least 99% sequence identity to any of nucleic acid sequences identified as SEQ ID NO: 38, 40, 42, or 44.

As stated, expression cassettes and expression vectors can include a nucleic acid segment encoding a PIF4 protein where the nucleic acid segment is operably linked to a promoter. Promoters provide for expression of mRNA from the PIF4 nucleic acids. The promoter can be heterologous to the PIF4 nucleic acid segment. In other words, such a heterologous promoter is not naturally linked to such a PIF4 nucleic acid segment. Instead, some expression cassettes and expression vectors have been recombinantly engineered to include a PIF4 nucleic acid segment operably linked to a heterologous promoter. A PIF4 nucleic acid is operably linked to the promoter, for example, when it is located downstream from the promoter.

A variety of promoters can be included in the expression cassettes and/or expression vectors. Promoter regions are typically found in the flanking DNA upstream from the coding sequence in both prokaryotic and eukaryotic cells. A promoter sequence provides for regulation of transcription of the downstream gene sequence and typically includes from about 50 to about 2,000 nucleotide base pairs. Promoter sequences can also contain regulatory sequences such as enhancer sequences that can influence the level of gene expression. Some isolated promoter sequences can provide for gene expression of heterologous DNAs, that is a DNA different from the native or homologous DNA.

Promoters can be strong or weak, or inducible. A strong promoter provides for a high level of gene expression, whereas a weak promoter provides for a very low level of gene expression. An inducible promoter is a promoter that provides for the turning on and off of gene expression in response to an exogenously added agent, or to an environmental or developmental stimulus. For example, a bacterial promoter such as the $P_{tac}$ promoter can be induced to vary levels of gene expression depending on the level of isothiopropylgalactoside added to the transformed cells. Promoters can also provide for tissue specific or developmental regulation. A strong promoter for heterologous DNAs can be advantageous because it provides for a sufficient level of gene expression for easy detection and selection of transformed cells and provides for a high level of gene expression when desired. In some cases, the promoter within such expression cassettes/vectors can be functional during plant development or growth.

Expression cassettes/vectors can include, but are not limited to, a plant promoter such as the CaMV 35S promoter (Odell et al., *Nature.* 313:810-812 (1985)), or others such as CaMV 19S (Lawton et al., *Plant Molecular Biology.* 9:315-324 (1987)), nos (Ebert et al., *Proc. Natl. Acad. Sci. USA.* 84:5745-5749 (1987)), Adh1 (Walker et al., *Proc. Natl. Acad. Sci. USA.* 84:6624-6628 (1987)), sucrose synthase (Yang et al., *Proc. Natl. Acad. Sci. USA.* 87:4144-4148 (1990)), α-tubulin, ubiquitin, actin (Wang et al., *Mol. Cell. Biol.* 12:3399 (1992)), cab (Sullivan et al., *Mol. Gen. Genet.* 215:431 (1989)), PEPCase (Hudspeth et al., *Plant Molecular Biology.* 12:579-589 (1989)) or those associated with the R gene complex (Chandler et al., *The Plant Cell.* 1:1175-1183 (1989)). Further suitable promoters include the poplar xylem-specific secondary cell wall specific cellulose synthase 8 promoter, cauliflower mosaic virus promoter, the Z10 promoter from a gene encoding a 10 kD zein protein, a Z27 promoter from a gene encoding a 27 kD zein protein, inducible promoters, such as the light inducible promoter derived from the pea rbcS gene (Coruzzi et al., *EMBO J.* 3:1671 (1971)) and the actin promoter from rice (McElroy et al., *The Plant Cell.* 2:163-171 (1990)). Seed specific promoters, such as the phaseolin promoter from beans, may also be used (Sengupta-Gopalan, *Proc. Natl. Acad. Sci. USA.* 83:3320-3324 (1985). Other promoters useful in the practice of the invention are available to those of skill in the art.

Alternatively, novel tissue specific promoter sequences may be employed in the practice of the present invention. cDNA clones from a particular tissue are isolated and those clones which are expressed specifically in that tissue are identified, for example, using Northern blotting. Preferably, the gene isolated is not present in a high copy number, but is relatively abundant in specific tissues. The promoter and control elements of corresponding genomic clones can then be localized using techniques well known to those of skill in the art.

A PIF4 nucleic acid can be combined with the promoter by standard methods to yield an expression cassette, for example, as described in Sambrook et al. (MOLECULAR CLONING: A LABORATORY MANUAL. Second Edition (Cold Spring Harbor, NY: Cold Spring Harbor Press (1989);

MOLECULAR CLONING: A LABORATORY MANUAL. Third Edition (Cold Spring Harbor, NY: Cold Spring Harbor Press (2000)). Briefly, a plasmid containing a promoter such as the 35S CaMV promoter can be constructed as described in Jefferson (*Plant Molecular Biology Reporter* 5:387-405 (1987)) or obtained from Clontech Lab in Palo Alto, California (e.g., pBI121 or pBI221). Typically, these plasmids are constructed to have multiple cloning sites having specificity for different restriction enzymes downstream from the promoter. The PIF4 nucleic acids can be subcloned downstream from the promoter using restriction enzymes and positioned to ensure that the DNA is inserted in proper orientation with respect to the promoter so that the DNA can be expressed as sense or antisense RNA. Once the PIF4 nucleic acid is operably linked to a promoter, the expression cassette so formed can be subcloned into a plasmid or other vector (e.g., an expression vector).

In some embodiments, a cDNA clone encoding a PIF4 protein is isolated or obtained from a selected plant type. In other embodiments, cDNA clones from other species (that encode a PIF4 protein) are isolated from selected plant tissues. For example, the nucleic acid encoding a PIF4 protein can be any nucleic acid with a coding region that hybridizes to SEQ ID NO:39 and that has PIF4 activity. In another example, the PIF4 nucleic acid can encode a PIF4 protein with at least 90% sequence identity to SEQ ID NO:38. Using restriction endonucleases, the entire coding sequence for the PIF4 nucleic acid is subcloned downstream of the promoter in a 5' to 3' sense orientation.

jazQ Mutations

A quintet of JAZ transcriptional repressor genes can be modified to improve insect resistance in plants. The quintet of JAZ transcriptional repressor genes can encode JAZ1, JAZ3, JAZ4, JAZ9, JAZ10, and/or related proteins. Reduction or deletion of genes that encode JAZ1, JAZ3, JAZ4, JAZ9, JAZ10, and/or related proteins can provide insect resistance to plants.

JAZ1 proteins are repressors of the jasmonic acid signaling pathway. One example, of an *Arabidopsis thaliana* jasmonate-zim-domain protein 1 (JAZ1) protein sequence is shown below (SEQ ID NO:48).

```
  1 MSLFPCEASN MDSMVQDVKP TNLFPRQPSF SSSSSSLPKE

41 DVLKMTQTTR SVKPESQTAP LTIFYAGQVI VFNDFSAEKA

81 KEVINLASKG TANSLAKNQT DIRSNIATIA NQVPHPRKTT

121 TQEPIQSSPT PLTELPIARR ASLHRFLEKR KDRVTSKAPY

161 QLCDPAKASS NPQTTGNMSW LGLAAEI
```

A chromosomal DNA sequence for the *Arabidopsis thaliana* jasmonate-zim-domain protein 1 (JAZ1) protein with SEQ ID NO:48 is shown below as SEQ ID NO:49.

```
   1 ATATTGGAGG TAGGAAGAAG AACTCTGCAA CCAAACCAAC

41 CAACCCCAAA GCCAAACAAA GTTTTATAGA GACCTTCCAT

121 TTCTCCCTCT CGTGAGAAAC GCAATTTGCA GAGAAGCAAC

201 AGCAACAACA AGAAGAAGAA GAAAAAGATT TGAGATTACT

241 TTGTATCGAT TTAGCTATTC GAGAAACTCT TGCCGTTTGA

281 AAGTTTTAAT TGTTAAAGAT GTCGAGTTCT ATGGAATGTT

321 CTGAGTTCGT CGGTAGCCGG AGATTACTG GGAAGAAGCC

361 TAGCTTCTCA CAGACGTGTA GTCGATTGAG TCAGTATCTA

401 AAAGAGAACG GTAGCTTTGG AGATCTGAGC TTAGGAATGG

441 CATGCAAGCC TGATGTCAAT GGTAAGAAAC CTTCTCTTTC

481 TCCTAGATCC ACTTCTTTTT TCGTTTTCTC TGTTTTTTAT

521 TTCTTGAATC TTGATCTTGA AAACTTTTCA AGAAAATTTT

561 GAATCGATTT CAAAGAAATT AGGGAGAGTT AGTTTGCTAA

601 ATTTTGACAT AGAAAATGAT TGGAGAGAGT TCTAACTTTT

641 GGATCATATA TATTTGCAGG AACTTTAGGC AACTCACGTC

681 AGCCGACAAC AACCATGAGT TTATTCCCTT GTGAAGCTTC

721 TAACATGGAT TCCATGGTTC AAGATGTTAA ACCGACGAAT

761 CTGTTTCCTA GGCAACCAAG CTTTTCTTCC TCATCTTCCT

801 CTCTTCCAAA GGAAGATGTT TTGAAAATGA CACAGACTAC

841 CAGATCTGTG AAACCAGAGT CTCAAACTGC ACCATTGACT

881 ATATTCTACG CCGGGCAAGT GATTGTATTC AATGACTTTT

921 CTGCTGAGAA AGCCAAAGAA GTGATCAACT TGGCGAGCAA

961 AGGCACCGCT AATAGCTTAG CCAAGAATCA AACCGATATC

1001 AGAAGCAACA TCGCTACTAT CGCAAACCAA GTTCCTCATC

1041 CAAGAAAAAC CACAACACAA GAGCCAATCC AATCCTCCCC

1081 AACACCATTG ACAGAACTTC CTATTGCTAG AAGAGCTTCA

1121 CTTCACCGGT TCTTGGAGAA GAGAAAGGAC AGAGTTACGT

1161 CAAAGGCACC ATACCAATTA TGCGATCCAG CCAAAGCGTC

1201 TTCAAACCCT CAAACCACAG GCAACATGTC GTGGCTCGGT

1241 TTAGCAGCTG AAATATGAAT GCTAACCACC CTCAAGCCGT

1281 ACCAAGAAAT TCTTTTGACG ACGTTGCTTC AAGACAAGAT

1321 ATAAAAGCTC CTATCTTCAT GCTTTTTGAT TTAAGATACA

1361 AACTACTCAA TGATTAGGAA ACTTCATATA TTTGTATGTA

1401 TTGATTAGTG ATCAATTATT GTTAGTATTC GTTATAGTCT

1441 GTTTTTCTAC TAGTTATTGT CGCCTGTCTA AATCCCCTTG

1481 CTATGGGTTA TCTCAAAATT AGTTTCGTAT GTAACTAATT

1521 TTGTAAGAAC AATAATTTTT GTTGACGAAC CATACTATCA

1561 AATACTCTAA ATTATATCTT GATAAATCTA CCTATCAGGT

1601 AAGTAGG
```

JAZ3 is also a repressor of jasmonate responses, and it is targeted by the SCF(COI1) complex for proteasome degradation in response to jasmonate. One example, of an *Arabidopsis thaliana* jasmonate-zim-domain protein 3 (JAZ3) protein sequence is shown below (SEQ ID NO:50).

```
  1 MERDFLGLGS KNSPITVKEE TSESSRDSAP NRGMNWSFSN

41 KVSASSSQFL SFRPTQEDRH RKSGNYHLPH SGSFMPSSVA

81 DVYDSTRKAP YSSVQGVRMF PNSNQHEETN AVSMSMPGFQ

121 SHHYAPGGRS FMNNNNNSQP LVGVPIMAPP ISILPPPGSI

161 VGTTDIRSSS KPIGSPAQLT IFYAGSVCVY DDISPEKAKA

201 IMLLAGNGSS MPQVFSPPQT HQQVVHHTRA SVDSSAMPPS

241 FMPTISYLSP EAGSSTNGLG ATKATRGLTS TYHNNQANGS

281 NINCPVPVSC STNVMAPTVA LPLARKASLA RFLEKRKERV

321 TSVSPYCLDK KSSTDCRRSM SECISSSLSS AT
```

A chromosomal DNA sequence for the *Arabidopsis thaliana* jasmonate-zim-domain protein 3 (JAZ3) protein with SEQ ID NO:50 is shown below as SEQ ID NO:51.

```
   1 GCGATTTGTT AATAAAACTA GAAATTGCGG TGAATTAACT
  41 TCATTCCACG TTTTTTCATT TTCTCCCTCA AAAGTCTCTG
  81 TTTTTTTTCC TTTTTCCGGC GAAGCTCTAT TTAGCTTGAT
 121 TCCGGCGTTT AACACGCGTT TTAATCGAAA CAGACATTTG
 161 AGATCGAATT AATTTTGTAG CGGGCTGTGT CTTTATTATA
 201 GATGGAGAGA GATTTTCTCG GGTTGGGTTC GAAAAATTCT
 241 CCGATCACTG TCAAGGAGGA AACCAGCGAA AGCTCTAGAG
 281 ATTCAGGTTA TTTATTACTC TTCTCAATTT TTCTGATTCT
 321 GATTGTTTTT AAATCGTAGA TTTGTTTGAT TGATTAGGAG
 361 TTATTAGGAC TACTTGTAGT ATGGAATTTG TTTTTGGATA
 401 GCTGATTTTA TGGCTTGCTC GGGAACTGGA ATTGTCAGTT
 441 TGTTGCTTGG AGCAGAACAT TGTCCTTTGC TTTTCTCGGG
 481 AGATGTAGAA TTTGGATTTG GAAAAACTAG TGTTCTTTTC
 521 CAAAGCCTTG TCTTAAACAT GCTTTCGGTC GGAGAAATTA
 561 ACGAGAACTA ATCTCAAGCT TCTAACATAA TTAAACTCGG
 601 TAAACTTTTT TTTACTAGAG TAAATTTTTT TGTTTTGTTT
 641 GAAGAGTCTT ATAATTGAGA AATACTTTAT TAGTTTATAC
 681 TAAAAAAAAA ACGAATACGT AAAATGTTGG AAAAGAGGGG
 721 ATGTATAGAG ACTGATACAA AAATGATAAA ATAGAGACGG
 761 TTGGTAGTAG GTAGAAAGAT TAAATATACT CAAAAGAGTG
 801 AGTTGGATTA GTTTATAAGA TGATTAACTT CTTGATTGTG
 841 TGAGTTGGAT TAGTTTATGA GATTATTAAA ATATTGATTG
 881 TGTATTTGTG TTGTGTGTTG ATTAAGCGGA ACTTGCGTTA
 921 GAATATTGTT CAAGGTACAA TGTGGAAATA ATAGTTTTCT
 961 CACCACGAGG AATATAATTA TTTCAACTTT GTTTTCTTAT
1001 CAGCCAAAAC GTGCCACACC ATAAAGTAG TGCATCAACA
1041 TGTGGTGTGG TGTGGTGGGG TTAAAGTTTG AATCTCTCTT
1081 TAATTTAAAC TATTAAAACA AACTTAAATT ATTGGAGTTT
1121 CGTACAATGA CTTTCAATCA AATGTTTTAG AATTAGACAC
1161 GGTTTTCGAA AGTGGTTTTC CCTCGTTGAA TTTGTCAACA
1201 GTATCAGATT CTACATTGTT GGTTACTAAT CTTTTCCTTG
1241 AAGTAGGTGT TGAATTAATC CTCTGTTGTT TATGTAAGGA
1281 GATCTCGAGA CATTTATGGT TAACAGTTAA CACTAGATGT
1321 TTGACTTTAA ACTGATTATC TTTTATTCTT TTTCTTTTGT
1361 AGCTCCCAAC AGAGGAATGA ACTGGTCTTT CTCAAACAAA
1401 GTATCAGCTT CTTCTTCTCA GTTTCTATCC TTCAGGCCAA
1441 CTCAAGAAGA TAGACATAGA AAGTCTGGAA ATTATCATCT
1481 TCCTCACTCT GGTTCCTTCA TGCCATCATC AGTAGCTGAT
1521 GTTTATGATT CAACCCGCAA AGCTCCTTAC AGTTCTGTAC
1561 AGGTATTTGT CATCAAAACC TATGTTAACC AAGACCCTTG
1601 TGTTTTTTTT ATCCTTCGCA AGATAGCTTT AAAAGTGAGC
1641 CCTGTTTTAT GAGCATATAG TAATTGGTTT TGAGTCTAGT
1681 TTAGCACAAG TTCATGGCAA TTAGTTTGTG GATCTAATCT
1721 TGGTTTAATA CTGATTCATT TTAAGTGTAA GCTAAGCTTC
1761 TCATTTTTGA TAAGTTAGTT CATACAATGC CTCACACCTA
1801 CTTTATGGCT TGTTACTCTC AGGGAGTGAG GATGTTCCCT
1841 AATTCCAATC AACACGAAGA AACTAACGCA GTTTCCATGT
1881 CGATGCCGGG TTTCCAGTCT CATCATTATG CACCAGGAGG
1921 AAGAAGCTTC ATGAACAATA ACAATAACTC ACAACCTTTG
1961 GTAGGAGTTC CTATCATGGC ACCTCCAATT TCAATCCTTC
2001 CTCCTCCAGG TTCCATTGTA GGGACTACTG ATATTAGGTA
2041 CCCACTAGTC ATCATATCAT ACAGAAACTC TTTCTACATT
2081 TTCATAGTTG ACTAAAGACT TATTTTTGTC AGATCTTCTT
2121 CCAAGCCAAT AGGTTCACCT GCGCAGTTGA CGATCTTTTA
2161 TGCCGGTTCA GTTTGTGTTT ACGATGACAT ATCTCCTGAA
2201 AAGGTATCTC AATCATTTTC TTCCATATAT GCATCTCTTT
2241 TACTCGTAAG GTATGGTACT CATTTGCTTT CTTTCATTTC
2281 TCAGGCAAAG GCGATAATGT TGCTAGCTGG AACGGTTCC
2321 TCTATGCCTC AAGTCTTTTC GCCGCCTCAA ACTCATCAAC
2361 AAGTGGTCCA TCATACTCGT GCCTCTGTCG ATTCTTCAGC
2401 TATGCCTCCT AGCTTCATGC CTACAATATC TTATCTTAGC
2441 CCTGAAGCTG GAAGTAGCAC AAACGGACTC GGAGCCACAA
2481 AAGCGACAAG AGGCTTGACG TCAACATATC ACAACAACCA
```

-continued

```
2521  AGCTAATGGA TCCAATATTA ACTGCCCAGT ACCAGTTTCT
2561  TGTTCTACCA ATGTAATGGC TCCAACAGGT AAAAAACAAA
2601  GTCAGAGACC TGATACTACA TTCGCCATCT AACTTACTAG
2641  TATTTTCATG GATGTAACTT CATTCTCGTT CTGTTTCTTA
2681  TGCAGTGGCA TTACCTCTGG CTCGCAAAGC ATCCCTGGCT
2721  AGGTTTTTAG AGAAACGCAA AGAAAGGTAC GCAACACTTC
2761  TTTAGAATAC ACCATTCAAT AGTTTCTTGG GCTAACTCTC
2801  TTTCTCGCTG TGGGTTTCTC AGGGTCACGA GCGTATCCCC
2841  ATATTGCTTA GACAAGAAGT CATCGACAGA TTGTCGCAGA
2881  TCAATGTCTG AATGCATTAG TTCTTCTCTC AGCTCTGCAA
2921  CCTAATTTCA TCTACAGTAA GAAGGTTGCT TTAGACCACT
2961  CCACATCCAT ATTTGCATTT CAATGGCGGT CTTTTCAATG
3001  TCTCAGTTAA TTTTTCCTCA CTCGCCACAC TGAGTTTCTC
3041  CTTAGCTTTA TATATACGAT AGTGTATACT TTGTTTACAT
3081  GTTTTTTGGT GGAATGGAAC TTATGAGAGC ATATCAGATA
3121  TGTACTTGGG AAAATTAGTA GAAACTGTTT GTTTCTTTTT
3161  TTTTAACTCT GTTCTTTTGT ATATATCACT GAAGCTCGCA
3201  TATGTATAAT TCATGTAATG GAATTGCATC GCTTCTGTTT
3241  CCCTAAGTTA TTT
```

JAZ4 is also a repressor of jasmonate responses. One example of an *Arabidopsis thaliana* jasmonate-zim-domain protein 4 (JAZ4) protein sequence is shown below (SEQ ID NO:52).

```
  1  MERDFLGLGS KLSPITVKEE TNEDSAPSRG MMDWSFSSKV
 41  GSGPQFLSFG TSQQETRVNT VNDHLLSSAA MDQNQRTYFS
 81  SLQEDRVFPG SSQQDQTTIT VSMSEPNYIN SFINHQHLGG
121  SPIMAPPVSV FPAPTTIRSS SKPLPPQLTI FYAGSVLVYQ
161  DIAPEKAQAI MLLAGNGPHA KPVSQPKPQK LVHHSLPTTD
201  PPTMPPSFLP SISYIVSETR SSGSNGVTGL GPTKTKASLA
241  STRNNQTAAF SMAPTVGLPQ TRKASLARFL EKRKERVINV
281  SPYYVDNKSS IDCRTLMSEC VSCPPAHHLH
```

A chromosomal DNA sequence for the *Arabidopsis thaliana* jasmonate-zim-domain protein 4 (JAZ4) protein with SEQ ID NO:52 is shown below as SEQ ID NO:53.

```
   1  ATTAGAGGAA TCATAAATCG GCGGTGTGTG TAACTTCAAC
  41  TCACGTTTTT CATTTCTCTC CAAAGTCCTT CAATTGTTAC
  81  TAATTCTCTC TGATCTCTCA TTTCTTCTCT TCTCCGGTGA
 121  CATTTTTTTT CTCCCCCGCG AAAGCTAAAC CGTTTTTGTA
 161  TTCTCAACGA TTGATAAGCC TGATGGAGAG AGATTTTCTC
 201  GGGCTGGGAT CAAAGTTATC TCCGATAACT GTGAAGGAGG
 241  AAACTAACGA AGATTCAGGT AATTCATCTT CAACATCTTC
 281  CATTATGATC TGATGATTGT GTTTTTCATC TCACTTTTTT
 321  TTGTTTCTAT TTTTGTAATC TCTTTTTTTG TTTATTGTTC
 361  AAGTACATAT ATATTGTTTT TCTAGCTTGA TTGGGAGTCC
 401  TACTGTCTGG TTTTTTCTTG AACAAGAAAT TTTTTCTTCG
 441  TTTTCTCGGG AAGAGAAAAA ATAAATTAGG GTTTCTTTTT
 481  TCTTGATATA TATTTAAGAA ATTAGGTTTT AGTACTATAG
 521  ACAGAAATTT AGCTACTCGA ATTTGTTTGA CGTAGCCGAT
 561  GAAAAAACAC GTTTTGGGAC TCGATAGTTA GAAAATTCAT
 601  ACGTTCACGA TCTACTTTTG AAGTTTTTTT CATTAAATAT
 641  TTTTTGCAAA CTACAAATGT ACAAGTATAC AACTATACAA
 681  GCAAACACCA AACTTGTTGA CGTTAGTAAT TTAACAAGTG
 721  TTAGTATTAT CTTTGAAAAA TAATATTCAG AGAACAAACT
 761  TGATTTTCTA GGTGACTAGG TGATGCATGT TTCTAAAGCT
 801  GTTGGTAATG TTGAGTGTTT TCAAAATAAT TTCGTTTTTT
 841  TCTTCAAACA GCCGACACCG ACAGAACAAA AATGCTATAT
 881  TTTTTTTGTT GCTTACAAAA TTGATCAATT GGTTTCAATA
 921  CAATAGTATC TTCTTTAGAA AAGATTGTTT TTTTCAAAGC
1001  CGGATTGAAT ATTGAGAATT AGAACATTGG CTGGTTATTC
1041  TTTTTGAAAA GTTTATGCCA TTTTTTAAGG TTTATTAAGC
1081  AACTTGAATT CTATCAGTAT TATTTAAAAA CGAAGACGTG
1121  AAATGTTGGG AAAAGAATGC GTTATATAGC GACCGGCTGA
1161  CGATTAGAGA TTTAACAACA AATGCAAGTT GAATTATATA
1201  AAAGCAAGAT TGATTGTGAC TTGATTAAGT TTTATTTCTA
1241  TCCAAGTAGA CTCATTGATT AAGTTAGGAT CATGTTGGGT
1281  ATTAAATTTA GATCAAGTTA CAATTGGAT GAATAATTTA
1321  CTTACCCACG AGGAATTTAA TAGTTAGTTC TTGTCTTTTT
1361  ATATTCCGAA ACGTGCCATT TCTTGAAAGT ATTTGTATGA
1401  TCACTATTTT CCCCAGTGTG TTTGGCTTTA TGCAGATTTG
1441  TTCATTGTTG ATGAATCTAA TGTTAAGAGT CGTCCACTTT
1481  AGCATAGCTA GATCTGAGTG TTTCCTAGTT TGATAAAATC
1521  TAAAGACATT TGCTCATGTT TCAGCCCCAA GTAGAGGTAT
1561  GATGGATTGG TCATTCTCAA GCAAAGTCGG TTCTGGTCCT
1601  CAGTTTCTTT CTTTTGGGAC ATCCCAACAA GAAACGCGTG
1641  TAAACACAGT CAATGATCAT TTGCTTTCTT CTGCTGCAAT
```

-continued

```
1681 GGATCAAAAC CAGAGAACTT ACTTCAGCTC ACTACAGGTT
1721 AGGCTATTTC TTGAAAAGAA AAAAAGTAGT GATAAAGTGT
1761 GATTTAGTGA CCTTGTAAGA AAGCTTGGCA ATTGGTTTAG
1801 TTTCTTCTGG TCTCAAAATT GATACAAAAT GATCTCAGGA
1841 AGACAGAGTG TTCCCAGGTT CCAGTCAGCA AGACCAAACA
1881 ACCATCACAG TCTCCATGTC CGAACCAAAC TACATCAACA
1921 GTTTCATAAA CCACCAACAT TTAGGAGGAT CTCCTATCAT
1961 GGCACCTCCA GTTTCAGTAT TTCCTGCTCC AACCACTATT
2001 AGGCATGCAC TGCATTCTAT CTTCTTCTGT TTAACATCAG
2041 ATACAGAACC TCTTTACTTC TATAGTTGAC TCGAGCTCCT
2081 TTATGTTCAT CTCCAGATCT TCTTCAAAAC CACTTCCCCC
2121 TCAGTTGACA ATCTTTTATG CCGGTTCAGT ATTAGTTTAC
2161 CAAGACATAG CTCCTGAAAA GGTAACCAAA TTTCCTTCAA
2221 TATGTGTTAC ATTACAGTCC AAGCTATCCA CTGACTAAGT
2241 ATTCAATCAA AGAAATAAGT TTCACGTATA GACATGCTGA
2281 AGTTATAGAA AGTTACTAAC CTGGTTTCAA CATACAGTAT
2321 GTTAATGATT CATAGATATG ATAAATCTTT GTCCTTACTT
2361 CTTCATTTAT TTTGTATTCA TAGGCCCAAG CTATCATGTT
2401 GCTAGCCGGA AATGGACCTC ATGCTAAACC GGTTTCACAA
2441 CCTAAACCTC AAAAACTGGT TCATCACTCT CTTCCAACCA
2481 CTGATCCTCC AACTATGCCT CCTAGTTTCC TGCCTTCCAT
2521 CTCTTACATT GTCTCTGAAA CCAGAAGTAG TGGATCCAAC
2561 GGGGTTACTG GACTTGGACC AACAAAAACA AAGGCGAGTT
2601 TAGCATCCAC GCGCAACAAC CAAACTGCTG CCTTCTCTAT
2641 GGCTCCAACA GGTTATAAAT GAAGTCTTAA CTCCTATTAA
2681 TGTTTTGTCA TCAAACTTCT ATCTTAGGTT TAGTTTGTTA
2721 TAACCAAAAA ATCTTGCTAT GATTTAATAC AGTGGGTTTA
2761 CCACAAACAC GCAAAGCATC CTTGGCTCGG TTCTTAGAGA
2801 AACGCAAAGA AAGGTACTGA GCTACAAGAT TATTCACTTA
2841 TTCACAATAT CAAAACACAG GTTTGCTGTA TATTGGCTTC
2881 GTTTTCTTGC AGGGTCATTA ACGTATCACC TTATTACGTA
2921 GACAACAAGT CATCAATAGA CTGTAGAACA CTGATGTCTG
2961 AATGTGTAAG CTGTCCTCCA GCTCATCATC TGCACTAAAA
3001 CCAATTTAGA CCCCTCATTG TTCTAAAGGC TTTTTCTTTT
3081 TTCTCTGGCT CTGTATCCTA TAGACTATAG TATAGTTGTT
3121 ATAGCTTTTG TTTATTCAGA TTTTAGTACA CTGGGCTTGT
3161 AAAAGCAAGT TATTTATATA TATCCTATAA ATTTAATTTG
3201 GATACTGTAT GTTTTGTCTT TACTCTTGCA TGTGTATAAA
3241 AAACATAAAA GTAAGACTAT TCAAGCT
```

JAZ9 is also a repressor of jasmonate responses. One example of an *Arabidopsis thaliana* jasmonate-zim-domain protein 9 (JAZ9) protein sequence is shown below (SEQ ID NO:54).

```
  1 MERDFLGLSD KQYLSNNVKH EVNDDAVEER GLSTKAAREW
 41 GKSKVFATSS EMPSSDFQEA KAFPGAYQWG SVSAANVFRR
 81 CQFGGAFQNA TPLLLGGSVP LPTHPSLVPR VASSGSSPQL
121 TIFYGGTISV FNDISPDKAQ AIMLCAGNGL KGETGDSKPV
161 REAERMYGKQ IHNTAATSSS SATHIDNFSR CRDTPVAATN
201 AMSMIESFNA APRNMIPSVP QARKASLARE LEKRKERLMS
241 AMPYKKMLLD LSTGESSGMN YSSTSPT
```

A chromosomal DNA sequence for the *Arabidopsis thaliana* jasmonate-zim-domain protein 9 (JAZ9) protein with SEQ ID NO:54 is shown below as SEQ ID NO:55.

```
   1 GCAAAGAGTT AAATAAGCCT CTCCAAAAGT GTGTCTGTAA
  41 CATTACCAAA ACGAAACCTT CCTTGTGGAT TCCCACTTCT
  81 TTCTTCTGTT TTCTTCTTCC TCTTCTTTAA ATTGGATGTT
 121 TTGGGCAAGA AACAGAGAGA AACACGTTAA TTTGAGAGTT
 161 TGTCATTGAA TATTTGGTTT GCAATGGAAA GAGATTTTCT
 201 GGGTTTGAGC GACAAGCAGT ATCTAAGTAA TAACGTTAAG
 241 CATGAGGTTA ACGATGATGC TGTCGAAGAA CGAGGTTTGT
 281 GTTCTTGTCT CGAGAATCTT TTATTTTAAT GTTTGAAGAA
 321 GAGATCAGTT TTCACTTTTA ACATAGCCGT ATAAAGTTGT
 361 TTATTTAAAT ATAATTTTTC AGATTCCAAA ACTTGAAAAA
 401 AAAAAGATTC CATTAAATCT TTTATAAAAA TGAGATTGGA
 441 TAGATTAGTC AAATTGACGA CCATAAAAAA TGATACTTAT
 481 AGGGTTAAGT ACGAAGGCAG CTAGAGAATG GGGGAAGTCA
 521 AAGGTTTTTG CTACTTCAAG TTTCATGCCT TCTTCAGATT
 561 TCCAGGTTGG TTCATCTTAA AATTTAACTT ACTCTGTATC
 601 AGTTTCAGAT GTTATGGCTA ATCTAATGGT TCTATAAGCT
 641 ACCGCATAAT CATGGTCGTC TTTTAGCATG TGCAAGAGGA
 681 GTACTCAATT ATGGTCTTGA TTAAAAAGAA GAATTTACTT
 721 TCAAATTATG TTAAACACAT CAATCACATA TTTATGAGAA
 761 AAGTTGTTTT CGTAAGAGAT AGCCACCGGA AAATGGTCGG
 801 ATAAATGGCC GAACTTTATC ATTTTTGTGT ATGTGGCCAA
 841 TCATTAACCA GGGAAAAAAA ATTGTTGGAT AAGTGCTAGT
 881 TAAGAGCTGG TAGGGTCGGT CGTCTGCCAG CCGCAAAGTT
 921 AGGGAAAAAA TAATTTAATA TTTTGTGGCG TTTGGTGTTT
 961 GGCGTTTGGA TCACGTTTAT TTCTTGGCAT TTTTCTAAAT
1001 TTAGAATGTA CAAAAAATTT AAAGACGTTG ACGATTAAAA
1041 TTTGAATTTA ACAAATTAGG AGGCTAAGGC GTTTCCGGGT
1081 GCATACCAGT GGGGATCAGT TTCTGCGGCC AATGTTTTCC
```

```
1121  GCAGATCCA ATTTGGTGGT GCGTTTCAAA ACGCGACGCC
1161  GCTTTTACTA GGCGGTTCAG TTCCTTTACC AACTCATCCT
1201  TCTCTTGTTC CACGGTAATT TCCATATTAT GATGCAAAAA
1241  CATTCAACAA TTTTTTTGCT CTTTTCATAT TTTGATTTGG
1281  TTATGTGGGT TTGTGGAAAC AGAGTGGCTT CCTCCGGATC
1321  ATCTCCTCAG CTCACAATCT TTTATGGCGG AACTATAAGC
1361  GTCTTTAATG ACATATCTCC CGATAAGGTA TATATAATCA
1401  AGATTCATAC AAATAACATT TACATAACAT TTACATGTTC
1441  TAAAACGGAC TATTCATGAT ATGTGAGTAG GCTCAAGCCA
1481  TCATGTTATG CGCCGGGAAC GGTTTGAAAG GTGAAACTGG
1521  AGATAGCAAA CCGGTTCGAG AAGCTGAAAG AATGTATGGA
1561  AAACAAATCC ATAACACTGC TGCTACCTCA TCAAGCTCTG
1601  CCACTCACAC TGATAATTTC TCAAGGTGTA GGGACACACC
1641  CGTTGCTGCG ACTAATGCAA TGAGCATGAT CGAATCATTC
1681  AATGCAGCTC CTCGTAACAT GATTCCTTCA GGTATGTGTG
1721  TCTAATATCA ACATCAAAAC AAAATATAAT CAAGATTTTT
1761  GCTTCCTCAA ATCATATGTC TAAACTCGAA AATTGCTTTT
1801  TTCCAGTCCC TCAAGCTCGG AAAGCATCCT TGGCTCGGTT
1841  CTTGGAGAAG CGCAAAGAGA GGTTTGATTT TGTATTTTTT
1881  TTCTTTATAG AAAATTTTGA GGTTTTTCAA TTGAATCTAA
1921  AAGAATTAT GTTTTGGTG CAGGCTTATG AGTGCAATGC
1961  CATACAAGAA GATGCTTCTT GATTTGTCGA CCGGAGAATC
2001  CAGTGGAATG AATTACTCTT CTACTTCTCC TACATAAAAC
2041  CTACACTTTT TTTTTTTTTT TTTACAATGG TAATTTGTAA
2081  TTGTAATCAT TAGATTATGA TTATATAGTT ACCATTTATA
2121  TTCTTACGAG CAGGAGAAGA CGTTAGGGCG TCTCTGTATT
2161  TGATCATTGT TTGTAATGCT TTGGTCTGTT TATTGTAGGA
2201  TTACATTATA ACTTTAAGAA CTAACAGATA TATGTTTGTC
2241  ATGGACTCAT GTCTGTCAAG AATTTAATAT CAAATAAAT
2281  TCACTATAAT TTTTTTT
```

JAZ10 is also a repressor of jasmonate responses. One example of an *Arabidopsis thaliana* jasmonate-zim-domain protein 10 (JAZ10) protein sequence is shown below (SEQ ID NO:56).

```
  1  MSKATIELDF LGLEKKQTNN APKPKFQKFL DRRRSFRDIQ
 41  GAISKIDPEI IKSLLASTGN NSDSSAKSRS VPSTPREDQP
 81  QIPISPVHAS LARSSTELVS GTVFMTIFYN GSVSVFQVSR
121  NKAGEIMKVA NEAASKKDES SMETDLSVIL PTTLRPKLFG
161  QNLEGDLPIA RRKSLQRFLE KRKERLVSTS PYYPTSA
```

A chromosomal DNA sequence for the *Arabidopsis thaliana* jasmonate-zim-domain protein 10 (JAZ10) protein with SEQ ID NO:56 is shown below as SEQ ID NO:57.

```
   1  AAAAACTCTC ACATGAGAAA TCAGAATCCG TTATTATTCC
  41  TCCATTTATT CATCTCAAAA CCCATATCTC TCTGTCTTGA
  81  TCTCTCTCTC ACTTTCTAAT AAGATCAAAG AAGATGTCGA
 121  AAGCTACCAT AGAACTCGAT TTCCTCGGAC TTGAGAAGAA
 161  AGAAACCAAC AACGCTCCTA AGCCTAAGTT CCAGAAATTT
 201  CTCGATCGCC GTCGTAGTTT CCGAGGTTCG TTTGGTTTTT
 241  AGTCGCTCTC TCTTTTTTTT TTCTTGCGAT AAATCGAATT
 281  TATTCATATG GAACTCCTGC AGATATTCAA GGTGCGATTT
 321  CGAAAATCGA TCCGGAGATT ATGAAATCGC TGTTAGCTTC
 361  CACTGGAAAC AATTCCGATT CATCGGCTAA ATCTCGTTCG
 401  GTTCCGTCTA CTCCGAGGGA AGATCAGCCT CAGATCCCGA
 441  TTTCTCCGGT CCACGCGTCT CTCGCCAGGT ATTTTTGTCT
 481  TTCCGGTAAA GTTTTTTTTT TCTTTCTAAC TTTTTTGGCG
 521  CTACCAGAAA AGACGAAAAA ATTTGAAATT CAAATTTTCA
 561  AAACATTCAT TTTCCTCAGG TCTAGTACCG AACTCGTTTC
 601  GGGAACTGTT CCTATGACGA TTTTCTACAA TGGAAGTGTT
 641  TCAGTTTTCC AAGTGTCTCG TAACAAAGCT GGTGAAATTA
 681  TGAAGGTCGC TAATGAAGCA GCATCTAAGA AAGACGAGTC
 721  GTCGATGGAG ACAGATCTTT CGGTAATTCT TCCGACCACT
 761  CTAAGACCAA AGCTCTTTGG CCAGAATCTA GAAGGAGGTT
 801  AGTATAATAA AAATAAAAAT CACTTAGTGC TGGATTCTTC
 841  TAGAATTTTA GTTACATATT ATTGCATGTA GAGATCTAAG
 881  AAGAGTTTGT TGTTAGAGAG GAATTGGTTG CTAATTAGTT
 921  TGGAATTAGA TATCAAAGAG TTAAAGACTA TAGTTTATGT
 961  CTATACGTAT TAATATACGT TATTAATAAA AGTATAAACA
1001  TGTTGTTTAA TTTCTGATAA GAAACTGGTT TATGCGTGTG
1041  TATGCAGATC TTCCCATCGC AAGGAGAAAG TCACTGCAA
1081  GTTTTCTCGA GAAGCGGAAG GAGAGGTAAT GATTCTTCAA
1121  CAATCCAAGG ATTTTTACCC CGAAATAATT AAAGAAAGGT
1161  TTTTATTTTT CTCTCTCTCG ACCTTTTTTT TACTATAAGT
1201  TATTTAAGAT AGTAATTATG GGTCCTGCCT CTTTTACTCT
1241  CACATACAAC TTAAGATTCA ACTAGTTTTG TTCAAGAACG
1281  CACATGCTTA TACGTAGATA GATAATGGAG ATCAGTAGTA
1321  ATATCGGTAT ACGTAGGTTA CTATTGTAAT GGAACTTTTA
1361  AAAAGCGCGT TGACTTTGAG TCTTTGACTC TAGTTCTGTT
1401  TGCTACACCG ACAAGTTATA TTTTTCAAAA TGATGAGAAA
1441  ACGAGGAGAA ACACCGGAAA AAAATTTGAA CTTTTACTTT
1481  TATCAGACCA TACGGCCAAA GAAAGATCTG TATATTATAT
1521  AAGTTATCAC AAAACGCGGT TTCACATTTT CTTTTTCGTC
1561  TTGTTGTGTT TGCAGATTAG TATCAACATC TCCTTACTAT
1601  CCGACATCGG CCTAAACGAT CTCTTTTTAG ATTGGGACAT
```

```
1641 GGACCAAATT TGTCTTTTTC AATCGGAAGA CATCCATGTT

1681 CGTTTTTGGA TTTGGCTTAT TTCCAATCTT CTTTTGAAGC

1721 CTTCTTCGTC GTTGCTAAAT CGTATACTAT TCACGACAAA

1761 CGTTTTTAGG AGATTACGTT ACCTACTAAG ATTATATATA

1801 TTGGTTTGTT TTTAAAAATG TCTATTATCT TTATTGTCAT

1841 TGATAGCTTG ATTTAAGAAG CTCTCTCTTA TCCCGTGACC

1881 TTCTACTTTT GTTTTATTTT TTAGTATATG GTAAAGAAAA

1921 TTATAAC
``` genes or chromosomal segments encoding jasmonic acid regulatory proteins can be modified to reduce or eliminate the expression and/or function of the encoded proteins.

The following are examples of "JAZ-related" proteins and nucleic acids that can be modified to reduce or eliminate the expression and/or function thereof, and thereby generate plants with improved resistance to insects.

One example of a *Brassica rapa* protein called TIFY 10A-like (NCBI accession no. XP_009117562.1; GI:685367109) has significant sequence identity to the *Arabidopsis thaliana* JAZ1 protein with SEQ ID NO:48, as illustrated by the sequence comparison shown below. Domains of sequence homology are identified by asterisks below the sequence comparison.

```
73.0% identity in 211 residues overlap; Score: 634.0; Gap frequency: 11.4%
Seq 48    1 MSLFPCEASNMDSMVQDVKPTNLFPRQPSFSSSSSSLPKEDVLKMTQ---
TTRSVKPESQ
Seq 58   63
MSLFPCEASNMEPIGQDVKPKNLFPRQPSFSSSSSSLPKEDILKMTQATSSTRSVKPEPQ
            **********  ***** ******************** *****   *******
*

Seq 48   58 TAPLTIFYAGQVIVFNDFSAEKAKEVINLASKGTANS------------------
LAKN
Seq 58  123
TAPLTIFYGGQVIVFNDFSAEKAKEVMDLASKGTANTFTGFTSNVNNNIQSVYTTNLANN
            ********  ****************  ********                       **
*

Seq 48   99 QTDIRSNIATIANQVPHPRKTTTQEPIQSSPTPLT-
ELPIARRASLHRFLEKRKDRVTSK
Seq 58  183
QTEMRSNIAPIPNQLPHLMKTTTQNPVQSSSTAMACELPIARRASLHRFLAKRKDRVTSK
            **  *****  * ** **  ***** *  *** *        **************
*********

Seq 48  158 APYQLCDPAKASSNPQTTGNM-SWLGLAAEI
Seq 58  243 APYQLNDPAKASSKPQTGDNTTSWLGLAAEM
            *****  ******  ***  *      ********
```

Chromosomal sequences that encode repressors of jasmonic acid responses from many plant types and species can be modified to reduce or eliminate the expression and/or function of the encoded protein. For example, chromosomal sequences encoding jasmonic acid repressor genes from agriculturally important plants such as alfalfa (e.g., forage legume alfalfa), algae, avocado, barley, broccoli, Brussels sprouts, cabbage, canola, cassava, cauliflower, cole vegetables, collards, corn, crucifers, grain legumes, grasses (e.g., forage grasses), jatropa, kale, kohlrabi, maize, miscanthus, mustards, nut sedge, oats, oil firewood trees, oilseeds, potato, radish, rape, rapeseed, rice, rutabaga, sorghum, soybean, sugar beets, sugarcane, sunflower, switchgrass, tobacco, tomato, turnips, and/or wheat can be modified reduce or eliminate the expression and/or function of one or more encoded jasmonic acid regulatory proteins.

In some cases, more than one gene or chromosomal segment encoding a jasmonic acid regulatory protein can be modified to reduce or eliminate the expression and/or function of the encoded protein(s). In some cases, more than two genes or chromosomal segments encoding jasmonic acid regulatory proteins can be modified to reduce or eliminate the expression and/or function of the encoded proteins. In some cases, more than three genes or chromosomal segments encoding jasmonic acid regulatory proteins can be modified to reduce or eliminate the expression and/or function of the encoded proteins. In some cases, more than four This JAZ-related *Brassica rapa* protein, called TIFY 10A-like (NCBI accession no. XP_009117562.1; GI:685367109), has the following sequence (SEQ ID NO:58).

```
  1  MSSPMESSDF AATRRFSRKP SFSQTCSRLS QYLKENGSFG

41  DLSLGMACKP EVNGISRQPT TTMSLFPCEA SNMEPIGQDV

81  KPKNLFPRQP SFSSSSSSLP KEDILKMTQA TSSTRSVKPE

121  PQTAPLTIFY GGQVIVFNDF SAEKAKEVMD LASKGTANTF

161  TGFTSNVNNN IQSVYTTNLA NNQTEMRSNI APIPNQLPHL

201  MKTTTQNPVQ SSSTAMACEL PIARRASLHR FLAKRKDRVT

241  SKAPYQLNDP AKASSKPQTG DNTTSWLGLA AEM
```

A cDNA encoding the SEQ ID NO:58 protein is available as NCBI accession number XM_009119314.1 (GI: 685367108), and a chromosomal segment encoding the SEQ ID NO:58 protein is available as NCBI accession number AENI01008623.1 (GI:339949964).

One example of a *Brassica oleracea* protein, also referred to as protein TIFY A-like (NCBI accession no. XP_013583936.1; GI:922487335), has significant sequence identity to the *Arabidopsis thaliana* JAZ1 protein with SEQ ID NO:48, as illustrated by the sequence comparison shown below. Domains of sequence homology are identified by asterisks below the sequence comparison.

```
72.9% identity in 192 residues overlap; Score: 633.0; Gap frequency: 2.6%
Seq 48    1 MSLFPCEASNMDSMV--QDVKPTNLFPRQPSFSSSSSSLPKEDVLKMTQTT-
RSVKPESQ
Seq 59   61
MSLFPCEASNVGSMAAAQDVKPKNLFPRQPSFSSSSSSIPKEDVPKMTQTTTRSLKPEPQ
               ********** **  ***** *************** ***** ****** ** ***
*

Seq 48   58
TAPLTIFYAGQVIVFNDFSAEKAKEVINLASKGTANSLAKNQTDIRSNIATIANQVPHPR
Seq 59  121
TAPLTIFYGGQVIVFNDFSAEKAKEVMNLANKGTANTFTGFTSTLNNNIAPTPNQVPHLM
          ******** *****************  *** *****           ***    *****

Seq 48  118 KTTTQEPIQSSPTPLT-
ELPIARRASLHRFLEKRKDRVTSKAPYQLCDPAKASSNPQTTG
Seq 59  181
KAATQDPKQTSSAAMACELPIARRASLHRFLAKRKDRVTSKAPYQLNDPAKAYSKPQTGN
          *  ** *  *    *************** *************** *  ***

Seq 48  177 NM-SWLGLAAEI
Seq 59  241 TTTSWLGLAADM
                *******
```

This JAZ-related *Brassica oleracea* protein referred to as protein TIFY 10A-like (NCBI accession no. XP_013583936.1; GI:922487335) has the following sequence (SEQ ID NO:59).

```
  1   MSSSMECSTT RRSSSGKPSF SLTCSRLSQY LKENGSFGDL
 41   SLGMSCKPDT NGMSRKPTTT MSLFPCEASN VGSMAAAQDV
 81   KPKNLFPRQP SFSSSSSSIP KEDVPKMTQT TTRSLKPEPQ
121   TAPLTIFYGG QVIVFNDFSA EKAKEVMNLA NKGTANTFTG
161   FTSTLNNNIA PTPNQVPHLM KAATQDPKQT SSAAMACELP
201   IARRASLHRF LAKRKDRVTS KAPYQLNDPA KAYSKPQTGN
241   TTTSWLGLAA DM
```

A cDNA encoding the SEQ ID NO:59 protein is available as NCBI accession number XM_013728482.1 (GI: 922487334), and a chromosomal segment encoding the SEQ ID NO:59 protein is available as NCBI accession number NC_027752.1 (GI:919506312).

An uncharacterized *Zea mays* protein referred to as LOC100276383 (NCBI accession no. NP_001308779.1 (GI: 1013071036) has significant sequence identity to the *Arabidopsis thaliana* JAZ1 protein with SEQ ID NO:48, as illustrated by the sequence comparison shown below. Domains of sequence homology are identified by asterisks below the sequence comparison.

This JAZ-related uncharacterized *Zea mays* protein referred to as LOC100276383 (NCBI accession no. NP_001308779.1 (GI:1013071036) has the following sequence (SEQ ID NO:60).

```
  1   MAASARPGER ATSFAVACSL LSRFVRQNGV AAADLGLRIK
 41   GEVEQQRTPA TTNSLPGAEG EEVERRKETM ELFPQSVGFS
 81   IKDAAAPREE QGDKEKPKQL TIFYGGKVLV FDDFPADKAK
121   DLMQLASKGS PVVQNVALPQ PSAAAAVTTD KAVLDPVISL
161   AAAKKPARTN ASDMPIMRKA SLHRFLEKRK DRLNAKTPYQ
201   TAPSDAAPVK KEPESQPWLG LGPNAVDSSL NLS
```

A cDNA encoding the SEQ ID NO:60 protein is available as NCBI accession number NM_001321850.1 (GI: 1013071035), and a chromosomal segment encoding the SEQ ID NO:60 protein is on *Zea mays* chromosome 7 at NC_024465.1 (165496371 ... 165497455), sequence available as NCBI accession number NC_024465.1 (GI: 662248746).

A *Glycine max* protein referred to as protein TIFY 10A-like (NCBI accession no. NP_001276307.1 (GI: 574584782)) has significant sequence identity to the 15 *Arabidopsis thaliana* JAZ1 protein with SEQ ID NO:48, as illustrated by the sequence comparison shown below. Domains of sequence homology are identified by asterisks below the sequence comparison.

```
39.0% identity in 123 residues overlap; Score: 201.0; Gap frequency: 0.8%
Seq 48   61
LTIFYAGQVIVFNDFSAEKAKEVINLASKGTANSLAKNQTDIRSNIATIANQVPHPRKTT
Seq 60  100
LTIFYGGKVLVFDDFPADKAKDLMQLASKGSPVVQNVALPQPSAAAAVTTDKAVLDPVIS
          ***** * ** ** * ***      ***** *****                    *

Seq 48  121
TQEPIQSSPTPLTELPIARRASLHRFLEKRKDRVTSKAPYQLCDPAKASSNPQTTGNMSW
Seq 60  160 LAAAKKPARTNASDMPIMRKASLHRFLEKRKDRLNAKTPYQTA-
PSDAAPVKKEPESQPW
                      ** * ************   * *  ***   *    *

Seq 48  181 LGL
Seq 60  219 LGL
                ***
```

```
45.5% identity in 145 residues overlap; Score: 271.0; Gap frequency: 4.8%
Seq 48  42
VLKMTQTTRSVKPESQTAPLTIFYAGQVIVFNDFSAEKAKEVINLASKGTANSLAKNQTD
Seq 61 101 IMVKSSAFKSMEKEPKAAQLTIFYAGQVVVFDDFPAEKLEEITSLAGKGISQS-----
QN
               *     *    * *********  ** ** ***  *    ** **     *

Seq 48 102
IRSNIATIANQVPHPRKTTTQEPIQSSPTPLTELPIARRASLHRFLEKRKDRVTSKAPYQ
Seq 61 156
TSAYAHTHNQQVNHPSFVPNISPQAPSRPLVCDLPIARKASLHRFLSKRKDRIAAKAPYQ
                    *   ** **         *   *     ***** ******* *****
*****

Seq 48 162 LCDPAKASSNPQTTGNMSWLGLAAE
Seq 61 216 INNPNSASSKPAE--SMSWLGLGAQ
                *   *** *      ****** *
```

This JAZ-related *Glycine max* protein referred to as protein TIFY 10A-like (NCBI accession no. NP_001276307.1 (GI: 574584782) has the following sequence (SEQ ID NO:61).

```
  1 MSSSSEYLVF SSHHPANSPA EKSTFSQTCS LLSQYIKEKG

41 TFGDLTLGMT CTAETNGSPE TSCHSATTME LFPTIITQRN

61 PTTVDFLSPQ TAYPHHSEVP IMVKSSAFKS MEKEPKAAQL

121 TIFYAGQVVV FDDFPAEKLE EITSLAGKGI SQSQNTSAYA

161 HTHNQQVNHP SFVPNISPQA PSRPLVCDLP IARKASLHRF

201 LSKRKDRIAA KAPYQINNPN SASSKPAESM SWLGLGAQST
```

A cDNA encoding the SEQ ID NO:61 protein is available as NCBI accession number NM_001289378.1 (GI: 574584781), and a chromosomal segment encoding the SEQ ID NO:61 protein is on *Glycine max* chromosome 13 at NC_016100.2 (22541885...22544240), sequence available as NCBI accession number NC_016100.2 (GI:952545303).

An *Oryza sativa* protein referred to as protein TIFY 10b (*Japonica* Group; NCBI accession no. XP_015647536.1 (GI:1002286463) has significant sequence identity to the *Arabidopsis thaliana* JAZ1 protein with SEQ ID NO:48, as illustrated by the sequence comparison shown below. Domains of sequence homology are identified by asterisks below the sequence comparison.

This JAZ-related *Oryza sativa* protein referred to as protein TIFY 10b (*Japonica* Group; NCBI accession no. XP_015647536.1 (GI:1002286463) has the following sequence (SEQ ID NO:62).

```
  1 MAASARPVGV GGERATSFAM ACSLLSRYVR QNGALLAELG

41 LGIRGEGEAP RAAPATMSLL PGEAERKKET MELFPQSAGF

81 GQQDAITADS AADAREQEPE KRQLTIFYGG KVLVFNDFPA

121 DKAKGLMQLA SKGSPVAPQN AAAPAPAAVT DNTKAPMAVP

161 APVSSLPTAQ ADAQKPARAN ASDMPIARKA SLHRFLEKRK

201 DRLNAKTPYQ ASPSDATPVK KEPESQPWLG LGPNAVVKPI

241 ERGQ
```

A cDNA encoding the SEQ ID NO:62 protein is available as NCBI accession number XM_015792050.1 (GI: 1002286462), and a chromosomal segment encoding the SEQ ID NO:62 protein is on *Oryza sativa* chromosome 7 at NC_029262.1 (25347990...25350243), sequence available as NCBI accession number NC_029262.1 (GI:996703426).

A *Zea mays* protein referred to as protein TIFY 6A-like (NCBI accession no. NP_001288506.1 (GI: 673921704) has significant sequence identity to the *Arabidopsis thaliana* JAZ3 protein with SEQ ID NO:50, as illustrated by the

```
38.5% identity in 156 residues overlap; Score: 213.0; Gap frequency: 4.5%
Seq 48  34
SSSLPKEDVLKMTQTTRSVKPESQTAPLTIFYAGQVIVFNDFSAEKAKEVINLASKGTA-
Seq 62  77
SAGFGQQDAITADSAADAREQEPEKRQLTIFYGGKVLVFNDFPADKAKGLMQLASKGSPV
     *      *            *     ***** * ***** * ***       *****

Seq 48  93 ---NSLAKNQTDIRSNI-ATIANQVPHPRKTTTQEPIQS-
SPTPLTELPIARRASLHPFL
Seq 62 137
APQNAAAPAPAAVTDNTKAPMAVPAPVSSLPTAQADAQKPARANASDMPIARKASLHRFL
        *  *      * *    *    * *   * *           ****
*******

Seq 48 148 EKRKDRVTSKAPYQLCDPAKASSNPQTTGNMSWLGL
Seq 62 197 EKRKDRLNAKTPYQ-ASPSDATPVKKEPESQPWLGL
           ******    *** *   *     *          ****
``` sequence comparison shown below. Domains of sequence homology are identified by asterisks below the sequence comparison.

```
36.6% identity in 161 residues overlap; Score: 165.0; Gap frequency: 6.8%
Seq 50 177
AQLTIFYAGSVCVYDDISPEKAKAIMLLAGNGSSMPQVFSPPQTHQQVVHHTRSVDSSA
Seq 63 167
AQLTIFYAGSVNVFNNVSAEKAQELMFLASRGSSAPVACKPEAPPTLAPAKVTAPEVLLP
        *********** *    * ***    * **   *** *    *          *

Seq 50 237 MPPSFMPTISYLSPEAGSSTNGLGATKATRGLTSTYH-NNQANGSNINCPVP-------
-
Seq 63 227
AKQMLFQKPQHLSPPPSSVPGILQSAALPRSASSSSNLDSPAPKSSVPLAVPPVSQAPPA
              ***    *    *   *    *           *  *        **

Seq 50 288 --VSCSTNVMAPTVALPLARKASLARFLEKRKERVTSVSPY
Seq 63 287 TLIATTTAAAIMPRAVPQARKASLARFLEKRKERVTTAAPY
             *      * * ****************** **
```

This JAZ-related *Zea mays* protein referred to as protein TIFY 6A-like (NCBI accession no. NP_001288506.1 (GI: 673921704) has the following sequence (SEQ ID NO:63).

```
  1 MERDFLAAIG KEQQHPRKEK AGGGAEESAY FGAAAVPAMD
 41 WSFASKPCAA PALMSFRSAA REEPSFPQFS ALDGTKNTAP
 81 RMLTHQRSFG PDSTQYAALH RAQNGARVVP VSSPFSQSNP
121 MFRVQSSPSL PNSTAFKQPP FAISNAVASS TVGSYGGTRD
161 AVRPRTAQLT IFYAGSVNVF NNVSAEKAQE LMFLASRGSS
201 APVACKPEAP PTLAPAKVTA PEVLLPAKQM LFQKPQHLSP
241 PPSSVPGILQ SAALPRSASS SSNLDSPAPK SSVPLAVPPV
281 SQAPPATLIA TTTAAAIMPR AVPQARKASL ARFLEKRKER
321 VTTAAPYPSA KSPLESSDTF GSGSASANAN DKSSCTDIAL
361 SSNHEESLCL GGQPRSIISF SEESPSTKLQ I
```

A cDNA encoding the SEQ ID NO:63 protein is available as NCBI accession number NM_001301577.1 (GI: 673921703), and a chromosomal segment encoding the SEQ ID NO:63 protein is on *Zea mays* chromosome 2 at NC_024460.1 (180086924 . . . 180089758, complement), sequence available as NCBI accession number NC_024460.1 (GI:662249846).

A *Glycine max* protein referred to as protein TIFY 6B-like isoform X1 (NCBI accession no. XP_003534135.1 (GI: 356531138) has significant sequence identity to the *Arabidopsis thaliana* JAZ3 protein with SEQ ID NO:50, as illustrated by the sequence comparison shown below. Domains of sequence homology are identified by asterisks below the sequence comparison.

```
38.9% identity in 378 residues overlap; Score: 417.0; Gap frequency: 8.5%
Seq 50   1 MERDFLGLGSKNSP-
ITVKEETSESSRDSAPNRGMNWSFSNKVSASSSQFLSFRPTQEDR
Seq 64   1 MEREFFGLSSKNGAWTTMKDDAVNKSRDQVRSSGMQWSFPNKVSALP-
QFLSFKTNQEDK
             *** * ** ***      * *      ***    ** *** *****   *****   ***

Seq 50  60 HRKSGNYHLPHSGSFMPSSVADVYDSTRKA--------------PYSSVQGVRMFPNS-
-
Seq 64  60 PRKTILEPLASSG-
YMAMSTQYAFDSNQKSFLGLTNRNLSISKHAAGNKQGMTVYPLQCC
             **    * **  *   *     **  *                          **   *

Seq 50 104 -NQHEETNAVSMSMPGFQ-----
SHHYAPGGRSFMNNNNNSQPLVGVPIMAPPISILPPP
Seq 64 119 DAQSEEARIFSVSNQSNQVSPVLQSNLASTGLNMVNSVIKPQPF-
GSKSSGTPLSILPSI
              * **   * *    *          *   *     ** *      * ****

Seq 50 158
GSIVGTTDIRSSSKPIGSPAQLTIFYAGSVCVYDDISPEKAKAIMLLAGNGSSMPQVFSP
Seq 64 178
GSIVGSTDLRNNSKSSTMPTQLTIFYAGSVCVYDDISPEKAKAIMLMAGNGYTPTEKMEL
            ***** ** *  **   *  * ****************************   ****

Seq 50 218 PQTHQQVVHHTRASVD----
SSAMPPSFMPTISYLSPEAGSSTNGLGATKATRGLTSTYH
Seq 64 238
PTVKLQPAISIPSKDDGFMISQSYPPSTFPTPLPLTSHVNSQPGGGSSSNKEISIIRQVG
              *     *      *    ***  *      *          *
```

-continued

```
Seq 50  274 NNQANGSNINCPV--
PVSCSTNVMAPTVALPLARKASLARFLEKRKERVTSVSPYCLDKK
Seq 64  298
PSTAPTNHLESPIIGSIGSASKEKAQPVCLPQARKASLARFLEKRKGRMMRTSPYLYMSK
            *       *       *  *  ** **************  *     ***
*

Seq 50  332 SSTDCRRSMSECISSSLS
Seq 64  358 KSPECSSSGSDSVSFSLN
            *  *  *  *    *  **
```

This JAZ-related *Glycine max* protein referred to as protein TIFY 6B-like isoform X1 (NCBI accession no. XP_003534135.1 (GI:356531138) has the following sequence (SEQ ID NO:64).

```
  1 MEREFFGLSS KNGAWTTMKD DAVNKSRDQV RSSGMQWSFP
 41 NKVSALPQFL SFKTNQEDKP RKTILEPLAS SGYMAMSTQY
 81 AFDSNQKSFL GLTNRNLSIS KHAAGNKQGM TVYPLQCCDA
121 QSEEARIFSV SNQSNQVSPV LQSNLASTGL NMVNSVIKPQ
161 PFGSKSSGTP LSILPSIGSI VGSTDLRNNS KSSTMPTQLT
201 IFYAGSVCVY DDISPEKAKA IMLMAGNGYT PTEKMELPTV
241 KLQPAISIPS KDDGFMISQS YPPSTFPTPL PLTSHVNSQP
281 GGGSSSNKEI SIIRQVGPST APTNHLESPI IGSIGSASKE
321 KAQPVCLPQA RKASLARFLE KRKGRMMRTS PYLYMSKKSP
361 ECSSSGSDSV SFSLNFSGSC SLPATN
```

A cDNA encoding the SEQ ID NO:64 protein is available as NCBI accession number XM_003534087.3 (GI: 955341633), and a chromosomal segment encoding the SEQ ID NO:64 protein is on *Glycine max* chromosome 9 at NC_016096.2 (39883473 ... 39889992), sequence available as NCBI accession number NC_016096.2 (GI:952545307).

An *Oryza sativa* protein referred to as protein TIFY 6b (NCBI accession no. XP_015612402.1 (GI:1002297967) has significant sequence identity to the *Arabidopsis thaliana* JAZ3 protein with SEQ ID NO:50, as illustrated by the sequence comparison shown below. Domains of sequence homology are identified by asterisks below the sequence comparison.

This JAZ-related *Oryza sativa* protein, referred to as protein TIFY 6b (NCBI accession no. XP_015612402.1 (GI:1002297967), has the following sequence (SEQ ID NO:65).

```
  1 MERDFLGAIG KDEEQRRHAE ERKESDYFGA GGGAAAAAMD
 41 WSFASRAALM SFRSSSSAAA AAAREETREL AFPHFSALDG
 81 AKMQQASHVL ARQKSFGAES HGIPQYALLA AVHGAHRGQP
121 PHVLNGARVI PASSPFNPNN PMFRVQSSPN LPNAVGAGGG
161 AFKQPPFAMG NAVAGSTVGV YGTRDMPKAK AAQLTIFYAG
201 SVNVFNNVSP EKAQELMFLA SRGSLPSAPT TVARMPEAHV
241 FPPAKVTVPE VSPTKPMMLQ KPQLVSSPVP AISKPISVVS
281 QATSLPRSAS SSNVDSNVTK SSGPLVVPPT SLPPPAQPET
321 LATTTAAAIM PRAVPQARKA SLARFLEKRK ERVTTVAPYP
361 LAKSPLESSD TMGSANDNKS SCTDIALSSN RDESLSLGQP
401 RTISFCEESP STKLQI
```

A cDNA encoding the SEQ ID NO:65 protein is available as NCBI accession number XM_015756916.1 (GI: 1002297966), and a chromosomal segment encoding the SEQ ID NO:65 protein is on *Oryza sativa* chromosome 9 at NC_029264.1 (14056084 ... 14060320, complement), sequence available as NCBI accession number NC_029264.1 (GI:996703424).

An uncharacterized *Zea mays* protein referred to as LOC100273108 (NCBI accession no. NP_001141029.1 (GI: 226500626) has significant sequence identity to the *Arabidopsis thaliana* JAZ4 protein with SEQ ID NO:52, as illustrated by the sequence comparison shown below.

```
37.3% identity in 177 residues overlap; Score: 142.0; Gap frequency: 10.2%

Seq 50  172 PIGSPAQLTIFYAGSVCVYDDISPEKAKAIMLLAGNGS---------SMPO--
VFSPPQT
Seq 65  187
PKAKAAQLTIFYAGSVNVFNNVSPEKAQELMFLASRGSLPSAPTTVARMPEAHVFPPAKV
                * ************** *  *****  *  ** **        **  ** *

Seq 50  221 HQQVVHHTRASV-DSSAMPPSFMPTISY---
LSPEAGSSTNGLGATKTRGLTSTYHNNQ
Seq 65  247
TVPEVSPTKPMMLQKPQLVSSPVPAISKPISVVSQATSLPRSASSSNVDSNVTKSSGPLV
            *   *           * * **        * *                *

Seq 50  277 ANGSNINCPV-PVSCSTNVMAPTV--ALPLARKASLARFLEKRKERVTSVSPYCLDK
Seq 65  307 VPPTSLPPPAQPETLATTTAAAIMPRAVPQARKASLARFLEKRKERVTTVAPYPLAK
             *    *      *    * ******************* **  * *
```

Domains of sequence homology are identified by asterisks below the sequence comparison.

```
55.0% identity in 40 residues overlap;
Score: 106.0; Gap frequency: 0.0%
Seq 52 138 RSSSKPLPPQLTIFYAGSVLVYQDIAPEKAQAIMLLAGNG
Seq 66 172 RDVVRPKTAQLTIFYAGSVNVFDNVSAEKAQELMLLASRG
            *  *  **********  *    ****  **** *

76.9% identity in 26 residues overlap;
Score: 102.0; Gap frequency: 0.0%
Seq 52 258 LPQTRKASLARFLEKRKERVINVSPY
Seq 66 321 VPQARKASLARFLEKRKERVTTAAPY
            ** ****************   **

48.0% identity in 25 residues overlap;
Score: 66.0; Gap frequency: 0.0%
Seq 52  25 SAPSRGMMDWSFSSKVGSGPQFLSF
Seq 66  47 AAAAAPAMDWSFASKPGAAPALMSF
             *    ***** **  *   **

38.5% identity in 26 residues overlap;
Score: 37.0; Gap frequency: 0.0%
Seq 52   1 MERDFLGLGSKLSPITVKEETNEDSA
Seq 66  14 MERDFLAAIGKEQQPHKEEAGAEES
           ******  *       ***
```

This JAZ-related uncharacterized *Zea mays* protein, referred to as LOC100273108 (NCBI accession no. NP_001141029.1 (GI:226500626), has the following sequence (SEQ ID NO:66).

```
  1 MAKSGASFPE SSWMERDFLA AIGKEQQHPH KEEAGAEESA
 41 YTGGAGAAAA APAMDWSFAS KPGAAPALMS FRSASFPQFS
 81 SFDGAKNPAP RILTHQRSFG PDSTHYAAAH RTQHALNGAR
121 VTPVSSPFNQ NSPMFRVQSS PSLPNGTAFK QPPFAINNNA
161 AASSTVGFYG TRDVVRPKTA QLTIFYAGSV NVFDNVSAEK
201 AQELMLLASR GSLPSSAPVA RKPEAPILAP AKVTAPEVLH
241 ATQMLFQKPQ HVSPPSSAIS KPIPGILQAA SLPRSASSSN
281 LDSPFPKSSV PFPVSPVSQA PRAQPATIAA TTAAAIMPRA
321 VPQARKASLA RFLEKRKERV TTAAPYPSAK SPMESSDTFG
361 SGSANDKSSC TDIALSSNHE ESLCLGQPRN ISFIQESPST
401 KLQI
```

A cDNA encoding the SEQ ID NO:66 protein is available as NCBI accession number NM_001147557.1 (GI: 226500625), and a chromosomal segment encoding the SEQ ID NO:66 protein is on *Zea mays* chromosome 7 at NC_024465.1 (108871356 . . . 108874213, complement), sequence available as NCBI accession number NC_024465.1 (GI:662248746).

A *Glycine max* protein, referred to as protein TIFY 6B isoform X5 (NCBI accession number XP_006580448.1 (GI: 571456655), has significant sequence identity to the *Arabidopsis thaliana* JAZ4 protein with SEQ ID NO:52, as illustrated by the sequence comparison shown below. Domains of sequence homology are identified with asterisks below the sequence comparison.

```
37.0% identity in 322 residues overlap; Score: 273.0; Gap frequency: 8.7%
Seq 52   1 MERDFLGLGSKLSPITVKEETNEDSAPSRG-----
MMDWSFSSKVGSGPQFLSFGTSQQE
Seq 67   1
MERDFMGLNLKEPLAVVKEEMNNDGCKNSGFKKGRIAQWPFSNKVSALPHLMSFKASQDD
           ***** **  *    **** * *      *    * ** **  *   ** **

Seq 52  56 TRVNTVNDHLLSSAAMD-
QNQRTYFSSLQEDRVFPGSSQQDQTTITVSMSEPNYINSFI-
Seq 67  61
KTKNTVSDTLSSSGFMSILSQEAFDTSQKRSAGEPQMFSVPNQAISVSLGNPFLKNHFAA
            *** * **  *       *       *       * **   *   * *

Seq 52 114 --NHQHLGGSPIMAP----
PVSVFPAPTTIRSSSKPLPPQLTIFYAGSVLVYQDIAPEKA
Seq 67 121
AGQKPLLGGIPVTTSHSVLPSAVAVAGMTESCNSVKPSAQLTIFYAGTVNIFDDISAEKA
                 *** *        *  * * *    *  ******* *   **
***

Seq 52 168 QAIMLLAGNG-
PHAKPVSQPKPOKLVHHSLPTTDPPTMPPSFLPSISYIVSETRSSGSNG
Seq 67 181
QAIMLLAGNSLSAASNMAQPNVQVPISKLGAGAGVPVSQPANTSPGSGLSSPLSVSSHTG
           *********    *   ** *                *   *   *  *   *
*

Seq 52 227 V-TGLPTKTKASLASTRNN--QTAAFSMAP----------
TVGLPQTRKASLARFLEKR
Seq 67 241
VQSGSGLTSTDEFLAAKTTGVPNTPICNVEPPKVVSATTMLTSAVPQARKASLARFLEKR
           *  *   *    **                              *  *    *  **
           ************
```

-continued

```
Seq 52  274 KERVINVSPYYVDNKSSIDCRT
Seq 67  301 KERVMSAAPYNL-NKKSEECAT
            ****  **  ** *  * *
```

This JAZ-related *Glycine max* protein, referred to as protein TIFY 6B isoform X5 (NCBI accession number XP_006580448.1 (GI:571456655), has the following sequence (SEQ ID NO:67).

```
  1 MERDFMGLNL KEPLAVVKEE MNNDGCKNSG FKKGRIAQWP
 41 FSNKVSALPH LMSFKASQDD KTKNTVSDTL SSSGFMSILS
 61 QEAFDTSQKR SAGEPQMFSV PNQAISVSLG NPFLKNHFAA
121 AGQKPLLGGI PVTTSHSVLP SAVAVAGMTE SCNSVKPSAQ
161 LTIFYAGTVN IFDDISAEKA QAIMLLAGNS LSAASNMAQP
201 NVQVPISKLG AGAGVPVSQP ANTSPGSGLS SPLSVSSHTG
241 VQSGSGLTST DEFLAAKTTG VPNTPICNVE PPKVVSATTM
281 LTSAVPQARK ASLARFLEKR KERVMSAAPY NLNKKSEECA
321 TAEYAGVNFS ATNTVLAKQG
```

A cDNA encoding the SEQ ID NO:67 protein is available as NCBI accession number XM_006580385.2 (GI: 955322108), and a chromosomal segment encoding the SEQ ID NO:67 protein is on *Glycine max* chromosome 5 at NC_016092.2 (41222014 . . . 41225906), sequence available as NCBI accession number NC_016092.2 (GI:952545311).

An *Oryza sativa* protein, referred to as protein TIFY 6a isoform X2 (NCBI accession number XP_015651050.1 (GI: 1002293416), has significant sequence identity to the *Arabidopsis thaliana* JAZ4 protein with SEQ ID NO:52, as illustrated by the sequence comparison shown below. Domains of sequence homology are identified by asterisks below each sequence comparison.

This JAZ-related *Oryza sativa* protein, referred to as protein TIFY 6a isoform X2 (NCBI accession number XP_015651050.1 (GI:1002293416), has the following sequence (SEQ ID NO:68).

```
  1 MERDFLGAIW RKEEAAGKPE EHSDYRGGGG GASAAMQWQF
 41 PATKVGAASS AFMSFRSSAA AAREEDPKEA AVFDRFSLSG
 81 FRPPPRPSPG DAFDGAAAMK QRQFGFNGRQ QYAAAAQHGH
121 REQGVDSYGV AAPHHFPSPS PSPRHPVPFG HANPMLRVHS
161 LPNVAGGSPY RNQSFSVGNS VAGSTVGVYG GPRDLQNPKV
201 TQMTIFYDGL VNVFDNIPVE KAQELMLLAS RASIPSPPSA
241 ARKSDSPISA AAKLTVPEAL PARQIVVQKP EASVPLVSGV
281 SNPITIVSQA VTLPKSFSSS NDSAGPKSGG LPLAVTPLSQ
321 ASPSQPIPVA TTNASAIMPR AVPQARKASL ARFLEKRKER
361 VSSVAPYPSS KSPLESSDTI GSPSTPSKSS CTDITPSTNN
401 CEDSLCLGQP RNISFSSQEP PSTKLQI
```

A cDNA encoding the SEQ ID NO:68 protein is available as NCBI accession number XM_015795564.1 (GI: 1002293415), and a chromosomal segment encoding the SEQ ID NO:68 protein is on *Oryza sativa* chromosome 8 at NC_029263.1 (20624989 . . . 20627964, complement), sequence available as NCBI accession number NC_029263.1 (GI:996703425).

A *Zea mays* protein referred to as putative tify domain/ CCT motif transcription factor family protein (NCBI accession no. DAA40037.1 (GI:414589466)) has significant

```
80.8% identity in 26 residues overlap; Score: 106.0; Gap frequency: 0.0%

Seq 52 258 LPQTRKASLARFLEKRKERVINVSPY
Seq 68 342 VPQARKASLARFLEKRKERVSSVAPY
               ** ****************  * **

44.7% identity in 47 residues overlap; Score: 87.0; Gap frequency: 0.0%

Seq 52 138 RSSSKPLPPQLTIFYAGSVLVYQDIAPEKAQAIMLLAGNGPHAKPVS
Seq 68 193 RDLQNPKVTQMTIFYDGLVNVFDNIPVEKAQELMLLASRASIPSPPS
           *    *   * **** * *   * **** ****          * *

41.7% identity in 24 residues overlap; Score: 39.0; Gap frequency: 0.0%

Seq 52   1 MERDFLGLGSKLSPITVKEETNED
Seq 68   1 MERDFLGAIWRKEEPAGKPEEHSD
           *******      * *    *

19.0% identity in 63 residues overlap; Score: 36.0; Gap  frequency: 0.0%

Seq 52 123 IMAPPVSVFPAPTTIRSSSKPLPPQLTIFYAGSVLVYQDIAPEKAQAIMLLAGNGPHAKP
Seq 68 227 LLASRASIPSPPSAARKSDSPISAAAKLTVPEALPARQIVVQKPEASVPLVSGVSNPITI
              *  *  * **  *                  *             * *

Seq 52 183 VSQ
Seq 68 287 VSQ
           ***
``` sequence identity to the *Arabidopsis thaliana* JAZ9 protein with SEQ ID NO:54, as illustrated by the sequence comparison shown below. Domains of sequence homology are identified by asterisks below each sequence comparison.

```
52.1% identity in 48 residues overlap; Score: 118.0; Gap frequency:
0.0%
Seq54  218 SVPQARKASLARFLEKRKERLMSAMPYKKMLLDLSTGESSGMNYSSTS
Seq69  263 AVPQARKASLARFLEKRKERVTTAAPYPSAKSPLESSDTFGSGSASAN
           ******************  * **     *      *     *

54.8% dentity in 31 residues overlap; Score: 96.0; Gap frequency:
0.0%
Seq54  119 QLTIFYGGTISVFNDISPDKAQAIMLCAGNG
Seq69  130 QLTIFYAGSVNVFNNVSAEKAQELMFLASRG
           ******  *   ***  *  ***  *    *    *

34.6% identity in 26 residues overlap; Score: 34.0; Gap frequency:
0.0%
Seq54  110 RVASSGSSPQLTIFYGGTISVFNDIS
Seq69   85 RVQSSPSLPNSTAFKQPPFAISNAVA
           ** **  *    *  *        *
```

This JAZ-related uncharacterized *Zea mays* protein, referred to as putative tify domain/CCT motif transcription factor family protein (NCBI accession no. DAA40037.1 (GI: 414589466)), has the following sequence (SEQ ID NO:69).

```
  1 MDWSFASKPC AAPALMSFRS AAREEPSFPQ FSALDGTKNT
 41 APRMLTHQRS FGPDSTQYAA LHRAQNGARV VPVSSPFSQS
 81 NPMFRVQSSP SLPNSTAFKQ PPFAISNAVA SSTVGSYGGT
121 RDAVRPRTAQ LTIFYAGSVN VFNNVSAEKA QELMFLASRG
161 SSAPVACKPE APPTLAPAKV TAPEVLLPAK QMLFQKPQHL
201 SPPPSSVPGI LQSAALPRSA SSSSNLDSPA PKSSVPLAVP
241 PVSQAPPATL IATTTAAAIM PRAMPQARRA SLARFLEKRK
281 ERVTTAAPYP SAKSPLESSD TFGSGSASAN ANDKSSCTDI
321 ALSSNHEESL CLGGQPRSII SFSEESPSTK LQI
```

A chromosomal segment encoding the SEQ ID NO:69 protein is on *Zea mays* chromosome 2 at NC_024460.1 (180086924 ... 180089758, complement), sequence available as NCBI accession number NC_024460.1 (GI: 662249846).

A *Glycine max* protein referred to as protein TIFY 6A isoform X6 (NCBI accession no XP_006580449.1 (GI: 571456657) has significant sequence identity to the *Arabidopsis thaliana* JAZ9 protein with SEQ ID NO:54, as illustrated by the sequence comparison shown below. Domains of sequence homology are identified by asterisks below each sequence comparison.

```
39.8% identity in 176 residues overlap; Score: 167.0; Gap frequency: 15.3%
Seq54  117 SPQLTIFYGGTISVFNDISPDKAQAIMLCAGNGLKGETGDSKP----------------
           -
Seq70  156
SAQLTIFYAGTVNIFDDISAEKAQAIMLLAGNSLSAASNMAQPNVQVPISKLGAGAGVPV
           * ****** **   * ***  ******* ***  *              *

Seq54  160 VREAERMYGKQIHN-------
TAATSSSSATHTDNFSRCRDTPVAATNAMSMIESFNAAP
Seq70  216
SQPANTSPGSGLSSPLSVSSHTGVQGSGLTSTDEFLAAKTTGVPNTPICNVEPPKVVSA
           *    *        *      *   * ** ****      **   *

Seq54  213 RNMIPS-VPQARKASLARFLEKRKERLMSAMPYK--KMLLDLSTGESSGMNYSSTS
Seq70  276 TTMLTSAVPQARKASLARFLEKRKERVMSAAPYNLNKKSEECATAEYAGVNFSATN
            *  *  ******************* *** **    *      *   * * ***

40.0% identity in 40 residues overlap; Score: 66.0; Gap frequency: 2.5%
Seq54   1 MERDFLGLSDKQYLSNNVKHEVNDDAVEERGLSTKAAREW
Seq70   1 MERDFMGLNLKEPLAV-VKEEMNNDGCKNSGFKKGRIAQW
          ***** **  *    **  * * *     *         *
```

This JAZ-related *Glycine max* protein, referred to as protein TIFY 6A isoform X6 (NCBI accession no. XP_006580449.1 (GI:571456657)) has the following sequence (SEQ ID NO:70).

```
  1 MERDFMGLNL KEPLAVVKEE MNNDGCKNSG FKKGRIAQWP
 41 FSNKVSALPH LMSFKASQDD KTKNTVSDTL SSSGFMSILS
 81 QEAFDTSQKR SAGEPQMFSV PNQAISVSLG NPFLKNHFAA
121 AGQKPLLGGI PVTTSHSVLP SAVAVAGMTE SCVKPSAQLT
161 IFYAGTVNIF DDISAEKAQA IMLLAGNSLS AASNMAQPNV
201 QVPISKLGAG AGVPVSQPAN TSPGSGLSSP LSVSSHTGVQ
241 SGSGLTSTDE FLAAKTTGVP NTPICNVEPP KVVSATTMLT
281 SAVPQARKAS LARFLEKRKE RVMSAAPYNL NKKSEECATA
321 EYAGVNFSAT NTVLAKQG
```

A cDNA encoding the SEQ ID NO:70 protein is available as NCBI accession number XM_006580386.2 (GI:

955322109), and a chromosomal segment encoding the SEQ ID NO:70 protein is on *Glycine max* chromosome 5 at NC_016092.2 (41222014 . . . 41225906), sequence available as NCBI accession number NC_016092.2 (GI:952545311).

An unknown *Oryza sativa* protein with NCBI accession no. BAD28520.1 (GI:50251455) has significant sequence identity to the *Arabidopsis thaliana* JAZ9 protein with SEQ ID NO:54, as illustrated by the sequence comparison shown below. Domains of sequence homology are identified by asterisks below each sequence comparison.

```
40.9% identity in 66 residues overlap; Score: 116.0; Gap frequency: 1.5%
Seq54    84
GGAFQNATPLLLGGSVPLPTHPSLVPRVASSGSSPQLTIFYGGTISVFNDISPDKAQAIM
Seq71    51GGAFKQP--
PFAMGNAVAGSTVGVYGTRDMPKAKAAQLTIFYAGSVNVFNNVSPEKAQELM
****      *  *  *   *       *      ******  *   ***  ** ***
 *

Seq54    144 LCAGNG
Seq71    110 FLASRG
              *  *

56.1% identity in 41 residues overlap; Score: 110.0; Gap frequency: 0.0%
Seq54    218 SVPQARKASLARFLEKRKERLMSAMPYKKMLLDLSTGESSG
Seq71    225 AVPQARKASLARFLEKRKERVTTVAPYPLAKSPLESSDTMG
              ******************  **    *      *
```

This JAZ-related *Oryza sativa* protein with NCBI accession no. BAD28520.1 (GI:50251455) has the following sequence (SEQ ID NO:71).

```
  1 MQQASHVLAR QPPHVLNGAR VIPASSPFNP NNPMFRVQSS

41 PNLPNAVGAG GGAFKQPPFA MGNAVAGSTV GVYGTRDMPK

81 AKAAQLTIFY AGSVNVFNNV SPEKAQELMF LASRGSLPSA

121 PTTVARMPEA HVFPPAKVTV PEVSPTKPMM LQKPQLVSSP

161 VPAISKPISV VSQATSLPRS ASSSNVDSNV TKSSGPLVVP

201 PTSLPPPAQP ETLATTTAAA IMPRAVPQAR KASLARFLEK

241 RKERVTTVAP YPLAKSPLES SDTMGSANDN KSSCTDIALS

281 SNRDESLSLG QPRTISFCEE SPSTKLQI
```

A chromosomal segment encoding the SEQ ID NO:71 protein is on *Oryza sativa* chromosome 9 at NC_029264.1 (14056084 . . . 14060320, complement), sequence available as NCBI accession number NC_029264.1 (GI:996703424).

An uncharacterized *Zea mays* protein referred to as LOC100384222 (NCBI accession no. NP_001182812.1 (GI:308044557)) has significant sequence identity to the *Arabidopsis thaliana* JAZ10 protein with SEQ ID NO:56, as illustrated by the sequence comparison shown below. Domains of sequence homology are identified by asterisks below each sequence comparison.

This JAZ-related uncharacterized *Zea mays* protein referred to as LOC100384222 (NCBI accession no. NP_001182812.1 (GI:308044557)) has the following sequence (SEQ ID NO:72).

```
  1 MAGHAPARDK TTTGFAATCS LLSQFLKEKK GGLQGLGGLA

41 MAPAPAAGAG AFRPPTTMNL LSALDAAKAT VGEPEGHGQR

81 TGGNPREAAG EEAQQLTIFY GGKVVVFDRF PSAKVKDLLQ

121 IVSPPGADAV VDGAGAGAAV PTQNLPRPSH DSLSADLPIA

161 RRNSLHRFLE KRKDRITAKA PYQVNSSVGA EASKAEKPWL

201 GLGQEQEGSD GRQAGEEM
```

A cDNA encoding the SEQ ID NO:72 protein is available as NCBI accession number NM_001195883.1 (GI:308044556), and a chromosomal segment encoding the SEQ ID NO:72 protein is on *Zea mays* chromosome 7 at NC_024465.1 (121257106 . . . 121259180, complement), sequence available as NCBI accession number NC_024465.1 (GI:662248746).

An uncharacterized *Glycine max* protein referred to as LOC100306524 (NCBI accession number NP_001236269.1 (GI:351723837) has significant sequence identity to the *Arabidopsis thaliana* JAZ10 protein with SEQ ID NO:56, as illustrated by the sequence comparison shown below. Domains of sequence homology are identified by asterisks below each sequence comparison.

```
36.2% identity in 94 residues overlap; Score: 126.0; Gap frequency: 3.2%
Seq56    105 MTIFYNGSVSVF-
QVSRNKAGEIMKVANEAASKKDESSMETDLSVILPTTLRPKLFGQL
Seq72    96 LTIFYGGKVVVFDRFPSAKVKDLLQIVSPPGA--
DAVVDGAGAGAAVPTQNLPRPSHDSL
             **** * * **           *           *       **  **

Seq56    164 EGDLPIARRKSLQRFLEKRKERLVSTSPYYPTSA
Seq72    154 SADLPIARRNSLHRFLEKRKDRITAKAPYQVNSS
                ******* ** ******* *    ** *
```

```
36.6% identity in 123 residues overlap; Score: 114.0; Gap frequency: 12.2%
Seq56       85  SPVHASLARSSTELVSGTVPMTIFYNGSVSVFQ-
VSRNKAGEIMKVANEAASKKDESSME
Seq73       38
SPNKSVPASGLDAVIPSANQLTIFYNGSVCVYDGIPAEKVHEIMLIAAAAAKSTEMKKIG
               **      *           ********  *         *  ***  *  **

Seq56      144  TDLSVILPTTLRP--------------
KLFGQNLEGDLPIARRKSLQRFLEKRKERLVST
Seq73       98
TQTTLISPAPSRPSSPHGITNNIGSSQKSSICRLQAEFPIARRHSLQRFLEKRRDRLGSK
                *  *  *  **              *      *    *****  ********* ** *

Seq56      190  SPY
Seq73      158  TPY
                 **
```

This JAZ-related uncharacterized *Glycine max* protein referred to as LOC100306524 (NCBI accession number NP_001236269.1 (GI:351723837) has the following sequence (SEQ ID NO:73).

```
  1 MAAGVTVKSE VLESSPPEGV CSNTVENALV QTNLSDGSPN
 41 KSVPASGLDA VIPSANQLTI FYNGSVCVYD GIPAEKVHEI
 81 MLIAAAAAKS TEMKKIGTQT TLISPAPSRP SSPHGITNNI
121 GSSQKSSICR LQAEFPIARR HSLQRFLEKR RDRLGSKTPY
161 PSSPTTKVAD NIENNTCADN APELISLNRS EEEFQPTVSA
201 S
```

A cDNA encoding the SEQ ID NO:73 protein is available as NCBI accession number NM_001249340.2 (GI: 402766138), and a chromosomal segment encoding the SEQ ID NO:73 protein is on *Glycine max* chromosome 15 at NC_016102.2 (18552881 ... 18556339), sequence available as NCBI accession number NC_016102.2 (GI:952545301).

An *Oryza sativa* protein referred to as protein TIFY 9 with NCBI accession no. XP_015634258.1 (GI:1002259863) has significant sequence identity to the *Arabidopsis thaliana* JAZ10 protein with SEQ ID NO:56, as illustrated by the sequence comparison shown below. Domains of sequence homology are identified by asterisks below each sequence comparison.

```
  1 MSTRAPVELD FLGLRAAAAD ADDRHAKSGG SSASSSSSIR
 41 GMETSAIARI GPHLLRRVIA AAGPPPPPST APVPEEMPGA
 81 AAAAAPMTLF YNGSVAVFDV SHDKAEAIMR MATEATKAKG
121 LARGNAIVGN FAKEPLTRTK SLQRFLSKRK ERLTSLGPYQ
161 VGGPAAVGAT TSTTTKSFLA KEEEHTAS
```

A cDNA encoding the SEQ ID NO:74 protein is available as NCBI accession number XM_015778772.1 (GI: 1002259862), and a chromosomal segment encoding the SEQ ID NO:74 protein is on *Oryza sativa* chromosome 4 at NC_029259.1 (19492605 ... 19497181), sequence available as NCBI accession number NC_029259.1 (GI:996703429).

Chromosomal sites encoding any of the conserved amino acids and conserved domains illustrated by the sequence comparisons shown above can be deleted or mutated to reduce the activity of the proteins described herein.

For example, a wild type plant can express JAZ polypeptides or JAZ-related polypeptides with at least 70%, or at least 75%, or at least 80%, or at least 85%, or at least 90%, or at least 95%, or at least 97%, or at least 98%, or at least 99% sequence identity to any of SEQ ID NOs:48, 50, 52, 54, 56, 58-73, or 74.

However, the mutant jazQ plant cells, plants, and/or seeds with increased jasmonic acid responses and improved insect resistance can express mutant JAZ and/or JAZ-related poly-

```
40.0% identity in 110 residues overlap; Score: 119.0; Gap frequency:
13.6%
Seq56       83
PISPVHASLARSSTELVSGTVPMTIFYNGSVSVFQVSRNKAGEIMKVANEAASKKDESSM
Seq74       65 PPPPSTAPVPEEMPGAAAAAAPMTLFYNGSVAVFDVSHDKAEAIMRMATEATKAKGLA-
-
                *  *  *        ***  ******  **  **  **  **   *  **       *

Seq56      143 ETDLSVILPTTLRPKLFGQNLEGDLPIARRKSLQRFLEKRKERLVSTSPY
Seq74      123 ------------RGNAIVGNFAKE-PLTRTKSLQRFLSKRKERLTSLGPY
                              *      *   *  ******* ******  *   **

66.7% identity in 12 residues overlap; Score: 44.0; Gap frequency:
0.0%
Seq56       2 SKATIELDFLGL
Seq74       3 TRAPVELDFLGL
                  *  *******
```

This JAZ-related *Oryza sativa* protein referred to as protein TIFY 9 with NCBI accession no. XP_015634258.1 (GI: 1002259863) has the following sequence (SEQ ID NO:74).

peptides that have reduced activity. Such JAZ and/or JAZ-related polypeptides that have reduced JAZ activity can have less than 99%, or less than 98%, or less than 95%, or less than 90%, or less than 85%, or less than 75%, or less than 60%, or less than 50%, or less than 40%, or less than 30%, or less than 20% sequence identity to any of SEQ ID NOs:48, 50, 52, 54, 56, 58-73, or 74.

The mutant JAZ and/or JAZ-related polypeptides can, for example, have mutations in at least one conserved amino acid position, or at least two conserved amino acid positions, or at least three conserved amino acid positions, or at least five conserved amino acid positions, or at least seven conserved amino acid positions, or at least eight conserved amino acid positions, or at least ten conserved amino acid positions, or at least fifteen amino acid positions, or at least twenty conserved amino acid positions, or at least twenty-five amino acid positions. In some cases, an entire conserved JAZ and/or JAZ-related domain or the entire endogenous JAZ and/or JAZ-related gene or chromosomal segment is deleted or mutated.

The conserved amino acids and/or domains are in some cases mutated by deletion or replacement with amino acids that have dissimilar physical and/or chemical properties. Examples of amino acids with different physical and/or chemical properties that can be employed are shown in Tables 1 and 2.

Transformation of Plant Cells

Mutations can be introduced into any of the MYC, MYC-related, JAZ, JAZ-related, PHYB or PHYB-related plant genomes by introducing targeting vectors, T-DNA, transposons, nucleic acids encoding TALENS, CRISPR, or ZFN nucleases, and combinations thereof into a recipient plant cell to create a transformed cell. In addition plant cells can be transformed to include a PIF4 transgene, for example, by transformation of the plant cells with a PIF4 expression cassette or expression vector.

The frequency of occurrence of cells taking up exogenous (foreign) DNA can sometimes be low. However, certain cells from virtually any dicot or monocot species can be stably transformed, and these cells can be regenerated into transgenic plants, through the application of the techniques disclosed herein. The plant cells, plants, and seeds can therefore be monocotyledons or dicotyledons.

The cell(s) that undergo transformation may be in a suspension cell culture or may be in an intact plant part, such as an immature embryo, or in a specialized plant tissue, such as callus, such as Type I or Type II callus.

Transformation of the cells of the plant tissue source can be conducted by any one of a number of methods available to those of skill in the art. Examples include: Transformation by direct DNA transfer into plant cells by electroporation (U.S. Pat. Nos. 5,384,253 and 5,472,869, Dekeyser et al., The Plant Cell. 2:591 602 (1990)); direct DNA transfer to plant cells by PEG precipitation (Hayashimoto et al., Plant Physiol. 93:857 863 (1990)); direct DNA transfer to plant cells by microprojectile bombardment (McCabe et al., Bio/Technology. 6:923 926 (1988); Gordon Kamm et al., The Plant Cell. 2:603 618 (1990); U.S. Pat. Nos. 5,489,520; 5,538,877; and 5,538,880) and DNA transfer to plant cells via infection with Agrobacterium. Methods such as microprojectile bombardment or electroporation can be carried out with "naked" DNA where the expression cassette may be simply carried on any E. coli derived plasmid cloning vector. In the case of viral vectors, it is desirable that the system retain replication functions, but lack functions for disease induction.

One method for dicot transformation, for example, involves infection of plant cells with Agrobacterium tumefaciens using the leaf disk protocol (Horsch et al., Science 227:1229 1231 (1985). Monocots such as Zea mays can be transformed via microprojectile bombardment of embryogenic callus tissue or immature embryos, or by electroporation following partial enzymatic degradation of the cell wall with a pectinase containing enzyme (U.S. Pat. Nos. 5,384,253; and 5,472,869). For example, embryogenic cell lines derived from immature Zea mays embryos can be transformed by accelerated particle treatment as described by Gordon Kamm et al. (The Plant Cell. 2:603 618 (1990)) or U.S. Pat. Nos. 5,489,520; 5,538,877 and 5,538,880, cited above. Excised immature embryos can also be used as the target for transformation prior to tissue culture induction, selection and regeneration as described in U.S. application Ser. No. 08/112,245 and PCT publication WO 95/06128. Furthermore, methods for transformation of monocotyledonous plants utilizing Agrobacterium tumefaciens have been described by Hiei et al. (European Patent 0 604 662, 1994) and Saito et al. (European Patent 0 672 752, 1995).

Methods such as microprojectile bombardment or electroporation can be carried out with "naked" DNA where the expression cassette may be simply carried, for example, on any E. coli derived plasmid cloning vector. In the case of viral vectors, it is desirable that the system retain replication functions, but lack functions for disease induction.

The choice of plant tissue source for transformation will depend on the nature of the host plant and the transformation protocol. Useful tissue sources include callus, suspension culture cells, protoplasts, leaf segments, stem segments, tassels, pollen, embryos, hypocotyls, tuber segments, meristematic regions, and the like. The tissue source is selected and transformed so that it retains the ability to regenerate whole, fertile plants following transformation, i.e., contains totipotent cells. Type I or Type II embryonic maize callus and immature embryos are exemplary Zea mays tissue sources. Selection of tissue sources for transformation of monocots is described in detail in U.S. application Ser. No. 08/112,245 and PCT publication WO 95/06128.

The transformation is carried out under conditions directed to the plant tissue of choice. The plant cells or tissue are exposed to the DNA or RNA carrying the targeting vector and/or other nucleic acids for an effective period of time. This may range from a less than one second pulse of electricity for electroporation to a 2-3 day co cultivation in the presence of plasmid bearing Agrobacterium cells. Buffers and media used will also vary with the plant tissue source and transformation protocol. Many transformation protocols employ a feeder layer of suspended culture cells (tobacco or Black Mexican Sweet corn, for example) on the surface of solid media plates, separated by a sterile filter paper disk from the plant cells or tissues being transformed.

Where one wishes to introduce DNA by means of electroporation, it is contemplated that the method of Krzyzek et al. (U.S. Pat. No. 5,384,253) may be advantageous. In this method, certain cell wall degrading enzymes, such as pectin degrading enzymes, are employed to render the target recipient cells more susceptible to transformation by electroporation than untreated cells. Alternatively, recipient cells can be made more susceptible to transformation, by mechanical wounding.

To effect transformation by electroporation, one may employ either friable tissues such as a suspension cell cultures, or embryogenic callus, or alternatively, one may transform immature embryos or other organized tissues directly. The cell walls of the preselected cells or organs can be partially degraded by exposing them to pectin degrading enzymes (pectinases or pectolyases) or mechanically wounding them in a controlled manner. Such cells would then be receptive to DNA uptake by electroporation, which may be carried out at this stage, and transformed cells then identified by a suitable selection or screening protocol dependent on the nature of the newly incorporated DNA.

A further advantageous method for delivering transforming DNA segments to plant cells is microprojectile bombardment. In this method, microparticles may be coated with DNA and delivered into cells by a propelling force. Exemplary particles include those comprised of tungsten, gold, platinum, and the like.

It is contemplated that in some instances DNA precipitation onto metal particles would not be necessary for DNA delivery to a recipient cell using microprojectile bombardment. In an illustrative embodiment, non-embryogenic cells were bombarded with intact cells of the bacteria *E. coli* or *Agrobacterium tumefaciens* containing plasmids with either the β-glucouronidase or bar gene engineered for expression in maize. Bacteria were inactivated by ethanol dehydration prior to bombardment. A low level of transient expression of the β-glucouronidase gene was observed 24-48 hours following DNA delivery. In addition, stable transformants containing the bar gene can be recovered following bombardment with either *E. coli* or *Agrobacterium tumefaciens* cells. It is contemplated that particles may contain DNA rather than be coated with DNA. Hence it is proposed that particles may increase the level of DNA delivery but are not, in and of themselves, necessary to introduce DNA into plant cells.

An advantage of microprojectile bombardment, in addition to being an effective means of reproducibly stably transforming monocots, is that the isolation of protoplasts (Christou et al., PNAS. 84:3962 3966 (1987)), the formation of partially degraded cells, or the susceptibility to *Agrobacterium* infection is not required. An illustrative embodiment of a method for delivering DNA into maize cells by acceleration is a Biolistics Particle Delivery System, which can be used to propel particles coated with DNA or cells through a screen, such as a stainless steel or Nytex screen, onto a filter surface covered with maize cells cultured in suspension (Gordon Kamm et al., The Plant Cell. 2:603 618 (1990)). The screen disperses the particles so that they are not delivered to the recipient cells in large aggregates. It is believed that a screen intervening between the projectile apparatus and the cells to be bombarded reduces the size of projectile aggregate and may contribute to a higher frequency of transformation, by reducing damage inflicted on the recipient cells by an aggregated projectile.

For bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. If desired, one or more screens are also positioned between the acceleration device and the cells to be bombarded. Through the use of techniques set forth here in one may obtain up to 1000 or more foci of cells transiently expressing a marker gene. The number of cells in a focus which express the exogenous gene product 48 hours post bombardment often range from about 1 to 10 and average about 1 to 3.

In bombardment transformation, one may optimize the prebombardment culturing conditions and the bombardment parameters to yield the maximum numbers of stable transformants. Both the physical and biological parameters for bombardment can influence transformation frequency. Physical factors are those that involve manipulating the DNA/microprojectile precipitate or those that affect the path and velocity of either the macroprojectiles or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmid DNA.

One may wish to adjust various bombardment parameters in small scale studies to fully optimize the conditions and/or to adjust physical parameters such as gap distance, flight distance, tissue distance, and helium pressure. One may also minimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. Execution of such routine adjustments will be known to those of skill in the art.

Examples of plants and/or plant cells that can be modified as described herein include alfalfa (e.g., forage legume alfalfa), algae, avocado, barley, broccoli, Brussels sprouts, cabbage, canola, cassava, cauliflower, cole vegetables, collards, corn, crucifers, grain legumes, grasses (e.g., forage grasses), jatropa, kale, kohlrabi, maize, miscanthus, mustards, nut sedge, oats, oil firewood trees, oilseeds, potato, radish, rape, rapeseed, rice, rutabaga, sorghum, soybean, sugar beets, sugarcane, sunflower, switchgrass, tobacco, tomato, turnips, and wheat. In some embodiments, the plant is a *Brassicaceae* or other *Solanaceae* species. In some embodiments, the plant or cell can be a maize plant or cell. In some embodiments, the plant is not a species of *Arabidopsis*, for example, in some embodiments, the plant is not *Arabidopsis thaliana*.

An exemplary embodiment of methods for identifying transformed cells involves exposing the bombarded cultures to a selective agent, such as a metabolic inhibitor, an antibiotic, herbicide or the like. Cells which have been transformed and have stably integrated a marker gene conferring resistance to the selective agent used, will grow and divide in culture. Sensitive cells will not be amenable to further culturing.

To use the bar-bialaphos or the EPSPS-glyphosate selective system, bombarded tissue is cultured for about 0-28 days on nonselective medium and subsequently transferred to medium containing from about 1-3 mg/l bialaphos or about 1-3 mM glyphosate, as appropriate. While ranges of about 1-3 mg/l bialaphos or about 1-3 mM glyphosate can be employed, it is proposed that ranges of at least about 0.1-50 mg/l bialaphos or at least about 0.1-50 mM glyphosate will find utility in the practice of the invention. Tissue can be placed on any porous, inert, solid or semi-solid support for bombardment, including but not limited to filters and solid culture medium. Bialaphos and glyphosate are provided as examples of agents suitable for selection of transformants, but the technique of this invention is not limited to them.

An example of a screenable marker trait is the red pigment produced under the control of the R-locus in maize. This pigment may be detected by culturing cells on a solid support containing nutrient media capable of supporting growth at this stage and selecting cells from colonies (visible aggregates of cells) that are pigmented. These cells may be cultured further, either in suspension or on solid media. The R-locus is useful for selection of transformants from bombarded immature embryos. In a similar fashion, the introduction of the C1 and B genes will result in pigmented cells and/or tissues.

The enzyme luciferase is also useful as a screenable marker in the context of the present invention. In the presence of the substrate luciferin, cells expressing luciferase emit light which can be detected on photographic or X-ray film, in a luminometer (or liquid scintillation counter), by devices that enhance night vision, or by a highly light sensitive video camera, such as a photon counting camera. All of these assays are nondestructive and transformed cells may be cultured further following identification. The photon counting camera is especially valuable as it allows one to identify specific cells or groups of cells which are expressing luciferase and manipulate those in real time.

It is further contemplated that combinations of screenable and selectable markers may be useful for identification of transformed cells. For example, selection with a growth inhibiting compound, such as bialaphos or glyphosate at concentrations below those that cause 100% inhibition followed by screening of growing tissue for expression of a screenable marker gene such as luciferase would allow one to recover transformants from cell or tissue types that are not amenable to selection alone. In an illustrative embodiment embryogenic Type II callus of Zea mays L. can be selected with sub-lethal levels of bialaphos. Slowly growing tissue was subsequently screened for expression of the luciferase gene and transformants can be identified.

Regeneration and Seed Production

Cells that survive the exposure to the selective agent, or cells that have been scored positive in a screening assay, are cultured in media that supports regeneration of plants. One example of a growth regulator that can be used for such purposes is dicamba or 2,4-D. However, other growth regulators may be employed, including NAA, NAA+2,4-D or perhaps even picloram. Media improvement in these and like ways can facilitate the growth of cells at specific developmental stages. Tissue can be maintained on a basic media with growth regulators until sufficient tissue is available to begin plant regeneration efforts, or following repeated rounds of manual selection, until the morphology of the tissue is suitable for regeneration, at least two weeks, then transferred to media conducive to maturation of embryoids. Cultures are typically transferred every two weeks on this medium. Shoot development signals the time to transfer to medium lacking growth regulators.

The transformed cells, identified by selection or screening and cultured in an appropriate medium that supports regeneration, can then be allowed to mature into plants. Developing plantlets are transferred to soilless plant growth mix, and hardened, e.g., in an environmentally controlled chamber at about 85% relative humidity, about 600 ppm $CO_2$, and at about 25-250 microeinsteins/sec·$m^2$ of light.

Plants can be matured either in a growth chamber or greenhouse. Plants are regenerated from about 6 weeks to 10 months after a transformant is identified, depending on the initial tissue. During regeneration, cells are grown on solid media in tissue culture vessels. Illustrative embodiments of such vessels are petri dishes and Plant Con™. Regenerating plants can be grown at about 19° C. to 28° C. After the regenerating plants have reached the stage of shoot and root development, they may be transferred to a greenhouse for further growth and testing.

Mature plants are then obtained from cell lines that are known to have the mutations. In some embodiments, the regenerated plants are self-pollinated. In addition, pollen obtained from the regenerated plants can be crossed to seed grown plants of agronomically important inbred lines. In some cases, pollen from plants of these inbred lines is used to pollinate regenerated plants. The trait is genetically characterized by evaluating the segregation of the trait in first and later generation progeny. The heritability and expression in plants of traits selected in tissue culture are of particular importance if the traits are to be commercially useful.

Regenerated plants can be repeatedly crossed to inbred plants in order to introgress the mutations into the genome of the inbred plants. This process is referred to as backcross conversion. When a sufficient number of crosses to the recurrent inbred parent have been completed in order to produce a product of the backcross conversion process that is substantially isogenic with the recurrent inbred parent except for the presence of the introduced myc, JAZ, or phyB mutations or PIF4 expression cassette, the plant is self-pollinated at least once in order to produce a homozygous backcross converted inbred containing the mutations. Progeny of these plants are true breeding.

Alternatively, seed from transformed mutant plant lines regenerated from transformed tissue cultures is grown in the field and self-pollinated to generate true breeding plants.

Seed from the fertile transgenic plants can then be evaluated for the presence of the desired MYC, JAZ, or PhyB mutation, the desired PIF4 expression cassette, and/or the expression of the desired mutant protein. Transgenic plant and/or seed tissue can be analyzed using standard methods such as SDS polyacrylamide gel electrophoresis, liquid chromatography (e.g., HPLC) or other means of detecting a mutation.

Once a transgenic plant with a mutant sequence and having improved growth and insect resistance is identified, seeds from such plants can be used to develop true breeding plants. The true breeding plants are used to develop a line of plants with an increase insect resistance relative to wild type, and acceptable growth characteristics while still maintaining other desirable functional agronomic traits. Adding the mutation to other plants can be accomplished by back-crossing with this trait and with plants that do not exhibit this trait and studying the pattern of inheritance in segregating generations. Those plants expressing the target trait (insect resistance, good growth) in a dominant fashion are preferably selected. Back-crossing is carried out by crossing the original fertile transgenic plants with a plant from an inbred line exhibiting desirable functional agronomic characteristics while not necessarily expressing the trait of an increased insect resistance and good plant growth. The resulting progeny are then crossed back to the parent that expresses the increased insect resistance and good plant growth. The progeny from this cross will also segregate so that some of the progeny carry the trait and some do not. This back-crossing is repeated until an inbred line with the desirable functional agronomic traits, and with expression of the trait involving an increase in insect resistance and good plant growth. Such insect resistance and good plant growth can be expressed in a dominant fashion.

The new transgenic plants can also be evaluated for a battery of functional agronomic characteristics such as growth, lodging, kernel hardness, yield, resistance to disease and insect pests, drought resistance, and/or herbicide resistance.

Plants that may be improved by these methods include but are not limited to agricultural plants of all types, oil and/or starch plants (canola, potatoes, lupins, sunflower and cottonseed), forage plants (alfalfa, clover and fescue), grains (maize, wheat, barley, oats, rice, sorghum, millet and rye), grasses (switchgrass, prairie grass, wheat grass, sudangrass, sorghum, straw-producing plants), softwood, hardwood and other woody plants (e.g., those used for paper production such as poplar species, pine species, and eucalyptus). In some embodiments the plant is a gymnosperm. Examples of plants useful for pulp and paper production include most pine species such as loblolly pine, Jack pine, Southern pine, Radiata pine, spruce, Douglas fir and others. Hardwoods that can be modified as described herein include aspen, poplar, eucalyptus, and others. Plants useful for making biofuels and ethanol include corn, grasses (e.g., miscanthus, switchgrass, and the like), as well as trees such as poplar, aspen, willow, and the like. Plants useful for generating dairy forage include legumes such as alfalfa, as well as forage grasses such as bromegrass, and bluestem.

Determination of Stably Transformed Plant Tissues

To confirm the presence of MYC, JAZ, and/or PHYB mutations and/or a PIF4 expression cassette in the regenerating plants, or seeds or progeny derived from the regenerated plant, a variety of assays may be performed. Such assays include, for example, molecular biological assays available to those of skill in the art, such as Southern and Northern blotting and PCR; biochemical assays, such as detecting the presence of a protein product, e.g., by immunological means (ELISAs and Western blots) or by enzymatic function; plant part assays, such as leaf, seed or root assays; and also, by analyzing the phenotype of the whole regenerated plant.

Whereas DNA analysis techniques may be conducted using DNA isolated from any part of a plant, RNA may only be expressed in particular cells or tissue types and so RNA for analysis can be obtained from those tissues. PCR techniques may also be used for detection and quantification of RNA produced from introduced MYC, JAZ, or PhyB mutations or of RNA expressed from an introduced PIF4 expression cassette. For example, PCR also be used to reverse transcribe RNA into DNA, using enzymes such as reverse transcriptase, and then this DNA can be amplified through the use of conventional PCR techniques.

For example, if no amplification of PHYB mRNAs is observed, then a deletion mutation has successfully been introduced.

Information about mutations can also be obtained by primer extension or single nucleotide polymorphism (SNP) analysis.

Further information about the nature of the RNA product may be obtained by Northern blotting. This technique will demonstrate the presence of an RNA species and give information about the integrity of that RNA. The presence of some mutations can be detected by Northern blotting. The presence or absence of an RNA species (e.g., PIF4 RNA) can also be determined using dot or slot blot Northern hybridizations. These techniques are modifications of Northern blotting and also demonstrate the presence or absence of an RNA species.

While Southern blotting and PCR may be used to detect the presence of MYC, JAZ, and/or PHYB mutations or the presence of a PIF4 expression cassette, they do not provide information as to whether the preselected DNA segment is being expressed. Expression may be evaluated by specifically identifying the protein products of the introduced PIF4 expression cassette or the introduced mutations, by detecting that no PHYB proteins are expressed, or evaluating the phenotypic changes brought about by such mutation.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange, liquid chromatography or gel exclusion chromatography. The unique structures of individual proteins offer opportunities for use of specific antibodies to detect their presence in formats such as an ELISA assay. Combinations of approaches may be employed with even greater specificity such as Western blotting in which antibodies are used to locate individual gene products, or the absence thereof, that have been separated by electrophoretic techniques. Additional techniques may be employed to absolutely confirm the identity of a mutation such as evaluation by screening for reduced transcription (or no transcription) of MYC, JAZ, and/or PHYB mRNAs, by screening for PIF4 expression, or by amino acid sequencing following purification. The Examples of this application also provide assay procedures for detecting and quantifying insect resistance and plant growth. Other procedures may be additionally used.

The expression of a gene product can also be determined by evaluating the phenotypic results of its expression. These assays also may take many forms including but not limited to analyzing changes in the insect resistance, growth characteristics, or other physiological properties of the plant. Expression of selected DNA segments encoding different amino acids or having different sequences and may be detected by amino acid analysis or sequencing.

The following Examples describe some of the experiments performed in the development of the invention.

Example 1: Materials and Methods

This Example describes some of the material and methods employed in the development of the invention.

Plant material and growth conditions. *Arabidopsis thaliana* Columbia ecotype (Col-0) was used as a wild-type (WT) parent for all experiments. Soil-grown plants were maintained at 20° C. (±1° C.) with 16 h light at a light intensity of 120 µE m$^{-2}$ s−1 and 8 h dark unless otherwise noted. For the first 10 days after seed sowing, trays containing potted plants were covered with a transparent plastic dome to increase humidity. For experiments involving growth of seedlings on agar plates, seeds were surface sterilized for 15 min in a solution containing 50% (v/v) bleach and 0.1% (v/v) Triton X-100, washed 10 times with sterile water and then stratified in dark at 4° C. for 2 days. Seeds were then sown on 0.7% (w/v) agar media containing half-strength Murashige and Skoog (MS; Caisson Labs) salts supplemented with 0.8% (w/v) sucrose.

Transfer DNA (T-DNA) insertion mutants used for construction of jazQ were obtained from the *Arabidopsis* Biological Research Center (ABRC; The Ohio State University) and named as follows: jaz1-SM (jaz1, JIC-SM.22668), jaz3-GK (jaz3, GK-097F09), jaz4-1 (jaz4, SALK_141628), jaz9-GK (jaz9, GK-265H05) and jaz10-1 (jaz10, SAIL_92_D08). See FIG. 1G.

The jaz3-GK and jaz9-GK lines were backcrossed to Col-0 to remove unlinked T-DNA insertions. The jaz10-1 was backcrossed to Col-0 to remove a qrtl-2 mutation present in the SAIL lines (McElver et al., *Genetics* 159, 1751-1763 (2001)). The jaz4-1 and jaz10-1 mutants are described by Jiang et al. (*Plant Cell* 26, 230-245 (2014)), and Sehr et al. (*Plant J* 63, 811-822 (2010)). The jazQ phyB sextuple mutant was obtained from a genetic cross between mutant jazQ and the mutant phyB reference allele phyB-9 (Reed et al., *Plant Cell* 5, 147-157 (1993)). The higher-order pifq (pif1-1/pif3-3/pif4-2/pif5-3) and dellaQ (gai-t6/rgat2/rgl1-1/rgl2-1/rgl3-1) mutants are discussed by Feng et al. (*Nature* 451, 475-479 (2008)) and Leivar et al., (*Curr Biol* 18, 1815-1823 (2008)).

PCR analysis. PCR-based genotyping of jazQ and lower-order mutants relied on primer sets flanking T-DNA insertion sites, together with a third primer recognizing the border of the inserted T-DNA. The forward, reverse, and border primers used were the following:

```
JAZ1 (At1g19180):
                               (SEQ ID NO: 75)
5'-ACCGAGACACATTCCCGATT-3', (SEQ ID NO: 76)
5'-CATCAGGCTTGCATGCCATT-3',
and (SEQ ID NO: 77)
5'-ACGAATAAGAGCGTCCATTTTAGAG-3';

JAZ3 (At3g17860):
                               (SEQ ID NO: 129)
5'-ACGGTTCCTCTATGCCTCAAGTC-3', (SEQ ID NO: 78)
5'-GTGGAGTGGTCTAAAGCAACCTTC-3',
and (SEQ ID NO: 79)
5'-ATAACGCTGCGGACATCTACATT-3';

JAZ4 (At1g48500):
                               (SEQ ID NO: 80)
5'-TCAGGAAGACAGAGTGTTCCC-3', (SEQ ID NO: 81)
5'-TGCGTTTCTCTAAGAACCGAG-3',
and (SEQ ID NO: 83)
5'-TTGGGTGATGGTTCACGTAG-3';

JAZ9 (At1g70700):
                               (SEQ ID NO: 84)
5'-TACCGCATAATCATGGTCGTC-3', (SEQ ID NO: 85)
5'-TCATGCTCATTGCATTAGTCG-3',
and (SEQ ID NO: 86)
5'-CTTTGAAGACGTGGTTGGAACG-3';

JAZ10 (At5g13220):
                               (SEQ ID NO: 87)
5'-ATTTCTCGATCGCCGTCGTAGT-3', (SEQ ID NO: 88)
5'-GCCAAAGAGCTTTGGTCTTAGAGTG-3',
and (SEQ ID NO: 89)
5'-GTCTAAGCGTCAATTTGTTTACACC-3'.
```

Reverse transcription-PCR (RT-PCR) was used to confirm the presence or absence of JAZ transcripts in wild type (WT) and mutant jazQ plants. For this purpose, RNA was extracted from eight-day-old seedlings grown on MS plates containing 20 µM MeJA. Frozen tissue was homogenized with a mortar and pestle and RNA was extracted using an RNeasy kit (Qiagen) with on-column DNase (Qiagen) treatment. cDNA was reverse transcribed from one pg total RNA with a High Capacity cDNA Reverse Transcription kit (Applied Biosystems, ABI). RT-PCR was performed using primer sets designed to amplify the five JAZ genes and the internal control ACTIN1 (At2g37620). The forward and reverse primer sets used were as follows:

```
JAZ1:
                               (SEQ ID NO: 90)
5'-ATGTCGAGTTCTATGGAATGTTCTG-3',
and (SEQ ID NO: 91)
5'-TCATATTTCAGCTGCTAAACCGAGCC-3';

JAZ3:
                               (SEQ ID NO: 92)
5'-ATGGAGAGAGATTTTCTCGGG-3',
and (SEQ ID NO: 93)
5'-TTAGGTTGCAGAGCTGAGAGAAG-3';

JAZ4:
                               (SEQ ID NO: 94)
5'-ATGGAGAGAGATTTTCTCGG-3',
and (SEQ ID NO: 95)
5'-CAGATGATGAGCTGGAGGAC-3;

JAZ9:
                               (SEQ ID NO: 96)
5'-ATGGAAAGAGATTTTCTGGGTTTG-3',
and (SEQ ID NO: 97)
5'-TTATGTAGGAGAAGTAGAAGAGTAATTCA-3';

JAZ10:
                               (SEQ ID NO: 98)
5'-ATGTCGAAAGCTACCATAGAAC-3',
and (SEQ ID NO: 99)
5'-GATAGTAAGGAGATGTTGATACTAATCTCT-3';

ACTIN1:
                               (SEQ ID NO: 100)
5'-ATGGCTGATGGTGAAGACATTCAA-3',
and (SEQ ID NO: 101)
5'-TCAGAAGCACTTCCTGTGAACAAT-3'.
```

RT-PCR reactions were performed with the following conditions: 94° C. for 5 min, followed by 30 cycles of denaturation (45 sec at 94° C.), annealing (30 sec at 52° C.), and elongation (1.5 min at 72° C.). Final elongation step was performed at 72° C. for 10 min and completed reactions were maintained at 12° C. Forty elongation cycles were used to detect the JAZ4 transcripts, which accumulate at low levels in WT plants (Chung et al., *Plant Physiol* 146, 952-964 (2008)).

Root growth assays. The effect of exogenous JA on seedling root growth inhibition has been described by Shyu et al. (*Plant Cell* 24, 536-550 (2012)). Seedlings were grown on square Petri plates (Fisher) containing MS medium supplemented with the indicated concentration of methyl-jasmonic acid (MeJA; Sigma-Aldrich). Plates were incubated vertically in a growth chamber maintained at 21° C. under continuous light for 8 days. Primary root length was measured using the ImageJ software (see website at imagej.nih.gov/ij/). WT and mutant lines were grown on the same plate to control for plate-to-plate variation.

Quantification of secondary metabolites. Anthocyanins were quantified as described by Kang et al. (*Plant Physiol* 164 (2014)), with minor modifications. Petioles were excised from 4-week-old plants and extracted in 1 ml methanol (MeOH) containing 1% (v/v) HCl. Samples were incubated overnight at 4° C. with constant agitation. Anthocyanin pigments in the resulting extract were measured spectrophotometrically and calculated as $A_{530}$-0.25($A_{657}$) $g^{-1}$ fresh weight. Glucosinolates were quantified as described by Barth & Jander (*Plant J* 46, 549-562 (2006)) with minor modifications. Eight-day-old seedlings grown on solid MS medium were collected into two-mL tubes (approximately 50 seedlings per tube) and immediately frozen in liquid nitrogen. WT and mutant lines were grown on the same plate to avoid plate-to-plate variation. Frozen tissue was lyophilized, ground to a fine powder and extracted with 1 ml 80% MeOH containing an internal standard (25 nmol sinigrin, Sigma-Aldrich). Samples were briefly vortexed, incubated at 75° C. for 15 min, and then centrifuged at 23° C. at 10,000×g for 10 min. Resulting supernatants were applied to Sephadex A-25 columns (Amersham). Glucosinolates were released from the columns as desulfoglucosinolates with a solution containing 30 μL of aryl sulfatase (3.0 mg ml$^{-1}$; Sigma) and 70 μL water (HPLC-grade). Following an overnight incubation in the dark at 23° C., samples were eluted from the columns with 200 μL 80% MeOH and 200 μL water. Samples were then lyophilized to complete dryness and re-dissolved in 100 μL water.

Desulfoglucosinoaltes were detected by HPLC and quantified as described by Barth & Jander (*Plant J* 46, 549-562 (2006)). Compound abbreviations in FIG. 1C correspond to the following: 3MSP, 3-methylsulfinylpropylglucosinolate; 4MSB, 4-methylsulfinylbutylglucosinolate; 5MSP, 5-methylsulfinylpentylyglucosinolate; 4OHI3M, 4-hydroxyindol-3-ylmethylglucosinolate; 7MSH, 7-methylsulfinylheptyl-glucosinolate; 4MTB, 4-methylthiobutylglucosinolate; 8MSO, 8-methylsulfinyloctyl-glucosinolate; I3M, indol-3-ylmethylglucosinolate; 4MI3M, 4-methoxyindol-3-ylmethylglucosinolate; 1MI3M, 1-methoxyindol-3-ylmethylglucosinolate; 7MTH, 7-methylthioheptylglucosinolate; and 8MTO, 8-methylthiooctylglucosinolate.

Insect feeding assays. Insect feeding assays were performed with soil-grown plants maintained in a growth chamber at 19° C. and a photoperiod of 8 h light (120 E m$^{-2}$ s$^{-1}$) and 16 h dark. Neonate *Trichoplusia ni* larvae (Benzon Research) were transferred to the center of fully expanded rosette leaves of 6-week-old plants, as previously described by Herde et al. (*Methods Mol Biol* 1011, 51-61 (2013)). Four larvae were reared on each of 12 plants per genotype. Plants were then covered with a transparent dome and returned to the chamber for 10 d, after which larval weights were measured.

Growth and flowering time measurements. Three-to-four week-old soil-grown plants were used for all measurements (10 plants per measurement), unless indicated otherwise. Petiole length of the third true leaf was measured with a caliper after leaf excision. Bolting time was measured in a separate set of plants by counting the number of true leaves on the main stem and the number of days from sowing until bolting (i.e., floral buds visible in the center of the rosette). The same set of plants was subsequently used to assess the length of time to opening of the first flower. Rosette diameter and leaf area were determined by photographing rosettes from the top with a Nikon D80 camera. The resulting images were used to calculate Feret diameter using ImageJ analysis. Total leaf area was determined with GIMP software (see website at gimp.org). Leaf dry weight was determined by weighing excised rosettes (without roots) after freeze drying for two days in a lyophilizer.

jazQ suppressor screen and identification of sjg11. Approximately 50,000 jazQ mutant seeds were further mutagenized by immersion in a solution of 0.1% or 0.2% (v/v) ethyl methanesulfonate (EMS, Sigma-Aldrich) for 16 hours at room temperature, with constant agitation. Seeds ($M_1$ generation) were thoroughly washed with water, stratified in the dark at 4° C. for two days and then immediately sown on soil. $M_2$ seed was collected from 16 pools of self-pollinated $M_1$ plants (approximately 1,000 $M_1$ plants/pool). Soil-grown $M_2$ plants (~2000 plants/pool) were visually screened for individuals having a larger rosette size than jazQ mutant seedlings. Putative sjq (suppressors of the jazQ) mutants were rescreened in the $M_3$ generation to confirm heritability of phenotypes. Insight into the causal mutation in sjg11 came from the observation that sjg11 seedlings grown on MS medium in continuous white light for 3 days have elongated hypocotyls. Subsequent hypocotyl growth assays in monochromatic red light (Warnasooriya & Montgomery, *Plant Physiol* 149, 424-433 (2009)) confirmed a defect in red light signaling. Briefly, sjg11 ($M_3$ generation) and control seeds were plated on MS medium lacking sucrose and stratified at 4° C. in the dark for two days. Mutant and control lines were grown on the same plate to control for plate-to-plate variation. A 3 hours a pulse of white light was then administered to improve synchronous seed germination. Plates were then returned to darkness for one day at 21° C. and then transferred to a monochromatic LED chamber outfitted to emit red light (670±20 nm; 25 μE μE m$^{-2}$ s$^{-1}$). As a control, a set of plates containing each genotype was maintained in darkness. Following three days of growth, seedling hypocotyls were measured by ImageJ software analysis of scanned images. Allelism tests performed with $F_1$ seedlings (obtained from the cross between sjg11 and phyB-9) revealed a lack of genetic complementation. Sequencing of the PHYB gene (AT2G18790) in sjg11 revealed a C→T transition that introduces a stop codon in a region of the gene that encodes the chromophore-binding domain of PHYB (see FIG. 2G).

Gene expression profiling. Global gene expression profiling in 8-day-old whole seedlings (Col-0 WT, mutant jazQ, mutant phyB-9, mutant jazQ phyB-9) was assessed by mRNA sequencing (RNA-seq) performed on the Ilumina HiSeq 2000 platform. Seedlings were grown in continuous light on solid MS medium supplemented with sucrose. For each replicate sample, approximately 200 seedlings were harvested for RNA extraction. WT and mutant seedlings were grown on the same plate to minimize plate-to-plate variation.

Three independent RNA samples (biological replicates) were sequenced per genotype. Total RNA was isolated as described above and RNA integrity was assessed with a 2100 Bioanalyzer (Agilent Technologies). All samples utilized had an integrity score of at least 7.0. Single-end (50 bp) sequencing was performed at the Michigan State University Research Technologies Service Facility (see website at rtsf.natsci.msu.edu). Barcoded sequencing libraries were constructed using the Illumina RNAseq kit according to the manufacturer's instructions and were multiplexed in six libraries per lane. The average number of sequencing reads was 18.4±4.3 million per sample. Raw sequencing reads were assessed with Illumina quality control tools filters and FASTX toolkit (see website at hannonlab.cshl.edu /fastx_toolkit/). Reads were mapped to gene models in TAIR10 with the program RSEM (version 1.2.11) set for default parameters (Li & Dewey, *BMC Bioinformatics* 12, 323, (2011)). Data was expressed as transcripts per million (TPM), and the average TPM±standard error for *Arabidopsis* genes.

DESeq (version 1.18.0; see Anders & Huber, *Genome Biol* 11, R106 (2010)) was used to normalize expected counts from RSEM and to assess differential gene expression by comparing normalized counts in WT to those in a particular mutant. Gene ontology (GO) analysis of enriched functional categories was performed using BiNGO (version 2.44; Maere et al., *Bioinformatics* 21, 3448-3449 (2005)). The hypergeometric test with Benjamini & Hochberg's FDR correction was used to calculate over-represented and under-represented GO categories among differentially expressed genes, using a P value<0.05.

For wounding experiments, three-week old soil-grown seedlings were wounded twice across the midvein of four leaves (leaves 3-6, counted from first rosette leaf). After 1 h, the wounded leaves of two plants were pooled and immediately frozen in liquid nitrogen. Equivalent leaves of two unwounded plants were pooled and collected as controls. The experiment was independently replicated twice, with each experiment consisting of 3-4 biological replicates. Frozen tissue was homogenized with a TissueLyser II (Qiagen) and RNA was extracted using an RNeasy kit (Qiagen) with on-column DNase (Qiagen) treatment, as per the manufacturer's instructions. RNA quality was assessed by $A_{260}/A_{280}$ ratios using a ND-1000 UV Nanodrop spectrophotometer (Thermo Scientific). cDNA was reverse transcribed using a High-Capacity cDNA Reverse Transcription kit (Applied Biosystems, ABI), as per the manufacturer's instructions, and cDNA was diluted to 0.5 ng/L with nuclease-free water. qRT-PCR was performed as described by Attaran et al. (*Plant Physiol* 165, 1302-1314 (2014)), with minor modifications. Briefly, reactions were performed on an ABI 7500 Fast qPCR instrument, and consisted of 5 L of 2×Power SYBR Green (ABI) master mix, 2 uL diluted cDNA template (1 ng total), 1 μL 5 uM forward and reverse primers, and nuclease-free water for 10 μL total reaction volume. The forward and reverse primers used were the following:

```
PP2A:
                                   (SEQ ID NO: 102)
5'-AAGCAGCGTAATCGGTAGG-3'
and (SEQ ID NO: 103)
5'-GCACAGCAATCGGGTATAAAG-3';

AOS:
                                   (SEQ ID NO: 104)
5'-GGAGAACTCACGATGGGAGCGATT-3'
and (SEQ ID NO: 105)
5'-GCGTCGTGGCTTTCGATAACCAGA-3';

LOX3:
                                   (SEQ ID NO: 106)
5'-GCTGGCGGTTCGACATG-3'
and (SEQ ID NO: 107)
5'-GCCATTCCTCTGCGAATTAGA-3';
and MYC2:
                                   (SEQ ID NO: 108)
5'-AGAAACTCCAAATCAAGAACCAGCTC-3'
and (SEQ ID NO: 109)
5'-CCGGTTTAATCGAAGAACACGAAGAC-3'.
```

Reactions were run with the following conditions: 95° C. for 10 min, then 40 cycles of 15 s at 95° C. for denaturation and 60 s at 60° C. for annealing and polymerization. A dissociation curve was performed at the end of each reaction to confirm primer specificity using default parameters (15 s at 95° C., 60 s at 60° C.-95° C. in 1° C. increments, and 15 s at 95° C.). Target gene expression was normalized to the expression of PP2a, which is stable under JA-inducing conditions. The normalization incorporated primer efficiencies determined for each primer pair using LinRegPCR v2012.0[46] from the log-linear phase of each amplification plot.

Overexpression of PIF4 in the mutant jazQ background. The 35S::PIF4-TAP overexpression construct (see Lee & Thomashow, *Proc Natl Acad Sci USA* 109, 15054-15059 (2012)). Transformation of mutant jazQ plants with *Agrobacterium tumefaciens* (strain C58C1) was performed using the flower dip method (Clough & Bent, *Plant J* 16, 735-743 (1998)). Multiple independent transformed lines (T1 generation) were selected on MS plates containing gentamycin and transferred to soil for subsequent analysis. Homozygous lines were selected by testing the T3 progeny for gentamycin resistance.

Photosynthesis measurements. Gas exchange measurements were obtained as described by Attaran et al. (*Plant Physiol* 165, 1302-1314 (2014)), and Li et al. (*Photosynth Res* 112, 49-61 (2012)). Plants were grown in plastic containers ("Cone-tainers", Steuwe and Sons, Tangent, OR, USA) on an 8 h light (19° C.)/16 h dark (16° C.) photoperiod and 120 μmol m$^{-2}$ s$^{-1}$ photosynthetic photon flux density (PPFD). Single mature rosette leaves (attached) from 8- to 10-week-old plants were used to obtain $CO_2$ response curves on a LI-6400XT system (LI-COR Biosciences, Lincoln, NE, USA) outfitted with a standard leaf chamber (chamber area=6 cm$^2$). Leaves were supplied with an artificial air mixture consisting of 20% $O_2$, 80% $N_2$, and 400 ppm $CO_2$ at intensity of light 500 μmol m$^{-2}$ s−1. Leaf temperature was maintained at ~20° C. (block temperature set to 18° C.). Leaves were acclimated under this condition for at least 30 min before the start of each experiment. Assimilation rates were normalized to projected leaf area as measured by image analysis with the GIMP software. Area-based and whole plant-based photosynthesis and respiration was determined at four time points of the *Arabidopsis* growth cycle as described by Weraduwage et al. (*Front Plant Sci* 6, 167 (2015)), in plants grown under short-day conditions.

In situ chlorophyll a fluorescence measurements were performed in a Percival AR41L2 (Geneva Scientific, see website at geneva-scientific.com) refitted as a Dynamic Environment Photosynthesis imager (DEPI), as described by Attaran et al. (*Plant Physiol* 165, 1302-1314 (2014)), Dutta et al. (*Plant J* 84, 428-442 (2015)), and Kramer et al. (WO 2013181433 A2 (2013)). Images were processed using visual phenomics software (Tessmer et al., *BMC Syst Biol* 7, (Suppl 6) S17 (2013)). The quantum yield of PSII ($\Phi$II) was calculated as $(F'_M-Fs)/F'_M$, where Fs is the steady-state fluorescence and $F'_M$ is the fluorescence maximum at steady state (Baker, *Annu Rev Plant Biol* 59, 89-113 (2008)).

Leaf thickness measurements. Leaf cross sections obtained from the 5$^{th}$ leaf of 22-day old rosette leaves were examined under an Olympus FluoView FV1000, Confocal Laser Scanning Microscope (Olympus, NJ, USA) in the Center for Advanced Microscopy, Michigan State University. Leaf thickness was measured as the distance between the abaxial and adaxial surfaces of the leaf as described by Weraduwage et al. (*Front Plant Sci* 6, 167 (2015)).

Measurement of total chlorophyll and Rubisco concentration in leaves. Extraction and quantification of chlorophyll was carried out using a protocol modified from Lichtenthaler & Wellburn (*Biochem Soc Trans* 11, 591-592 (1983)). Total chlorophyll was extracted from 54-d old *Arabidopsis* rosette leaves with 96% ethanol. Absorbance of the extracted chlorophyll was measured spectrophotometrically at 665 nm and 649 nm and the total chlorophyll was calculated using the following equation:

$$Chl_a + Chl_b = (13.95A_{665} - 6.88A_{649}) + (24.96A_{649} - 7.32A_{665}).$$

Total protein was extracted from 54-d old *Arabidopsis* rosette leaves using a Plant Total Protein Extraction Kit (Sigma-Aldrich, MO, USA). A modified Lowry Assay was performed to measure the total protein concentration in the extract and the purity and quality of the extracted protein were determined by denaturing polyacrylamide gel electrophoresis. Equal amounts of total protein were loaded onto an automated capillary-based size western blotting system (ProteinSimple Wes System, San Jose CA, USA). All procedures were performed with manufacturer's reagents according to their user manual. Protein separation and immunodetection were performed automatically on the individual capillaries using the default settings.

Antibodies raised against the large subunit of Rubisco (rabbit antibodies, AS03 037; Agrisera, Sweden; dilution used 1:650) were used to detect Rubisco in each protein sample. For quantification, all subsequent data generated was analyzed with the 'Compass Software' provided by manufacturer (ProteinSimple, San Jose CA). Peak heights of the fluorescence signals were used to calculate relative differences of Rubisco concentration between samples. Rubisco concentration per unit leaf area was calculated based on the total protein concentration and measurements of leaf area per unit mass.

Example 2: Mutants with Enhanced Jasmonate (JA)-Regulated Defense Against Insects A genetic screen was performed to identify mutants of *Arabidopsis* that display enhanced jasmonate (JA)-regulated defense against insect herbivory without an associated reduction in leaf growth. This screen leveraged a signaling model predicting that removal of JAZ repressor proteins would constitutively activate defense and inhibit growth (FIG. 1A). A mutant plant line (jaz quintuple or jazQ) was developed with T-DNA insertion mutations in five (JAZ1/3/4/9/10) of the 13 *Arabidopsis* JAZ genes (FIG. 1G). These JAZs were selected on the basis of their phylogenetic relationship, their demonstrated role in inhibiting MYC transcription factors, and their capacity to interact with DELLA proteins that antagonistically link JA signaling to gibberellic acid (GA)-mediated growth responses (FIG. 1A).

Figure 1B:
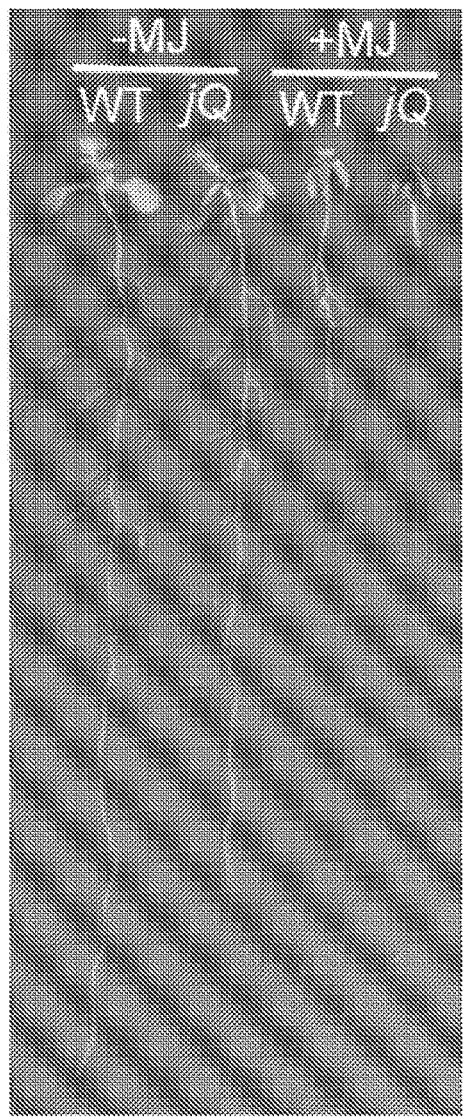
Figure 1C:
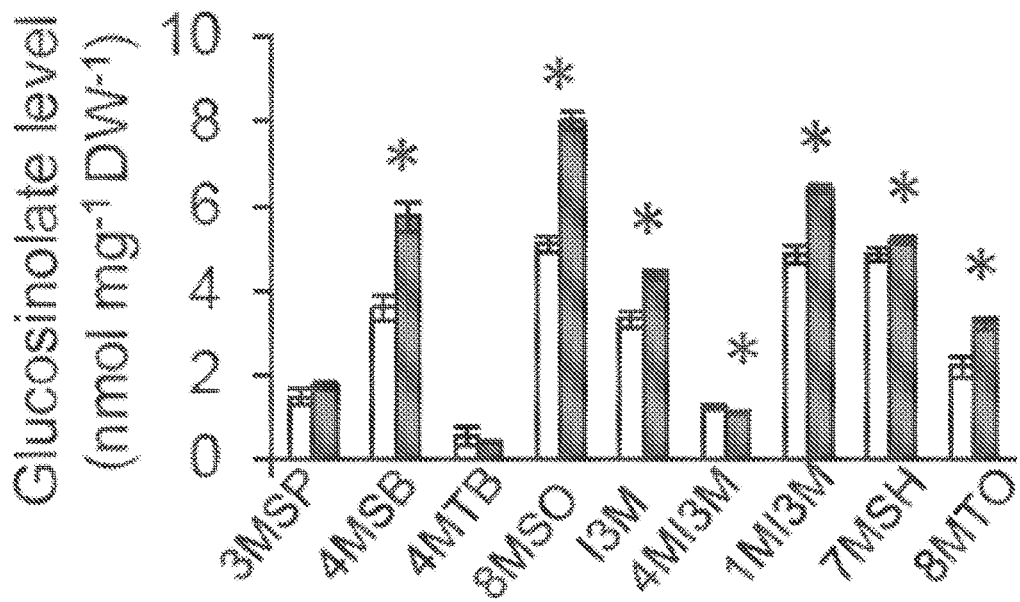
Figure 1D:
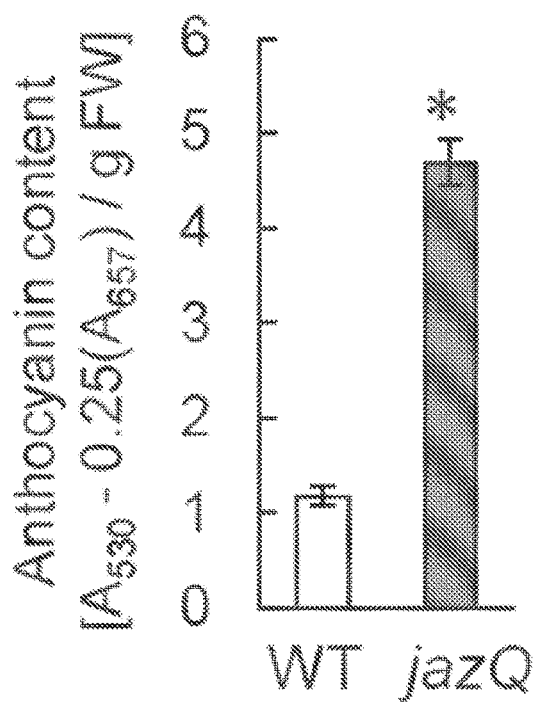
Figure 1E:
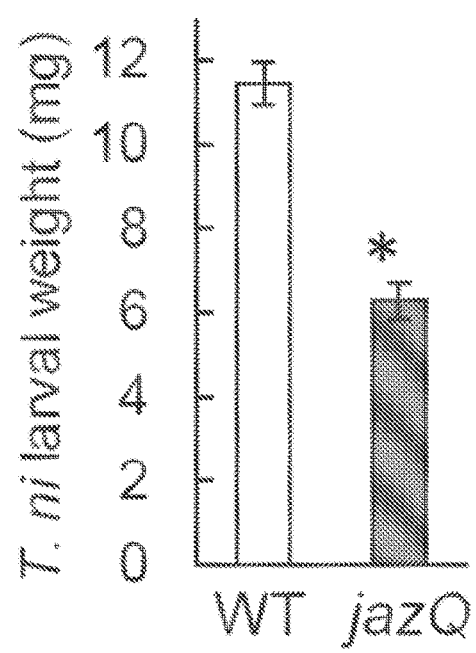
Figure 1F:
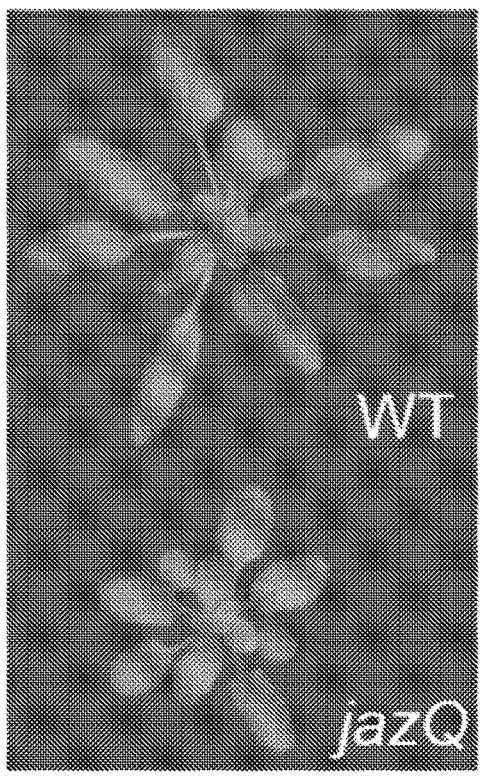
Figure 1G:
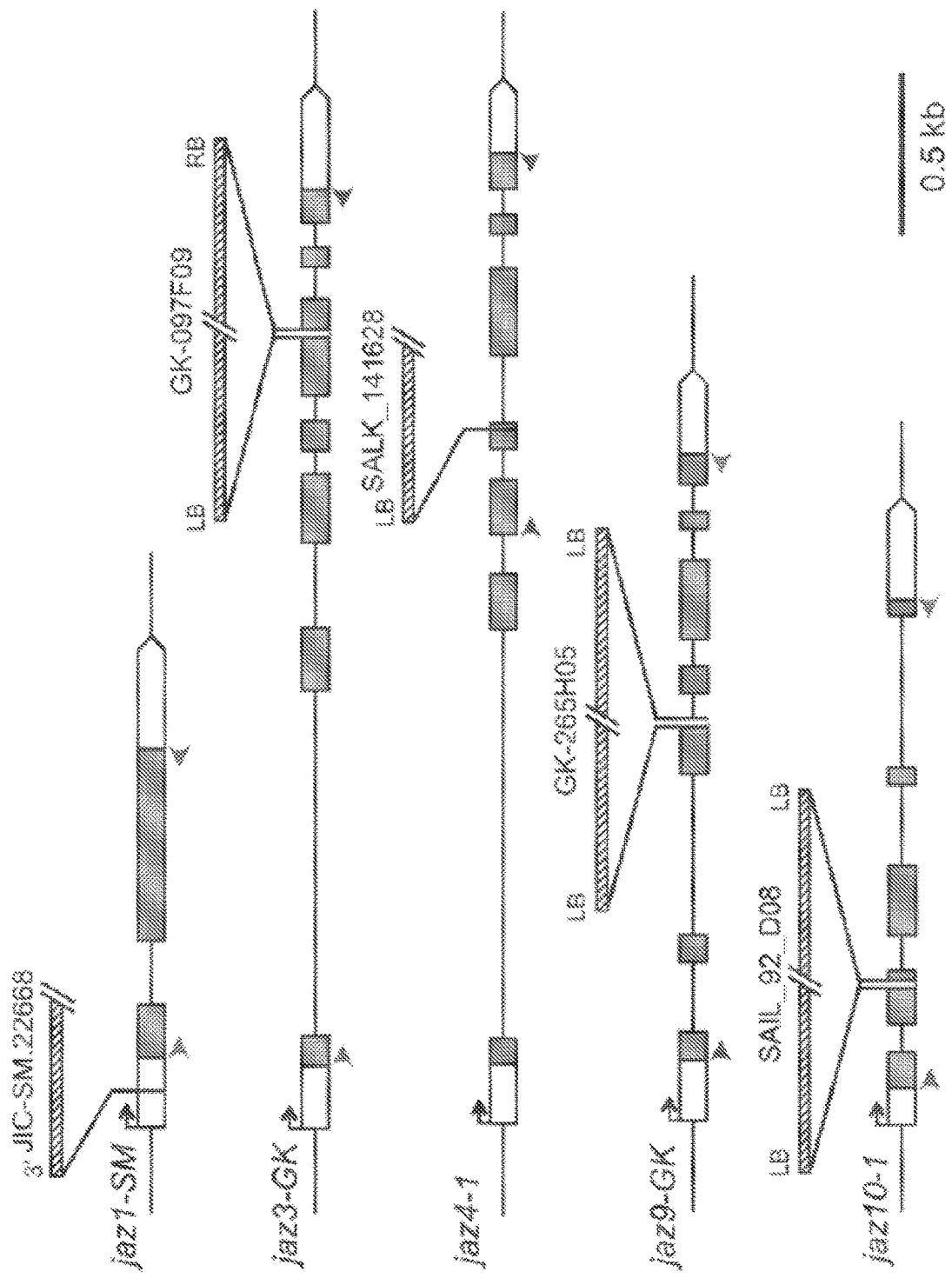
Figure 1I:
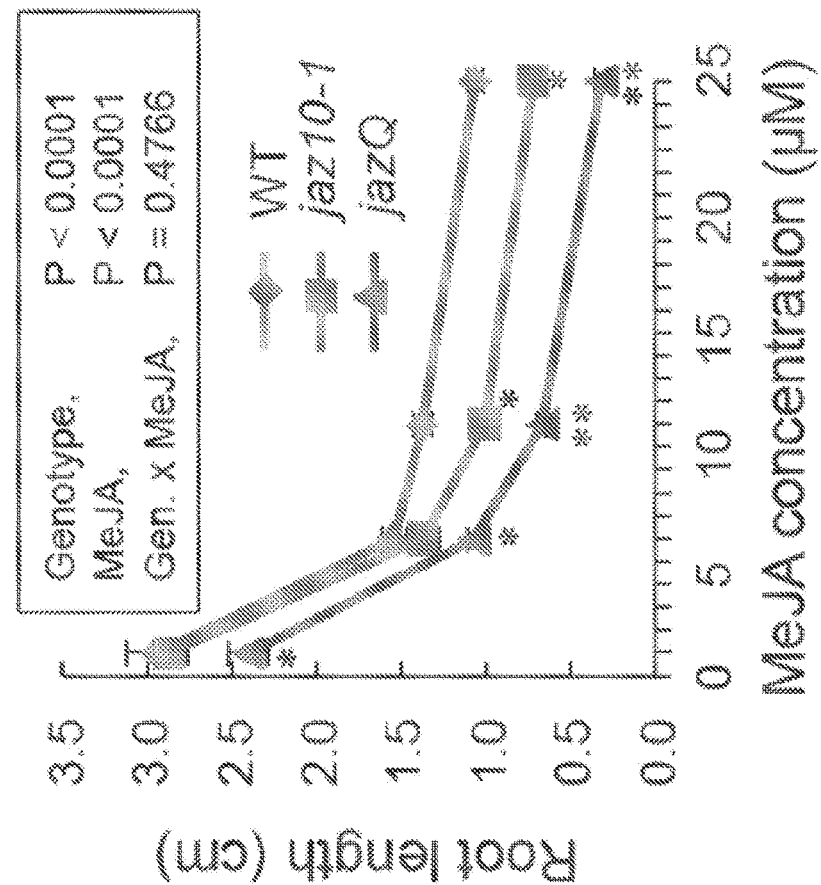
Figure 1H:
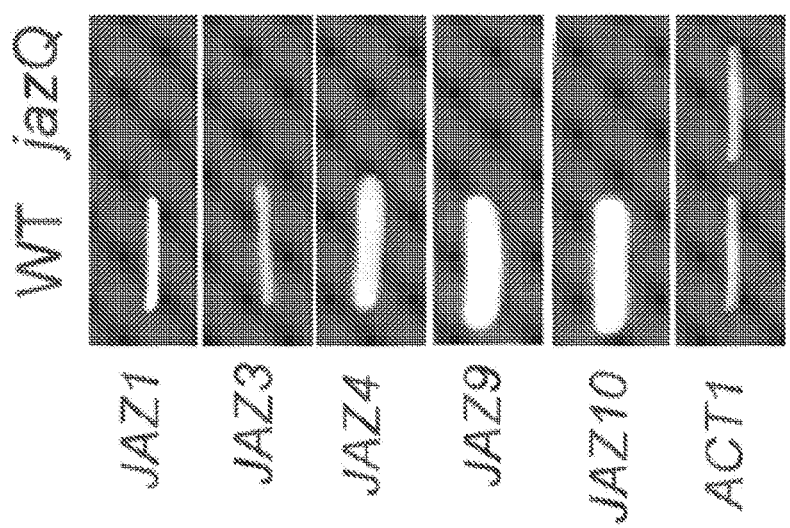

Root growth assays showed that mutant jazQ seedlings have both an increased sensitivity to exogenous JA and a constitutive short-root phenotype (FIGS. 1B and 1I). The short root phenotype is consistent with recent genetic analysis of JA signaling in roots (Gasperini et al., *PLoS Genet* 11, e1005300 (2015)). Glucosinolates and anthocyanins, whose biosynthesis in *Arabidopsis* is positively regulated by jasmonic acid, accumulated to higher levels in jazQ mutant seedlings than in wild type (WT) seedlings (FIG. 1C-1D). Soil-grown jazQ mutant plants had remarkably heightened resistance to attack by the generalist herbivore *Trichoplusia ni* (FIG. 1E). In contrast to these elevated defense traits, leaf area, petiole length, and rosette dry weight were all reduced in jazQ mutants relative to WT (FIG. 1F). The jazQ mutations also delayed the time to bolting but did not affect the number of leaves at the time of bolting. These results demonstrate that jazQ mutant plants exhibit constitutive growth-defense antagonism (i.e., reduced growth with enhanced defense) and thus provide a unique genetic model with which to interrogate how JA-triggered immunity inhibits growth.

Figure 2A:
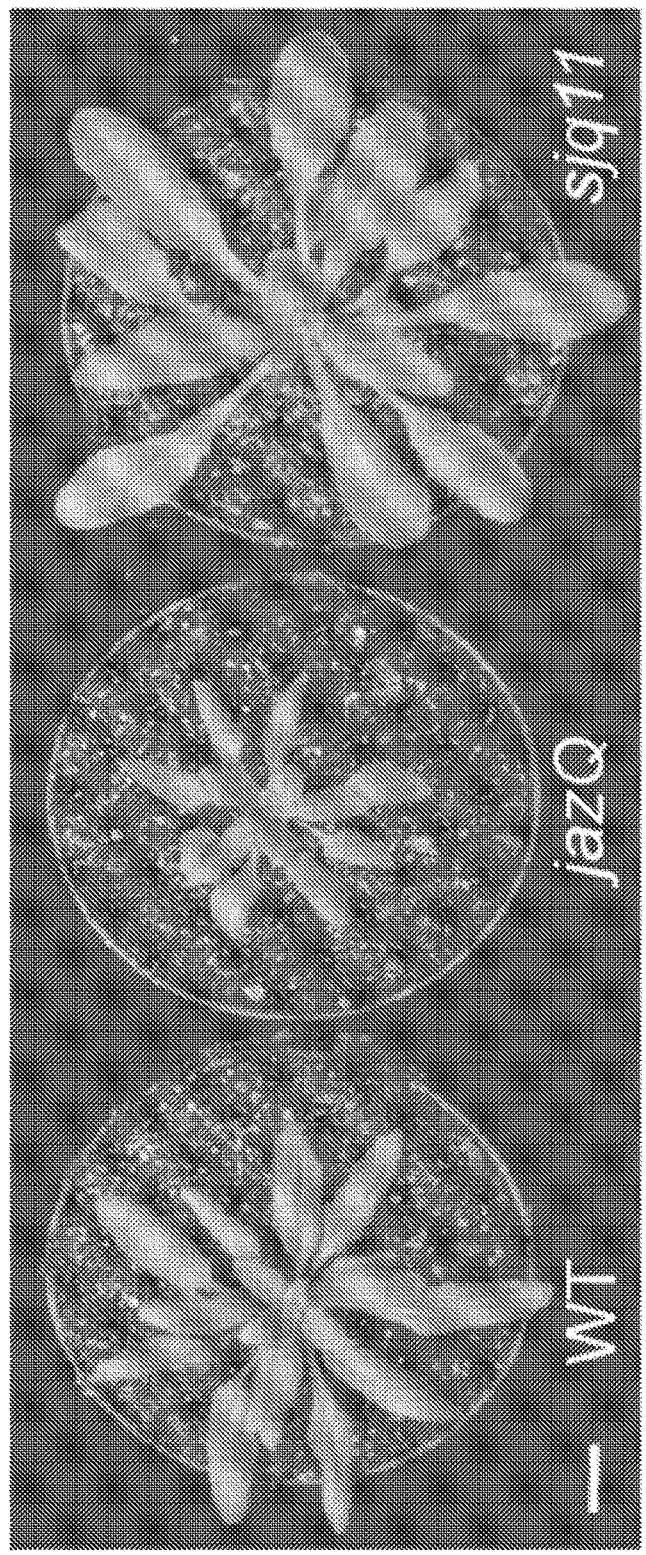
FIG. 2A-2H illustrate that mutant jazQ phyB plants simultaneously grow well and defend against insect infestation.
Figure 2B:
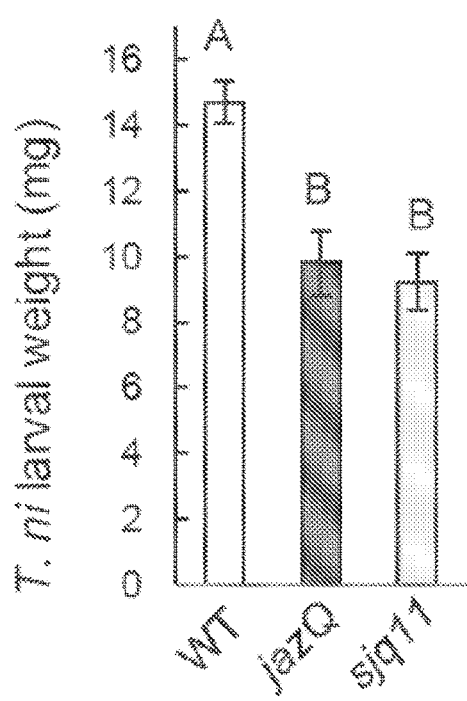
Figure 2C:
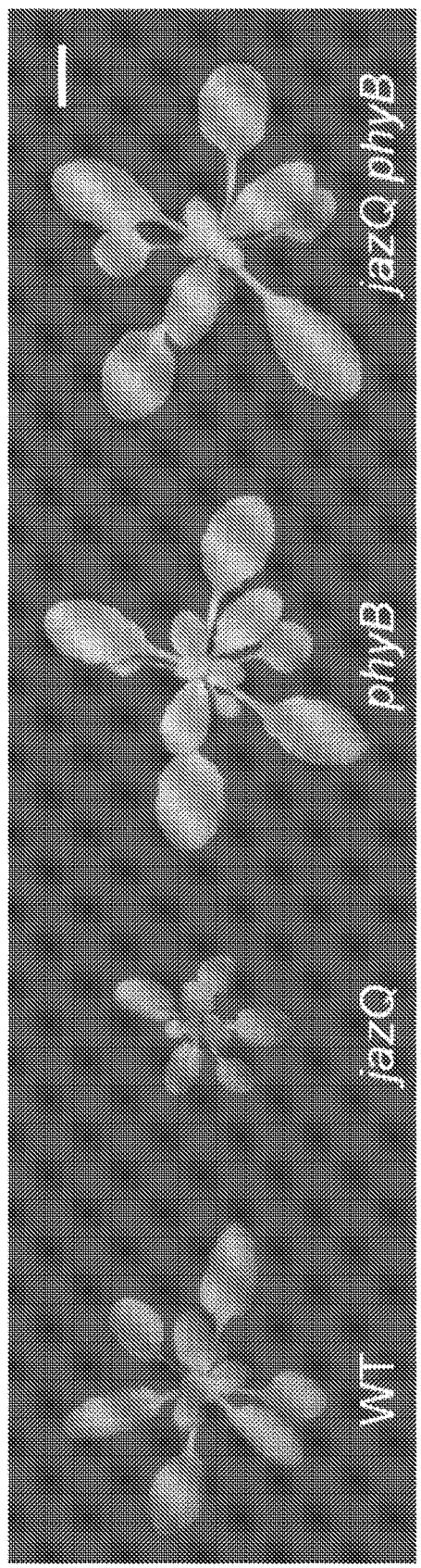

Example 3: Screen for Mutants with Enhanced Jasmonate (JA)-Regulated Defense Against Insects without Reduced Leaf Growth An ethyl methanesulfonate (EMS)-mutagenized population of jazQ was visually screened for mutants with increased rosette size and persistence of elevated leaf anthocyanin content. Among several suppressor of jazQ (sjq) mutants identified, one line (sjg11) showed a particularly striking leaf growth pattern that was heritable in the $M_3$ generation (FIG. 2A). Importantly, bioassays performed with T. ni larvae showed that sjg11 plants also maintained heightened defenses (FIG. 2B). Characterization of sjg11 plants revealed phenotypes similar to those described for phytochrome B (phyB) photoreceptor mutants, including early flowering time, as well as elongated hypocotyls and petioles under continuous white light. Genetic allelism tests and DNA sequencing confirmed that sjg11 harbors a null mutation in the PHYB gene (FIG. 2G). To eliminate the possibility that additional EMS mutations contribute to the sjg11 phenotype, further studies were performed with a jazQ phyB sextuple mutant obtained by crossing the reference phyB-9 null allele into the jazQ mutant background.

Example 4: Analysis of Growth and Defense Traits in jazQ phyB Plants

Analysis of growth and defense traits in jazQ phyB mutant plants showed that the jazQ and phyB "single" mutant phenotypes were largely additive and often tissue specific. Mutant jazQ phyB seedlings, for example, retained the JA-hypersensitive root growth inhibition and red-light insensitive hypocotyl elongation phenotypes of jazQ and phyB, respectively. Adult jazQ phyB mutant plants grown in soil resembled phyB in having elongated petioles, flat rosette leaves, and early flowering time (FIG. 2). The phyB mutation is thus epistatic to jazQ for these traits. The rosette diameter, projected leaf area, and dry mass of jazQ phyB rosette leaves exceeded that of the jazQ and phyB parents, indicating that the combination of jazQ and phyB has transgressive effects on leaf growth (FIG. 2D).

Figure 2F:
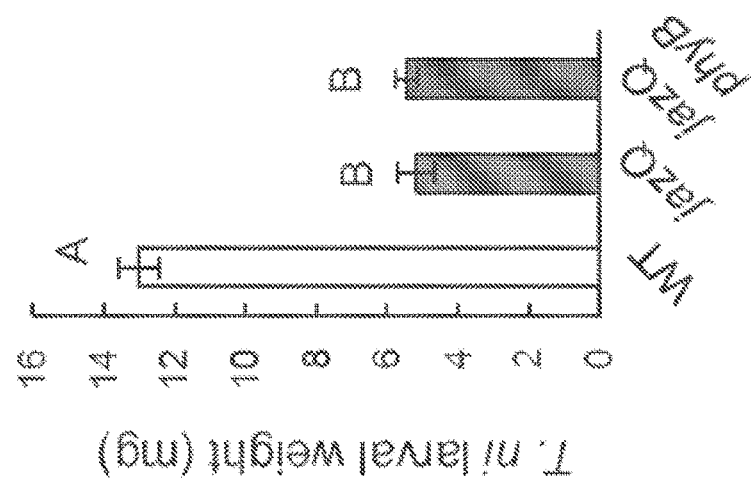
Figure 2E:
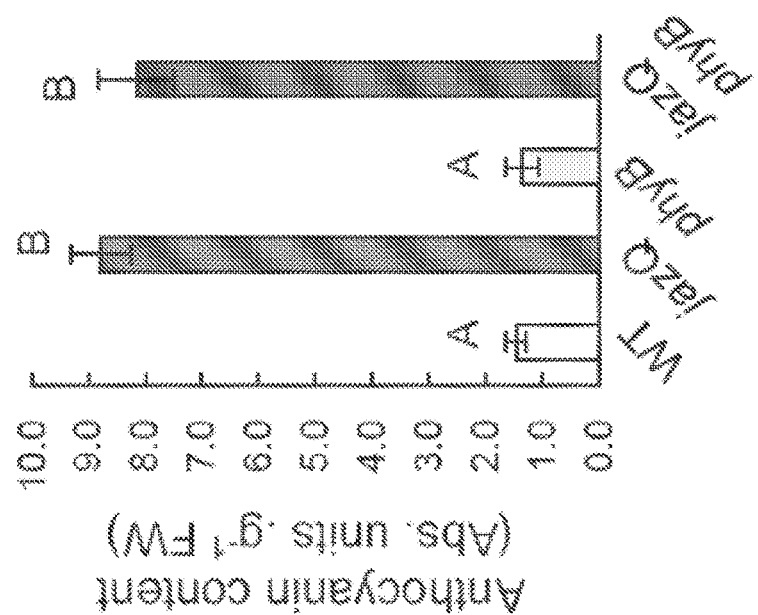
Figure 2D:
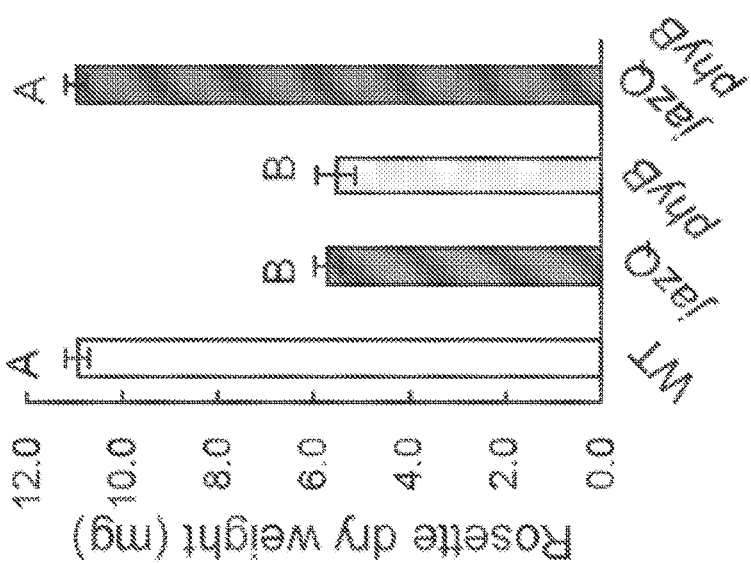
Figure 2G:
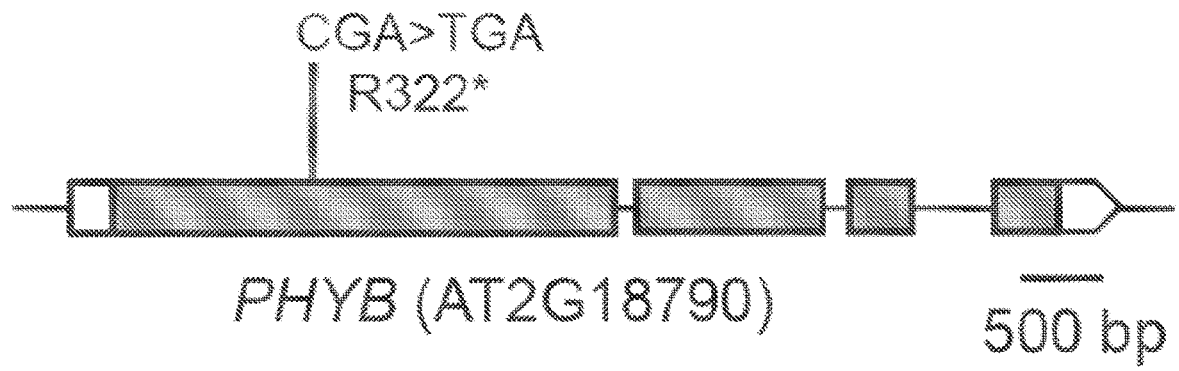
Figure 2H:
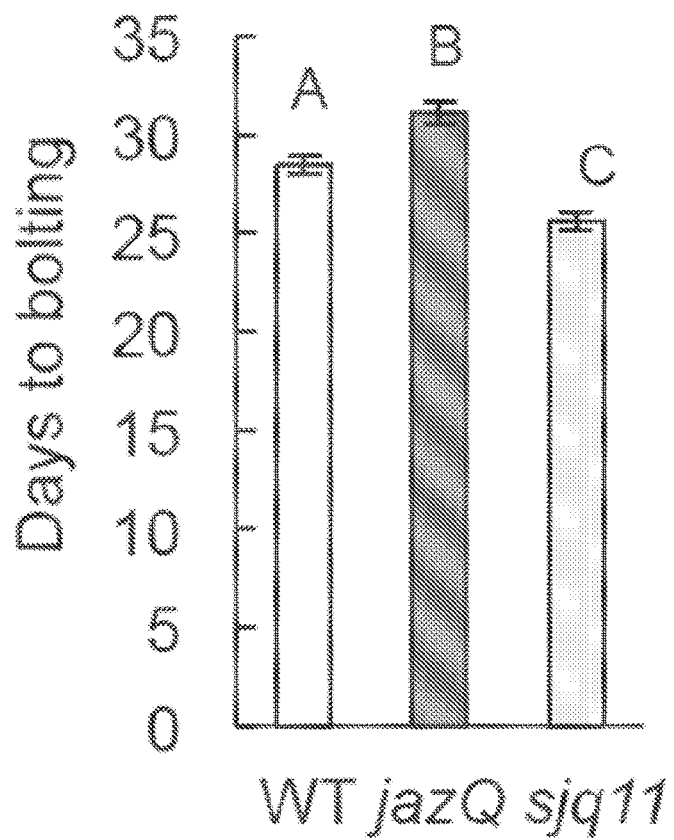

Despite its robust vegetative growth, jazQ phyB mutant plants maintained the heightened anti-insect defense and anthocyanin content of jazQ (FIG. 2E-2F). The effect of combining jazQ and phyB mutations on resistance to T. ni feeding was particularly striking because phyB mutations alone cause high susceptibility to this herbivore. The jazQ phenotype is therefore epistatic to phyB with respect to leaf defense traits. These data demonstrate that phyB mutations fully suppresses the slow growth of mutant jazQ rosette leaves without compromising heightened resistance to T. ni feeding.

The JA and PHYB signaling pathways interact to mediate growth-defense balance during the shade avoidance response. Within this signaling network, GA stimulates cell extension growth by promoting the degradation of DELLA proteins that repress PIF transcription factors (FIG. 1A; see also de Lucas et al. *Nature* 451, 480-484 (2008)). Reciprocal antagonism between the JA and GA pathways involves JAZ-DELLA interactions that prevent these repressors from inhibiting their cognate transcription factors (Hou et al., *Dev Cell* 19, 884-894 (2010); Yang et al., *Proc Natl Acad Sci USA* 109, 1192-1200 (2012)). JA-GA crosstalk is integrated with the shade avoidance response through PHYB-mediated perception of changes in the ratio of red to far red (R:FR) light. Low R:FR ratios indicative of leaf shading reduce PHYB activity to relieve repression on PIFs, thereby promoting rapid growth through the concerted action of auxin and brassinosteroids (FIG. 1A). Concurrent with this growth response to plant competitors, inactivation of PHYB by low R:FR (or phyB mutation) also leads to depletion of DELLA proteins, increased JAZ stability, accelerated turnover of MYCs, and suppression of JA-triggered immune responses.

Example 5: Expression Patterns of Wild Type,jazQ, phyB, and jazQ phyB Seedlings

This Example describes transcript profiles obtained by mRNA sequencing of WT, mutant jazQ, mutant phyB, and mutant jazQ phyB seedling tissues to ascertain how the combination of phyB and jazQ mutations affects gene expression.

Figure 3:
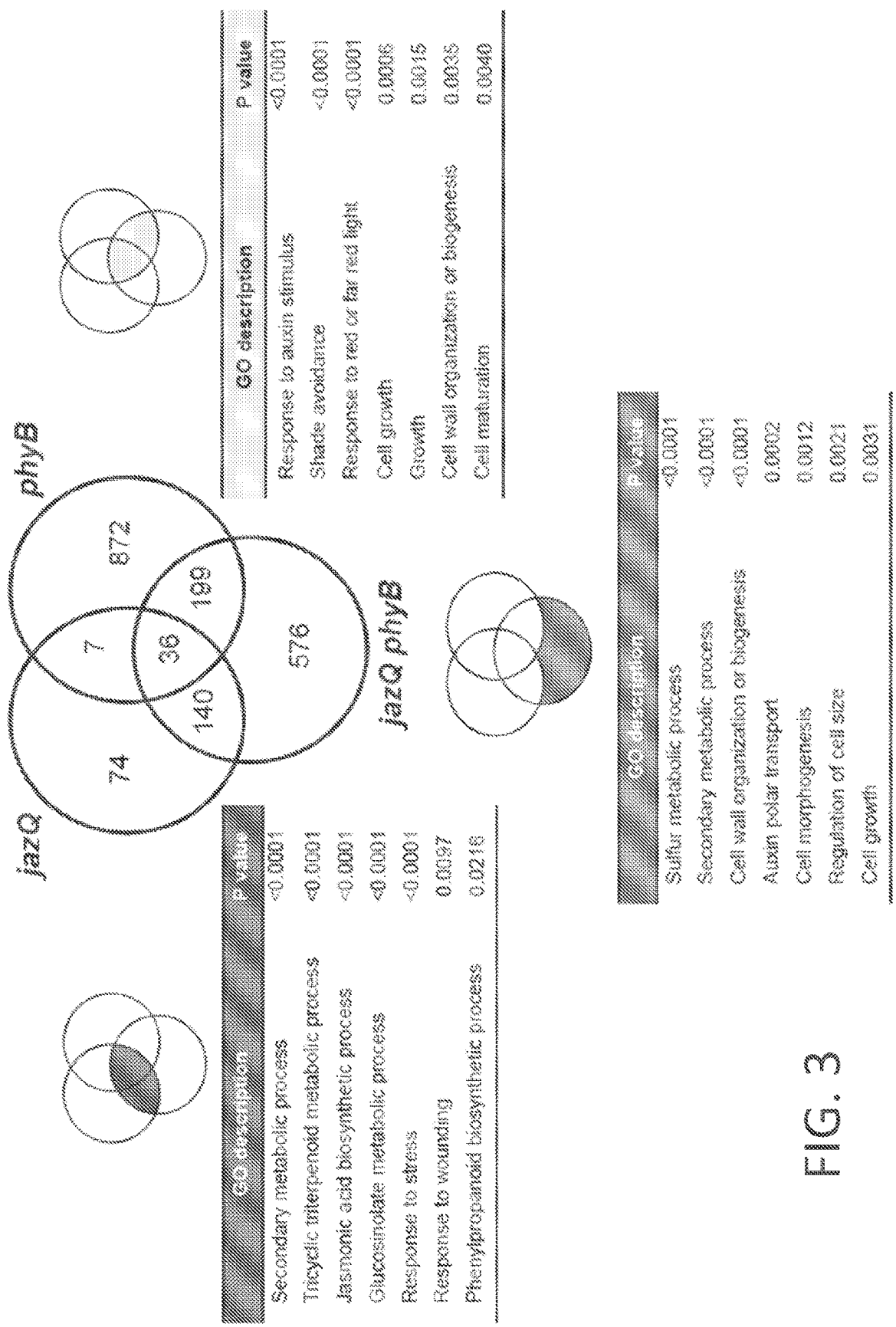
FIG. 3 illustrates that the combination of jazQ and phyB mutations promotes expression of growth-related and defense-related genes. WT, mutant jazQ, mutant phyB and mutant jazQ/phyB seedlings were grown for 8 days in continuous white light prior to RNA extraction and analysis of gene expression by mRNA sequencing. The Venn diagram shows the number of genes upregulated in comparisons between WT and each of the three mutants. GO analysis of functional categories was performed with gene sets that are shared between mutant jazQ and mutant jazQ phyB (blue intersect), shared between mutant phyB and mutant jazQ phyB (yellow intersect), or unique to mutant jazQ phyB (green shade).

"Secondary metabolism" and "response to stress" and were among the biological processes most significantly overrepresented in ontologies of 257 genes expressed to higher levels in jazQ than in WT (FIG. 3). This gene set included glucosinolate biosynthesis genes that are direct targets of MYC2, as well as genes involved in the synthesis of triterpenoids, jasmonates, and various defense proteins.

Consistent with their enhanced defense stature, jazQ phyB plants maintained increased expression of the majority (68%) of genes that are upregulated in jazQ (FIG. 3). By comparison, analysis of growth-related genes revealed that the set of 235 genes upregulated in both phyB and jazQ phyB genetic backgrounds is enriched for functional classes involved in responses to auxin, shade avoidance, cell wall organization, and light stimulus (FIG. 3). Several genes within this group have been shown to be direct targets for PIF transcription factor binding (Oh et al., *Nat Cell Biol* 14, 802-809 (2012); Hornitschek et al., *Plant J* 71, 699-711 (2012); and Zhang et al., *PLoS Genet* 9, e1003244 (2013)). These data indicate that the combination of jazQ and phyB mutations promotes simultaneous expression of defense and growth-related genes that are controlled, at least in part, by the MYC and PIF transcriptional modules, respectively.

Among the 576 transcripts whose abundance was significantly increased in jazQ phyB mutants but not jazQ or phyB mutants, there was a strong over-representation of GO terms related to secondary metabolism, cell wall organization, growth, and auxin transport (FIG. 3). These data indicate that the combination of jazQ and phyB mutations leads to increased expression of certain growth and defense responses in jazQ phyB mutant plants. Quantitative PCR analysis showed that wound-induced expression of select JA-response genes was significantly higher in jazQ phyB mutant leaves than WT leaves, which may also contribute to the heightened defense of jazQ phyB mutant plants relative to WT. The synergistic effects of jazQ and phyB mutations on gene expression may thus result from functional interaction between MYCs and PIFs at the level of protein-protein interaction or altered binding to common cis-regulatory elements in target genes.

Example 6: Photosynthetic Efficiency

This Example describes investigations of whether jazQ and phyB mutations interact to modulate leaf photosynthetic efficiency.

PIF activity can repress chloroplast development and photosynthetic competency, and the inventors have observed that "photosynthesis" was a characteristic most significantly overrepresented among genes that are repressed in both phyB mutant and jazQ phyB mutant seedlings. Non-invasive, whole-plant chlorophyll fluorescence imaging (Attaran et al., *Plant Physiol* 165, 1302-1314 (2014)) was used to determine how genetic perturbations within the PHYB-GA-JA signaling network affect photosystem II efficiency ($\Phi_{II}$) under various light regimes, including those designed to simulate natural environments (see FIG. 4A).

Figure 4A:
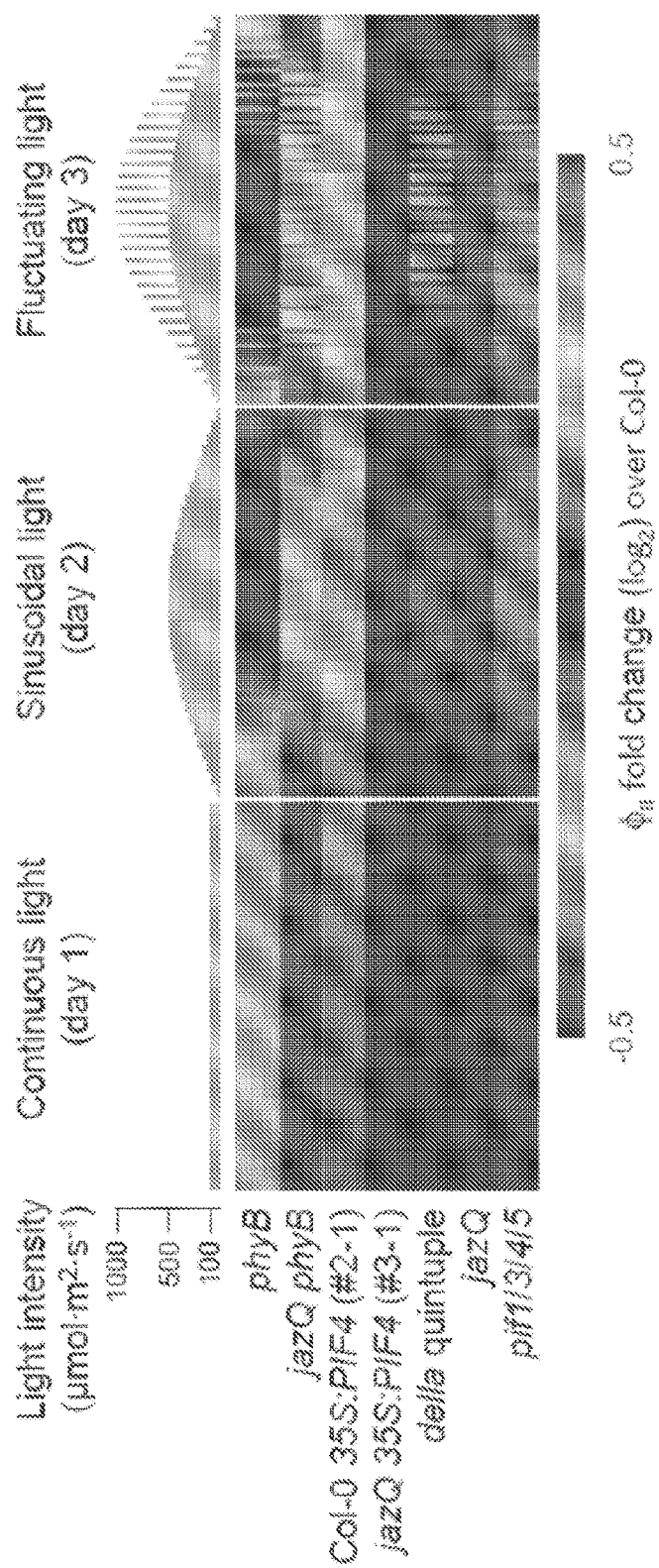
FIGS. 4A-4E illustrate that jazQ and phyB mutations interact to modulate photosynthesis and leaf architecture.

Mutant phyB plants had reduced ($\Phi_{II}$) under continuous low light intensity and this effect was exacerbated under the sinusoidal and fluctuating light regimes. A similar decrease in ($\Phi_{II}$) was observed in Col-0 transgenic plants (35S:PIF4) that overexpressed PIF4. Interestingly, the negative effect of phyB mutations and 35S:PIF4 on ($\Phi_{II}$ was rescued by jazQ mutations, which alone had little (or very weak positive) effect on $\Phi_{II}$ (FIG. 4A). Consistent with the role of PIFs in repressing photosynthesis, a pifII/3/4/5 quadruple mutant (pifq) showed increased ($\Phi_{II}$) under fluctuating light conditions, whereas loss of DELLAs in the della quintuple mutant (dellaQ) reduced $\Phi_{II}$. That $\Phi_{II}$ was lower in phyB leaves than in dellaQ leaves suggests that phyB has a predominate role in repressing PIF activity in leaves under these growth conditions.

To obtain additional insight into physiological processes that underlie growth-defense vigor of jazQ phyB mutant plants, the relationship between photosynthesis and leaf growth was investigated to obtain an estimate of leaf construction costs. Gas exchange experiments showed that phyB mutant eaves have significantly lower photosynthetic rate per unit leaf area whereas photosynthetic capacity of jazQ mutant plants relating to leaf area or dry weight basis was comparable to WT (FIG. 4B), consistent with our chlorophyll fluorescence measurements. Mutant phyB leaves also contained less area-based chlorophyll and Rubisco (D-ribulose-1,5-bisphosphate carboxylase/oxygenase) than WT.

Figure 4C:
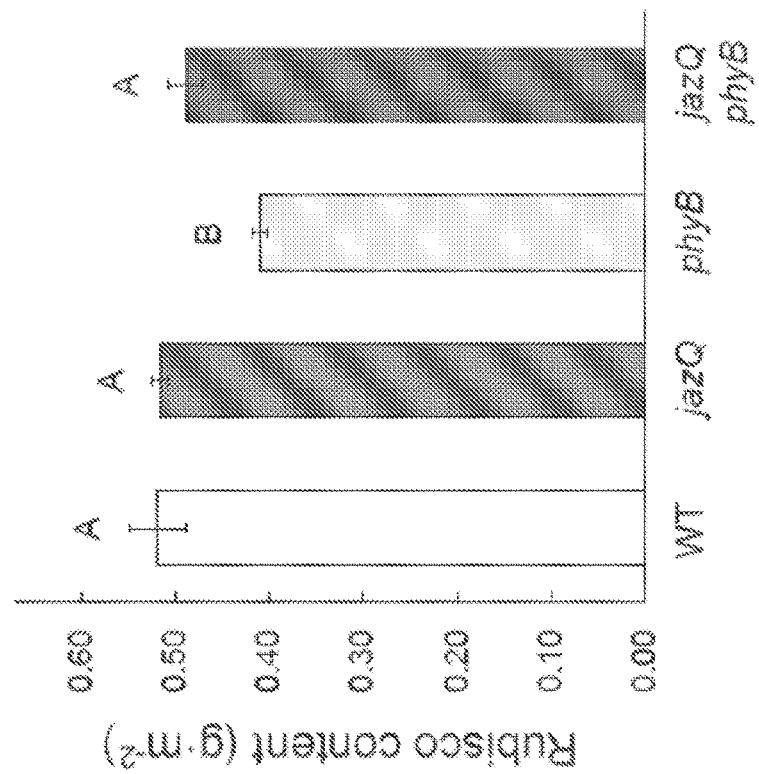
Figure 4B:
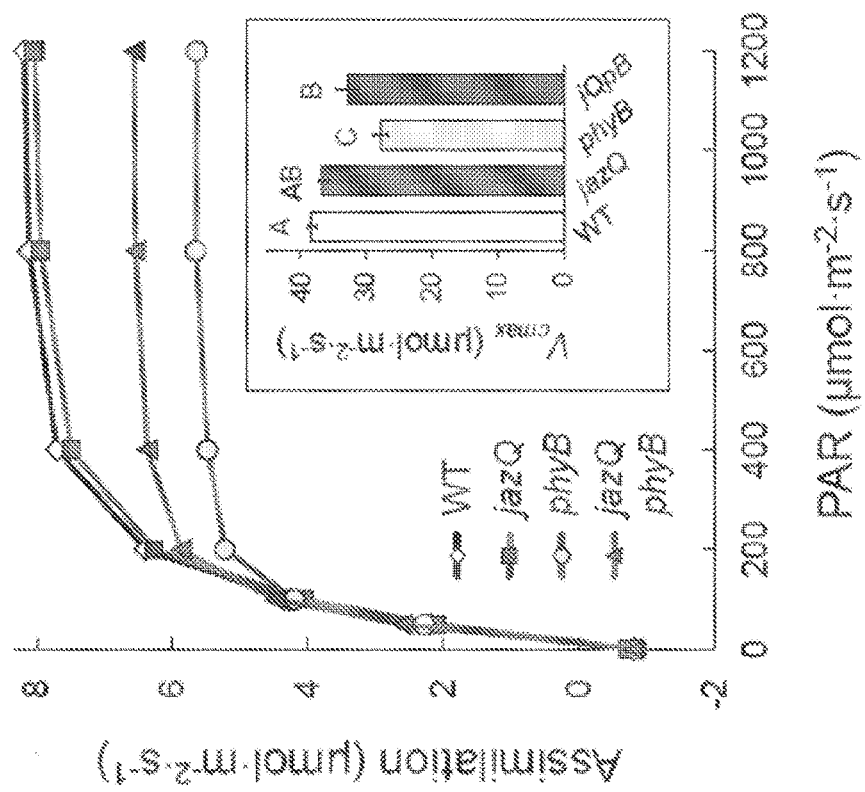
Figure 4E:
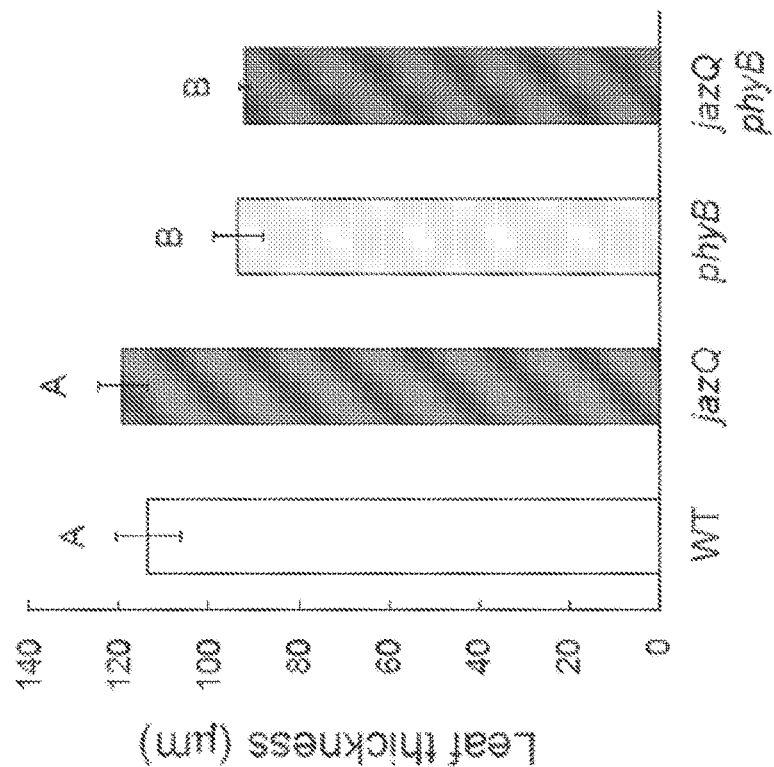
Figure 4D:
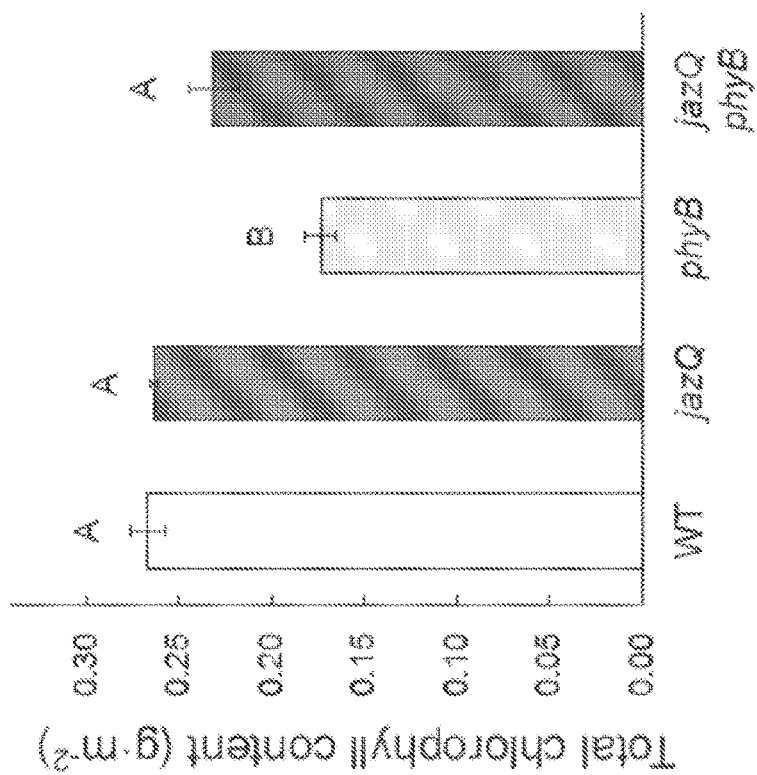
Figure 5D:
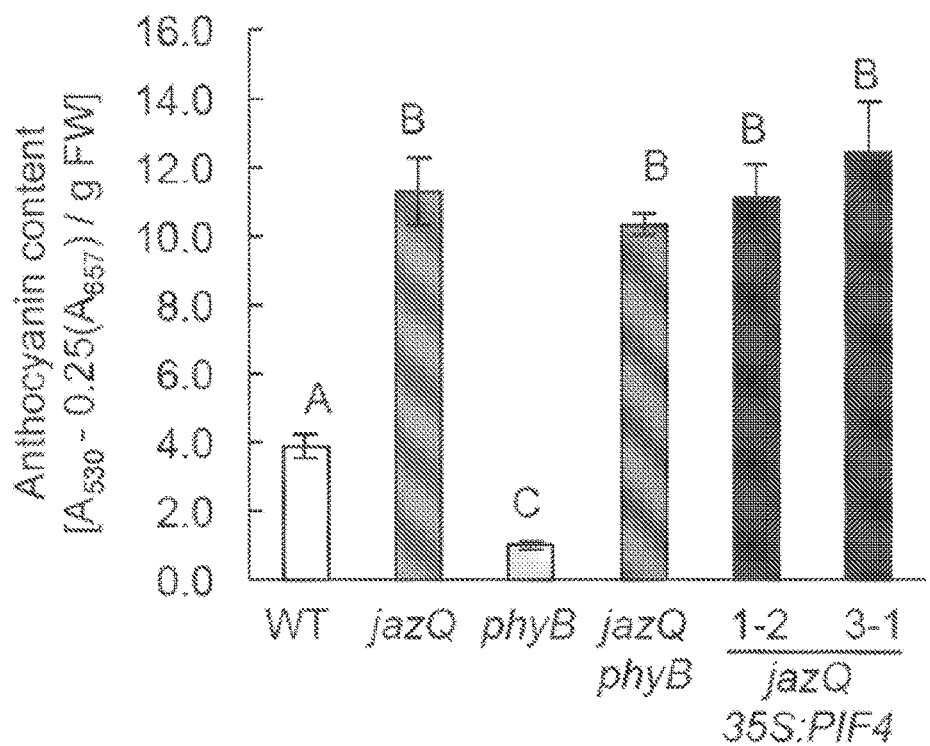
Figure 5E:
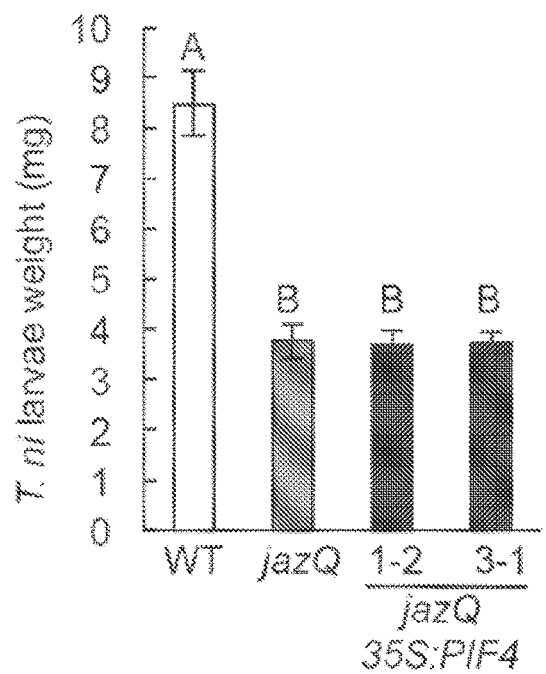

Modeling of photosynthetic parameters showed that the reduced photosynthetic capacity of mutant phyB at high light results in part from a limitation in Rubisco activity. Mutations in jazQ partially rescued the low photosynthetic capacity of phyB leaves, as well as the low area-based Rubisco and chlorophyll content of phyB mutations (FIG. 4C-4D). In addition, mutant phyB leaves were thinner than WT and mutant jazQ leaves; this trait was retained in jazQ phyB mutant plants (FIG. 4D).

Because of the greater projected leaf area available to intercept light (due to longer petioles and flatter, thinner leaves), the whole plant photosynthetic rate in jazQ phyB mutant plants was similar to WT. Thus, costs associated with jazQ phyB mutations one leaf structure may be lowered through increased partitioning of carbon to leaf area at the expense of leaf thickness. These data suggest that changes in leaf architecture rather than increased efficiency of the photosynthetic apparatus may contribute to the growth-defense vigor of jazQ phyB mutant plants relative to WT plants.

In summary, an unbiased genetic approach was employed to show that JA-mediated growth-defense antagonism can be effectively eliminated through genetic removal of JAZ and phyB repressors that respectively restrain the MYC and PIF transcription modules in WT plants. In highlighting a general role for transcriptional repressors in tuning photoassimilate use efficiency in mature plants, the results described herein provide new insight into how JA and light signaling pathways are integrated to control the balance between growth and immune responses. Note also that the expression of genes involved in abiotic stress response is repressed in jazQ phyB mutant plants.

The ability of jazQ phyB mutant leaves to grow and at the same time defend against insects and other threats indicates that JA signaling does not simply divert photoassimilates or other metabolic resources to defense processes at the expense of growth. The data described herein support a conclusion that the linkage between JA-triggered immunity and growth inhibition is more accurately viewed as a phenotypic consequence of interconnected transcriptional networks that evolved to optimize fitness in the face of episodic, unpredictable encounters with plant consumers and competitors.

Genetic removal of transcriptional repressors that coordinate growth and immune responses provides an approach to combine desirable traits in new ways, and increase the productivity of densely planted crops with less dependence on pesticides.

Example 7: Overexpression of PIF4 in the jazQ Background Leads to Partial Rescue of Growth without Compromising Defense The phyB-Jasmonic acid crosstalk led the inventors to test the hypothesis that the combination of jazQ and phyB mutations causes concomitant de-repression of the MYC and PIF transcriptional programs to drive growth and defense simultaneously (FIG. 1A). The inventors then tested what effect overexpression of PIF4 would have in the jazQ mutant background.

As shown in FIG. 5A-5E, overexpression of PIF4 partially rescued the small rosette size and short petiole length of jazQ mutations without affecting anthocyanin accumulation and resistance to $T.\ ni$ feeding. This finding indicates that increased PIF4-mediated growth does not attenuate the defense status of jazQ mutation on leaf structures. These findings also indicate that other PIFs may contribute to the growth vigor of jazQ phyB mutant plants.

Example 8: MYC3L$^{152A}$ and MYC3$^{E148A/M155A}$ Mutants

Figure 7A:
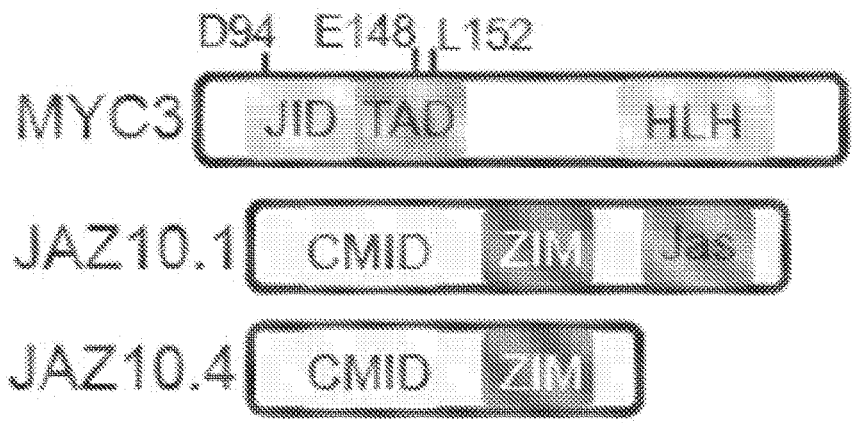
FIG. 7A-7E illustrate structure-based design of dominant MYC transcription factors.
Figure 7B:
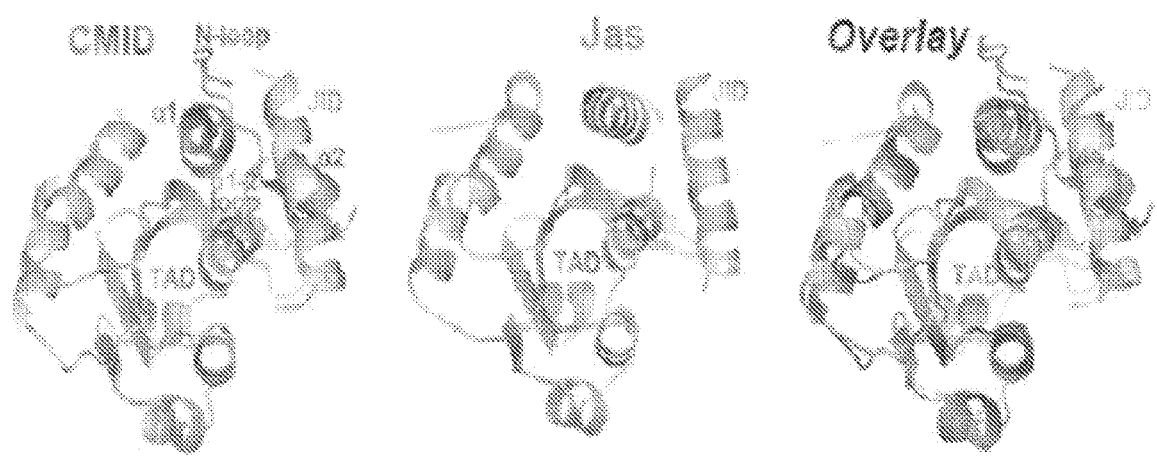

JAZ proteins contain two distinct structural motifs that bind to the JAZ-interacting domain (JID) of MYC (FIG. 7A-7B). All JAZ proteins contain a C-terminal Jas motif that, in the absence of jasmonic acid, forms an extended α-helix that binds JID (Zhang et al. 2015; Katsir et al. 2008; Melotto et al. 2008). A subset of JAZ proteins (e.g., JAZ10 and JAZ1) contain a cryptic MYC-interaction domain (CMID) near the N-terminus that also binds the JID (Moreno et al. 2013; Chung and Howe 2009; Goossens et al. 2015). Comparison of the x-ray crystal structures of the MYC3-JAZ10$^{CMID}$ and MYC3-JAZ10$^{Jas}$ complexes showed that whereas the Jas motif binds MYC as a single continuous α-helix, the CMID adopts a bipartite structure in which one helix occupies the Jas-binding groove of MYC and a second helix makes contact with the backside of this groove (FIG. 7B). This clamp-like action of the CMID engages MYCs with higher affinity than the Jas helix and also effectively masks the MED25 binding site of MYC (Zhang et al. 2017). Sequence alignments indicate that CMID-containing JAZs are present in diverse plant species but none have been characterized to date.

The inventors have used structural information for rational design of dominant MYC transcription factors (MYC$^D$ TFs) that are insensitive to binding by both the Jas and CMID of JAZ. The inventors hypothesize that such dominant mutant MYC proteins can strongly activate defense gene expression in the absence of JA elicitation. Three AtMYC$^D$ variants have been reported in the literature: MYC3$^{D94N}$ (atr2D allele)(Smolen et al. 2002), the corresponding MYC2 mutant (MYC2$^{D105N}$)(Goossens et al. 2015), and MYC2$^{E165K}$ (myc2-322B) (Gasperini et al. 2015). These MYC variants exhibit weak constitutive JA responses as a consequence of losing interaction with the Jas motif of JAZ.

The inventors hypothesize that design of MYC$^D$ TFs that are insensitive to both Jas and CMID binding will result in much stronger activation of JA-dependent defenses, and that the combination of these myc$^D$ alleles with phyB will drive robust growth and defense simultaneously.

The structural information from the MYC3-CMID complex was used to generate site-directed mutants of MYC3 that have reduced interaction with the JAZ10.4 splice variant, which contains a CMID but not a Jas motif (Chung and Howe 2009). Several promising mutants were made.

Binding studies were performed to evaluate the mutant MYC proteins. AtMYC2 and its paralogs (MYC3, MYC4, and MYC5) within subclade IIIe of the bHLH superfamily bind to G-box motifs to promote the expression of a large portion of JA-responsive genes in cells containing elevated JA levels (Fernandez-Calvo et al. 2011; Schweizer et al. 2013; Major et al. 2017). Low levels of JA stabilize JAZs to permit JAZ binding to the JAZ-interacting domain (JID) of MYCs. JAZ binding to the JID represses MYC activity by two distinct mechanisms.

First, JAZs use their EAR and ZIM motifs to recruit the TOPLESS (TPL) co-repressor and associated chromatin-modifying enzymes (Shyu et al. 2012; Pauwels et al. 2010). Second, JAZ binding to the JID competitively inhibits MYC interaction with the MED25 subunit of the Mediator of RNA polymerase II transcription complex, which promotes transcription by bridging DNA-bound transcription factors to RNA polymerase II (Zhang et al. 2015). Although the JID and adjacent transactivation domain (TAD) of MYC were initially mapped as discrete regions (Kazan & Manners 2013), recent structural analysis of JAZ9-MYC3 complexes revealed that the JID and TAD functionally overlap to form a continuous groove that binds both JAZ and the MED25 in a competitive manner (Zhang et al. 2015).

The interactions of mutants MYC3$^{L152A}$ and MYC3$^{E148A/M155A}$ with JAZ10.4 and MED25 was evaluated using yeast two-hybrid analyses to visualize MED25 and JAZ10.4 (bait) interactions with wild-type MYC3 and MYC3 point mutants (prey).

Figure 7C:
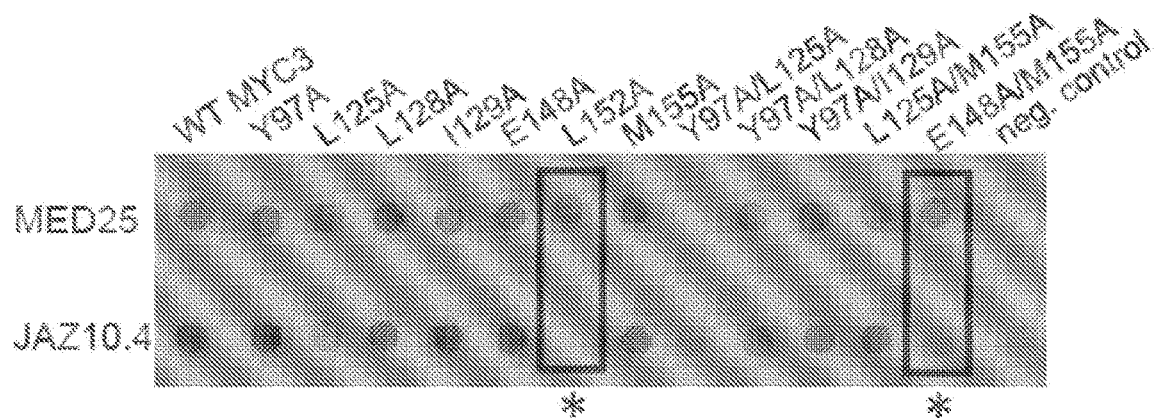

The MYC3$^{L152A}$ and MYC3$^{E148A/M155A}$ mutant protein exhibited strongly reduced JAZ10.4 interaction but still interacted with MED25 (FIG. 7C).

Functional analysis of these and other MYC$^D$ transcription factors in planta was performed by overexpressing the transcription factors in *Arabidopsis* with subsequent testing of the resulting transgenic lines for increased resistance to 5-methyl tryptophan (5-MT), a toxic analog of the amino acid tryptophan.

Figure 7D:
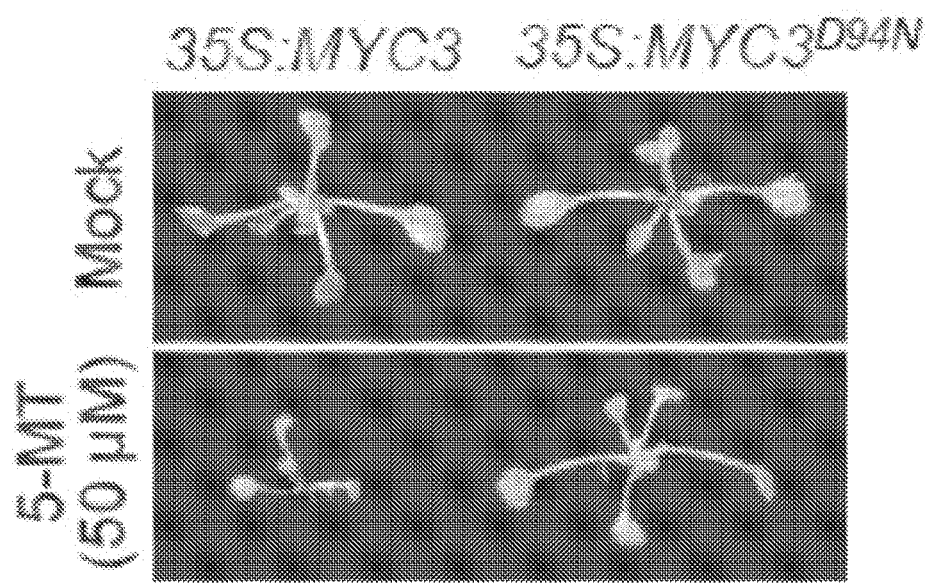

For example, a dominant allele (atr2D allele) encoding MYC3$^{D94N}$ was identified in a genetic screen for 5-MT-resistant plants (Smolen et al. 2002). Preliminary results show that overexpression from the 35S promoter of MYC3$^{D94N}$ but not wild-type MYC3 confers 5-MT resistance (FIG. 7D).

Similarly, overexpression in *Arabidopsis* of a tomato (*Solanum lycopersicum*) MYC2 protein with SEQ ID NO:19 that was modified to have a D132N mutation confers resistance of the genetically modified *Arabidopsis* plants to 5-MT (data not shown).

Example 9: Expression of Dominant Mutant Myc2 Reduces Primary Root Inhibition This Example illustrates that overexpression of a dominant MYC2 mutant transcription factor (with D105N+ E165K mutations) in *Arabidopsis* reduces primary root inhibition in response to treatment with 5-methyltryptophan.

Methods

Primary root length in the presence of 15 µM 5-MT was evaluated for 14-day-old seedlings of non-transgenic (NT) phyB-9 mutant plants or phyB-9 mutant plants that overexpressed either wild-type (WT) MYC2 or a MYC2$^{D105N/E165K}$ mutant allele that harbors two point mutations (D105N and E165K) that prevent JAZ binding. Primary root length was determined as the root length of a given genotype grown in the presence of 15 µM 5-MT normalized to the root length of the same genotype grown in the absence of 5-MT.

Results

Figure 7E:
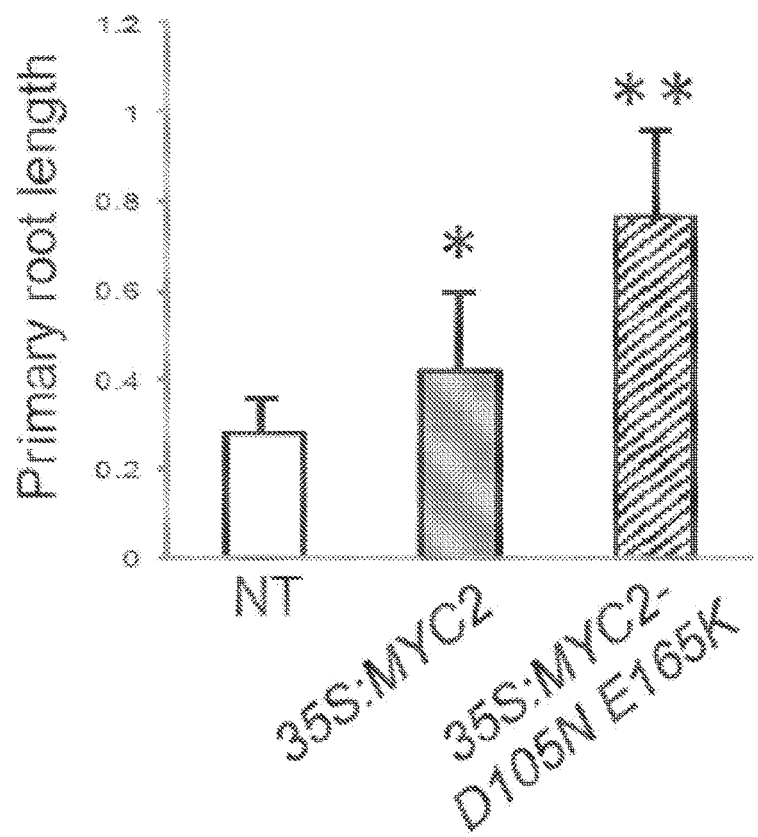

FIG. 7E graphically illustrates that the primary root length of 14-day-old seedlings of non-transgenic (NT)phyB-9 mutant plants (left bar) was less than observed for the phyB-9 mutant plants that overexpress either wild-type (WT) MYC2 (middle bar) or a MYC2 derivative (MYC2$^{D105N/E165K}$; right bar) harboring two point mutations (D105N and E165K) that prevent JAZ binding. Asterisks indicate significant differences in relative root length (* P=0.0017, ** P=2E-08) in comparisons to phyB. Error bars represent SEM, n>20. Hence, expression of such dominant MYC transcription factors conferred resistance to 15 µM 5-MT and fostered growth of the plant as indicated by the significantly increased length of the plants' primary root.

These findings provide proof-of-concept that 5-MT resistance can be used to quantify MYC$^D$ activity in planta for rationale design of dominant MYC TFs.

In summary, the inventors have developed a structure-guided pipeline (that incorporates site-directed mutagenesis, yeast two-hybrid analysis of JAZ repressor and MED25 co-activator interaction, and functional analysis of 5-MT resistance in *Arabidopsis*) to design and characterize MYC$^D$ TFs, from any plant species. Plants engineered to express dominant MYC transcription factors in a phyB mutant background can exhibit enhanced growth and defense at the same time.

REFERENCES

1. Stamp, N. Out of the quagmire of plant defense hypotheses. Q Rev Biol 78, 23-55 (2003).
2. Zust, T., Rasmann, S. & Agrawal, A. A. Growth-defense tradeoffs for two major anti-herbivore traits of the common milkweed *Asclepias syriaca*. Oikos 124, 1404-1415 (2015).
3. Herms, D. A. & Mattson, W. J. The dilemma of plants—To grow or defend. Q Rev Biol 67, 283-335 (1992).
4. Huot, B., Yao, J., Montgomery, B. L. & He, S. Y. Growth-defense tradeoffs in plants: a balancing act to optimize fitness. Mol Plant 7, 1267-1287 (2014).
5. Moreno, J. E., Tao, Y., Chory, J. & Ballare, C. L. Ecological modulation of plant defense via phytochrome control of jasmonate sensitivity. Proc Natl Acad Sci USA 106, 4935-4940 (2009).
6. Havko, N. E. et al. Control of carbon assimilation and partitioning by jasmonate: An accounting of growth-defense balance. Plants 5, 7 (2016).
7. Kliebenstein, D. J. False idolatry of the mythical growth versus immunity tradeoff in molecular systems plant pathology. Physiol Mol Plant Pathol, in press, doi: 10.1016/j.pmpp.2016.02.004 (2016).
8. Hu, P. et al. JAV1 controls jasmonate-regulated plant defense. Mol Cell 50, 504-515 (2013).
9. Leone, M., Keller, M. M., Cerrudo, I. & Ballare, C. L. To grow or defend? Low red:far-red ratios reduce jasmonate sensitivity in *Arabidopsis* seedlings by promoting DELLA degradation and increasing JAZ10 stability. New Phytol 204, 355-367 (2014).
10. Thireault, C. et al. Repression of jasmonate signaling by a non-TIFY JAZ protein in *Arabidopsis*. Plant J 82, 669-679 (2015).
11. Thines, B. et al. JAZ repressor proteins are targets of the SCF$^{COI1}$ complex during jasmonate signalling. Nature 448, 661-665 (2007).
12. Chini, A. et al. The JAZ family of repressors is the missing link in jasmonate signalling. Nature 448, 666-671 (2007).
13. Yan, Y. et al. A downstream mediator in the growth repression limb of the jasmonate pathway. Plant Cell 19, 2470-2483 (2007).
14. Hou, X., Lee, L. Y., Xia, K., Yan, Y. & Yu, H. DELLAs modulate jasmonate signaling via competitive binding to JAZs. Dev Cell 19, 884-894 (2010).
15. Yang, D. L. et al. Plant hormone jasmonate prioritizes defense over growth by interfering with gibberellin signaling cascade. Proc Natl Acad Sci USA 109, 1192-1200 (2012).
16. Fernandez-Calvo, P. et al. The *Arabidopsis* bHLH Transcription Factors MYC3 and MYC4 are targets of JAZ repressors and act additively with MYC2 in the activation of jasmonate responses. Plant Cell 23, 701-715 (2011).
17. Schweizer, F. et al. *Arabidopsis* basic helix-loop-helix transcription factors MYC2, MYC3, and MYC4 regulate glucosinolate biosynthesis, insect performance, and feeding behavior. Plant Cell 25, 3117-3132 (2013).
18. Gasperini, D. et al. Multilayered organization of jasmonate signalling in the regulation of root growth. PLoS Genet 11, e1005300 (2015).
19. Qi, T. et al. The Jasmonate-ZIM-domain proteins interact with the WD-Repeat/bHLH/MYB complexes to regulate jasmonate-mediated anthocyanin accumulation and trichome initiation in *Arabidopsis thaliana*. Plant Cell 23, 1795-1814 (2011).
20. de Lucas, M. et al. A molecular framework for light and gibberellin control of cell elongation. Nature 451, 480-484 (2008).
21. Casal, J. J. Photoreceptor signaling networks in plant responses to shade. Annu Rev Plant Biol 64, 403-427 (2013).
22. Ballare, C. L. Light regulation of plant defense. Annu Rev Plant Biol 65, 335-363 (2014).
23. Oh, E., Zhu, J. Y. & Wang, Z. Y. Interaction between BZR1 and PIF4 integrates brassinosteroid and environmental responses. Nat Cell Biol 14, 802-809 (2012).
24. Chico, J. M. et al. Repression of jasmonate-dependent defenses by shade involves differential regulation of protein stability of MYC transcription factors and their JAZ repressors in *Arabidopsis*. *Plant Cell* 26, 1967-1980 (2014).

Hornitschek, P. et al. Phytochrome interacting factors 4 and 5 control seedling growth in changing light conditions by directly controlling auxin signaling. *Plant J* 71, 699-711 (2012).

26 Zhang, Y. et al. A quartet of PIF bHLH factors provides a transcriptionally centered signaling hub that regulates seedling morphogenesis through differential expression-patterning of shared target genes in *Arabidopsis*. *PLoS Genet* 9, e1003244 (2013).

27 Leivar, P. & Monte, E. PIFs: systems integrators in plant development. *Plant Cell* 26, 56-78 (2014).

28 Attaran, E. et al. Temporal dynamics of growth and photosynthesis suppression in response to jasmonate signaling. *Plant Physiol* 165, 1302-1314 (2014).

29 Boccalandro, H. E. et al. Phytochrome B enhances photosynthesis at the expense of water-use efficiency in *Arabidopsis*. *Plant Physiol* 150, 1083-1092 (2009).

Weraduwage, S. M. et al. The relationship between leaf area growth and biomass accumulation in *Arabidopsis thaliana*. *Front Plant Sci* 6, 167 (2015).

31 McElver, J. et al. Insertional mutagenesis of genes required for seed development in *Arabidopsis thaliana*. *Genetics* 159, 1751-1763 (2001).

32 Jiang, Y., Liang, G., Yang, S. & Yu, D. *Arabidopsis* WRKY57 functions as a node of convergence for jasmonic acid- and auxin-mediated signaling in jasmonic acid-induced leaf senescence. *Plant Cell* 26, 230-245 (2014).

33 Sehr, E. M. et al. Analysis of secondary growth in the *Arabidopsis* shoot reveals a positive role of jasmonate signalling in cambium formation. *Plant J* 63, 811-822 (2010).

34 Reed, J. W., Nagpal, P., Poole, D. S., Furuya, M. & Chory, J. Mutations in the gene for the red/far-red light receptor phytochrome B alter cell elongation and physiological responses throughout *Arabidopsis* development. *Plant Cell* 5, 147-157 (1993).

Feng, S. H. et al. Coordinated regulation of *Arabidopsis thaliana* development by light and gibberellins. *Nature* 451, 475-479 (2008).

36 Leivar, P. et al. Multiple phytochrome-interacting bHLH transcription factors repress premature seedling photomorphogenesis in darkness. *Curr Biol* 18, 1815-1823 (2008).

37 Chung, H. S. et al. Regulation and function of *Arabidopsis JASMONATE ZIM*-domain genes in response to wounding and herbivory *Plant Physiol* 146, 952-964 (2008).

38 Shyu, C. et al. JAZ8 lacks a canonical degron and has an EAR motif that mediates transcriptional repression of jasmonate responses in *Arabidopsis*. *Plant Cell* 24, 536-550 (2012).

39 Kang, J. H. et al. The flavonoid biosynthetic enzyme chalcone isomerase modulates terpenoid production in glandular trichomes of tomato. *Plant Physiol* 164 (2014).

Barth, C. & Jander, G. *Arabidopsis* myrosinases TGG1 and TGG2 have redundant function in glucosinolate breakdown and insect defense. *Plant J* 46, 549-562 (2006).

41 Herde, M., Koo, A. J. & Howe, G. A. Elicitation of jasmonate-mediated defense responses by mechanical wounding and insect herbivory. *Methods Mol Biol* 1011, 51-61 (2013).

42 Warnasooriya, S. N. & Montgomery, B. L. Detection of spatial-specific phytochrome responses using targeted expression of biliverdin reductase in *Arabidopsis*. *Plant Physiol* 149, 424-433 (2009).

43 Li, B. & Dewey, C. N. RSEM: accurate transcript quantification from RNA-Seq data with or without a reference genome. *BMC Bioinformatics* 12, 323, (2011).

44 Anders, S. & Huber, W. Differential expression analysis for sequence count data. *Genome Biol* 11, R106 (2010).

45 Maere, S., Heymans, K. & Kuiper, M. BiNGO: a Cytoscape plugin to assess overrepresentation of Gene Ontology categories in biological networks. *Bioinformatics* 21, 3448-3449 (2005).

46 Ruijter, J. M. et al. Amplification efficiency: linking baseline and bias in the analysis of quantitative PCR data. *Nucleic Acids Res* 37, e45 (2009).

47 Lee, C. M. & Thomashow, M. F. Photoperiodic regulation of the C-repeat binding factor (CBF) cold acclimation pathway and freezing tolerance in *Arabidopsis thaliana*. *Proc Natl Acad Sci USA* 109, 15054-15059 (2012).

48 Clough, S. J. & Bent, A. F. Floral Dip: A simplified method for Agrobacterium-mediated transformation of *Arabidopsis thaliana*. *Plant J* 16, 735-743 (1998).

49 Li, Z. R., Gao, J. P., Benning, C. & Sharkey, T. D. Characterization of photosynthesis in *Arabidopsis* ER-to-plastid lipid trafficking mutants. *Photosynth Res* 112, 49-61 (2012).

50 Dutta, S. et al. Non-invasive, whole-plant imaging of chloroplast movement and chlorophyll fluorescence reveals photosynthetic phenotypes independent of chloroplast photorelocation defects in chloroplast division mutants. *Plant J* 84, 428-442 (2015).

51 Kramer, D., Cruz, J., Hall, C., Kovac, W. K. & Zegarac, R. Plant phenometrics systems and methods and devices related thereto. United States Patent WO 2013181433 A2 (2013).

52 Tessmer, O. L., Jiao, Y., Cruz, J. A., Kramer, D. M. & Chen, J. Functional approach to high-throughput plant growth analysis. *BMC Syst Biol* 7, (Suppl 6) S17 (2013).

53 Baker, N. R. Chlorophyll fluorescence: a probe of photosynthesis in vivo. *Annu Rev Plant Biol* 59, 89-113 (2008).

54 Lichtenthaler, H. K. & Wellburn, A. R. Determinations of total carotenoids and chlorophylls a and b of leaf extracts in different solvents. *Biochem Soc Trans* 11, 591-592 (1983).

55 Sonderby, I. E., Geu-Flores, F. & Halkier, B. A. Biosynthesis of glucosinolates—gene discovery and beyond. *Trends Plant Sci* 15, 283-290 (2010).

56. Zhang et al., Structural basis of JAZ repression of MYC transcription factors in jasmonate signalling, *Nature* 525: 269-273 (2015).

57. Katsir et al., COI1 is a critical component of a receptor for jasmonate and the bacterial virulence factor coronatine, *Proc. Natl. Acad. Sci. U.S.A.* 105(19): 7100-7105 (2008).

58. Melotto et al., A critical role of two positively charged amino acids in the Jas motif of *Arabidopsis* JAZ proteins in mediating coronatine- and jasmonoyl isoleucine-dependent interactions with the COI1 F-box protein, *The Plant journal: for cell and molecular biology* 55(6): 979-988 (2008).

59. Smolen et al., Dominant alleles of the basic helix-loop-helix transcription factor ATR2 activate stress-responsive genes in *Arabidopsis*, *Genetics* 161(3): 1235-1246 (2002).

60. Moreno et al., Negative feedback control of jasmonate signaling by an alternative splice variant of JAZ10, *Plant physiology* 162(2): 1006-1017 (2013).

61. Chung & Howe, A critical role for the TIFY motif in repression of jasmonate signaling by a stabilized splice variant of the JASMONATE ZIM-domain protein JAZ10 in *Arabidopsis*, The Plant Cell 21(1): 131-145 (2009).
62. Goossens et al., Change of a conserved amino acid in the MYC2 and MYC3 transcription factors leads to release of JAZ repression and increased activity, The New Phytologist 206(4): 1229-1237 (2015).
63. Zhang et al., Structural insights into alternative splicing-mediated desensitization of jasmonate signaling, *Proc. Natl. Acad. Sci. U.S.A.* 114(7): 1720-1725 (2017).
64. Major et al., Regulation of growth-defense balance by the JASMONATE ZIM-DOMAIN (JAZ)-MYC transcriptional module, The New Phytologist (2017).
65. Pauwels et al., NINJA connects the co-repressor TOPLESS to jasmonate signalling, Nature 464(7289): 788-791 (2010).
66. Kazan & Manners, MYC2: the master in action, Molecular Plant 6(3): 686-703 (2013).

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The following statements are intended to describe and summarize various embodiments of the invention according to the foregoing description in the specification.

Statements

1. A plant, plant cell, or plant seed comprising at least one mutant MYC protein with at least one mutation within or outside of a JAZ-interacting domain (JID) of the MYC protein, and a phyB loss-of-function mutation.
2. The plant, plant cell, or plant seed of statement 1, wherein the mutation within or outside of the JAZ-interacting domain (JID) reduces binding of the MYC protein to a JAZ protein selected from a JAZ1 protein, JAZ2 protein, JAZ3 protein, JAZ4 protein, JAZ5 protein, JAZ6 protein, JAZ7 protein, JAZ8 protein, JAZ9 protein, JAZ10 protein, JAZ11 protein, JAZ12 protein, JAZ13 protein, or a combination thereof.
3. The plant, plant cell, or plant seed of statement 1 or 2, wherein the mutation within or outside of the JAZ-interacting domain (JID) reduces binding of the MYC protein to a JAZ protein selected from a JAZ1 protein, JAZ2 protein, JAZ3 protein, JAZ4 protein, JAZ5 protein, JAZ6 protein, JAZ7 protein, JAZ8 protein, JAZ9 protein, JAZ10 protein, JAZ11 protein, JAZ12 protein, JAZ13 protein, or a combination thereof by at least 20%, or at least 30%, or at least 40%, or at least 50%, or at least 60%, or at least 70%, or at least 80%, or at least 90%, or at least 95%, or at least 97%, or at least 99% compared to wild type plant cells, plants, and seeds of the same species (that do not have the MYC mutation(s)).
4. The plant, plant cell, or plant seed of statement 1, 2, or 3, wherein the JAZ-interacting domain (JID) has less than 100%, or less than 99.5%, or less than 99%, or less than 98%, or at less than 97%, or less than 96%, or less than 95%, or less than 94%, or less than 93%, or less than 92%, or less than 91%, or less than 90% sequence identity to any of SEQ ID NOs: 2, 4, 6, 8, 10, 12, 14, 16, 18, 20, 22, 24, 26, or 28.
5. The plant, plant cell, or plant seed of statement 1-3 or 4, wherein the mutant MYC protein has less than 100%, or less than 99.5%, or less than 99%, or less than 98%, or at less than 97%, or less than 96%, or less than 95%, or less than 94%, or less than 93%, or less than 92%, or less than 91%, or less than 90% sequence identity to any of SEQ ID NOs:1, 3, 5, 7, 9, 11, 13, 15, 17, 19, 21, 23, 25, or 27.
6. The plant, plant cell, or plant seed of statement 1-4 or 5, wherein the mutant MYC protein has at least 40%, or at least 50%, or at least 60%, or at least 70%, or at least 80%, or at least 90%, or at least 95%, or at least 97%, or at least 99% sequence identity to any of SEQ ID NOs:1, 3, 5, 7, 9, 11, 13, 15, 17, 19, 21, 23, 25, or 27.
7. The plant, plant cell, or plant seed of statement 1-5 or 6, wherein the mutant MYC protein is expressed from a dominant MYC genomic allele, from an expression cassette encoding the mutant MYC protein, or from an expression cassette encoding a dominant mutant MYC protein.
8. The plant, plant cell, or plant seed of statement 1-6 or 7, comprising a heterologous MYC transgene or MYC expression cassette that encodes the mutant MYC protein.
9. The plant, plant cell, or plant seed of statement 1-7 or 8, comprising a heterologous MYC transgene comprising a promoter operably linked to a nucleic acid segment encoding the mutant MYC protein.
10. The plant, plant cell, or plant seed of statement 1-8 or 9, comprising a heterologous MYC transgene comprising a promoter operably linked to a cDNA encoding the mutant MYC protein.
11. The plant, plant cell, or plant seed of statement 1-9 or 10, wherein the plant, plant cell, or plant seed (or plant grown from the plant seed) has reduced PHYB activity compared to a wild type plant without the phyB loss-of-function mutation.
12. The plant, plant cell, or plant seed of statement 1-10 or 11, wherein the plant, plant cell, or plant seed expresses a PHYB protein with less than 99%, or less than 98%, or less than 95%, or less than 90%, or less than 85%, or less than 75%, or less than 60%, or less than 50%, or less than 40%, or less than 30%, or less than 20% sequence identity to any of SEQ ID NOs:30, 32, 33, 34, 35, 36, or 37.
13. The plant, plant cell, or plant seed of statement 1-11 or 12, wherein the plant, plant cell, or plant seed comprises a deletion in a chromosomal PhyB or PhyB-related chromosomal site, a substitution within a chromosomal PhyB or PhyB-related chromosomal site, or an insertion into a chromosomal PhyB or PhyB-related chromosomal site.
14. The plant, plant cell, or plant seed of statement 1-12 or 13, wherein the plant, plant cell, or plant seed comprises a deletion, substitution, or insertion of a chromosomal PhyB or PhyB-related chromosomal site so that a truncated PHYB polypeptide, a mutant PHYB polypeptide, or no PHYB polypeptide is expressed.
15. The plant, plant cell, or plant seed of statement 1-13 or 14, comprising at least one loss-of-function mutation(s) in at least four or five genes encoding transcriptional repressors of jasmonic acid (JAZ) responses.
16. The plant, plant cell, or plant seed of statement 1-14 or 15, comprising at least one loss-of-function mutation(s) in at least four or five genes encoding transcriptional repressors of jasmonic acid (JAZ) responses that comprise one or more deletions, substitutions, or insertions into at least four or five genomic nucleic acids encoding transcriptional repressors of jasmonic acid response proteins with at least at least 70%, or at least 75%, or at least 80%, or at least 85%, or at least 90%, or at least 95%, or at least 97%, or at least 98%, or at least 99% sequence identity to any of amino acid sequence SEQ ID NO:48, 50, 52, 54, 56, 58-73, or 74.

17. The plant, plant cell, or plant seed of statement 1-15 or 16, wherein the plant or a plant grown from the seed has less leaf damage from insect feeding than a wild type plant of the same species (but without phyB, phyB-related, or MYC gene mutations) grown under the same environmental conditions.

18. The plant, plant cell, or plant seed of statement 1-16 or 17, wherein the plant or a plant grown from the seed has 5% less, or 10% less, or 20% less, or 30% less, or 40% less, or 50% less, or 60% less, or 70% less, or 80% less, or 90% less, or 100% less leaf damage from insect feeding than a wild type plant of the same species (but without PHYB, PHYB-related, or MYC gene mutations) grown under the same environmental conditions.

19. The plant, plant cell, or plant seed of statement 1-17 or 18, further comprising a heterologous PIF4 transgene or PIF4 expression cassette.

20. The plant, plant cell, or plant seed of statement 1-18 or 19, further comprising a heterologous PIF4 transgene comprising a promoter operably linked to a nucleic acid segment encoding a PIF4 polypeptide.

21. The plant, plant cell, or plant seed of statement 1-19 or 20, further comprising a heterologous PIF4 transgene encoding a PIF4 protein with at least 70% sequence identity, or at least 80% sequence identity, or at least 85% sequence identity, or at least 90% sequence identity, or at least 95% sequence identity, or at least 97% sequence identity, or at least 98% sequence identity, or at least 99% sequence identity to any of amino acid sequences identified as SEQ ID NO: 38, 40, 42, or 44.

22. The plant, plant cell, or plant seed of statement 1-20 or 21, further comprising a heterologous PIF4 transgene comprising a promoter operably linked to a cDNA encoding a PIF4 polypeptide.

23. The plant, plant cell, or plant seed of statement 1-21 or 22, further comprising a heterologous PIF4 transgene comprising a promoter operably linked to a cDNA encoding a PIF4 polypeptide, where the promoter functions (e.g., promotes transcription) during plant development or growth.

24. The plant, plant cell, or plant seed of statement 1-22 or 23, wherein the plant or a plant grown from the seed exhibits resistance to environmental stress compared to a wild type plant of the same species under the same environmental conditions.

25. The plant, plant cell, or plant seed of statement 1-23 or 24, wherein the plant or a plant grown from the seed has at least about 10%, or at least about 20%, or at least about 30%, or at least about 40%, or at least about 50%, or at least about 60%, or at least about 70%, or at least about 80%, or at least about 90% fewer insects or insect larvae than a wild type plant of the same species grown under the same environmental conditions.

26. The plant, plant cell, or plant seed of statement 1-24 or 25, wherein rosette weight of the plant or a plant grown from the seed is about 80% to about 120%, or about 90% to about 110% of the rosette dry weight of wild type plants grown for the same time and under the same conditions.

27. The plant, plant cell, or plant seed of statement 1-25 or 26, which is a food crop species (e.g., sugar beets, beets, tomatoes, lettuce, spinach, carrots, peppers, peas, broccoli, beans, asparagus), a legume species (e.g., peas, beans, lentils, peanuts), a fiber-containing plant species, a tree species, flax, a grain species (e.g., maize, wheat, barley, oats, rice, sorghum, millet, and rye), a grass species (e.g., switchgrass, prairie grass, wheat grass, sudangrass, sorghum, straw-producing plants), a woody plant species (e.g., a poplar species, pine species, or eucalyptus species), a softwood, a hardwood, an oil and/or starch producing plant species (e.g., canola, potatoes, lupins, sunflower and cottonseed), a forage plant species (e.g., alfalfa, clover, or fescue).

28. A method comprising cultivating the plant or plant seed of statement 1-26 or 27.

29. The method of statement 28, wherein the plant or plant grown from the plant seed has less insect damage than a plant or plant grown from a seed without the mutation(s) but cultivated under similar growing conditions.

30. The method of statements 28 or 29, wherein the plant or plant grown from the plant seed has less insect larval and/or adult insect feeding than a plant or plant grown from a seed without the mutation(s) but cultivated under similar growing conditions.

31. The method of statement 28, 29, or 30, further comprising harvesting the plant or harvesting seeds, grain, fruit, vegetables, or biomass of the plant.

32. A method comprising (a) introducing into one or more plant cell at least one chromosomal loss-of-function mutation in a PHYB or PHYB-related gene and introducing at least one mutation into an endogenous MYC gene; and (b) generating a plant from the one or more plant cell(s).

33. The method of statement 32, wherein the mutation in the MYC gene is within or outside of a MYC JAZ-interacting domain (JID) encoded by the MYC gene.

34. The method of statement 32 or 33, wherein the mutation in the MYC gene is a dominant mutation.

35. The method of statement 32, 33, or 34, wherein the mutation in the MYC gene reduces binding of an encoded MYC protein to a JAZ protein selected from a JAZ1 protein, JAZ2 protein, JAZ3 protein, JAZ4 protein, JAZ5 protein, JAZ6 protein, JAZ7 protein, JAZ8 protein, JAZ9 protein, JAZ10 protein, JAZ11 protein, JAZ12 protein, JAZ13 protein, or a combination thereof.

36. The method of statement 32-34 or 35, wherein the mutation in the MYC gene reduces binding of an encoded MYC protein to a JAZ protein selected from a JAZ1 protein, JAZ2 protein, JAZ3 protein, JAZ4 protein, JAZ5 protein, JAZ6 protein, JAZ7 protein, JAZ8 protein, JAZ9 protein, JAZ10 protein, JAZ11 protein, JAZ12 protein, JAZ13 protein, or a combination thereof by at least 20%, or at least 30%, or at least 40%, or at least 50%, or at least 60%, or at least 70%, or at least 80%, or at least 90%, or at least 95%, or at least 97%, or at least 99% compared to a wild type plant of the same species (that does not have the MYC mutation(s)).

37. The method of statement 32-35 or 36, wherein the MYC gene encodes a JAZ-interacting domain (JID) that has less than 100%, or less than 99.5%, or less than 99%, or less than 98%, or at less than 97%, or less than 96%, or less than 95%, or less than 94%, or less than 93%, or less than 92%, or less than 91%, or less than 90% sequence identity to any of SEQ ID NOs: 2, 4, 6, 8, 10, 12, 14, 16, 18, 20, 22, 24, 26, or 28.

38. The method of statement 32-36 or 37, wherein the MYC gene encodes a MYC protein less than 100%, or less than 99.5%, or less than 99%, or less than 98%, or at less than 97%, or less than 96%, or less than 95%, or less than 94%, or less than 93%, or less than 92%, or less than 91%, or less than 90% sequence identity to any of SEQ ID NOs:1, 3, 5, 7, 9, 11, 13, 15, 17, 19, 21, 23, 25, or 27.

39. The method of statement 32-37 or 38, wherein the MYC protein has at least 40%, or at least 50%, or at least 60%, or at least 70%, or at least 80%, or at least 90%, or at least 95%, or at least 97%, or at least 99% sequence identity to any of SEQ ID NOs:1, 3, 5, 7, 9, 11, 13, 15, 17, 19, 21, 23, 25, or 27.

40. The method of statement 32-38 or 39, wherein the plant has reduced PHYB activity compared to a wild type plant without the PhyB loss-of-function mutation.

41. The method of statement 32-39 or 40, wherein the plant expresses a PHYB protein with less than 99%, or less than 98%, or less than 95%, or less than 90%, or less than 85%, or less than 75%, or less than 60%, or less than 50%, or less than 40%, or less than 30%, or less than 20% sequence identity to any of SEQ ID NOs:30, 32, 33, 34, 35, 36, or 37.

42. The method of statement 32-40 or 41, wherein the plant comprises a deletion of a chromosomal PhyB or PhyB-related chromosomal site, a substitution within a chromosomal PhyB or PhyB-related chromosomal site, or an insertion into a chromosomal PhyB or PhyB-related chromosomal site.

43. The method of statement 32-41 or 42, wherein the plant comprises a deletion, substitution, or insertion of a chromosomal PhyB or PhyB-related chromosomal site so that a truncated PHYB polypeptide, a mutant PHYB polypeptide, or no PHYB polypeptide is expressed.

44. The method of statement 32-42 or 43, wherein the plant cell comprises at least one loss-of-function mutation(s) in at least four or five genes encoding transcriptional repressors of jasmonic acid (JAZ) responses.

45. The method of statement 32-43 or 44, further comprising introducing into one or more plant cell at least one chromosomal loss-of-function mutation in at least four or five genes encoding transcriptional repressors of jasmonic acid (JAZ) responses.

46. The method of statement 32-44 or 45, wherein the plant comprises one or more deletions, substitutions, or insertions into at least four or five genomic nucleic acids encoding transcriptional repressors of jasmonic acid response proteins with at least at least 70%, or at least 75%, or at least 80%, or at least 85%, or at least 90%, or at least 95%, or at least 97%, or at least 98%, or at least 99% sequence identity to any of amino acid sequence SEQ ID NO:48, 50, 52, 54, 56, 58-73, or 74.

47. The method of statement 32-45 or 46, wherein the plant exhibits resistance to environmental stress compared to a wild type plant of the same species under the same environmental conditions.

48. The method of statement 32-46 or 47, further comprising obtaining seeds from the plant.

49. The method of statement 32-47 or 48, further comprising harvesting the plant or harvesting grain, fruit, vegetables, or biomass of the plant.

50. A method comprising (a) introducing into one or more plant cell at least one transgene or expression cassette encoding a mutant MYC nucleic acid segment that encodes a mutant MYC protein; and (b) generating a plant from the one or more plant cell(s).

51. The method of statement 50, wherein the mutant MYC nucleic acid segment has at least one mutation within or outside of an encoded MYC JAZ-interacting domain (JID).

52. The method of statement 50 or 51, wherein the mutant MYC nucleic acid has a dominant mutation.

53. The method of statement 50, 51 or 52, wherein the mutant MYC protein has reduced binding to a JAZ protein selected from a JAZ1 protein, JAZ2 protein, JAZ3 protein, JAZ4 protein, JAZ5 protein, JAZ6 protein, JAZ7 protein, JAZ8 protein, JAZ9 protein, JAZ10 protein, JAZ11 protein, JAZ12 protein, JAZ13 protein, or a combination thereof.

54. The method of statement 50-52 or 53, wherein the mutant MYC protein has binding to a JAZ protein selected from a JAZ1 protein, JAZ2 protein, JAZ3 protein, JAZ4 protein, JAZ5 protein, JAZ6 protein, JAZ7 protein, JAZ8 protein, JAZ9 protein, JAZ10 protein, JAZ11 protein, JAZ12 protein, JAZ13 protein, or a combination thereof that is reduced by at least 20%, or at least 30%, or at least 40%, or at least 50%, or at least 60%, or at least 70%, or at least 80%, or at least 90%, or at least 95%, or at least 97%, or at least 99% compared to a wild type plant of the same species (that does not have the MYC mutation(s)).

55. The method of statement 50-53 or 54, wherein the mutant MYC protein has a JAZ-interacting domain (JID) that has less than 100%, or less than 99.5%, or less than 99%, or less than 98%, or at less than 97%, or less than 96%, or less than 95%, or less than 94%, or less than 93%, or less than 92%, or less than 91%, or less than 90% sequence identity to any of SEQ ID NOs: 2, 4, 6, 8, 10, 12, 14, 16, 18, 20, 22, 24, 26, or 28.

56. The method of statement 50-54 or 55, wherein the mutant MYC protein has less than 100%, or less than 99.5%, or less than 99%, or less than 98%, or at less than 97%, or less than 96%, or less than 95%, or less than 94%, or less than 93%, or less than 92%, or less than 91%, or less than 90% sequence identity to any of SEQ ID NOs:1, 3, 5, 7, 9, 11, 13, 15, 17, 19, 21, 23, 25, or 27.

57. The method of statement 50-55 or 56, wherein the mutant MYC protein has at least 40%, or at least 50%, or at least 60%, or at least 70%, or at least 80%, or at least 90%, or at least 95%, or at least 97%, or at least 99% sequence identity to any of SEQ ID NOs:1, 3, 5, 7, 9, 11, 13, 15, 17, 19, 21, 23, 25, or 27.

58. The method of statement 50-56 or 57, wherein the plant has reduced PHYB activity compared to a wild type plant without the PhyB loss-of-function mutation.

59. The method of statement 50-57 or 58, wherein the plant expresses a PHYB protein with less than 99%, or less than 98%, or less than 95%, or less than 90%, or less than 85%, or less than 75%, or less than 60%, or less than 50%, or less than 40%, or less than 30%, or less than 20% sequence identity to any of SEQ ID NOs:30, 32, 33, 34, 35, 36, or 37.

60. The method of statement 50-58 or 59, wherein the plant comprises a deletion of a chromosomal PhyB or PhyB-related chromosomal site, a substitution within a chromosomal PhyB or PhyB-related chromosomal site, or an insertion into a chromosomal PhyB or PhyB-related chromosomal site.

61. The method of statement 50-59 or 60, wherein the plant comprises a deletion, substitution, or insertion of a chromosomal PhyB or PhyB-related chromosomal site so that a truncated PHYB polypeptide, a mutant PHYB polypeptide, or no PHYB polypeptide is expressed.

62. The method of statement 50-60 or 61, wherein the plant cell comprises at least one loss-of-function mutation(s) in at least four or five genes encoding transcriptional repressors of jasmonic acid (JAZ) responses.

63. The method of statement 50-61 or 62, further comprising introducing into one or more plant cell at least one chromosomal loss-of-function mutation in one to five genes encoding transcriptional repressors of jasmonic acid (JAZ) responses.

64. The method of statement 50-62 or 63, wherein the plant comprises one or more deletions, substitutions, or insertions into one or five genomic nucleic acids encoding transcriptional repressors of jasmonic acid response proteins with at least at least 70%, or at least 75%, or at least 80%, or at least 85%, or at least 90%, or at least 95%, or at least 97%, or at least 98%, or at least 99% sequence identity to any of amino acid sequence SEQ ID NO:48, 50, 52, 54, 56, 58-73, or 74.

65. The method of statement 50-63 or 64, wherein the plant exhibits resistance to environmental stress compared to a wild type plant of the same species under the same environmental conditions.

66. The method of statement 50-64 or 65, further comprising obtaining seeds from the plant.

67. The method of statement 50-65 or 67, further comprising harvesting the plant or harvesting grain, fruit, vegetables, or biomass of the plant.

68. A plant, plant cell, or plant seed comprising at least one chromosomal loss-of-function mutation in a PHYB or PHYB-related gene and a loss-of-function mutation in at least one gene encoding a transcriptional repressor of jasmonic acid responses.

69. The plant, plant cell, or plant seed of statement 68, comprising at least one chromosomal loss-of-function mutation in a PHYB or PHYB-related gene and a loss-of-function mutation in at least two or at least three genes encoding transcriptional repressors of jasmonic acid responses.

70. The plant, plant cell, or plant seed of statement 68 or 69, comprising at least one loss-of-function mutation(s) in at least four or five genes encoding transcriptional repressors of jasmonic acid responses.

71. The plant, plant cell, or plant seed of statement 68, 69 or 70, wherein the loss-of-function mutation(s) comprise one or more deletions, substitutions, or insertions into at least four or five genomic nucleic acids encoding transcriptional repressors of jasmonic acid response (JAZ) proteins with at least at least 70%, or at least 75%, or at least 80%, or at least 85%, or at least 90%, or at least 95%, or at least 97%, or at least 98%, or at least 99% sequence identity to any of amino acid sequence SEQ ID NO:48, 50, 52, 54, 56, 58-73, or 74.

72. The plant, plant cell, or plant seed of statement 68-70 or 71, wherein the loss-of-function mutation(s) comprise one or more insertions into at least four or five genomic nucleic acids encoding transcriptional repressors of jasmonic acid response (JAZ) proteins with at least at least 70%, or at least 75%, or at least 80%, or at least 85%, or at least 90%, or at least 95%, or at least 97%, or at least 98%, or at least 99% sequence identity to any of amino acid sequence SEQ ID NO:48, 50, 52, 54, 56, 58-73, or 74.

73. The plant, plant cell, or plant seed of statement 68-71 or 72, wherein the loss-of-function mutation(s) comprise one or more deletions in genomic nucleic acids encoding transcriptional repressors of jasmonic acid response (JAZ) proteins with at least at least 70%, or at least 75%, or at least 80%, or at least 85%, or at least 90%, or at least 95%, or at least 97%, or at least 98%, or at least 99% sequence identity to any of amino acid sequence SEQ ID NO:48, 50, 52, 54, 56, 58-73, or 74.

74. The plant, plant cell, or plant seed of statement 68-72 or 74, wherein the loss-of-function mutation(s) comprise one or more nucleotide substitutions in genomic nucleic acids encoding transcriptional repressors of jasmonic acid response (JAZ) proteins with at least at least 70%, or at least 75%, or at least 80%, or at least 85%, or at least 90%, or at least 95%, or at least 97%, or at least 98%, or at least 99% sequence identity to any of SEQ ID NO:48, 50, 52, 54, 56, 58-73, or 74.

75. The plant, plant cell, or plant seed of statement 68-73 or 74, wherein the loss-of-function mutation(s)s reduce transcription of genomic nucleic acids encoding transcriptional repressors of jasmonic acid response (JAZ) proteins by at least 70%, or at least 75%, or at least 80%, or at least 85%, or at least 90%, or at least 95%, or at least 97%, or at least 98%, or at least 99% compared to a wild type plant of the same species (without the loss-of-function mutations) grown under the same conditions.

76. The plant, plant cell, or plant seed of statement 68-74 or 75, wherein the chromosomal loss-of-function mutation(s) comprise one or more deletions, substitutions, or insertions into one or more genomic nucleic acid that encodes a PHYB protein or a PHYB-related protein with at least at least 70%, or at least 75%, or at least 80%, or at least 85%, or at least 90%, or at least 95%, or at least 97%, or at least 98%, or at least 99% sequence identity to any of SEQ ID NOs: 30, 32, 33, 34, 35, 36, or 37.

77. The plant, plant cell, or plant seed of statement 68-75 or 76, wherein the loss-of-function mutations reduce transcription and/or translation of at least three genes encoding transcriptional repressors of jasmonic acid responses by at least 20%, or at least 30%, or at least 40%, or at least 50%, or at least 60%, or at least 70%, or at least 80%, or at least 90%, or at least 95%, or at least 97%, or at least 99% compared to wild type plant cells, plants, and seeds of the same species (that do not have mutations in genes encoding transcriptional repressors of jasmonic acid response).

78. The plant, plant cell, or plant seed of statement 68-76 or 77, wherein the loss-of-function mutations reduce transcription and/or translation of the phyB gene, or of the phyB-related gene by at least 20%, or at least 30%, or at least 40%, or at least 50%, or at least 60%, or at least 70%, or at least 80%, or at least 90%, or at least 95%, or at least 97%, or at least 99% compared to wild type plant cells, plants, and seeds of the same species (that do not have phyB, phyB-related, or transcriptional repressors of jasmonic acid response gene mutations).

79. The plant, plant cell, or plant seed of statement 68-77 or 78, wherein the plant or a plant grown from the seed has less leaf damage from insect feeding than a wild type plant of the same species (but without phyB, phyB-related, or transcriptional repressors of jasmonic acid response gene mutations) grown under the same conditions.

80. The plant, plant cell, or plant seed of statement 68-78 or 79, wherein the plant or a plant grown from the seed has 5% less, or 10% less, or 20% less, or 30% less, or 40% less, or 50% less, or 60% less, or 70% less, or 80% less, or 90% less, or 100% less leaf damage from insect feeding than a wild type plant of the same species (but without PHYB, PHYB-related, or transcriptional repressors of jasmonic acid response gene mutations) grown under the same conditions.

81. The plant, plant cell, or plant seed of statement 68-79 or 80, wherein the plant or a plant grown from the seed has at least about 10%, or at least about 20%, or at least about 30%, or at least about 40%, or at least about 50%, or at least about 60%, or at least about 70%, or at least about 80%, or at least about 90% fewer insects or insect larvae than a wild type plant of the same species grown under the same conditions.

82. The plant, plant cell, or plant seed of statement 68-80 or 81, wherein rosette weight of the plant or a plant grown from the seed is about 80% to about 120%, or about 90% to about 110% of the rosette dry weight of wild type plants grown for the same time and under the same conditions.

83. The plant, plant cell, or plant seed of statement 68-81 or 82, further comprising a heterologous PIF4 transgene or PIF4 expression cassette.

84. The plant, plant cell, or plant seed of statement 68-82 or 83, further comprising a heterologous PIF4 transgene comprising a promoter operably linked to a nucleic acid segment encoding a PIF4 polypeptide.

85. The plant, plant cell, or plant seed of statement 68-83 or 84, further comprising a heterologous PIF4 transgene encoding a PIF4 protein with at least 70% sequence identity, or at least 80% sequence identity, or at least 85% sequence identity, or at least 90% sequence identity, or at least 95% sequence identity, or at least 97% sequence identity, or at least 98% sequence identity, or at least 99% sequence identity to any of amino acid sequences identified as SEQ ID NO: 38, 40, 42 or 44.

86. The plant, plant cell, or plant seed of statement 68-84 or 85, further comprising a heterologous PIF4 transgene comprising a promoter operably linked to a cDNA encoding a PIF4 polypeptide.

87. The plant, plant cell, or plant seed of statement 68-85 or 86, further comprising a heterologous PIF4 transgene comprising a promoter operably linked to a cDNA encoding a PIF4 polypeptide, where the promoter functions (e.g., promotes transcription) during plant development or growth.

88. A method comprising cultivating the plant or plant seed of statement 50-86 or 87.

89. The method of statement 88, wherein less insecticide is needed or less insecticide is applied to a plant or plant grown from the seed than would be applied to a plant or plant grown from a seed without the mutation(s) but cultivated under similar growing conditions.

90. The method of statement 88 or 89, wherein the plant or plant grown from the plant seed has less insect damage than a plant or plant grown from a seed without the mutation(s) but cultivated under similar growing conditions.

91. The method of statement 88, 89, or 90, wherein the plant or plant grown from the plant seed has less insect larval and/or adult insect feeding than a plant or plant grown from a seed without the mutation(s) but cultivated under similar growing conditions.

92. A method comprising (a) introducing at least one chromosomal loss-of-function mutation in a PHYB or PHYB-related gene and introducing at least one loss-of-function mutation in at least one gene encoding a transcriptional repressor of jasmonic acid responses into one or more plant cells; and (b) generating a plant from the one or more plant cells.

93. A method comprising (a) introducing at least one chromosomal loss-of-function mutation in a PHYB or PHYB-related gene and introducing at least one loss-of-function mutation in at least three genes encoding transcriptional repressors of jasmonic acid responses into one or more plant cells; and (b) generating a plant from the one or more plant cells.

94. The method of statement 92 or 93, further comprising introducing a heterologous PIF4 transgene comprising a promoter operably linked to a cDNA encoding a PIF4 polypeptide into the one or more plant cells.

95. The method of statement 92, 93 or 94, further comprising introducing at least one mutation in at least one JAZ interacting domain (JID) of a MYC protein encoded by a MYC gene into the one or more plant cells.

96. The method of statement 92-94 or 95, further comprising obtaining seeds from the plant.

97. The method of statement 28-67, 88-95 or 96, wherein the plant has a primary root that 1.5-fold longer, of 2-fold longer, or 2.3-fold longer, or 2.5-fold longer, or 2.7-fold longer, or 3-fold longer than the average primary root length of wild type plants grown for the same time and under the same conditions.

98. The method of statement 97, wherein the conditions are environmental stress conditions.

99. The method of statement 97 or 98, wherein the conditions comprise growth in the presence of 5-methyl-tryptophan.

100. The plant, plant cell, or plant seed of statement 1-26, 68-86, or 87, wherein the plant has a primary root that 1.5-fold longer, of 2-fold longer, or 2.3-fold longer, or 2.5-fold longer, or 2.7-fold longer, or 3-fold longer than the average primary root length of wild type plants grown for the same time and under the same conditions.

101. The plant, plant cell, or plant seed of statement 100, wherein the conditions are environmental stress conditions.

102. The plant, plant cell, or plant seed of statement 100 or 101, wherein the conditions comprise growth in the presence of 5-methyl-tryptophan.

The specific compositions and methods described herein are representative, exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by embodiments and optional features, modification and variation of the concepts herein disclosed may be resorted to by those skilled in the art, and that such modifications and variations are considered to be within the scope of this invention as defined by the appended claims and statements of the invention.

The invention illustratively described herein may be practiced in the absence of any element or elements, or limitation or limitations, which is not specifically disclosed herein as essential. The methods and processes illustratively described herein may be practiced in differing orders of steps, and the methods and processes are not necessarily restricted to the orders of steps indicated herein or in the claims.

As used herein and in the appended claims, the singular forms "a," "an," and "the" include plural reference unless the context clearly dictates otherwise. Thus, for example, a reference to "a plant" or "a seed" or "a cell" includes a plurality of such plants, seeds or cells, and so forth. In this document, the term "or" is used to refer to a nonexclusive or, such that "A or B" includes "A but not B," "B but not A," and "A and B," unless otherwise indicated.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

The Abstract is provided to comply with 37 C.F.R. § 1.72(b) to allow the reader to quickly ascertain the nature and gist of the technical disclosure. The Abstract is submitted with the understanding that it will not be used to interpret or limit the scope or meaning of the claims.

What is claimed:

1. A genetically modified and non-naturally occurring mutant plant cell, a mutant plant, or a mutant plant seed obtained thereof, comprising:
   (a) a PhyB loss-of-function mutation comprising at least one mutation to an amino acid in the amino acid sequence as set forth in SEQ ID NO: 33; and
   (b) a modified MYC nucleic acid encoding a mutant MYC protein comprising at least one mutation within a JAZ-interacting domain (JID) region of the mutant MYC protein that reduces or eliminates interaction of the mutant MYC protein with JAZ proteins, wherein the JAZ interacting domain (JID) has less than 100% and more than 95% amino acid sequence identity to the amino acid sequence as set forth in SEQ ID NO: 10, and wherein the mutant MYC protein has less than 100% amino acid sequence identity and at least 95% amino acid sequence identity to the amino acid sequence as set forth in SEQ ID NO: 9, and
   wherein the genetically modified and non-naturally occurring mutant plant cell, the mutant plant, or the mutant plant seed obtained thereof is a transgenic mutant, and wherein expression or lack of expression of the PhyB loss-of-function mutant protein, and expression of the MYC mutant protein rescues wild-type plant biomass and concurrently provides JA (jasmonic acid)-controlled defense in the genetically modified and non-naturally occurring mutant plant cell, the mutant plant, or the mutant plant seed obtained thereof as compared to a control plant of the same species that is grown under the same conditions, and wherein said JA-controlled defense is resistance to an environmental stress.

2. The genetically modified and non-naturally occurring mutant plant cell, the mutant plant, or the mutant plant seed obtained thereof, of claim 1, wherein the PhyB loss-of-function mutation comprises a deletion, substitution, or insertion of a wild-type chromosomal PhyB gene encoding the PhyB polypeptide of SEQ ID NO: 33 so that a truncated PHYB polypeptide, a mutant PHYB polypeptide, or no PHYB polypeptide is expressed.

3. The genetically modified and non-naturally occurring mutant plant cell, the mutant plant, or the mutant plant seed obtained thereof, of claim 1, wherein the mutant MYC protein has reduced binding to a JAZ protein from *Zea mays* as set forth in SEQ ID NO: 60, and wherein the binding is reduced by at least 20% as compared to a corresponding wild type MYC protein that does not have said at least one MYC mutation.

4. The genetically modified and non-naturally occurring mutant plant cell, the mutant plant, or the mutant plant seed obtained thereof, of claim 1, wherein the modified MYC nucleic acid is a modification by having a deletion, substitution, or insertion of a chromosomal wild-type MYC gene encoding the protein of SEQ ID NO: 9 to encode the mutant MYC protein.

5. The genetically modified and non-naturally occurring mutant plant cell, the mutant plant, or the mutant plant seed obtained thereof, of claim 1, comprising one or more deletions, substitutions, or insertions into one or five wild-type genomic JAZ nucleic acids that encode JAZ proteins with at least 95% amino acid sequence identity to the amino acid sequences as set forth in SEQ ID NO: 60.

6. The genetically modified and non-naturally occurring mutant plant cell, the mutant plant, or the mutant plant seed obtained thereof, of claim 1, comprising a loss-of-function chromosomal mutation in an endogenous *Zea mays* JAZ gene encoding the JAZ protein as set forth in SEQ ID NO: 60.

7. The genetically modified and non-naturally occurring mutant plant cell, the mutant plant, or the mutant plant seed obtained thereof, of claim 1, wherein the mutant plant or a mutant plant grown from the seed exhibits resistance to the environmental stress compared to a wild type plant of the same species grown under the same environmental conditions, and wherein the environmental stress is insect stress or oxidative stress.

8. A method comprising:
(a) providing one or more genetically modified and non-naturally occurring mutant plant cells comprising a PhyB loss-of-function mutation comprising at least one mutation to an amino acid in the amino acid sequence as set forth in SEQ ID NO: 33;
(b) introducing into at least one of the mutant plant cells at least one transgene or expression cassette encoding a mutant MYC nucleic acid segment that encodes a mutant MYC protein to generate one or more transformed plant cell(s), wherein the mutant MYC protein has less than 100% amino acid sequence identity and at least 95% amino acid sequence identity to the amino acid sequence as set forth in SEQ ID NO: 9, and wherein the mutant MYC protein comprises at least one mutation within a JAZ-interacting domain (JID) region that reduces or eliminates interaction of the mutant MYC protein with JAZ proteins, wherein the JAZ interacting domain (JID) has less than 100% and more than 95% amino acid sequence identity to the amino acid sequence as set forth in SEQ ID NO: 10; and
(c) generating a genetically modified and non-naturally occurring mutant plant from the one or more transformed plant cells,
wherein expression or lack of expression of the PhyB loss-of-function mutant protein, and expression of the MYC mutant protein rescues wild-type plant biomass and concurrently provides JA (jasmonic acid)-controlled defense in the genetically modified and non-naturally occurring mutant plant as compared to a control plant of the same species that is grown under the same conditions, and wherein said JA-controlled defense is resistance to an environmental stress.

9. The method of claim 8, further comprising introducing into said at least one of the transformed plant cells one or more deletions, substitutions, or insertions into one or five wild-type genomic JAZ nucleic acids that encode JAZ proteins with at least 95% amino acid sequence identity to the amino acid sequences as set forth in SEQ ID NO: 60.

10. The method of claim 8, wherein the mutant MYC nucleic acid segment that encodes the mutant MYC protein is a dominant MYC mutation.

11. The method of claim 8, wherein the mutant MYC protein has reduced binding to a JAZ protein from *Zea mays* as set forth in SEQ ID NO: 60, and wherein the binding is reduced by at least 20% as compared to a corresponding wild type MYC protein that does not have said at least one MYC mutation.

12. The method of claim 8, wherein the genetically modified and non-naturally occurring mutant plant exhibits resistance to the environmental stress as compared to a wild type plant of the same species grown under the same environmental conditions, and wherein the environmental stress is insect stress or oxidative stress.

* * * * *